(12) United States Patent
Nakao et al.

(10) Patent No.: US 6,608,070 B1
(45) Date of Patent: Aug. 19, 2003

(54) 2,3-SUBSTITUTED INDOLE COMPOUNDS AS ANTI-INFLAMMATORY AND ANALGESIC AGENTS

(76) Inventors: Kazunari Nakao, 29-1, Sinbayashi, Shinbayahi-cho, Chiryu-shi, Aichi-ken (JP), 472-0017; Rodney William Stevens, 3-4-26, Seoshiro-cho, Handa-shi, Aichi-ken (JP), 484-0081; Kiyoshi Kawamura, 40-1, Daimonsaki, Inuyama, Inuyama-shi, Aichi-ken (JP), 484-0081; Chikara Uchida, 118-401, Miyaji-cho, Handa-shi, Aichi-ken (JP), 475-0902; Hiroki Koike, 1-100 Souga-cho, Handa-shi, Aichi-ken (JP), 475-0801; Stephane Caron, 600 Meridian St. Extension-Apt. 509, Groton, CT (US) 06340

( * ) Notice: Subject to any disclaimer, the term of this patent is extended or adjusted under 35 U.S.C. 154(b) by 0 days.

(21) Appl. No.: 09/355,494

(22) PCT Filed: Dec. 18, 1998

(86) PCT No.: PCT/IB98/02065

§ 371 (c)(1),
(2), (4) Date: Aug. 18, 2000

(87) PCT Pub. No.: WO99/35130

PCT Pub. Date: Jul. 15, 1999

(51) Int. Cl.[7] .............................................. A01N 43/90
(52) U.S. Cl. ...................... 514/264; 548/153; 546/195; 544/3; 544/98; 544/336; 540/200; 540/470; 540/480; 540/484; 540/553; 540/596; 514/415; 514/210.21; 514/211.08; 514/211.15; 514/217.08; 514/218; 514/227.8; 514/231.5; 514/252.13; 514/320; 514/365; 514/374
(58) Field of Search ........................... 548/153; 514/264, 514/415, 210.21, 211.08, 211.15, 217.08, 218, 227.8, 231.5, 252.13, 320, 365, 374; 540/200, 470, 480, 484, 653, 394; 544/3, 98, 336; 546/195

(56) References Cited

U.S. PATENT DOCUMENTS 5,510,368 A * 4/1996 Lau et al. .................... 514/419
5,604,253 A * 2/1997 Lau et al. .................... 514/415
6,476,042 B1 * 11/2002 Harrison ................. 514/263.31

FOREIGN PATENT DOCUMENTS

WO         96/37469         11/1996

* cited by examiner

Primary Examiner—D. Margaret Seaman
(74) Attorney, Agent, or Firm—Peter C. Richardson; Paul H. Ginsburg; Richard L. Catania

(57) ABSTRACT

This invention provides a compound of the following formula:

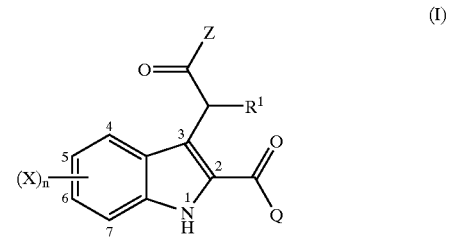

or the pharmaceutically acceptable salts thereof wherein Z is OH, C1-6 alkoxy, —NR2R3 or heterocycle; Q is selected from the following: (a) an optionally substituted phenyl, (b) an optionally substituted 6-membered monocyclic aromatic group containing one, two, three or four nitrogen atom(s), (c) an optionally substituted 5-membered monocyclic aromatic group containing one heteroatom selected from O, S and N and optionally containing one, two or three nitrogen atom(s) in addition to said heteroatom, (d) an optionally substituted C3–7 cycloalkyl and (e) an optionally substituted benzo-fuzed heterocycle; R1 is hydrogen, C1–4 alkyl or halo; R2 and R3 are independently hydrogen, OH, C1–4 alkoxy, C1–4 alkyl or C1–4 alkyl substituted with halo, OH, C1–4 alkoxy or CN; X is independently selected from H, halo, C1–4 alkyl, halo-substituted C1–4 alkyl, OH, C1–4 alkoxy, halo-substituted C1–4 alkoxy, C1–4 alkylthio, NO2, NH2, di-(C1–4 alkyl)amino and CN; and n is 0, 1, 2, 3 and 4.

This invention also provides a pharmaceutical composition useful for the treatment of a medical condition in which prostaglandins are implicated as pathogens.

14 Claims, No Drawings

2,3-SUBSTITUTED INDOLE COMPOUNDS AS ANTI-INFLAMMATORY AND ANALGESIC AGENTS

This application is a 371 of International Application No. PCT/IB98/02065, filed Dec. 18, 1998, which claims the benefit of International Application No. PCT/IB98/00003, filed Jan. 5, 1998.

TECHNICAL FIELD

This invention relates to novel 2,3-substituted indoles as pharmaceutical agents. This invention specifically relates to compounds, compositions and methods for the treatment or alleviation of pain and inflammation and other inflammation-associated disorders, such as arthritis.

BACKGROUND ART

Nonsteroidal antiinflammatory drugs (NSAIDs) are widely used in treating pain and the signs and symptoms of arthritis because of their analgesic and anti-inflammatory activity. It is accepted that common NSAIDs work by blocking the activity of cyclooxygenase (COX), also known as prostaglandin G/H synthase (PGHS), the enzyme that converts arachidonic acid into prostanoids. Prostaglandins, especially prostaglandin $E_2$ ($PGE_2$), which is the predominant eicosanoid detected in inflammation conditions are mediators of pain, fever and other symptoms associated with inflammation. Inhibition of the biosynthesis of prostaglandins has been a therapeutic target of anti-inflammatory drug discovery. The therapeutic use of conventional NSAIDs is, however, limited due to drug associated side effects, including life threatening ulceration and renal toxicity. An alternative to NSAIDs is the use of corticosteriods, however, long term therapy can also result in severe side effects.

Recently, two forms of COX were identified, a constitutive isoform (COX-1) and an inducible isoform (COX-2) of which expression is upregulated at sites of inflammation (Vane, J. R.; Mitchell, J. A.; Appleton, I.; Tomlinson, A.; Bishop-Bailey, D.; Croxtoll, J.; Willoughby, D. A. *Proc. Natl. Acad Sci. USA*, 1994, 91, 2046). COX-1 is thought to play a physiological role and to be responsible for gastrointestinal and renal protection. On the other hand, COX-2 appears to play a pathological role and to be the predominant isoform present in inflammation conditions. A pathological role for prostaglandins has been implicated in a number of human disease states including rheumatoid and osteoarthritis, pyrexia, asthma, bone resorption, cardiovascular diseases, nephrotoxicity, atherosclerosis, hypotension, shock, pain, cancer, and Alzheimer disease. The NSAIDs currently on market inhibit both isoforms of COX with little variation for selectivity, explaining their beneficial (inhibition of COX-2) and deleterious effects (inhibition of COX-1). It is believed that compounds that would selectively inhibit the biosynthesis of prostaglandins by intervention of the induction phase of the inducible enzyme cyclooxygenase-2 and/or by intervention of the activity of the enzyme cyclooxygenase-2 on arachidonic acid would provide alternate therapy to the use of NSAIDs or corticosteriods in that such compounds would exert anti-inflammatory effects without the adverse side effects associated with COX-1 inhibition.

A variety of indole compounds are known and are disclosed in several patent applications. The International Publication Numbers WO 96/32379 discloses N-substituted indole compounds as cGMP-PDE Inhibitors. The International Publication Numbers WO 96/37467, WO 96/37469, UK Patent Publication GB 2283745 A and U.S. Pat. No. 5,510,368 disclose 2-methyl-N-substituted indole compounds as cyclooxygenase-2 Inhibitors. Also, a variety of indole compounds are disclosed as agents for controlling underwater fouling organisms in European Patent Publication Number 0 556 949 A2 by Konya, Kazumi et. al. Specifically, the International Publication Numbers WO 97/09308 discloses indole compounds as neuropeptide receptor antagonists. Besides, in Sci. Pharm. 64, 577 (1996), a process for preparing a 2-ester-substituted indoline is disclosed.

BRIEF DISCLOSURE OF THE INVENTION

The present invention provides a compound of the following formula:

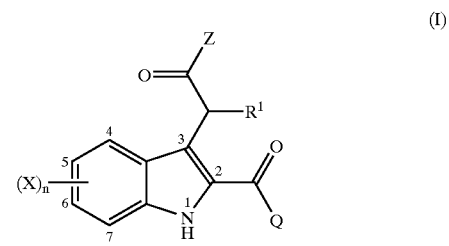

(I)

or the pharmaceutically acceptable salts thereof wherein
Z is OH, $C_{1-6}$ alkoxy, —$NR^2R^3$ or a group of the formula (II) or (III):

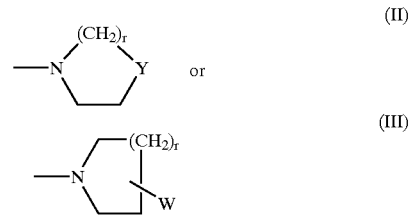

wherein r is 1, 2, 3 or 4, Y is a direct bond, O, S or $NR^4$, and W is OH or —$NR^2R^3$;

Q is selected from the following:
  (a) phenyl optionally substituted with one, two or three substituents independently selected from
    (a-1) halo, $C_{1-4}$ alkyl, halo-substituted $C_{1-4}$ alkyl, OH, $C_{1-4}$ alkoxy, halo-substituted $C_{1-4}$ alkoxy, $C_{1-4}$ alkylthio, $NO_2$, $NH_2$, di-($C_{1-4}$ alkyl)amino, $C_{1-4}$ alkylamino, CN, HO—($C_{1-4}$)alkyl, $C_{1-4}$ alkoxy-$C_{1-4}$ alkyl, $C_{1-4}$ alkylsulfonyl, aminosulfonyl, —$NH_2S(O)_2NR^2R^3$, acetyl, —COOH, —C(O)O—$C_{1-4}$ alkyl, $C_{1-4}$ alkylsulfonylamino and $C_{3-7}$ cycloalkyl,
    (a-2) aryl or —O—$(CH_2)_n$-aryl, and the aryl or aryl moiety being optionally substituted with one, two or three substituents independently selected from halo, $C_{1-4}$ alkyl, halo-substituted $C_{1-4}$ alkyl, OH, $C_{1-4}$ alkoxy, halo-substituted $C_{1-4}$ alkoxy, $C_{1-4}$ alkylthio, $NO_2$, $NH_2$, di-($C_{1-4}$ alkyl)amino, $C_{1-4}$ alkylamino and CN,
    (a-3) 5-membered monocyclic aromatic group optionally substitued with one, two or three substituents independently selected from halo, $C_{1-4}$ alkyl, halo-substituted $C_{1-4}$ alkyl, OH, $C_{1-4}$ alkoxy, halo-substituted $C_{1-4}$ alkoxy, $C_{1-4}$ alkylthio, $NO_2$, $NH_2$, di-($C_{1-4}$ alkyl)amino, $C_{1-4}$ alkylamino and CN, (a-4) 6-membered monocyclic aromatic group optionally substitued with one, two or three substituents independently selected from halo, $C_{1-4}$ alkyl, halo-substituted $C_{1-4}$ alkyl, OH, $C_{1-4}$ alkoxy, halo-substituted $C_{1-4}$ alkoxy, $C_{1-4}$ alkylthio, $NO_2$, $NH_2$, di-($C_{1-4}$ alkyl)amino, $C_{1-4}$ alkylamino and CN, (b) a 6-membered monocyclic aromatic group containing one, two, three or four nitrogen atom(s), and said monocyclic aromatic group being optionally substituted with one, two or three substituents independently selected from the above group (a-1), (a-2), (a-3) and (a-4), (c) a 5-membered monocyclic aromatic group containing one heteroatom selected from O, S and N and optionally containing one, two or three nitrogen atom(s) in addition to said heteroatom, and said monocyclic aromatic group being optionally substituted with one, two or three substituents independently selected from the above group (a-1), (a-2), (a-3) and (a-4);

(d) $C_{3-7}$ cycloalkyl optionally substituted with one or two substituents independently selected from OH, $C_{1-4}$ alkyl, halo and halo-substituted $C_{1-4}$ alkyl; and (e) a benzo-fuzed heterocycle optionally substituted with one, two or three substituents independently selected from the group (a-1);

$R^1$ is hydrogen, $C_{1-4}$ alkyl or halo;

$R^2$ and $R^3$ are independently H, OH, $C_{1-4}$ alkoxy, $C_{1-4}$ alkyl or $C_{1-4}$ alkyl substituted with halo, OH, $C_{1-4}$ alkoxy, $NH_2$ or CN;

$R^4$ is hydrogen or $C_{1-4}$ alkyl;

X is independently selected from halo, $C_{1-4}$ alkyl, halo-substituted $C_{1-4}$ alkyl, OH, $C_{1-4}$ alkoxy, halo-substituted $C_{1-4}$ alkoxy, $C_{1-4}$ alkylthio, $NO_2$, $NH_2$, di-($C_{1-4}$ alkyl)amino, $C_{1-4}$ alkylamino, CN, HO—($C_{1-4}$)alkyl, $C_{1-4}$ alkoxy-$C_{1-4}$ alkyl, $C_{1-4}$ alkylsulfonyl, aminosulfonyl, —$NH_2S(O)_2NR^2NR^3$, acetyl, —COOH, —C(O)O—$C_{1-4}$ alkyl, $C_{1-4}$ alkylsulfonylamino and $C_{3-7}$ cycloalkyl; and n is 0, 1, 2, 3 or 4.

The indole compounds of the present invention exhibit inhibition of COX activity. Preferably compounds of this invention exhibit inhibitory activity against COX-2, with more preferable compounds having COX-2 selectivity.

Accordingly, the present invention also provides a pharmaceutical composition, useful for the treatment of a medical condition in which prostaglandins are implicated as pathogens, which comprises a compound of the formula (I) and the pharmaceutically acceptable salts thereof.

Further, the present invention provides a method for the treatment of a medical condition in which prostaglandins are implicated as pathogens, in a mammalian subject, which comprises administering to said subject a therapeutically effective amount of said pharmaceutical composition.

The medical conditions in which prostaglandins are implicated as pathogens, include the relief of pain, fever and inflammation of a variety of conditions including rheumatic fever, symptoms associated with influenza or other viral infections, common cold, low back and neck pain, dysmenorrhea, headache, toothache, sprains and strains, myositis, neuralgia, synovitis, arthritis including rheumatoid arthritis, degenerative joint disease (osteoarthritis), gout, ankylosing spondylitis, systemic lumpus erythematosus and juvenile arthritis, bursitis, burns, injuries following surgical and dental procedures.

The compounds and pharmaceutical composition of this invention may inhibit cellular neoplastic transformations and metastatic tumor growth and thus may be used in the treatment and/or prevention of cancers in the colon, breast, skin, esophagus, stomach, urinary bladder, lung and liver. The compounds and pharmaceutical composition of this invention were used in the treatment and/or prevention of cyclooxygenase-mediated proliferation disorders such as which occur in diabetic retinopathy and tumor angiogenesis.

The compounds and pharmaceutical composition of this invention may inhibit prostaniod-induced smooth muscle contraction by preventing the synthesis of contractile prostanoids, and thus may be of use in the treatment of dysmenorrhea, premature labor, asthma and eosinophil related disorders and in the treatment of neurodegenerative diseases such as Alzheimer's and Parkinson's disease, and for the treatment of bone loss (treatment of osteoarthritis), stroke, seizures, migraine, multiple sclevosis, AIDS and encephaloathy.

By virtue of the COX-2 activity and/or specificity for COX-2 over COX-1, such compounds will prove useful as an alternative to conventional NSAIDs particularly where such NSAIDs may be contra-indicated such as in patients with ulcers (such as peptic ulcers and gastric ulcers), gastritis, regional enterotis, ulcerative colitis, diverticulitis or with a recurrent history of GI lesions, GI bleeding, coagulation disorders including anemia such as hypoprothrombinemia, haemophilia and other bleeding problems; kidney disease; prior to surgery of taking of anticoagulants.

Also, the present invention provides a compound of formula 7-VI:

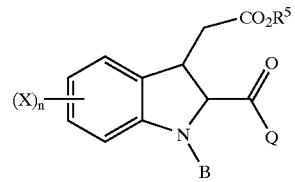

7-VI wherein B is a suitable protecting group;
Q is selected from the following:
(a) phenyl optionally substituted with one, two or three substituents independently selected from
(a-1) halo, $C_{1-4}$ alkyl, halo-substituted $C_{1-4}$ alkyl, OH, $C_{1-4}$ alkoxy, halo-substituted $C_{1-4}$ alkoxy, $C_{1-4}$ alkylthio, $NO_2$, $NH_2$, di-($C_{1-4}$ alkyl)amino, $C_{1-4}$ alkylamino, CN, HO—($C_{1-4}$)alkyl, $C_{1-4}$ alkoxy-$C_{1-4}$ alkyl, $C_{1-4}$ alkylsulfonyl, aminosulfonyl, —$NH_2S(O)_2NR^2R^3$, acetyl, —COOH, —C(O)O—$C_{1-4}$ alkyl, $C_{1-4}$ alkylsulfonylamino and $C_{3-7}$ cycloalkyl, (a-2) aryl or —O—$(CH_2)_n$-aryl, and the aryl or aryl moiety being optionally substituted with one, two or three substituents independently selected from halo, $C_{1-4}$ alkyl, halo-substituted $C_{1-4}$ alkyl, OH, $C_{1-4}$ alkoxy, halo-substituted $C_{1-4}$ alkoxy, $C_{1-4}$ alkylthio, $NO_2$, $NH_2$, di-($C_{1-4}$ alkyl)amino, $C_{1-4}$ alkylamino and CN, (a-3) 5-membered monocyclic aromatic group optionally substitued with one, two or three substituents independently selected from halo, $C_{1-4}$ alkyl, halo-substituted $C_{1-4}$ alkyl, OH, $C_{1-4}$ alkoxy, halo-substituted $C_{1-4}$ alkoxy, $C_{1-4}$ alkylthio, $NO_2$, $NH_2$, di-($C_{1-4}$ alkyl)amino, $C_{1-4}$ alkylamino and CN, (a-4) 6-membered monocyclic aromatic group optionally substitued with one, two or three substituents independently selected from halo, $C_{1-4}$ alkyl, halo-substituted $C_{1-4}$ alkyl, OH, $C_{1-4}$ alkoxy, halo-substituted $C_{1-4}$ alkoxy, $C_{1-4}$ alkylthio, $NO_2$, $NH_2$, di-($C_{1-4}$ alkyl)amino, $C_{1-4}$ alkylamino and CN, (b) a 6-membered monocyclic aromatic group containing one, two, three or four nitrogen atom(s), and said monocyclic aromatic group being optionally substituted with one, two or three substituents independently selected from the above group (a-1), (a-2), (a-3) and (a-4), (c) a 5-membered monocyclic aromatic group containing one heteroatom selected from O, S and N and optionally containing one, two or three nitrogen atom(s) in addition to said heteroatom, and said monocyclic aromatic group being optionally substituted with one, two or three substituents independently selected from the above group (a-1), (a-2), (a-3) and (a-4);

(d) $C_{3-7}$ cycloalkyl optionally substituted with one or two substituents independently selected from OH, $C_{1-4}$ alkyl, halo and halo-substituted $C_{1-4}$ alkyl; and (e) a benzo-fuzed heterocycle optionally substituted with one, two or three substituents independently selected from the group (a-1);

$R^2$ and $R^3$ are independently H, OH, $C_{1-4}$ alkoxy, $C_{1-4}$ alkyl or $C_{1-4}$ alkyl substituted with halo, OH, $C_{1-4}$ alkoxy, $NH_2$ or CN;

X is independently selected from halo, $C_{1-4}$ alkyl, halo-substituted $C_{1-4}$ alkyl, OH, $C_{1-4}$ alkoxy, halo-substituted $C_{1-4}$ alkoxy, $C_{1-4}$ alkylthio, $NO_2$, $NH_2$, di-($C_{1-4}$ alkyl)amino, $C_{1-4}$ alkylamino, CN, HO—($C_{1-4}$)alkyl, $C_{1-4}$ alkoxy-$C_{1-4}$ alkyl, $C_{1-4}$ alkylsulfonyl, aminosulfonyl, —$NH_2S(O)_2NR^2NR^3$, acetyl, —COOH, —C(O)O—$C_{1-4}$ alkyl, $C_{1-4}$ alkylsulfonylamino and $C_{3-7}$ cycloalkyl; $R^5$ is $C_{1-6}$ alkyl; and n is 0, 1, 2, 3 or 4.

Also, the present invention provides a compound of formula 7-V:

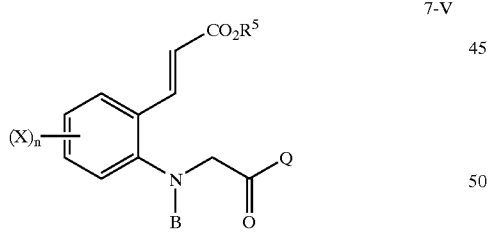

7-V wherein B is a suitable protecting group;

Q is selected from the following:
(a) phenyl optionally substituted with one, two or three substituents independently selected from
(a-1) halo, $C_{1-4}$ alkyl, halo-substituted $C_{1-4}$ alkyl, OH, $C_{1-4}$ alkoxy, halo-substituted $C_{1-4}$ alkoxy, $C_{1-4}$ alkylthio, $NO_2$, $NH_2$, di-($C_{1-4}$ alkyl)amino, $C_{1-4}$ alkylamino, CN, HO—($C_{1-4}$)alkyl, $C_{1-4}$ alkoxy-$C_{1-4}$ alkyl, $C_{1-4}$ alkylsulfonyl, aminosulfonyl, —$NH_2S(O)_2NR^2NR^3$, acetyl, —COOH, —C(O)O—$C_{1-4}$ alkyl, $C_{1-4}$ alkylsulfonylamino and $C_{3-7}$ cycloalkyl,
(a-2) aryl or —O—$(CH_2)_n$-aryl, and the aryl or aryl moiety being optionally substituted with one, two or three substituents independently selected from halo, $C_{1-4}$ alkyl, halo-substituted $C_{1-4}$ alkyl, OH, $C_{1-4}$ alkoxy, halo-substituted $C_{1-4}$ alkoxy, $C_{1-4}$ alkylthio, $NO_2$, $NH_2$, di-($C_{1-4}$ alkyl)amino, $C_{1-4}$ alkylamino and CN, (a-3) 5-membered monocyclic aromatic group optionally substitued with one, two or three substituents independently selected from halo, $C_{1-4}$ alkyl, halo-substituted $C_{1-4}$ alkyl, OH, $C_{1-4}$ alkoxy, halo-substituted $C_{1-4}$ alkoxy, $C_{1-4}$ alkylthio, $NO_2$, $NH_2$, di-($C_{1-4}$ alkyl)amino, $C_{1-4}$ alkylamino and CN, (a-4) 6-membered monocyclic aromatic group optionally substitued with one, two or three substituents independently selected from halo, $C_{1-4}$ alkyl, halo-substituted $C_{1-4}$ alkyl, OH, $C_{1-4}$ alkoxy, halo-substituted $C_{1-4}$ alkoxy, $C_{1-4}$ alkylthio, $NO_2$, $NH_2$, di-($C_{1-4}$ alkyl)amino, $C_{1-4}$ alkylamino and CN, (b) a 6-membered monocyclic aromatic group containing one, two, three or four nitrogen atom(s), and said monocyclic aromatic group being optionally substituted with one, two or three substituents independently selected from the above group (a-1), (a-2), (a-3) and (a-4), (c) a 5-membered monocyclic aromatic group containing one heteroatom selected from O, S and N and optionally containing one, two or three nitrogen atom(s) in addition to said heteroatom, and said monocyclic aromatic group being optionally substituted with one, two or three substituents independently selected from the above group (a-1), (a-2), (a-3) and (a-4);

(d) $C_{3-7}$ cycloalkyl optionally substituted with one or two substituents independently selected from OH, $C_{1-4}$ alkyl, halo and halo-substituted $C_{1-4}$ alkyl; and (e) a benzo-fuzed heterocycle optionally substituted with one, two or three substituents independently selected from the group (a-1);

$R^2$ and $R^3$ are independently H, OH, $C_{1-4}$ alkoxy, $C_{1-4}$ alkyl or $C_{1-4}$ alkyl substituted with halo, OH, $C_{1-4}$ alkoxy, $NH_2$ or CN;

X is independently selected from halo, $C_{1-4}$ alkyl, halo-substituted $C_{1-4}$ alkyl, OH, $C_{1-4}$ alkoxy, halo-substituted $C_{1-4}$ alkoxy, $C_{1-4}$ alkylthio, $NO_2$, $NH_2$, di-($C_{1-4}$ alkyl)amino, $C_{1-4}$ alkylamino, CN, HO—($C_{1-4}$)alkyl, $C_{1-4}$ alkoxy-$C_{1-4}$ alkyl, $C_{1-4}$ alkylsulfonyl, aminosulfonyl, —$NH_2S(O)_2NR^2NR^3$, acetyl, —COOH, —C(O)O—$C_{1-4}$ alkyl, $C_{1-4}$ alkylsulfonylamino and $C_{3-7}$ cycloalkyl; $R^5$ is $C_{1-6}$ alkyl; and n is 0, 1, 2, 3 or 4.

DETAILED DISCLOSURE OF THE INVENTION

As used herein, "halo" is fluoro, chloro, bromo or iodo.

As used herein, the term "$C_{1-4}$ alkyl" means straight or branched chain saturated radicals of 1 to 4 carbon atoms, including, but not limited to methyl, ethyl, n-propyl, isopropyl, n-butyl, isobutyl, sec-butyl, tert-butyl, and the like.

As used herein, an example of "propyl" is n-propyl and isopropyl.

As used herein, an example of "butyl" is n-butyl, isobutyl, sec-butyl and tert-butyl.

As used herein, an example of "alkoxy" is methoxy, ethoxy, n-propoxy, isopropoxy, n-butoxy, isobutoxy, sec-butoxy, tert-butoxy, and the like.

As used herein, an example of "alkylthio" is methylthio, ethylthio, n-propylthio, isopropylthio, n-butylthio, isobutylthio, sec-butylthio, tert-butylthio, and the like.

As used herein, an example of "di-($C_{1-4}$ alkyl)amino" is dimethylamino, diethylamino, dipropylamino, N-methyl-N-ethylamino, N-methyl-N-propylamino, N-methyl-N-butylamino, N-ethyl-N-propylamino, and the like.

As used herein, an example of "$C_{1-4}$ alkylamino" is methylamino, ethylamino, n-propylamino, isopropylamino, n-butylamino, isobutylamino, sec-butylamino, tert-butylamino, and the like.

As used herein, an example of "HO—($C_{1-4}$)alkyl" is hydroxymethyl, hydroxyethyl (e.g., 1-hydroxyethyl and 2-hydroxyethyl), hydroxypropyl (e.g., 1-hydroxypropyl, 2-hydroxypropyl and 3-hydroxypropyl).

As used herein, an example of "$C_{1-4}$ alkoxy-$C_{1-4}$ alkyl" is methoxymethyl, methoxyethyl, methoxypropyl, methoxybutyl, ethoxymethyl, ethoxyethyl, ethoxypropyl, and the like.

As used herein, the term "halo-substituted alkyl" refers to an alkyl radical as described above substituted with one or more halogens included, but not limited to, chloromethyl, dichloromethyl, fluoromethyl, difluoromethyl, trifluoromethyl, 2,2,2-trichloroethyl, and the like.

As used herein, an example of "halo-substituted alkoxy" is chloromethoxy, dichloromethoxy, fluoromethoxy, difluoromethoxy, trifluoromethoxy, 2,2,2-trichloroethoxy, and the like.

As used herein, the term "$C_{3-7}$ cycloalkyl" means carbocyclic radicals, of 3 to 7 carbon atoms, including, but not limited to cyclopropyl, cyclobutyl, cyclopentyl, cyclohexyl, cycloheptyl, and the like.

As used herein, an example of "aryl" is phenyl and naphthyl.

As used herein, a 5-membered monocyclic aromatic group usually has one heteroatom selected from O, S and N in the ring. In addition to said heteroatom, the monocyclic aromatic group may optionally have up to three N atoms in the ring. For example, the 5-membered monocyclic aromatic group includes thienyl, furyl, thiazolyl (e.g., 1,3-thiazolyl, 1,2-thiazolyl), imidazolyl, pyrrolyl, oxazolyl (e.g., 1,3-oxazolyl, 1,2-oxazolyl, isoxazolyl), pyrazolyl, tetrazolyl, triazolyl (e.g., 1,2,3-triazolyl, 1,2,4-triazolyl), oxadiazolyl (e.g., 1,2.3-oxadiazolyl), thiadiazolyl (e.g., 1,3,4-thiadiazolyl, 1,2,3-thiadiazolyl) and the like.

As used herein, an example of a 6-membered monocyclic aromatic group includes pyridyl, pyrazinyl, pyrimidinyl, pyridazinyl, triazinyl (e.g., 1,3,5-triazinyl), tetrazinyl and the like.

As used herein, an example of a benzo-fuzed heterocycle includes quinolyl, isoquinolyl, cinnolinyl, quinoxalinyl, benzoimidazolyl, benzothiazolyl, benzoxazolyl, benzofuranyl, benzothiophenyl, indolyl, isoindolyl, 1H-indazolyl, quinazolinyl, phthalazinyl and the like.

As used herein, an example of (ethyl)(ethoxy)pyridyl includes 3-ethoxy-4-ethyl-2-pyridyl, 4-ethoxy-3-ethyl-2-pyridyl and the like.

As used herein, an example of (chloro)(ethyl)pyridyl includes 3-chloro-4-ethyl-2-pyridyl, 4-chloro-3-ethyl-2-pyridyl and the like.

As used herein, an example of (fluoro)(ethyl)phenyl includes 3-fluoro-4-ethyl-2-pyridyl, 4-fluoro-3-ethyl-2-pyridyl and the like.

Preferred compounds of this invention are those of the formula (I) wherein

Z is OH, $C_{1-6}$ alkoxy, dimethylamino, methylamino, amino, N-methoxy-N-methylamino, 2-cyanoethylamino, 2-hydroxyethylamino, pyrrolidinyl, piperidino, piperazinyl, N-methyl-piperazinyl, morpholino, methoxyamino, piperazynyl, aminopyrrolidinyl or aminoethylamino.

Further preferred compounds of this invention are those of the formula (I) wherein Z is OH or $C_{1-6}$ alkoxy; and Q is selected from the following:
(a) phenyl optionally substituted with one, two or three substituents independently selected from
  (a-1) halo, $C_{1-4}$ alkyl, halo-substituted $C_{1-4}$ alkyl, OH, $C_{1-4}$ alkoxy, halo-substituted $C_{1-4}$ alkoxy, $C_{1-4}$ alkylthio, $NO_2$, $NH_2$, di-($C_{1-4}$ alkyl)amino, $C_{1-4}$ alkylamino, CN, HO—($C_{1-4}$)alkyl, $C_{1-4}$ alkoxy-$C_{1-4}$ alkyl, $C_{1-4}$ alkylsulfonyl, aminosulfonyl, —$NH_2S(O)_2NR^2R^3$, acetyl, —COOH, —C(O)O—$C_{1-4}$ alkyl, $C_{1-4}$ alkylsulfonylamino and $C_{3-7}$ cycloalkyl,
  (a-2) aryl or —O—$(CH_2)_n$-aryl, and the aryl or aryl moiety being optionally substituted with one, two or three substituents independently selected from halo, $C_{1-4}$ alkyl, halo-substituted $C_{1-4}$ alkyl, OH, $C_{1-4}$ alkoxy, halo-substituted $C_{1-4}$ alkoxy, $C_{1-4}$ alkylthio, $NO_2$, $NH_2$, di-($C_{1-4}$ alkyl)amino, $C_{1-4}$ alkylamino and CN,
  (a-3) 5-membered monocyclic aromatic group optionally substitued with one, two or three substituents independently selected from halo, $C_{1-4}$ alkyl, halo-substituted $C_{1-4}$ alkyl, OH, $C_{1-4}$ alkoxy, halo-substituted $C_{1-4}$ alkoxy, $C_{1-4}$ alkylthio, $NO_2$, $NH_2$, di-($C_{1-4}$ alkyl)amino, $C_{1-4}$ alkylamino and CN,
  (a-4) 6-membered monocyclic aromatic group optionally substitued with one, two or three substituents independently selected from halo, $C_{1-4}$ alkyl, halo-substituted $C_{1-4}$ alkyl, OH, $C_{1-4}$ alkoxy, halo-substituted $C_{1-4}$ alkoxy, $C_{1-4}$ alkylthio, $NO_2$, $NH_2$, di-($C_{1-4}$ alkyl)amino, $C_{1-4}$ alkylamino and CN,
(b) a 6-membered monocyclic aromatic group containing one, two, three or four nitrogen atom(s), and said monocyclic aromatic group being optionally substituted with one, two or three substituents independently selected from the above group (a-1), (a-2), (a-3) and (a-4),
(c) a 5-membered monocyclic aromatic group containing one heteroatom selected from O, S and N and optionally containing one, two or three nitrogen atom(s) in addition to said heteroatom, and said monocyclic aromatic group being optionally substituted with one, two or three substituents independently selected from the above group (a-1), (a-2), (a-3) and (a-4);
(d) $C_{3-7}$ cycloalkyl selected from cyclopropyl, cyclobutyl, cyclopentyl and cyclohexyl, and the said cycloalkyl being optionally substituted with one substituent selected from OH, methyl, ethyl, propyl, F, Cl and $CF_3$; and
(e) a benzo-fuzed heterocycle selected from quinolyl, isoquinolyl, cinnolinyl, quinoxalinyl, benzoimidazolyl, benzothiazolyl, benzoxazolyl, benzofuranyl, benzothiophenyl and indolyl, and the benzo-fuzed heterocycle being optionally substituted with one, two, or three substituents independently selected from the group (a-1).

Further preferred compounds of this invention are those of the formula (I) wherein Q is selected from the following:
(a) phenyl optionally substituted with one, two or three substituents independently selected from
  (a-1) halo, $C_{1-4}$ alkyl, halo-substituted $C_{1-4}$ alkyl, OH, $C_{1-4}$ alkoxy, halo-substituted $C_{1-4}$ alkoxy, $C_{1-4}$ alkylthio, $NO_2$, $NH_2$, di-($C_{1-4}$ alkyl)amino, $C_{1-4}$ alkylamino, CN, HO—($C_{1-4}$)alkyl, $C_{1-4}$ alkoxy-$C_{1-4}$ alkyl, $C_{1-4}$ alkylsulfonyl, aminosulfonyl, —$NH_2S(O)_2NR^2R^3$, acetyl, —COOH, —C(O)O—$C_{1-4}$ alkyl, $C_{1-4}$ alkylsulfonylamino and $C_{3-7}$ cycloalkyl,
  (a-2) aryl or —O—$(CH_2)_n$-aryl, and the aryl or aryl moiety being optionally substituted with one, two or three substituents independently selected from halo, $C_{1-4}$ alkyl, halo-substituted $C_{1-4}$ alkyl, OH, $C_{1-4}$ alkoxy, halo-substituted $C_{1-4}$ alkoxy, $C_{1-4}$ alkylthio, $NO_2$, $NH_2$, di-($C_{1-4}$ alkyl)amino, $C_{1-4}$ alkylamino and CN,
  (a-3) 5-membered monocyclic aromatic group optionally substituted with one, two or three substituents independently selected from halo, $C_{1-4}$ alkyl, halo-substituted $C_{1-4}$ alkyl, OH, $C_{1-4}$ alkoxy, halo-substituted $C_{1-4}$ alkoxy, $C_{1-4}$ alkylthio, $NO_2$, $NH_2$, di-($C_{1-4}$ alkyl)amino, $C_{1-4}$ alkylamino and CN,
  (a-4) 6-membered monocyclic aromatic group optionally substituted with one, two or three substituents independently selected from halo, $C_{1-4}$ alkyl, halo-substituted $C_{1-4}$ alkyl, OH, $C_{1-4}$ alkoxy, halo-substituted $C_{1-4}$ alkoxy, $C_{1-4}$ alkylthio, $NO_2$, $NH_2$, di-($C_{1-4}$ alkyl)amino, $C_{1-4}$ alkylamino and CN,
(b) a 6-membered monocyclic aromatic group containing one, two, three or four nitrogen atom(s), and said monocyclic aromatic group being optionally substituted with one, two or three substituents independently selected from the above group (a-1), (a-2), (a-3) and (a-4),
(c) a 5-membered monocyclic aromatic group containing one heteroatom selected from O, S and N and optionally containing one, two or three nitrogen atom(s) in addition to said heteroatom, and said monocyclic aromatic group being optionally substituted with one, two or three substituents independently selected from the above group (a-1), (a-2), (a-3) and (a-4);
(d) cyclopropyl, cyclobutyl and cyclohexyl; and
(e) quinolyl or isoquinolyl, and said quinolyl or isoquinolyl being optionally substituted with one substituent selected from the group halo, $C_{1-4}$ alkyl, $NH_2$, OH, $C_{1-4}$ alkoxy and $C_{1-4}$ halo-substituted alkyl.

Further preferred compounds of this invention are those of the formula (I) wherein Z is OH, $C_{1-6}$ alkoxy;
Q is selected from the following:
(a) phenyl optionally substituted with one, two or three substituents independently selected from
  (a-1) halo, $C_{1-4}$ alkyl, halo-substituted $C_{1-4}$ alkyl, OH, $C_{1-4}$ alkoxy, halo-substituted $C_{1-4}$ alkoxy, $C_{1-4}$ alkylthio, $NO_2$, $NH_2$, di-($C_{1-4}$ alkyl)amino, $C_{1-4}$ alkylamino, CN, HO—($C_{1-4}$)alkyl, $C_{1-4}$ alkoxy-$C_{1-4}$ alkyl, $C_{1-4}$ alkylsulfonyl, aminosulfonyl, —$NH_2S(O)_2NR^2R^3$, acetyl, —COOH, —C(O)O—$C_{1-4}$ alkyl, $C_{1-4}$ alkylsulfonylamino and $C_{3-7}$ cycloalkyl,
  (a-2) aryl or —O—$(CH_2)_n$-aryl, and the aryl or aryl moiety being optionally substituted with one, two or three substituents independently selected from halo, $C_{1-4}$ alkyl, halo-substituted $C_{1-4}$ alkyl, OH, $C_{1-4}$ alkoxy, halo-substituted $C_{1-4}$ alkoxy, $C_{1-4}$ alkylthio, $NO_2$, $NH_2$, di-($C_{1-4}$ alkyl)amino, $C_{1-4}$ alkylamino and CN,
  (a-3) 5-membered monocyclic aromatic group optionally substituted with one, two or three substituents independently selected from halo, $C_{1-4}$ alkyl, halo-substituted $C_{1-4}$ alkyl, OH, $C_{1-4}$ alkoxy, halo-substituted $C_{1-4}$ alkoxy, $C_{1-4}$ alkylthio, $NO_2$, $NH_2$, di-($C_{1-4}$ alkyl)amino, $C_{1-4}$ alkylamino and CN,
  (a-4) 6-membered monocyclic aromatic group optionally substituted with one, two or three substituents independently selected from halo, $C_{1-4}$ alkyl, halo-substituted $C_{1-4}$ alkyl, OH, $C_{1-4}$ alkoxy, halo-substituted $C_{1-4}$ alkoxy, $C_{1-4}$ alkylthio, $NO_2$, $NH_2$, di-($C_{1-4}$ alkyl)amino, $C_{1-4}$ alkylamino and CN,
(b) a 6-membered monocyclic aromatic group containing one, two, three or four nitrogen atom(s), and said monocyclic aromatic group being optionally substituted with one, two or three substituents independently selected from the above group (a-1), (a-2), (a-3) and (a-4),
(c) a 5-membered monocyclic aromatic group containing one heteroatom selected from O, S and N and optionally containing one, two or three nitrogen atom(s) in addition to said heteroatom, and said monocyclic aromatic group being optionally substituted with one, two or three substituents independently selected from the above group (a-1), (a-2), (a-3) and (a-4); and
(e) isoquinolyl;

$R^1$ is hydrogen or $C_{1-4}$ alkyl;
$R^2$ and $R^3$ are independently H or methyl;
X is independently selected from halo, $C_{1-4}$ alkyl, halo-substituted $C_{1-4}$ alkyl, OH, $C_{1-4}$ alkoxy, halo-substituted $C_{1-4}$ alkoxy, $C_{1-4}$ alkylthio $NO_2$, $NH_2$, di-($C_{1-4}$ alkyl)amino, $C_{1-4}$ alkylamino, CN, HO—($C_{1-4}$) alkyl, $C_{1-4}$ alkoxy-$C_{1-4}$ alkyl, $C_{1-4}$ alkylsulfonyl, aminosulfonyl, —$NH_2S(O)_2NR^2NR^3$, acetyl, —$COOR^4$, $C_{1-4}$ alkylsulfonylamino and $C_{3-7}$ cycloalkyl; and
n is 0, 1, 2, or 3.

Further preferred compounds of this invention are those of the formula (I) wherein Z is OH, methoxy, ethoxy, n-propoxy, iso-propoxy, n-butoxy, iso-butoxy or tert-butoxy;
Q is selected from the following:
(a) phenyl optionally substituted with one or two substituents independently selected from
  (a-1) halo, $C_{1-4}$ alkyl, halo-substituted $C_{1-4}$ alkyl, OH, $C_{1-4}$ alkoxy, halo-substituted $C_{1-4}$ alkoxy, $C_{1-4}$ alkylthio, HO—($C_{1-4}$)alkyl, $C_{1-4}$ alkoxy-$C_{1-4}$ alkyl, —COOH, $C_{1-4}$ alkylsulfonylamino, nitro, $C_{1-4}$ alkylsulfonyl and cyano,
  (a-2) phenyl or benzyloxy, and the phenyl or phenyl moiety of benzyloxy being optionally substituted with one substituent selected from $C_{1-4}$ alkyl, halo-substituted $C_{1-4}$ alkyl, halo, OH, $C_{1-4}$ alkoxy, halo-substituted $C_{1-4}$ alkoxy and $NH_2$,
  (a-3) 5-membered monocyclic aromatic group selected from imidazolyl, thiazolyl, furyl, thienyl, pyrrolyl, tetrazolyl, triazolyl, oxazolyl, isoxazolyl, thiadiazolyl and pyrazolyl, and the 5-membered monocyclic aromatic group optionally being substitued with one substituent selected from $C_{1-4}$ alkyl, halo-substituted $C_{1-4}$ alkyl, halo, OH, $C_{1-4}$ alkoxy, halo-substituted $C_{1-4}$ alkoxy and $NH_2$, (a-4) 6-membered monocyclic aromatic group selected from pyridyl, pyrazinyl, pyrimidinyl and pyridazinyl, and the 6-membered monocyclic aromatic group optionally being substitued with one substituent selected from $C_{1-4}$ alkyl, halo-substituted $C_{1-4}$ alkyl, halo, OH, $C_{1-4}$ alkoxy, halo-substituted $C_{1-4}$ alkoxy and $NH_2$, (b) a 6-membered monocyclic aromatic group selected from pyridyl, pyrazinyl, pyrimidinyl and pyridazinyl, and said monocyclic armomatic group being optionally substituted with one or two substituents independently selected from the above group (a-1), (a-2), (a-3) and (a-4), (c) a 5-membered monocyclic aromatic group selected from imidazolyl, thiazolyl, furyl, thienyl, pyrrolyl, tetrazolyl, triazolyl, oxazolyl, isoxazolyl, thiadiazolyl and pyrazolyl, and said monocyclic aromatic group being optionally substituted with one or two substituents independently selected from the above group (a-1), (a-2), (a-3) and (a-4);

$R^1$ is hydrogen, methyl, ethyl, n-propyl, iso-propyl, n-butyl, iso-butyl or tert-butyl;

X is independently selected from halo, $C_{1-4}$ alkyl, halo-substituted $C_{1-4}$ alkyl, OH, $C_{1-4}$ alkoxy, halo-substituted $C_{1-4}$ alkoxy, $C_{1-4}$ alkylthio, $NO_2$, $NH_2$, di-$(C_{1-4}$ alkyl)amino, $C_{1-4}$ alkylamino, CN, HO—$(C_{1-4})$alkyl, $C_{1-4}$ alkoxy-$C_{1-4}$ alkyl, $C_{1-4}$ alkylsulfonyl and aminosulfonyl; and n is 0, 1, 2, or 3.

Further preferred compounds of this invention are those of the formula (I) wherein Z is OH, methoxy, ethoxy, n-propoxy, iso-propoxy, n-butoxy, iso-butoxyor or tert-butoxy;

Q is selected from the following:
  (a) phenyl optionally substituted with one or two substituents independently selected from
    (a-1) fluoro, chloro, bromo, iodo, methyl, ethyl, propyl, butyl, $CH_2F$, $CHF_2$, $CF_3$, methoxy, ethoxy, n-propoxy, n-butoxy, isopropoxy, $CH_2F$—O—, $CHF_2$—O—, $CF_3$—O—, methylthio, ethylthio, hydroxymethyl, methoxymethyl, methoxyethyl, ethoxymethyl, hydroxy, nitro, methylsulfonyl, cyano, $(HO)(H_3C)_2C$—, acetyl and methylsulfonylamino,
    (a-2) phenyl or benzyloxy, and the phenyl or phenyl moiety of benzyloxy being optionally substituted with one substituent selected from methyl, ethyl, propyl, $CF_3$, F, Cl, OH, methoxy, ethoxy and $NH_2$,
    (a-3) 5-membered monocyclic aromatic group selected from furyl, thienyl and pyrrolyl, and the 5-membered monocyclic aromatic group optionally being substitued with one substituent selected from methyl, ethyl, propyl, $CF_3$, F, Cl, OH, methoxy, ethoxy and $NH_2$,
    (a-4) pyridyl optionally substitued with one substituent selected from methyl, ethyl, propyl, $CF_3$, F, Cl, OH, methoxy, ethoxy and $NH_2$,
  (b) pyridyl optionally substituted with one, two or three substituents independently selected from the above group (a-1), (a-1), (a-2), (a-3) and (a-4),
  (c) imidazolyl, thiazolyl, furyl, thienyl, isoxazolyl, 1,2,3-thiadiazolyl or pyrrolyl, and said imidazolyl, thiazolyl, furyl, thienyl, isoxazolyl, 1,2,3-thiadiazolyl or pyrrolyl being optionally substituted with one or two substituents independently selected from the above group (a-1), (a-2), (a-3) and (a-4);

$R^1$ is hydrogen, methyl, ethyl, n-propyl, iso-propyl;

X is independently selected from fluoro, chloro, bromo, methyl, ethyl, propyl, butyl, $CH_2F$, $CHF_2$, $CF_3$, methoxy, $CF_3O$ or ethoxy; and n is 0, 1 or 2.

Further preferred compounds of this invention are those of the formula (I) wherein Z is OH, ethoxy or methoxy; Q is phenyl, chlorophenyl, fluorophenyl, bromophenyl, methylphenyl, methoxyphenyl, (furyl)phenyl, trifluoromethylphenyl, trifluoromethoxyphenyl, pyridyl, methylpyridyl, ethylpyridyl, propylpyridyl, dimethlylpyridyl, chloropyridyl, fluoropyridyl, trifluoromethylpyridyl, methoxypyridyl, (ethyl)(ethoxy)pyridyl, (chloro)(ethyl)pyridyl, thiazolyl, methylthiazolyl, furyl, methoxymethylfuryl, isoquinolyl, cyclohexyl, methoxyphenyl, (fluoro)(ethyl)pyridyl, dimethylpyridyl or (ethoxy)(ethyl)pyridyl;

$R^1$ is hydrogen; X is fluoro, chloro, methyl, ethyl, isopropyl, tert-butyl, $CF_3$ or methoxy; and n is 1 or 2.

Further preferred compounds of this invention are those of the formula (I) wherein Z is OH, ethoxy or methoxy; Q is phenyl, chlorophenyl, pyridyl, methylpyridyl, ethylpyridyl, propylpyridyl or chloropyridyl; $R^1$ is hydrogen; X is fluoro, chloro, methyl or $CF_3$; and n is 1 or 2.

Preferred individual compounds of this invention are:

ethyl(2-benzoyl-6-chloro-1H-indol-3-yl)acetate;

(2-benzoyl-6-chloro-1H-indol-3-yl)acetic acid;

(2-benzoyl-6-chloro-1H-indol-3-yl)acetic acid, sodium salt;

[6-chloro-2-(2-methylbenzoyl)-1H-indol-3-yl]acetic acid;

[6-chloro-2-(3-methylbenzoyl)-1H-indol-3-yl]acetic acid;

[6-chloro-2-(4-methylbenzoyl)-1H-indol-3-yl]acetic acid;

[6-chloro-2-(3-chlorobenzoyl)-1H-indol-3-yl]acetic acid;

methyl[6-chloro-2-(4-chlorobenzoyl)-1H-indol-3-yl] acetate;

[6-chloro-2-(4-chlorobenzoyl)-1H-indol-3-yl]acetic acid;

[6-chloro-2-(3-fluorobenzoyl)-1H-indol-3-yl]acetic acid;

[6-chloro-2-(4-fluorobenzoyl)-1H-indol-3-yl]acetic acid;

[2-(3-bromobenzoyl)-6-chloro-1H-indol-3-yl]acetic acid;

[2-(4-bromobenzoyl)-6-chloro-1H-indol-3-yl]acetic acid;

[6-chloro-2-(3-trifluoromethylbenzoyl)-1H-indol-3-yl] acetic acid;

[6-chloro-2-(4-trifluoromethylbenzoyl)-1H-indol-3-yl] acetic acid;

[6-chloro-2-(3,4-dichlorobenzoyl)-1H-indol-3-yl]acetic acid;

(2-benzoyl-4-chloro-1H-indol-3-yl)acetic acid;

[5-chloro-2-(3-methylbenzoyl)-1H-indol-3-yl]acetic acid;

[5-chloro-2-(4-chlorobenzoyl)-1H-indol-3-yl]acetic acid;

[5-chloro-2-(3-chlorobenzoyl)-1H-indol-3-yl]acetic acid;
[2-(4-chlorobenzoyl)-5-fluoro-1H-indol-3-yl]acetic acid;
[2-(3-chlorobenzoyl)-5-fluoro-1H-indol-3-yl]acetic acid;
[5-methoxy-2-(3-methylbenzoyl)-1H-indol-3-yl]acetic acid;
(2-benzoyl-7-chloro-1H-indol-3-y)acetic acid;
(2-benzoyl-4,5-dichloro-1H-indol-3-yl)acetic acid;
(2-benzoyl-4,6-dichloro-1H-indol-3-yl)acetic acid;
(2-benzoyl-5,6-dichloro-1H-indol-3-yl)acetic acid;
dl-2-(2-benzoyl-6-chloro-1H-indol-3-yl)propanoic acid;
less polar antipode, 2-(2-benzoyl-6-chloro-1H-indol-3-yl)propanoic acid;
more polar antipode, 2-(2-benzoyl-6-chloro-1H-indol-3-yl)propanoic acid;
[6-chloro-2-(4-methylpyridine-2-carbonyl)-1H-indol-3-yl]acetic acid;
[6-chloro-2-(5-methylpyridine-2-carbonyl)-1H-indol-3-yl]acetic acid;
methyl[6-chloro-2-(4-chloropyridine-2-carbonyl)-1H-indol-3-yl]acetate;
[6-chloro-2-(4-chloropyridine-2-carbonyl)-1H-indol-3-yl]acetic acid;
[6-chloro-2-(pyridine-2-carbonyl)-1H-indol-3-yl]acetic acid;
[5-chloro-2-(4-methylpyridine-2-carbonyl)-1H-indol-3-yl]acetic acid;
methyl[5-chloro-2-(6-methylpyridine-2-carbonyl)-1H-indol-3-yl]acetate;
[5-chloro-2-(6-methylpyridine-2-carbonyl)-1H-indol-3-yl]acetic acid;
[6-chloro-2-(1-methylimidazole-2-carbonyl)-1H-indol-3-yl]acetic acid;
methyl[5-chloro-2-(thiazole-2-carbonyl)-1H-indol-3-yl]acetate;
[5-chloro-2-(thiazole-2-carbonyl)-1H-indol-3-yl]acetic acid;
methyl(2-benzoyl-6-chloro-1H-indol-3-yl)acetate;
(2-benzoyl-6-chloro-1H-indol-3-yl)-N,N-dimethylacetamide;
(2-benzoyl-6-chloro-1H-indol-3-yl)-N-methylacetamide;
(2-benzoyl-6-chloro-1H-indol-3-yl)acetamide;
(2-benzoyl-6-chloro-1H-indol-3-yl)-N-methoxy-N-methylacetamide;
2-(2-benzoyl-6-chloro-1H-indol-3-yl)-1-piperidino-1-ethanone;
2-(2-benzoyl-6-chloro-1H-indol-3-yl)-1-(4-methyl-1-piperazinyl)-1-ethanone;
(2-benzoyl-6-chloro-1H-indol-3-yl)-N-(2-cyanoethyl)acetamide;
(2-benzoyl-6-chloro-1H-indol-3-yl)-N-(2-hydroxyethyl)acetamide;
2-(2-benzoyl-6-chloro-1H-indol-3-yl)-1-morpholino-1-ethanone;
[2-(4-chlorobenzoyl)-1H-indol-3-yl]acetic acid;
[6-chloro-2-(2-furylcarbonyl)-1H-indol-3-yl]acetic acid;
[6-chloro-2-(cyclohexanecarbonyl)-1H-indol-3-yl]acetic acid;
methyl[6-chloro-2-(4-methoxybenzoyl)-1H-indol-3-yl]acetate;
[6-chloro-2-(4-methoxybenzoyl)-1H-indol-3-yl]acetic acid;
methyl[6-chloro-2-(4-ethylpyridine-2-carbonyl)-1H-indol-3-yl]acetate;
[6-chloro-2-(4-ethylpyridine-2-carbonyl)-1H-indol-3-yl]acetic acid;
methyl[5-chloro-2-(4-ethylpyridine-2-carbonyl)-1H-indol-3-yl]acetate;
[5-chloro-2-(4-ethyl pyridine-2-carbonyl)-1H-indol-3-yl]acetic acid;
methyl[6-chloro-2-(4-isopropylpyridine-2-carbonyl)-1H-indol-3-yl]acetate;
[6-chloro-2-(4-isopropylpyridine-2-carbonyl)-1H-indol-3-yl]acetic acid;
methyl[5-chloro-2-(4-isopropylpyridine-2-carbonyl)-1H-indol-3-yl]acetate;
[5-chloro-2-(4-isopropylpyridine-2-carbonyl)-1H-indol-3-yl]acetic acid;
methyl[6-chloro-2-(4-propylpyridine-2-carbonyl)-1H-indol-3-yl]acetate;
[6-chloro-2-(4-propylpyridine-2-carbonyl)-1H-indol-3-yl]acetic acid;
methyl[5-chloro-2-(4-propylpyridine-2-carbonyl)-1H-indol-3-yl]acetate;
[5-chloro-2-(4-propylpyridine-2-carbonyl)-1H-indol-3-yl]acetic acid;
methyl[2-(4-tert-butylpyridine-2-carbonyl)-6-chloro-1H-indol-3-yl]acetate;
[2-(4-tert-butylpyridine-2-carbonyl)-6-chloro-1H-indol-3-yl]acetic acid;
methyl[2-(4-tert-butylpyridine-2-carbonyl)-5-chloro-1H-indol-3-yl]acetate;
[2-(4-tert-butylpyridine-2-carbonyl)-5-chloro-1H-indol-3-yl]acetic acid;
methyl[6-chloro-2-(3-methylpyridine-2-carbonyl)-1H-indol-3-yl]acetate;
[6-chloro-2-(3-methylpyridine-2-carbonyl)-1H-indol-3-yl]acetic acid;
methyl[5-chloro-2-(3-methylpyridine-2-carbonyl)-1H-indol-3-yl]acetate;
[5-chloro-2-(3-methylpyridine-2-carbonyl)-1H-indol-3-yl]acetic acid;
methyl[6-chloro-2-(6-methylpyridine-2-carbonyl)-1H-indol-3-yl]acetate;
[6-chloro-2-(6-methylpyridine-2-carbonyl)-1H-indol-3-yl]acetic acid;
methyl[5-chloro-2-(5-methylpyridine-2-carbonyl)-1H-indol-3-yl]acetate;
[5-chloro-2-(5-methylpyridine-2-carbonyl)-1H-indol-3-yl]acetic acid;
methyl[6-chloro-2-[5-(trifluoromethyl)pyridine-2-carbonyl]-1H-indol-3-yl]acetate;
[6-chloro-2-[5-(trifluoromethyl)pyridine-2-carbonyl]-1H-indol-3-yl]acetic acid;
methyl[5-chloro-2-[5-(trifluoromethyl)pyridine-2-carbonyl]-1H-indol-3-yl]acetate;
[5-chloro-2-[5-(trifluoromethyl)pyridine-2-carbonyl]-1H-indol-3-yl]acetic acid;
methyl[5-chloro-2-(5-chloropyridine-2-carbonyl)-1H-indol-3-yl]acetate;
[5-chloro-2-(5-chloropyridine-2-carbonyl)-1H-indol-3-yl]acetic acid;
methyl[6-chloro-2-(5-chloropyridine-2-carbonyl)-1H-indol-3-yl]acetate;

[6-chloro-2-(5-chloropyridine-2-carbonyl)-1H-indol-3-yl]acetic acid;
methyl[5-chloro-2-(4-chloropyridine-2-carbonyl)-1H-indol-3-yl]acetate;
[5-chloro-2-(4-chloropyridine-2-carbonyl)-1H-indol-3-yl]acetic acid;
methyl[6-chloro-2-(pyridine-3-carbonyl)-1H-indol-3-yl]acetate;
[6-chloro-2-(pyridine-3-carbonyl)-1H-indol-3-yl]acetic acid;
methyl[6-chloro-2-(pyridine-4-carbonyl)-1H-indol-3-yl]acetate;
[6-chloro-2-(pyridine-4-carbonyl)-1H-indol-3-yl]acetic acid;
methyl[6-chloro-2-[4-(hydroxymethyl)pyridine-2-carbonyl-1H-indol-3-yl]acetate;
[6-chloro-2-[4-(hydroxymethyl)pyridine-2-carbonyl]-1H-indol-3-yl]acetic acid;
methyl[5-chloro-2-[4-(hydroxymethyl)pyridine-2-carbonyl]-1H-indol-3-yl]acetate;
[5-chloro-2-[4-(hydroxymethyl)pyridine-2-carbonyl]-1H-indol-3-yl]acetic acid;
methyl[5-chloro-2-(3,4-dimethylpyridine-2-carbonyl)-1H-indol-3-yl]acetate;
[5-chloro-2-(3,4-dimethylpyridine-2-carbonyl)-1H-indol-3-yl]acetic acid;
methyl[5-chloro-2-(4,5-dimethylpyridine-2-carbonyl)-1H-indol-3-yl]acetate;
[5-chloro-2-(4,5-dimethylpyridine-2-carbonyl)-1H-indol-3-yl]acetic acid;
methyl[6-chloro-2-(4,5-dimethylpyridine-2-carbonyl)-1H-indol-3-yl]acetate;
[6-chloro-2-(4,5-dimethylpyridine-2-carbonyl)-1H-indol-3-yl]acetic acid;
methyl[6-chloro-2-(4-methoxypyridine-2-carbonyl)-1H-indol-3-yl]acetate;
[6-chloro-2-(4-methoxypyridine-2-carbonyl)-1H-indol-3-yl]acetic acid;
methyl[5-chloro-2-(4-methoxypyridine-2-carbonyl)-1H-indol-3-yl]acetate;
[5-chloro-2-(4-methoxypyridine-2-carbonyl)-1H-indol-3-yl]acetic acid;
methyl[6-chloro-2-(3,5-dimethylpyridine-2-carbonyl)-1H-indol-3-yl]acetate;
[6-chloro-2-(3,5-dimethylpyridine-2-carbonyl)-1H-indol-3-yl]acetic acid;
methyl[5-chloro-2-(4-ethyl-3-fluoropyridine-2-carbonyl)-1H-indol-3-yl]acetate;
[5-chloro-2-(4-ethyl-3-fluoropyridine-2-carbonyl)-1H-indol-3-yl]acetic acid;
methyl[6-chloro-2-(4-ethyl-3-fluoropyridine-2-carbonyl)-1H-indol-3-yl]acetate;
[6-chloro-2-(3-ethoxy-4-ethylpyridine-2-carbonyl)-1H-indol-3-yl]acetic acid;
methyl[6-chloro-2-(3-chloro-4-ethylpyridine-2-carbonyl)-1H-indol-3-yl]acetate;
[6-chloro-2-(3-chloro-4-ethylpyridine-2-carbonyl)-1H-indol-3-yl]acetic acid;
methyl[5-chloro-2-(3-chloro-4-ethylpyridine-2-carbonyl)-1H-indol-3-yl]acetate;
[5-chloro-2-(3-chloro-4-ethylpyridine-2-carbonyl)-1H-indol-3-yl]acetic acid;
methyl[5-chloro-2-(4,6-dimethylpyridine-2-carbonyl)-1H-indol-3-yl]acetate;
[5-chloro-2-(4,6-dimethylpyridine-2-carbonyl)-1H-indol-3-yl]acetic acid;
methyl[6-chloro-2-(4,6-dimethylpyridine-2-carbonyl)-1H-indol-3-yl]acetate;
[6-chloro-2-(4,6-dimethylpyridine-2-carbonyl)-1H-indol-3-yl]acetic acid;
methyl[5,6-dichloro-2-(4-methylpyridine-2-carbonyl)-1H-indol-3-yl]acetate;
[5,6-dichloro-2-(4-methylpyridine-2-carbonyl)-1H-indol-3-yl]acetic acid;
methyl[5-methyl-2-(4-methylpyridine-2-carbonyl)-1H-indol-3-yl]acetate;
[5-methyl-2-(4-methylpyridine-2-carbonyl)-1H-indol-3-yl]acetic acid;
methyl[5-fluoro-2-(4-methylpyridine-2-carbonyl)-1H-indol-3-yl]acetate;
[5-fluoro-2-(4-methylpyridine-2-carbonyl)-1H-indol-3-yl]acetic acid;
methyl[5-methoxy-2-(4-methylpyridine-2-carbonyl)-1H-indol-3-yl]acetate;
[5-methoxy-2-(4-methylpyridine-2-carbonyl)-1H-indol-3-yl]acetic acid;
methyl[6-methoxy-2-(4-methylpyridine-2-carbonyl)-1H-indol-3-yl]acetate;
[6-methoxy-2-(4-methylpyridine-2-carbonyl)-1H-indol-3-yl]acetic acid;
methyl[5-ethyl-2-(4-methylpyridine-2-carbonyl)-1H-indol-3-yl]acetate;
[5-ethyl-2-(4-methylpyridine-2-carbonyl)-1H-indol-3-yl]acetic acid;
methyl[5-ethyl-2-(4-ethylpyridine-2-carbonyl)-1H-indol-3-yl]acetate;
[5-ethyl-2-(4-ethylpyridine-2-carbonyl)-1H-indol-3-yl]acetic acid;
methyl[6-ethyl-2-(4-methylpyridine-2-carbonyl)-1H-indol-3-yl]acetate;
[6-ethyl-2-(4-methylpyridine-2-carbonyl)-1H-indol-3-yl]acetic acid;
methyl[5-isopropyl-2-(4-methylpyridine-2-carbonyl)-1H-indol-3-yl]acetate;
[5-isopropyl-2-(4-methylpyridine-2-carbonyl)-1H-indol-3-yl]acetic acid;
methyl[2-(4-methylpyridine-2-carbonyl)-6-trifluoromethyl-1H-indol-3-yl]acetate;
[2-(4-methylpyridine-2-carbonyl)-6-trifluoromethyl-1H-indol-3-yl]acetic acid;
methyl[5-tert-butyl-2-(4-methylpyridine-2-carbonyl)-1H-indol-3-yl]acetate;
[5-tert-butyl-2-(4-methylpyridine-2-carbonyl)-1H-indol-3-yl]acetic acid;
methyl[2-(4-methylpyridine-2-carbonyl)-5-trifluoromethoxy-1H-indol-3-yl]acetate;
[2-(4-methyl-2-pyridine-2-carbonyl)-5-trifluoromethoxy-1H-indol-3-yl]acetic acid;
methyl[2-(4-ethylpyridine-2-carbonyl)-5-trifluoromethoxy-1H-indol-3-yl]acetate;
[2-(4-ethylpyridine-2-carbonyl)-5-trifluoromethoxy-1H-indol-3-yl]acetic acid;
methyl[6-methyl-2-(4-methylpyridine-2-carbonyl)-1H-indol-3-yl]acetate;

[6-methyl-2-(4-methyl pyridine-2-carbonyl)-1H-indol-3-yl]acetic acid;
methyl[2-(4-methylpyridine-2-carbonyl)-5-trifluoromethyl-1H-indol-3-yl]acetate;
[2-(4-methylpyridine-2-carbonyl)-5-trifluoromethyl-1H-indol-3-yl]acetic acid;
methyl[2-(4-ethylpyridine-2-carbonyl)-5-trifluoromethyl-1H-indol-3-yl]acetate;
[2-(4-ethylpyridine-2-carbonyl)-5-trifluoromethyl-1H-indol-3-yl]acetic acid;
methyl(2-benzoyl-1H-indol-3-yl)acetate;
(2-benzoyl-1H-indol-3-yl)acetic acid;
methyl[2-(4-chlorobenzoyl)-6-methyl-1H-indol-3-yl]acetate;
[2-(4-chlorobenzoyl)-6-methyl-1H-indol-3-yl]acetic acid;
[2-(4-chlorobenzoyl)-5-methyl-1H-indol-3-yl]acetic acid;
methyl[6-methoxy-2-(4-chlorobenzoyl)-1H-indol-3-yl]acetate;
[6-methoxy-2-(4-chlorobenzoyl)-1H-indol-3-yl]acetic acid;
[2-(4-chlorobenzoyl)-6-trifluoromethyl-1H-indol-3-yl]acetic acid;
methyl[2-(4-chlorobenzoyl)-5-ethyl-1H-indol-3-yl]acetate;
[2-(4-chlorobenzoyl)-5-ethyl-1H-indol-3-yl]acetic acid;
methyl[2-(4-chlorobenzoyl)-5-methoxy-1H-indol-3-yl]acetate;
[2-(4-chlorobenzoyl)-5-methoxy-1H-indol-3-yl]acetic acid;
methyl[2-(4-chlorobenzoyl)-5-isopropyl-1H-indol-3-yl]acetate;
[2-(4-chlorobenzoyl)-5-isopropyl-1H-indol-3-yl]acetic acid;
methyl[2-(4-chlorobenzoyl)-5-trifluoromethyl-1H-indol-3-yl]acetate;
[2-(4-chlorobenzoyl)-5-trifluoromethyl-1H-indol-3-yl]acetic acid;
methyl[2-(4-chlorobenzoyl)-5-trifluoromethoxy-1H-indol-3-yl]acetate;
[2-(4-chlorobenzoyl)-5-trifluoromethoxy-1H-indol-3-yl]acetic acid;
methyl[6-chloro-2-(2-methoxybenzoyl)-1H-indol-3-yl]acetate;
[6-chloro-2-(2-methoxybenzoyl)-1H-indol-3-yl]acetic acid;
methyl[6-chloro-2-(3-methoxybenzoyl)-1H-indol-3-yl]acetate;
[6-chloro-2-(3-methoxybenzoyl)-1H-indol-3-yl]acetic acid;
methyl[6-chloro-2-(3-benzyloxybenzoyl)-1H-indol-3-yl]acetate;
[6-chloro-2-(3-benzyloxybenzoyl)-1H-indol-3-yl]acetic acid;
methyl[6-chloro-2-(3-hydroxybenzoyl)-1H-indol-3-yl]acetate;
[6-chloro-2-(3-hydroxybenzoyl)-1H-indol-3-yl]acetic acid;
methyl[6-chloro-2-(4-benzoxybenzyloyl)-1H-indol-3-yl]acetate;
[6-chloro-2-(4-benzyloxybenzoyl)-1H-indol-3-yl]acetic acid;
methyl[6-chloro-2-(4-hydroxybenzoyl)-1H-indol-3-yl]acetate;
[6-chloro-2-(4-hydroxybenzoyl)-1H-indol-3-yl]acetic acid;
methyl[6-chloro-2-(4-isopropoxybenzoyl)-1H-indol-3-yl]acetate;
[6-chloro-2-(4-isopropoxybenzoyl)-1H-indol-3-yl]acetic acid;
methyl[6-chloro-2-(4-phenylbenzoyl)-1H-indol-3-yl]acetate;
[6-chloro-2-(4-phenylbenzoyl)-1H-indol-3-yl]acetic acid;
methyl[6-chloro-2-(4-trifluoromethoxybenzoyl)-1H-indol-3-yl]acetate;
[6-chloro-2-(4-trifluoromethoxybenzoyl)-1H-indol-3-yl]acetic acid;
methyl[5-chloro-2-(4-trifluoromethoxybenzoyl)-1H-indol-3-yl]acetate;
[5-chloro-2-(4-trifluoromethoxybenzoyl)-1H-indol-3-yl]acetic acid;
methyl[5-chloro-2-(4-methoxybenzoyl)-1H-indol-3-yl]acetate;
[5-chloro-2-(4-methoxybenzoyl)-1H-indol-3-yl]acetic acid;
methyl[6-chloro-2-(4-nitrobenzoyl)-1H-indol-3-yl]acetate;
[6-chloro-2-(4-nitrobenzoyl)-1H-indol-3-yl]acetic acid;
methyl[6-chloro-2-[(4-methylsulfonyl)benzoyl]-1H-indol-3-yl]acetate;
[6-chloro-2-[(4-methylsulfonyl)benzoyl]-1H-indol-3-yl]acetic acid;
methyl[6-chloro-2-[4-(methylsulfonylamino)benzoyl]-1H-indol-3-yl]acetate;
[6-chloro-2-[4-(methylsulfonylamino)benzoyl]-1H-indol-3-yl]acetic acid;
[6-chloro-2-(2-chlorobenzoyl)-1H-indol-3-yl]acetic acid;
[6-chloro-2-(2,4-dichlorobenzoyl)-1H-indol-3-yl]acetic acid;
methyl[6-chloro-2-(4-chloro-3-fluorobenzoyl)-1H-indol-3-yl]acetate;
[6-chloro-2-(4-chloro-3-fluorobenzoyl)-1H-indol-3-yl]acetic acid;
methyl[6-chloro-2-(4-cyanobenzoyl)-1H-indol-3-yl]acetate;
methyl[6-chloro-2-[4-bromobenzoyl]-1H-indol-3-yl]acetate;
methyl[6-chloro-2-[4-(2-thienyl)benzoyl]-1H-indol-3-yl]acetate;
[6-chloro-2-[4-(2-thienyl)benzoyl]-1H-indol-3-yl]acetic acid;
methyl[6-chloro-2-[4-(2-furyl)benzoyl]-1H-indol-3-yl]acetate;
[6-chloro-2-[4-(2-furyl)benzoyl]-1H-indol-3-yl]acetic acid;
methyl[6-chloro-2-[4-(3-pyridyl)benzoyl]-1H-indol-3-yl]acetate;
[6-chloro-2-[4-(3-pyridyl)benzoyl]-1H-indol-3-yl]acetic acid;
methyl[6-chloro-2-[4-(2-thiazolyl)benzoyl]-1H-indol-3-yl]acetate;

[6-chloro-2-[4-(2-thiazolyl)benzoyl]-1H-indol-3-yl] acetic acid;
methyl[6-chloro-2-(3-bromobenzoyl)-1H-indol-3-yl] acetate;
methyl[6-chloro-2-[3-(2-furyl)benzoyl]-1H-indol-3-yl] acetate;
[6-chloro-2-[3-(2-furyl)benzoyl]-1H-indol-3-yl]acetic acid;
methyl dl-2-[6-chloro-2-(4-chlorobenzoyl)-1H-indol-3-yl]propionate;
dl-2-[2-(4-chlorobenzoyl)-6-chloro-1H-indol-3-yl] propionic acid;
methyl[5-chloro-2-(isoquinoline-3-carbonyl)-1H-indol-3-yl]acetate;
[5-chloro-2-(isoquinoline-3-carbonyl)-1H-indol-3-yl] acetic acid;
methyl[6-chloro-2-(isoquinolne-3-carbonyl)-1H-indol-3-yl]acetate;
[6-chloro-2-(isoquinoline-3-carbonyl)-1H-indol-3-yl] acetic acid;
methyl[5-chloro-2-(5-methylisoxazole-3-carbonyl)-1H-indol-3-yl]acetate;
[5-chloro-2-(5-methylisoxazole-3-carbonyl)-1H-indol-3-yl]acetic acid;
methyl[6-chloro-2-(5-methylisoxazole-3-carbonyl)-1H-indol-3-yl]acetate;
[6-chloro-2-(5-methylisoxazole-3-carbonyl)-1H-indol-3-yl]acetic acid;
methyl[5-chloro-2-(4-methyl-1,2,3-thiadiazole-5-carbonyl)-1H-indol-3-yl]acetate;
[5-chloro-2-(4-methyl-1,2,3-thiadiazole-5-carbonyl)-1H-indol-3-yl]acetic acid;
methyl[6-chloro-2-(4-methyl-1,2,3-thiadiazole-5-carbonyl)-1H-indol-3-yl]acetate;
[6-chloro-2-(4-methyl-1,2,3-thiadiazole-5-carbonyl)-1H-indol-3-yl]acetic acid;
methyl[5-chloro-2-(5-methylthiazole-2-carbonyl)-1H-indol-3-yl]acetate;
[5-chloro-2-(5-methylthiazole-2-carbonyl)-1H-indol-3-yl]acetic acid;
methyl[6-chloro-2-(5-methylthiazole-2-carbonyl)-1H-indol-3-yl]acetate;
[6-chloro-2-(5-methylthiazole-2-carbonyl)-1H-indol-3-yl]acetic acid;
[6-chloro-2-(2-thienyl)carbonylindol-3-yl]acetic acid;
methyl[6-chloro-2-[3-(1-hydroxy-1-methylethyl)-2-furoyl]-1H-indol-3-yl]acetate;
[6-chloro-2-[3-(1-hydroxy-1-methylethyl)-2-furoyl]-1H-indol-3-yl]acetic acid;
methyl[6-chloro-2-[3-methoxymethyl-2-furoyl]-1H-indol-3-yl]acetate;
[6-chloro-2-[3-methoxymethyl-2-furoyl]-1H-indol-3-yl] acetic acid;
[6-chloro-2-(1-methylimidazole-2-carbonyl)-1H-indol-3-yl]acetic acid;
methyl[6-chloro-2-(1-methylimidazole-2-carbonyl)-1H-indol-3-yl]acetate;
methyl[5-chloro-2-(1-methylimidazole-2-carbonyl)-1H-indol-3-yl]acetate;
[5-chloro-2-(1-methylimidazole-2-carbonyl)-1H-indol-3-yl]acetic acid;
methyl[5-chloro-2-(imidazole-2-carbonyl)-1H-indol-3-yl]acetate;
[5-chloro-2-(imidazole-2-carbonyl)-1H-indol-3-yl]acetic acid;
methyl[6-chloro-2-(imidazole-2-carbonyl)-1H-indol-3-yl]acetate;
[6-chloro-2-(imidazole-2-carbonyl)-1H-indol-3-yl]acetic acid;
methyl[5-chloro-2-(4-methylthiazole-2-carbonyl)-1H-indol-3-yl]acetate;
[5-chloro-2-(4-methylthiazole-2-carbonyl)-1H-indol-3-yl]acetic acid;
methyl[5-chloro-2-(1-methylpyrrole-2-carbonyl)-1H-indol-3-yl]acetate;
[5-chloro-2-(1-methylpyrrole-2-carbonyl)-1H-indol-3-yl] acetic acid;
methyl[5-chloro-2-(2-methylimidazole-4-carbonyl)-1H-indol-3-yl]acetate;
[5-chloro-2-(2-methylimidazole-4-carbonyl)-1H-indol-3-yl]acetic acid;
methyl[5-chloro-2-(thiazole-5-carbonyl)-1H-indol-3-yl] acetate;
[5-chloro-2-(thiazole-5-carbonyl)-1H-indol-3-yl]acetic acid;
methyl(6-chloro-2-(4-methylthiazole-2-carbonyl)-1H-indol-3-yl]acetate;
[6-chloro-2-(4-methylthiazole-2-carbonyl)-1H-indol-3-yl]acetic acid;
methyl[5-chloro-2-[3-(ethoxypropyl)isoxazole-5-carbonyl]-1H-indol-3-yl]acetate;
[5-chloro-2-[3-(carboxy)isoxazole-5-carbonyl]-1H-indol-3-yl]acetic acid;
methyl[6-chloro-2-cyclopropanecarbonyl-1H-indol-3-yl] acetate;
[6-chloro-2-cyclopropanecarbonyl-1H-indol-3-yl]acetic acid;
methyl[6-chloro-2-cyclobutanecarbonyl-1H-indol-3-yl] acetate;
[6-chloro-2-cyclobutanecarbonyl-1H-indol-3-yl)acetic acid;
methyl[5-(tert-butyl)-2-(4-chlorobenzoyl)-1H-indol-3-yl] acetate;
[5-(tert-butyl)-2-(4-chlorobenzoyl)-1H-indol-3-yl]acetic acid;
[6-chloro-2-(4-methylpyridine-2-carbonyl)-1H-indol-3-yl]-N,N-dimethylacetamide;
[6-chloro-2-(4-methylpyridine-2-carbonyl)-1H-indol-3-yl]-N-methylacetamide;
[5-chloro-2-(4-methylpyridine-2-carbonyl)-1H-indol-3-yl]-N-(2-hydroxyethyl)acetamide;
[5-chloro-2-(4-methylpyridine-2-carbonyl)-1H-indol-3-yl]-N-methoxyacetamide;
2-[5-chloro-2-(4-methylpyridine-2-carbonyl)-1H-indol-3-yl]-1-piperazinyl-1-ethanone;
[5-chloro-2-(4-methylpyridine-2-carbonyl)-1H-indol-3-yl]-N-(2-aminoethyl)acetamide;
2-[5-chloro-2-(4-methylpyridine-2-carbonyl)-1H-indol-3-yl]-1-(3-amino-1-pyrrolidinyl)-1-ethanone;
[6-chloro-2-(4-chlorobenzoyl)-5-fluoro-1H-indol-3-yl] acetic acid;
methyl[6-chloro-5-fluoro-2-(4-methylpyridine-2-carbonyl)-1H-indol-3-yl]acetate;
[6-chloro-5-fluoro-2-(4-methylpyridine-2-carbonyl)-1H-indol-3-yl]acetic acid;

methyl[6-chloro-2-[4-(1-hydroxyethyl)pyridine-2-carbonyl]-1H-indol-3-yl]acetate;
[6-chloro-2-[4-(1-hydroxyethyl)pyridine-2-carbonyl]-1H-indol-3-yl]acetic acid;
[6-chloro-2-(4-ethyl-3-fluoropyridine-2-carbonyl)-1H-indol-3-yl]acetic acid;
[6-chloro-2-(2-nitrobenzoyl)-1H-indol-3-yl]acetic acid;
[6-chloro-2-(2,4-dimethoxybenzoyl)-1H-indol-3-yl]acetic acid;
[6-chloro-2-(4-difuluoromethoxybenzoyl)-1H-indol-3-yl]acetic acid;
[6-chloro-2-(2,5-dimethoxybenzoyl)-1H-indol-3-yl]acetic acid;
methyl[5-acetyl-2-(4-chlorobenzoyl)-1H-indol-3-yl]acetate;
[5-acetyl-2-(4-chlorobenzoyl)-1H-indol-3-yl]acetic acid;
methyl[6-chloro-2-(4-chlorobenzoyl)-5-fluoro-1H-indol-3-yl]acetate;
methyl[6-fluoro-2-(4-methylpyridine-2-carbonyl]-1H-indol-3-yl]acetate;
[6-fluoro-2-(4-methylpyridine-2-carbonyl)-1H-indol-3-yl]acetic acid;
methyl[6-fluoro-2-(4-chlorobenzoyl)-1H-indol-3-yl]acetate;
[6-fluoro-2-(4-chlorobenzoyl)-1H-indol-3-yl]acetic acid;
[2-(4-methylpyridine-2-carbonyl)-5-methylthio-1H-indol-3-yl]acetic acid;
[2-(4-methylpyridine-2-carbonyl)-5-methylthio-1H-indol-3-yl]acetic acid, and a salt thereof.
Preferred individual compounds of this invention are:
ethyl(2-benzoyl-6-chloro-1H-indol-3-yl)acetate;
(2-benzoyl-6-chloro-1H-indol-3-yl)acetic acid;
(2-benzoyl-6-chloro-1H-indol-3-yl)acetic acid, sodium salt;
[6-chloro-2-(2-methylbenzoyl)-1H-indol-3-yl]acetic acid;
[6-chloro-2-(3-methylbenzoyl)-1H-indol-3-yl]acetic acid;
[6-chloro-2-(4-methylbenzoyl)-1H-indol-3-yl]acetic acid;
[6-chloro-2-(3-chlorobenzoyl)-1H-indol-3-yl]acetic acid;
methyl[6-chloro-2-(4-chlorobenzoyl)-1H-indol-3-yl]acetate;
[6-chloro-2-(4-chlorobenzoyl)-1H-indol-3-yl]acetic acid;
[6-chloro-2-(3-fluorobenzoyl)-1H-indol-3-yl]acetic acid;
[6-chloro-2-(4-fluorobenzoyl)-1H-indol-3-yl]acetic acid;
[2-(3-bromobenzoyl)-6-chloro-1H-indol-3-yl]acetic acid;
[2-(4-bromobenzoyl)-6-chloro-1H-indol-3-yl]acetic acid;
[6-chloro-2-(3-trifluoromethylbenzoyl)-1H-indol-3-yl]acetic acid;
[6-chloro-2-(4-trifluoromethylbenzoyl)-1H-indol-3-yl]acetic acid;
[6-chloro-2-(3,4-dichlorobenzoyl)-1H-indol-3-yl]acetic acid;
(2-benzoyl-4-chloro-1H-indol-3-yl)acetic acid;
[5-chloro-2-(3-methylbenzoyl)-1H-indol-3-yl]acetic acid;
[5-chloro-2-(4-chloro benzoyl)-1H-indol-3-yl]acetic acid;
[5-chloro-2-(3-chlorobenzoyl)-1H-indol-3-yl]acetic acid;
[2-(4-chlorobenzoyl)-5-fluoro-1H-indol-3-yl]acetic acid;
[2-(3-chlorobenzoyl)-5-fluoro-1H-indol-3-yl]acetic acid;
[5-methoxy-2-(3-methylbenzoyl)-1H-indol-3-yl]acetic acid;
(2-benzoyl-7-chloro-1H-indol-3-yl)acetic acid;
(2-benzoyl-4,5-dichloro-1H-indol-3-yl)acetic acid;
(2-benzoyl-4,6-dichloro-1H-indol-3-yl)acetic acid;
(2-benzoyl-5,6-dichloro-1H-indol-3-yl)acetic acid;
dl-2-(2-benzoyl-6-chloro-1H-indol-3-yl)propanoic acid;
less polar antipode, 2-(2-benzoyl-6-chloro-1H-indol-3-yl)propanoic acid;
more polar antipode, 2-(2-benzoyl-6-chloro-1H-indol-3-yl)propanoic acid;
[6-chloro-2-(4-methylpyridine-2-carbonyl)-1H-indol-3-yl]acetic acid;
[6-chloro-2-(5-methylpyridine-2-carbonyl)-1H-indol-3-yl]acetic acid;
methyl[6-chloro-2-(4-chloropyridine-2-carbonyl)-1H-indol-3-yl]acetate;
[6-chloro-2-(4-chloropyridine-2-carbonyl)-1H-indol-3-yl]acetic acid;
[6-chloro-2-(pyridine-2-carbonyl)-1H-indol-3-yl]acetic acid;
[5-chloro-2-(4-methylpyridine-2-carbonyl)-1H-indol-3-yl]acetic acid;
methyl[5-chloro-2-(6-methylpyridine-2-carbonyl)-1H-indol-3-yl]acetate;
[5-chloro-2-(6-methylpyridine-2-carbonyl)-1H-indol-3-yl]acetic acid;
[6-chloro-2-(1-methylimidazole-2-carbonyl)-1H-indol-3-yl]acetic acid;
methyl[5-chloro-2-(thiazole-2-carbonyl)-1H-indol-3yl]acetate;
[5-chloro-2-(thiazole-2-carbonyl)-1H-indol-3-yl]acetic acid;
methyl(2-benzoyl-6-chloro-1H-indol-3-yl)acetate;
[2-(4-chlorobenzoyl)-1H-indol-3-yl]acetic acid;
[6-chloro-2-(2-methylcarbonyl)-1H-indol-3-yl]acetic acid;
[6-chloro-2-(cyclohexanecarbonyl)-1H-indol-3-yl]acetic acid;
methyl[6-chloro-2-(4-methoxybenzoyl)-1H-indol-3-yl]acetate;
[6-chloro-2-(4-methoxybenzoyl)-1H-indol-3-yl]acetic acid;
methyl[6-chloro-2-(4-ethylpyridine-2-carbonyl)-1H-indol-3-yl]acetate;
[6-chloro-2-(4-ethylpyridine-2-carbonyl)-1H-indol-3-yl]acetic acid;
[5-chloro-2-(4-ethylpyridine-2-carbonyl)-1H-indol-3-yl]acetic acid;
[6-chloro-2-(4-isopropylpyridine-2-carbonyl)-1H-indol-3-yl]acetic acid;
[5-chloro-2-(4-isopropylpyridine-2-carbonyl)-1H-indol-3-yl]acetic acid;
[6-chloro-2-(4-propylpyridine-2-carbonyl)-1H-indol-3-yl]acetic acid;
[5-chloro-2-(4-propylpyridine-2-carbonyl)-1H-indol-3-yl]acetic acid;
[2-(4-tert-butylpyridine-2-carbonyl)-6-chloro-1H-indol-3-yl]acetic acid;
[2-(4-tert-butylpyridine-2-carbonyl)-5-chloro-1H-indol-3-yl]acetic acid;

[6-chloro-2-(3-methylpyridine-2-carbonyl)-1H-indol-3-yl]acetic acid;
[5-chloro-2-(3-methylpyridine-2-carbonyl)-1H-indol-3-yl]acetic acid;
[6-chloro-2-(6-methylpyridine-2-carbonyl)-1H-indol-3-yl]acetic acid;
[5-chloro-2-(5-methylpyridine-2-carbonyl)-1H-indol-3-yl]acetic acid;
[6-chloro-2-[5-(trifluoromethyl)pyridine-2-carbonyl]-1H-indol-3-yl]acetic acid;
[5-chloro-2-[5-(trifluoromethyl)pyridine-2-carbonyl]-1H-indol-3-yl]acetic acid;
[5-chloro-2-(5-chloropyridine-2-carbonyl)-1H-indol-3-yl]acetic acid;
[6-chloro-2-(5-chloropyridine-2-carbonyl)-1H-indol-3-yl]acetic acid;
[5-chloro-2-(4-chloropyridine-2-carbonyl)-1H-indol-3-yl]acetic acid;
[6-chloro-2-(pyridine-3-carbonyl)-1H-indol-3-yl]acetic acid;
[6-chloro-2-(pyridine-4-carbonyl)-1H-indol-3-yl]acetic acid;
[6-chloro-2-[4-(hydroxymethyl)pyridine-2-carbonyl]-1H-indol-3-yl]acetic acid;
[5-chloro-2-[4-(hydroxymethyl)pyridine-2-carbonyl]-1H-indol-3-yl]acetic acid;
[5-chloro-2-(3,4-dimethylpyridine-2-carbonyl)-1H-indol-3-yl]acetic acid;
[5-chloro-2-(4,5-dimethylpyridine-2-carbonyl)-1H-indol-3-yl]acetic acid;
[6-chloro-2-(4,5-dimethylpyridine-2-carbonyl)-1H-indol-3-yl]acetic acid;
[6-chloro-2-(4-methoxypyridine-2-carbonyl)-1H-indol-3-yl]acetic acid;
[5-chloro-2-(4-methoxypyridine-2-carbonyl)-1H-indol-3-yl]acetic acid;
[6-chloro-2-(3,5-dimethylpyridine-2-carbonyl)-1H-indol-3-yl]acetic acid;
[5-chloro-2-(4-ethyl-3-fluoropyridine-2-carbonyl)-1H-indol-3-yl]acetic acid;
[6-chloro-2-(3-ethoxy-4-ethylpyridine-2-carbonyl)-1H-indol-3-yl]acetic acid;
[6-chloro-2-(3-chloro-4-ethyl pyridine-2-carbonyl)-1H-indol-3-yl]acetic acid;
[5-chloro-2-(3-chloro-4-ethylpyridine-2-carbonyl)-1H-indol-3-yl]acetic acid;
[6-chloro-2-(4,6-dimethylpyridine-2-carbonyl)-1H-indol-3-yl]acetic acid;
[6-chloro-2-(4,6-dimethylpyridine-2-carbonyl)-1H-indol-3-yl]acetic acid;
[5,6-dichloro-2-(4-methylpyridine-2-carbonyl)-1H-indol-3-yl]acetic acid;
[5-methyl-2-(4-methylpyridine-2-carbonyl)-1H-indol-3-yl]acetic acid;
[5-fluoro-2-(4-methylpyridine-2-carbonyl)-1H-indol-3-yl]acetic acid;
[5-methoxy-2-(4-methylpyridine-2-carbonyl)-1H-indol-3-yl]acetic acid;
[6-methoxy-2-(4-methylpyridine-2-carbonyl)-1H-indol-3-yl]acetic acid;
[5-ethyl-2-(4-methylpyridine-2-carbonyl)-1H-indol-3-yl]acetic acid;
[5-ethyl-2-(4-ethylpyridine-2-carbonyl)-1H-indol-3-yl]acetic acid;
[6-ethyl-2-(4-methylpyridine-2-carbonyl)-1H-indol-3-yl]acetic acid;
[5-isopropyl-2-(4-methylpyridine-2-carbonyl)-1H-indol-3-yl]acetic acid;
[2-(4-methylpyridine-2-carbonyl)-6-trifluoromethyl-1H-indol-3-yl]acetic acid;
[5-tert-butyl-2-(4-methylpyridine-2-carbonyl)-1H-indol-3-yl]acetic acid;
[2-(4-methyl-2-pyridine-2-carbonyl)-5-trifluoromethoxy-1H-indol-3-yl]acetic acid;
[2-(4-ethylpyridine-2-carbonyl)-5-trifluoromethoxy-1H-indol-3-yl]acetic acid;
[6-methyl-2-(4-methylpyridine-2-carbonyl)-1H-indol-3-yl]acetic acid;
[2-(4-methylpyridine-2-carbonyl)-5-trifluoromethyl-1H-indol-3-yl]acetic acid;
[2-(4-ethylpyridine-2-carbonyl)-5-trifluoromethyl-1H-indol-3-yl]acetic acid;
(2-benzoyl-1H-indol-3-yl)acetic acid;
[2-(4-chlorobenzoyl)-6-methyl-1H-indol-3-yl]acetic acid;
[2-(4-chlorobenzoyl)-5-methyl-1H-indol-3-yl]acetic acid;
[6-methoxy-2-(4-chlorobenzoyl)-1H-indol-3-yl]acetic acid;
[2-(4-chlorobenzoyl)-6-trifluoromethyl-1H-indol-3-yl]acetic acid;
[2-(4-chlorobenzoyl)-5-ethyl-1H-indol-3-yl]acetic acid;
[2-(4-chlorobenzoyl)-5-methoxy-1H-indol-3-yl]acetic acid;
[2-(4-chlorobenzoyl)-5-isopropyl-1H-indol-3-yl]acetic acid;
[2-(4-chlorobenzoyl)-5-trifluoromethyl-1H-indol-3-yl]acetic acid;
[2-(4-chlorobenzoyl)-5-trifluoromethoxy-1H-indol-3-yl]acetic acid;
[6-chloro-2-(2-methoxybenzoyl)-1H-indol-3-yl]acetic acid;
[6-chloro-2-(3-methoxybenzoyl)-1H-indol-3-yl]acetic acid;
[6-chloro-2-(3-benzyloxybenzoyl)-1H-indol-3-yl]acetic acid;
[6-chloro-2-(3-hydroxybenzoyl)-1H-indol-3-yl]acetic acid;
[6-chloro-2-(4-benzyloxybenzoyl)-1H-indol-3-yl]acetic acid;
[6-chloro-2-(4-hydroxybenzoyl)-1H-indol-3-yl]acetic acid;
[6-chloro-2-(4-isopropoxybenzoyl)-1H-indol-3-yl]acetic acid;
[6-chloro-2-(4-phenylbenzoyl)-1H-indol-3-yl]acetic acid;
[6-chloro-2-(4-trifluoromethoxybenzoyl)-1H-indol-3-yl]acetic acid;
[5-chloro-2-(4-trifluoromethoxybenzoyl)-1H-indol-3-yl]acetic acid;
[5-chloro-2-(4-methoxybenzoyl)-1H-indol-3-yl]acetic acid;
[6-chloro-2-(4-nitrobenzoyl)-1H-indol-3-yl]acetic acid;
[6-chloro-2-[(4-methylsulfonyl)benzoyl]-1H-indol-3-yl]acetic acid;

[6-chloro-2-[4-(methylsulfonylamino)benzoyl]-1H-indol-3-yl]acetic acid;
[6-chloro-2-(2-chlorobenzoyl)-1H-indol-3-yl]acetic acid;
[6-chloro-2-(2,4-dichlorobenzoyl)-1H-indol-3-yl]acetic acid;
[6-chloro-2-(4-chloro-3-fluorobenzoyl)-1H-indol-3-yl]acetic acid;
methyl[6-chloro-2-(4-cyanobenzoyl)-1H-indol-3-yl]acetate;
methyl[6-chloro-2-[4-bromobenzoyl]-1H-indol-3-yl]acetate;
[6-chloro-2-[4-(2-thienyl)benzoyl]-1H-indol-3-yl]acetic acid;
[6-chloro-2-[4-(2-furyl)benzoyl]-1H-indol-3-yl]acetic acid;
[6-chloro-2-[4-(3-pyridyl)benzoyl]-1H-indol-3-yl]acetic acid;
[6-chloro-2-[4-(2-thiazolyl)benzoyl]-1H-indol-3-yl]acetic acid;
methyl[6-chloro-2-(3-bromobenzoyl)-1H-indol-3-yl]acetate;
[6-chloro-2-[3-(2-furyl)benzoyl]-1H-indol-3-yl]acetic acid;
dl-2-[2-(4-chlorobenzoyl)-6-chloro-1H-indol-3-yl]propionic acid;
[5-chloro-2-(isoquinoline-3-carbonyl)-1H-indol-3-yl]acetic acid;
[6-chloro-2-(isoquinoline-3-carbonyl)-1H-indol-3-yl]acetic acid;
[5-chloro-2-(5-methylisoxazole-3-carbonyl)-1H-indol-3-yl]acetic acid;
[6-chloro-2-(5-methylisoxazole-3-carbonyl)-1H-indol-3-yl]acetic acid;
[5-chloro-2-(4-methyl-1,2,3-thiadiazole-5-carbonyl)-1H-indol-3-yl]acetic acid;
[6-chloro-2-(4-methyl-1,2,3-thiadiazole-5-carbonyl)-1H-indol-3-yl]acetic acid;
[5-chloro-2-(5-methylthiazole-2-carbonyl)-1H-indol-3-yl]acetic acid;
[6-chloro-2-(5-methylthiazole-2-carbonyl)-1H-indol-3-yl]acetic acid;
[6-chloro-2-(2-thienyl)carbonylindol-3-yl]acetic acid;
[6-chloro-2-[3-(1-hydroxy-1-methylethyl)-2-furoyl]-1H-indol-3-yl]acetic acid;
[6-chloro-2-[3-methoxymethyl-2-furoyl]-1H-indol-3-yl]acetic acid;
[6-chloro-2-(1-methylimidazole-2-carbonyl)-1H-indol-3-yl]acetic acid;
methyl[5-chloro-2-(1-methylimidazole-2-carbonyl)-1H-indol-3-yl]acetate;
[5-chloro-2(1-methylimidazole-2-carbonyl)-1H-indol-3-yl]acetic acid;
[5-chloro-2-(imidazole-2-carbonyl)-1H-indol-3-yl]acetic acid;
[6-chloro-2-(imidazole-2-carbonyl)-1H-indol-3-yl]acetic acid;
[5-chloro-2-(4-methylthiazole-2-carbonyl)-1H-indol-3-yl]acetic acid;
[5-chloro-2-(1-methylpyrrole-2-carbonyl)-1H-indol-3-yl]acetic acid;
[5-chloro-2-(2-methylimidazole-4-carbonyl)-1H-indol-3-yl]acetic acid;
[5-chloro-2-(thiazole-5-carbonyl)-1H-indol-3-yl]acetic acid;
[6-chloro-2-(4-methylthiazole-2-carbonyl)-1H-indol-3-yl]acetic acid;
[5-chloro-2-[3-(carboxy)isoxazole-5-carbonyl]-1H-indol-3-yl]acetic acid;
[6-chloro-2-cyclopropanecarbonyl-1H-indol-3-yl]acetic acid;
[6-chloro-2-cyclobutanecarbonyl-1H-indol-3-yl]acetic acid;
[5-(tert-butyl)-2-(4-chlorobenzoyl)-1H-indol-3-yl]acetic acid;
[6-chloro-2-(4-chlorobenzoyl)-5-fluoro-1H-indol-3-yl]acetic acid;
[6-chloro-5-fluoro-2-(4-methylpyridine-2-carbonyl)-1H-indol-3-yl]acetic acid;
methyl[6-chloro-2-[4-(1-hydroxyethyl)pyridine-2-carbonyl]-1H-indol-3-yl]acetate;
[6-chloro-2-[4-(1-hydroxyethyl)pyridine-2-carbonyl]-1H-indol-3-yl]acetic acid;
[6-chloro-2-(4-ethyl-3-fluoro-pyridine-2-carbonyl)-1H-indol-3-yl]acetic acid;
[6-chloro-2-(2-nitrobenzoyl)-1H-indol-3-yl]acetic acid;
[6-chloro-2-(2,4-dimethoxybenzoyl)-1H-indol-3-yl]acetic acid;
[6-chloro-2-(4-difuluoromethoxybenzoyl)-1H-indol-3-yl]acetic acid;
[6-chloro-2-(2,5-dimethoxybenzoyl)-1H-indol-3-yl]acetic acid;
[5-acetyl-2-(4-chlorobenzoyl)-1H-indol-3-yl]acetic acid, and a salt thereof.

Preferred individual compounds of this invention are:
ethyl(2-benzoyl-6-chloro-1H-indol-3-yl)acetate;
(2-benzoyl-6-chloro-1H-indol-3-yl)acetic acid;
[6-chloro-2-(3-methylbenzoyl)-1H-indol-3-yl]acetic acid;
[6-chloro-2-(4-methylbenzoyl)-1H-indol-3-yl]acetic acid;
[6-chloro-2-(3-chlorobenzoyl)-1H-indol-3-yl]acetic acid;
methyl[6-chloro-2-(4-chlorobenzoyl)-1H-indol-3-yl]acetate;
[6-chloro-2-(4-chlorobenzoyl)-1H-indol-3-yl]acetic acid;
[6-chloro-2-(3-fluorobenzoyl)-1H-indol-3-yl]acetic acid;
[6-chloro-2-(4-fluorobenzoyl)-1H-indol-3-yl]acetic acid;
[2-(3-bromobenzoyl)-6-chloro-1H-indol-3-yl]acetic acid;
[2-(4-bromobenzoyl)-6-chloro-1H-indol-3-yl]acetic acid;
[6-chloro-2-(3-trifluoromethylbenzoyl)-1H-indol-3-yl]acetic acid;
[6-chloro-2-(4-trifluoromethylbenzoyl)-1H-indol-3-yl]acetic acid;
(2-benzoyl-4-chloro-1H-indol-3-yl)acetic acid;
[5-chloro-2-(3-methylbenzoyl)-1H-indol-3-yl]acetic acid;
[5-chloro-2-(4-chlorobenzoyl)-1H-indol-3-yl]acetic acid;
[5-chloro-2-(3-chlorobenzoyl)-1H-indol-3-yl]acetic acid;
[2-(4-chlorobenzoyl)-5-fluoro-1H-indol-3-yl]acetic acid;
[2-(3-chlorobenzoyl)-5-fluoro-1H-indol-3-yl]acetic acid;
(2-benzoyl-4,5-dichloro-1H-indol-3-yl)acetic acid;
(2-benzoyl-4,6-dichloro-1H-indol-3-yl)acetic acid;
(2-benzoyl-5,6-dichloro-1H-indol-3-yl)acetic acid;

dl-2-(2-benzoyl-6-chloro-1H-indol-3-yl)propanoic acid;
less polar antipode, 2-(2-benzoyl-6-chloro-1H-indol-3-yl)propanoic acid;
more polar antipode, 2-(2-benzoyl-6-chloro-1H-indol-3-yl)propanoic acid;
[6-chloro-2-(4-methylpyridine-2-carbonyl)-1H-indol-3-yl]acetic acid;
[6-chloro-2-(5-methylpyridine-2-carbonyl)-1H-indol-3-yl]acetic acid;
methyl[6-chloro-2-(4-chloropyridine-2-carbonyl)-1H-indol-3-yl]acetate;
[6-chloro-2-(4-chloropyridine-2-carbonyl)-1H-indol-3-yl]acetic acid;
[6-chloro-2-(pyridine-2-carbonyl)-1H-indol-3-yl]acetic acid;
[5-chloro-2-(4-methylpyridine-2-carbonyl)-1H-indol-3-yl]acetic acid;
methyl[5-chloro-2-(6-methylpyridine-2-carbonyl)-1H-indol-3-yl]acetate;
[5-chloro-2-(6-methylpyridine-2-carbonyl)-1H-indol-3-yl]acetic acid;
[6-chloro-2-(6-methylimidazole-2-carbonyl)-1H-indol-3-yl]acetic acid;
methyl[5-chloro-2-(thiazole-2-carbonyl)-1H-indol-3-yl]acetate;
[5-chloro-2-(thiazole-2-carbonyl)-1H-indol-3-yl]acetic acid;
methyl(2-benzoyl-6-chloro-1H-indol-3-yl)acetate;
[6-chloro-2-(2-furylcarbonyl)-1H-indol-3-yl]acetic acid;
[6-chloro-2-(cyclohexanecarbonyl)-1H-indol-3-yl]acetic acid;
methyl[6-chloro-2-(4-methoxybenzoyl)-1H-indol-3-yl]acetate;
[6-chloro-2-(4-methoxybenzoyl)-1H-indol-3-yl]acetic acid;
methyl[6-chloro-2-(4-ethylpyridine-2-carbonyl)-1H-indol-3-yl]acetate;
[6-chloro-2-(4-ethylpyridine-2-carbonyl)-1H-indol-3-yl]acetic acid;
methyl[5-chloro-2-(4-ethylpyridine-2-carbonyl)-1H-indol-3-yl]acetate;
[5-chloro-2-(4-ethylpyridine-2-carbonyl)-1H-indol-3-yl]acetic acid;
methyl[6-chloro-2-(4-isopropylpyridine-2-carbonyl)-1H-indol-3-yl]acetate;
[6-chloro-2-(4-isopropylpyridine-2-carbonyl)-1H-indol-3-yl]acetic acid;
methyl[6-chloro-2-(4-propylpyridine-2-carbonyl)-1H-indol-3-yl]acetate;
[6-chloro-2-(4-propylpyridine-2-carbonyl)-1H-indol-3-yl]acetic acid;
methyl[5-chloro-2-(4-propylpyridine-2-carbonyl)-1H-indol-3-yl]acetate;
[5-chloro-2-(4-propylpyridine-2-carbonyl)-1H-indol-3-yl]acetic acid;
methyl[2-(4-tert-butylpyridine-2-carbonyl)-6-chloro-1H-indol-3-yl]acetate;
[2-(4-tert-butylpyridine-2-carbonyl)-6-chloro-1H-indol-3-yl]acetic acid;
methyl[6-chloro-2-(3-methylpyridine-2-carbonyl)-1H-indol-3-yl]acetate;
[6-chloro-2-(3-methylpyridine-2-carbonyl)-1H-indol-3-yl]acetic acid;
methyl[6-chloro-2-(6-methylpyridine-2-carbonyl)-1H-indol-3-yl]acetate;
[6-chloro-2-(6-methylpyridine-2-carbonyl)-1H-indol-3-yl]acetic acid;
methyl[5-chloro-2-(5-methylpyridine-2-carbonyl)-1H-indol-3-yl]acetate;
[5-chloro-2-(5-methylpyridine-2-carbonyl)-1H-indol-3-yl]acetic acid;
methyl[6-chloro-2-[5-(trifluoromethyl)pyridine-2-carbonyl]-1H-indol-3-yl]acetate;
[6-chloro-2-[5-(trifluoromethyl)pyridine-2-carbonyl]-1H-indol-3-yl]acetic acid;
methyl[5-chloro-2-[5-(trifluoromethyl)pyridine-2-carbonyl]-1H-indol-3-yl]acetate;
[5-chloro-2-[5-(trifluoromethyl)pyridine-2-carbonyl]-1H-indol-3-yl]acetic acid;
methyl[5-chloro-2-(5-chloropyridine-2-carbonyl)-1H-indol-3-yl]acetate;
[5-chloro-2-(5-chloropyridine-2-carbonyl)-1H-indol-3-yl]acetic acid;
methyl[6-chloro-2-(5-chloropyridine-2-carbonyl)-1H-indol-3-yl]acetate;
[6-chloro-2-(5-chloropyridine-2-carbonyl)-1H-indol-3-yl]acetic acid;
methyl[5-chloro-2-(4-chloropyridine-2-carbonyl)-1H-indol-3-yl]acetate;
[5-chloro-2-(4-chloropyridine-2-carbonyl)-1H-indol-3-yl]acetic acid;
methyl[5-chloro-2-[4-(hydroxymethyl)pyridine-2-carbonyl]-1H-indol-3-yl]acetate;
[5-chloro-2-[4-(hydroxymethyl)pyridine-2-carbonyl]-1H-indol-3-yl]acetic acid;
methyl[5-chloro-2-(4,5-dimethylpyridine-2-carbonyl)-1H-indol-3-yl]acetate;
[5-chloro-2-(4,5-dimethylpyridine-2-carbonyl)-1H-indol-3-yl]acetic acid;
methyl[6-chloro-2-(4,5-dimethylpyridine-2-carbonyl)-1H-indol-3-yl]acetate;
[6-chloro-2-(4,5-dimethylpyridine-2-carbonyl)-1H-indol-3-yl]acetic acid;
methyl[6-chloro-2-(4-methoxypyridine-2-carbonyl)-1H-indol-3-yl]acetate;
[6-chloro-2-(4-methoxypyridine-2-carbonyl)-1H-indol-3-yl]acetic acid;
methyl[5-chloro-2-(4-methoxypyridine-2-carbonyl)-1H-indol-3-yl]acetate;
[5-chloro-2-(4-methoxypyridine-2-carbonyl)-1H-indol-3-yl]acetic acid;
methyl[6-chloro-2-(3,5-dimethylpyridine-2-carbonyl)-1H-indol-3-yl]acetate;
[6-chloro-2-(3,5-dimethylpyridine-2-carbonyl)-1H-indol-3-yl]acetic acid;
methyl[5-chloro-2-(4-ethyl-3-fluoropyridine-2-carbonyl)-1H-indol-3-yl]acetate;
[5-chloro-2-(4-ethyl-3-fluoropyridine-2-carbonyl)-1H-indol-3-yl]acetic acid;
methyl[6-chloro-2-(4-ethyl-3-fluoropyridine-2-carbonyl)-1H-indol-3-yl]acetate;
[6-chloro-2-(3-ethoxy-4-ethylpyridine-2-carbonyl)-1H-indol-3-yl]acetic acid;

methyl[6-chloro-2-(3-chloro-4-ethylpyridine-2-carbonyl)-1H-indol-3-yl]acetate;
[6-chloro-2-(3-chloro-4-ethylpyridine-2-carbonyl)-1H-indol-3-yl]acetic acid;
methyl[5-chloro-2-(3-chloro-4-ethylpyridine-2-carbonyl)-1H-indol-3-yl]acetate;
[5-chloro-2-(3-chloro-4-ethylpyridine-2-carbonyl)-1H-indol-3-yl]acetic acid;
methyl[5-chloro-2-(4,6-dimethylpyridine-2-carbonyl)-1H-indol-3-yl]acetate;
[5-chloro-2-(4,6-dimethylpyridine-2-carbonyl)-1H-indol-3-yl]acetic acid;
methyl[6-chloro-2-(4,6-dimethylpyridine-2-carbonyl)-1H-indol-3-yl]acetate;
[6-chloro-2-(4,6-dimethylpyridine-2-carbonyl)-1H-indol-3-yl]acetic acid;
methyl[5,6-dichloro-2-(4-methylpyridine-2-carbonyl)-1H-indol-3-yl]acetate;
[5,6-dichloro-2-(4-dimethylpyridine-2-carbonyl)-1H-indol-3-yl]acetic acid;
methyl[5-methyl-2-(4-methylpyridine-2-carbonyl)-1H-indol-3-yl]acetate;
[5-methyl-2-(4-methylpyridine-2-carbonyl)-1H-indol-3-yl]acetic acid;
methyl[5-fluoro-2-(4-methylpyridine-2-carbonyl)-1H-indol-3-yl]acetate;
[5-fluoro-2-(4-methylpyridine-2-carbonyl)-1H-indol-3-yl]acetic acid;
methyl[5-methoxy-2-(4-methylpyridine-2-carbonyl)-1H-indol-3-yl]acetate;
[5-methoxy-2-(4-methylpyridine-2-carbonyl)-1H-indol-3-yl]acetic acid;
methyl[6-methoxy-2-(4-methylpyridine-2-carbonyl)-1H-indol-3-yl]acetate;
[6-methoxy-2-(4-methylpyridine-2-carbonyl)-1H-indol-3-yl]acetic acid;
methyl[5-ethyl-2-(4-methylpyridine-2-carbonyl)-1H-indol-3-yl]acetate;
[5-ethyl-2-(4-methylpyridine-2-carbonyl)-1H-indol-3-yl]acetic acid;
methyl[5-ethyl-2-(4-ethylpyridine-2-carbonyl)-1H-indol-3-yl]acetate;
[5-ethyl-2-(4-ethylpyridine-2-carbonyl)-1H-indol-3-yl]acetic acid;
methyl[6-ethyl-2-(4-methylpyridine-2-carbonyl)-1H-indol-3-yl]acetate;
[6-ethyl-2-(4-methylpyridine-2-carbonyl)-1H-indol-3-yl]acetic acid;
methyl[5-isopropyl-2-(4-methylpyridine-2-carbonyl)-1H-indol-3-yl]acetate;
[5-isopropyl-2-(4-methylpyridine-2-carbonyl)-1H-indol-3-yl]acetic acid;
methyl[2-(4-methylpyridine-2-carbonyl)-6-trifluoromethyl-1H-indol-3-yl]acetate;
[2-(4-methylpyridine-2-carbonyl)-6-trifluoromethyl-1H-indol-3-yl]acetic acid;
methyl[5-tert-butyl-2-(4-methylpyridine-2-carbonyl)-1H-indol-3-yl]acetate;
[5-tert-butyl-2-(4-methylpyridine-2-carbonyl)-1H-indol-3-yl]acetic acid;
methyl[2-(4-methylpyridine-2-carbonyl)-5-trifluoromethyl-1H-indol-3-yl]acetate;
[2-(4-methyl-2-pyridine-2-carbonyl)-5-trifluoromethyl-1H-indol-3-yl]acetic acid;
methyl[6-methyl-2-(4-methylpyridine-2-carbonyl)-1H-indol-3-yl]acetate;
[6-methyl-2-(4-methylpyridine-2-carbonyl)-1H-indol-3-yl]acetic acid;
methyl[2-(4-methylpyridine-2-carbonyl)-5-trifluoromethyl-1H-indol-3-yl]acetate;
[2-(4-methylpyridine-2-carbonyl)-5-trifluoromethyl-1H-indol-3-yl]acetic acid;
methyl[2-(4-ethylpyridine-2-carbonyl)-5-trifluoromethyl-1H-indol-3-yl]acetate;
[2-(4-ethylpyridine-2-carbonyl)-5-trifluoromethyl-1H-indol-3-yl]acetic acid;
methyl[2-(4-chlorobenzoyl)-6-methyl-1H-indol-3-yl]acetate;
[2-(4-chlorobenzoyl)-6-methyl-1H-indol-3-yl]acetic acid;
[2-(4-chlorobenzoyl)-5-methyl-1H-indol-3-yl]acetic acid;
methyl[2-(4-chlorobenzoyl)-5-trifluoromethyl-1H-indol-3-yl]acetate;
[2-(4-chlorobenzoyl)-5-trifluoromethyl-1H-indol-3-yl]acetic acid;
methyl[2-(4-chlorobenzoyl)-5-trifluoromethoxy-1H-indol-3-yl]acetate;
[2-(4-chlorobenzoyl)-5-trifluoromethoxy-1H-indol-3-yl]acetic acid;
methyl[6-chloro-2-(3-methoxybenzoyl)-1H-indol-3-yl]acetate;
[6-chloro-2-(3-methoxybenzoyl)-1H-indol-3-yl]acetic acid;
methyl[6-chloro-2-(4-trifluoromethoxybenzoyl)-1H-indol-3-yl]acetate;
[6-chloro-2-(4-trifluoromethoxybenzoyl)-1H-indol-3-yl]acetic acid;
methyl[5-chloro-2-(4-trifluoromethoxybenzoyl)-1H-indol-3-yl]acetate;
[5-chloro-2-(4-trifluoromethoxybenzoyl)-1H-indol-3-yl]acetic acid;
methyl[5-chloro-2-(4-methoxybenzoyl)-1H-indol-3-yl]acetate;
[5-chloro-2-(4-methoxybenzoyl)-1H-indol-3-yl]acetic acid;
methyl[6-chloro-2-[4-(2-furyl)benzoyl]-1H-indol-3-yl]acetate;
[6-chloro-2-[4-(2-furyl)benzoyl]-1H-indol-3-yl]acetic acid;
methyl[5-chloro-2-(isoquinoline-3-carbonyl)-1H-indol-3-yl]acetate;
[5-chloro-2-(isoquinoline-3-carbonyl)-1H-indol-3-yl]acetic acid;
methyl[6-chloro-2-(isoquinoline-3-carbonyl)-1H-indol-3-yl]acetate;
[6-chloro-2-(isoquinoline-3-carbonyl)-1H-indol-3-yl]acetic acid;
methyl[6-chloro-2-(5methylisoxazole-3-carbonyl)-1H-indol-3-yl]acetate;
[6-chloro-2-(5-methylisoxazole-3-carbonyl)-1H-indol-3-yl]acetic acid;
methyl[5-chloro-2-(5-methylthiazole-2-carbonyl)-1H-indol-3-yl]acetate;

[5-chloro-2-(5-methylthiazole-2-carbonyl)-1H-indol-3-yl]acetic acid;
methyl[6-chloro-2-(5-methylthiazole-2-carbonyl)-1H-indol-3-yl]acetate;
[6-chloro-2-(5-methylthiazole-2-carbonyl)-1H-indol-3-yl]acetic acid;
methyl[6-chloro-2-[3-methoxymethyl-2-furoyl]-1H-indol-3-yl]acetate;
[6-chloro-2-[3-methoxymethyl-2-furoyl]-1H-indol-3-yl]acetic acid;
[6-chloro-2-(5-methylimidazole-2-carbonyl)-1H-indol-3-yl]acetic acid;
methyl[5-chloro-2-(4-methylthiazole-2-carbonyl)-1H-indol-3-yl]acetate;
[5-chloro-2-(4-methylthiazole-2-carbonyl)-1H-indol-3-yl]acetic acid;
methyl[5-chloro-2-(2-methylimidazole-4-carbonyl)-1H-indol-3-yl]acetate;
[5-chloro-2-(2-methylimidazole-4-carbonyl)-1H-indol-3-yl]acetic acid;
methyl[6-chloro-2-(4-methylthiazole-2-carbonyl)-1H-indol-3-yl]acetate;
[6-chloro-2-(4-methylthiazole-2-carbonyl)-1H-indol-3-yl]acetic acid;
[6-chloro-2-(4-chlorobenzoyl)-5-fluoro-1H-indol-3-yl]acetic acid;
methyl[6-chloro-2-[4-(1-hydroxyethyl)pyridine-2-carbonyl]-1H-indol-3-yl]acetate;
[6-chloro-2-[4-(1-hydroxyethyl)pyridine-2-carbonyl]-1H-indol-3-yl]acetic acid;
[6-chloro-2-(4-ethyl-3-fluoropyridine-2-carbonyl)-1H-indol-3-yl]acetic acid;
methyl[6-chloro-2-(4-chlorobenzoyl)-5-fluoro-1H-indol-3-yl]acetate, and a salt thereof.

Preferred individual compounds of this invention are:
ethyl(2-benzoyl-6-chloro-1H-indol-3-yl)acetate;
(2-benzoyl-6-chloro-1H-indol-3-yl)acetic acid;
[6-chloro-2-(3-methylbenzoyl)-1H-indol-3-yl]acetic acid;
[6-chloro-2-(4-methylbenzoyl)-1H-indol-3-yl]acetic acid;
[6-chloro-2-(3-chlorobenzoyl)-1H-indol-3-yl]acetic acid;
methyl[6-chloro-2-(4-chlorobenzoyl)-1H-indol-3-yl]acetate;
[6-chloro-2-(4-chlorobenzoyl)-1H-indol-3-yl]acetic acid;
[6-chloro-2-(3-fluorobenzoyl)-1H-indol-3-yl]acetic acid;
[6-chloro-2-(4-fluorobenzoyl)-1H-indol-3-yl]acetic acid;
[2-(3-bromobenzoyl)-6-chloro-1H-indol-3-yl]acetic acid;
[2-(4-bromobenzoyl)-6-chloro-1H-indol-3-yl]acetic acid;
[6-chloro-2-(3-trifluoromethylbenzoyl)-1H-indol-3-yl]acetic acid;
[6-chloro-2-(4-trifluoromethylbenzoyl)-1H-indol-3-yl]acetic acid;
(2-benzoyl-4-chloro-1H-indol-3-yl)acetic acid;
[5-chloro-2-(3-methylbenzoyl)-1H-indol-3-yl]acetic acid;
[5-chloro-2-(4-chlorobenzoyl)-1H-indol-3-yl]acetic acid;
[5-chloro-2-(3-chlorobenzoyl)-1H-indol-3-yl]acetic acid;
[2-(4-chlorobenzoyl)-5-fluoro-1H-indol-3-yl]acetic acid;
[2-(3-chlorobenzoyl)-5-fluoro-1H-indol-3-yl]acetic acid;
(2-benzoyl-4,5-dichloro-1H-indol-3-yl)acetic acid;
(2-benzoyl-4,6-dichloro-1H-indol-3-yl)acetic acid;
(2-benzoyl-5,6-dichloro-1H-indol-3-yl)acetic acid;
dl-2-(2-benzoyl-6-chloro-1H-indol-3-yl)propanoic acid;
less polar antipode, 2-(2-benzoyl-6-chloro-1H-indol-3-yl)propanoic acid;
more polar antipode, 2-(2-benzoyl-6-chloro-1H-indol-3-yl)propanoic acid;
[6-chloro-2-(4-methylpyridine-2-carbonyl)-1H-indol-3-yl]acetic acid;
[6-chloro-2-(5-methylpyridine-2-carbonyl)-1H-indol-3-yl]acetic acid;
methyl[6-chloro-2-(4-chloropyridine-2-carbonyl)-1H-indol-3-yl]acetate;
[6-chloro-2-(4-chloropyridine-2-carbonyl)-1H-indol-3-yl]acetic acid;
[6-chloro-2-(pyridine-2-carbonyl)-1H-indol-3-yl]acetic acid;
[5-chloro-2-(4-methylpyridine-2-carbonyl)-1H-indol-3-yl]acetic acid;
methyl[5-chloro-2-(6-methylpyridine-2-carbonyl)-1H-indol-3-yl]acetate;
[5-chloro-2-(6-methylpyridine-2-carbonyl)-1H-indol-3-yl]acetic acid;
[6-chloro-2-(1-methylimidazole-2-carbonyl)-1H-indol-3-yl]acetic acid;
methyl[5-chloro-2-(thiazole-2-carbonyl)-1H-indol-3-yl]acetate;
[5-chloro-2-(thiazole-2-carbonyl)-1H-indol-3-yl]acetic acid;
methyl(2-benzoyl-6-chloro-1H-indol-3-yl)acetate;
[6-chloro-2-(2-furylcarbonyl)-1H-indol-3-yl]acetic acid;
[6-chloro-2-(cyclohexanecarbonyl)-1H-indol-3-yl]acetic acid;
methyl[6-chloro-2-(4-methoxybenzoyl)-1H-indol-3-yl]acetate;
[6-chloro-2-(4-methoxybenzoyl)-1H-indol-3-yl]acetic acid;
methyl[6-chloro-2-(4-ethylpyridine-2-carbonyl)-1H-indol-3-yl]acetate;
[6-chloro-2-(4-ethylpyridine-2-carbonyl)-1H-indol-3-yl]acetic acid;
[5-chloro-2-(4-ethylpyridine-2-carbonyl)-1H-indol-3-yl]acetic acid;
[6-chloro-2-(4-isopropylpyridine-2-carbonyl)-1H-indol-3-yl]acetic acid;
[6-chloro-2-(4-propylpyridine-2-carbonyl)-1H-indol-3-yl]acetic acid;
[5-chloro-2-(4-propylpyridine-2-carbonyl)-1H-indol-3-yl]acetic acid;
[2-(4-tert-butylpyridine-2-carbonyl)-6-chloro-1H-indol-3-yl]acetic acid;
[6-chloro-2-(3-methylpyridine-2-carbonyl)-1H-indol-3-yl]acetic acid;
[6-chloro-2-(6-methylpyridine-2-carbonyl)-1H-indol-3-yl]acetic acid;
[5-chloro-2-(5-methylpyridine-2-carbonyl)-1H-indol-3-yl]acetic acid;
[6-chloro-2-[5-(trifluoromethyl)pyridine-2-carbonyl]-1H-indol-3-yl]acetic acid;
[5-chloro-2-[5-(trifluoromethyl)pyridine-2-carbonyl]-1H-indol-3-yl]acetic acid;

[5-chloro-2-(5-chloropyridine-2-carbonyl)-1H-indol-3-yl]acetic acid;
[6-chloro-2-(5-chloropyridine-2-carbonyl)-1H-indol-3-yl]acetic acid;
[5-chloro-2-(4-chloropyridine-2-carbonyl)-1H-indol-3-yl]acetic acid;
[5-chloro-2-[4-(hydroxymethyl)pyridine-2-carbonyl]-1H-indol-3-yl]acetic acid;
[5-chloro-2-(4,5-dimethylpyridine-2-carbonyl)-1H-indol-3-yl]acetic acid;
[6-chloro-2-(4,5-dimethylpyridine-2-carbonyl)-1H-indol-3-yl]acetic acid;
[6-chloro-2-(4-methoxypyridine-2-carbonyl)-1H-indol-3-yl]acetic acid;
[5-chloro-2-(4-methoxypyridine-2-carbonyl)-1H-indol-3-yl]acetic acid;
[6-chloro-2-(3,5-dimethylpyridine-2-carbonyl)-1H-indol-3-yl]acetic acid;
[5-chloro-2-(4-ethyl-3-fluoropyridine-2-carbonyl)-1H-indol-3-yl]acetic acid;
[6-chloro-2-(3-ethoxy-4-ethylpyridine-2-carbonyl)-1H-indol-3-yl]acetic acid;
[6-chloro-2-(3-chloro-4-ethylpyridine-2-carbonyl)-1H-indol-3-yl]acetic acid;
[5-chloro-2-(3-chloro-4-ethylpyridine-2-carbonyl)-1H-indol-3-yl]acetic acid;
[5-chloro-2-(4,6-dimethylpyridine-2-carbonyl)-1H-indol-3-yl]acetic acid;
[6-chloro-2-(4,6-dimethylpyridine-2-carbonyl)-1H-indol-3-yl]acetic acid;
[5,6-dichloro-2-(4-methylpyridine-2-carbonyl)-1H-indol-3-yl]acetic acid;
[5-methyl-2-(4-methylpyridine-2-carbonyl)-1H-indol-3-yl]acetic acid;
[5-fluoro-2-(4-methylpyridine-2-carbonyl)-1H-indol-3-yl]acetic acid;
[5-methoxy-2-(4-methylpyridine-2-carbonyl)-1H-indol-3-yl]acetic acid;
[6-methoxy-2-(4-methylpyridine-2-carbonyl)-1H-indol-3-yl]acetic acid;
[5-ethyl-2-(4-methylpyridine-2-carbonyl)-1H-indol-3-yl]acetic acid;
[5-ethyl-2-(4-ethylpyridine-2-carbonyl)-1H-indol-3-yl]acetic acid;
[6-ethyl-2-(4-methylpyridine-2-carbonyl)-1H-indol-3-yl]acetic acid;
[5-isopropyl-2-(4-methylpyridine-2-carbonyl)-1H-indol-3-yl]acetic acid;
[2-(4-methylpyridine-2-carbonyl)-6-trifluoromethyl-1H-indol-3-yl]acetic acid;
[5-tert-butyl-2-(4-methylpyridine-2-carbonyl)-1H-indol-3-yl]acetic acid;
[2-(4-methyl-2-pyridine-2-carbonyl)-5-trifluoromethoxy-1H-indol-3-yl]acetic acid;
[6-methyl-2-(4-methylpyridine-2-carbonyl)-1H-indol-3-yl]acetic acid;
[2-(4-methylpyridine-2-carbonyl)-5-trifluoromethyl-1H-indol-3-yl]acetic acid;
[2-(4-ethylpyridine-2-carbonyl)-5-trifluoromethyl-1H-indol-3-yl]acetic acid;
[2-(4-chlorobenzoyl)-6-methyl-1H-indol-3-yl]acetic acid;
[2-(4-chlorobenzoyl)-5-methyl-1H-indol-3-yl]acetic acid;
[2-(4-chlorobenzoyl)-5-trifluoromethyl-1H-indol-3-yl]acetic acid;
[2-(4-chlorobenzoyl)-5-trifluoromethoxy-1H-indol-3-yl]acetic acid;
[6-chloro-2-(3-methoxybenzoyl)-1H-indol-3-yl]acetic acid;
[6-chloro-2-(4-trifluoromethoxybenzoyl)-1H-indol-3-yl]acetic acid;
[5-chloro-2-(4-trifluoromethoxybenzoyl)-1H-indol-3-yl]acetic acid;
[5-chloro-2-(4-methoxybenzoyl)-1H-indol-3-yl]acetic acid;
[6-chloro-2-[4-(2-furyl)benzoyl]-1H-indol-3-yl]acetic acid;
[5-chloro-2-(isoquinoline-3-carbonyl)-1H-indol-3-yl]acetic acid;
[6-chloro-2-(isoquinoline-3-carbonyl)-1H-indol-3-yl]acetic acid;
[6-chloro-2-(5-methylisoxazole-3-carbonyl)-1H-indol-3-yl]acetic acid;
[5-chloro-2-(5-methylthiazole-2-carbonyl)-1H-indol-3-yl]acetic acid;
[6-chloro-2-(5-methylthiazole-2-carbonyl)-1H-indol-3-yl]acetic acid;
[6-chloro-2-[3-methoxymethyl-2-furoyl]-1H-indol-3-yl]acetic acid;
[6-chloro-2-(1-methylimidazole-2-carbonyl)-1H-indol-3-yl]acetic acid;
[5-chloro-2-(4-methylthiazole-2-carbonyl)-1H-indol-3-yl]acetic acid;
[5-chloro-2-(2-methylimidazole-4-carbonyl)-1H-indol-3-yl]acetic acid;
[6-chloro-2-(4-methylthiazole-2-carbonyl)-1H-indol-3-yl]acetic acid;
[6-chloro-2-(4-chlorobenzoyl)-5-fluoro-1H-indol-3-yl]acetic acid;
methyl[6-chloro-2-[4-(1-hydroxyethyl)pyridine-2-carbonyl]-1H-indol-3-yl]acetate;
[6-chloro-2-[4-(1-hydroxyethyl)pyridine-2-carbonyl]-1H-indol-3-yl]acetic acid;
2-{6-chloro-2-[(4-ethyl-3-fluoro-2-pyridinyl)carbonyl]-1H-indol-3-yl}acetic acid;
methyl[6-chloro-2-(4-chlorobenzoyl)-5-fluoro-1H-indol-3-yl]acetate, and a salt thereof.

Preferred individual compounds of this invention are:
(2-benzoyl-6-chloro-1H-indol-3-yl)acetic acid;
[6-chloro-2-(4-methylbenzoyl)-1H-indol-3-yl]acetic acid;
[6-chloro-2-(3-chlorobenzoyl)-1H-indol-3-yl]acetic acid;
methyl[6-chloro-2-(4-chlorobenzoyl)-1H-indol-3-yl]acetate;
[6-chloro-2-(4-chlorobenzoyl)-1H-indol-3-yl]acetic acid;
[6-chloro-2-(3-fluorobenzoyl)-1H-indol-3-yl]acetic acid;
[6-chloro-2-(4-fluorobenzoyl)-1H-indol-3-yl]acetic acid;
[2-(3-bromobenzoyl)-6-chloro-1H-indol-3-yl]acetic acid;
[2-(4-bromobenzoyl)-6-chloro-1H-indol-3-yl]acetic acid;
[6-chloro-2-(4-trifluoromethylbenzoyl)-1H-indol-3-yl]acetic acid;
[5-chloro-2-(3-methylbenzoyl)-1H-indol-3-yl]acetic acid;

[5-chloro-2-(4-chlorobenzoyl)-1H-indol-3-yl]acetic acid;
[5-chloro-2-(3-chlorobenzoyl)-1H-indol-3-yl]acetic acid;
[2-(4-chlorobenzoyl)-5-fluoro-1H-indol-3-yl]acetic acid;
[2-(3-chlorobenzoyl)-5-fluoro-1H-indol-3-yl]acetic acid;
(2-benzoyl-4,5-dichloro-1H-indol-3-yl)acetic acid;
(2-benzoyl-4,6-dichloro-1H-indol-3-yl)acetic acid;
(2-benzoyl-5,6-dichloro-1H-indol-3-yl)acetic acid;
[6-chloro-2-(4-methylpyridine-2-carbonyl)-1H-indol-3-yl]acetic acid;
[6-chloro-2-(5-methylpyridine-2-carbonyl)-1H-indol-3-yl]acetic acid;
methyl[6-chloro-2-(4-chloropyridine-2-carbonyl)-1H-indol-3-yl]acetate;
[6-chloro-2-(4-chloropyridine-2-carbonyl)-1H-indol-3-yl]acetic acid;
[6-chloro-2-(pyridine-2-carbonyl)-1H-indol-3-yl]acetic acid;
[5-chloro-2-(4-methylpyridine-2-carbonyl)-1H-indol-3-yl]acetic acid;
methyl[5-chloro-2-(6-methylpyridine-2-carbonyl)-1H-indol-3-yl]acetate;
[5-chloro-2-(6-methylpyridine-2-carbonyl)-1H-indol-3-yl]acetic acid;
methyl[5-chloro-2-(thiazole-2-carbonyl)-1H-indol-3-yl]acetate;
[5-chloro-2-(thiazole-2-carbonyl)-1H-indol-3-yl]acetic acid;
methyl(2-benzoyl-6-chloro-1H-indol-3-yl)acetate;
[6-chloro-2-(cyclohexanecarbonyl)-1H-indol-3-yl]acetic acid;
methyl[6-chloro-2-(4-methoxybenzoyl)-1H-indol-3-yl]acetate;
[6-chloro-2-(4-methoxybenzoyl)-1H-indol-3-yl]acetic acid;
methyl[6-chloro-2-(4-ethylpyridine-2-carbonyl)-1H-indol-3-yl]acetate;
[6-chloro-2-(4-ethylpyridine-2-carbonyl)-1H-indol-3-yl]acetic acid;
methyl[5-chloro-2-(4-ethylpyridine-2-carbonyl)-1H-indol-3-yl]acetate;
[5-chloro-2-(4-ethylpyridine-2-carbonyl)-1H-indol-3-yl]acetic acid;
methyl[6-chloro-2-(4-isopropylpyridine-2-carbonyl)-1H-indol-3-yl]acetate;
[6-chloro-2-(4-isopropylpyridine-2-carbonyl)-1H-indol-3-yl]acetic acid;
methyl[6-chloro-2-(4-propylpyridine-2-carbonyl)-1H-indol-3-yl]acetate;
[6-chloro-2-(4-propylpyridine-2-carbonyl)-1H-indol-3-yl]acetic acid;
methyl[6-chloro-2-(6-methylpyridine-2-carbonyl)-1H-indol-3-yl]acetate;
[6-chloro-2-(6-methylpyridine-2-carbonyl)-1H-indol-3-yl]acetic acid;
methyl[5-chloro-2-(5-methylpyridine-2-carbonyl)-1H-indol-3-yl]acetate;
[5-chloro-2-(5-methylpyridine-2-carbonyl)-1H-indol-3-yl]acetic acid;
methyl[6-chloro-2-[5-(trifluoromethyl)pyridine-2-carbonyl]-1H-indol-3-yl]acetate;
[6-chloro-2-[5-(trifluoromethyl)pyridine-2-carbonyl]-1H-indol-3-yl]acetic acid;
methyl[5-chloro-2-[5-(trifluoromethyl)pyridine-2-carbonyl]-1H-indol-3-yl]acetate;
[5-chloro-2-[5-(trifluoromethyl)pyridine-2-carbonyl]-1H-indol-3-yl]acetic acid;
methyl[5-chloro-2-(5-chloropyridine-2-carbonyl)-1H-indol-3-yl]acetate;
[5-chloro-2-(5-chloropyridine-2-carbonyl)-1H-indol-3-yl]acetic acid;
methyl[6-chloro-2-(5-chloropyridine-2-carbonyl)-1H-indol-3-yl]acetate;
[6-chloro-2-(5-chloropyridine-2-carbonyl)-1H-indol-3-yl]acetic acid;
methyl[5-chloro-2-(4-chloropyridine-2-carbonyl)-1H-indol-3-yl]acetate;
[5-chloro-2-(4-chloropyridine-2-carbonyl)-1H-indol-3-yl]acetic acid;
methyl[5-chloro-2-(4,5-dimethylpyridine-2-carbonyl)-1H-indol-3-yl]acetate;
[5-chloro-2-(4,5-dimethylpyridine-2-carbonyl)-1H-indol-3-yl]acetic acid;
methyl[6-chloro-2-(4,5-dimethylpyridine-2-carbonyl)-1H-indol-3-yl)acetate;
[6-chloro-2-(4,5-dimethylpyridine-2-carbonyl)-1H-indol-3-yl]acetic acid;
methyl[6-chloro-2-(4-methoxypyridine-2-carbonyl)-1H-indol-3-yl]acetate;
[6-chloro-2-(4-methoxypyridine-2-carbonyl)-1H-indol-3-yl]acetic acid;
methyl[5-chloro-2-(4-ethyl-3-fluoropyridine-2-carbonyl)-1H-indol-3-yl]acetate;
[5-chloro-2-(4-ethyl-3-fluoropyridine-2-carbonyl)-1H-indol-3-y ]acetic acid;
methyl[6-chloro-2-(4-ethyl-3-fluoropyridine-2-carbonyl)-1H-indol-3-yl]acetate;
[6-chloro-2-(3-ethoxy-4-ethylpyridine-2-carbonyl)-1H-indol-3-yl]acetic acid;
methyl[6-chloro-2-(3-chloro-4-ethylpyridine-2-carbonyl)-1H-indol-3-yl]acetate;
[6-chloro-2-(3-chloro-4-ethylpyridine-2-carbonyl)-1H-indol-3-yl]acetic acid;
methyl[5-chloro-2-(4,6-dimethylpyridine-2-carbonyl)-1H-indol-3-yl]acetate;
[5-chloro-2-(4,6-dimethylpyridine-2-carbonyl)-1H-indol-3-yl]acetic acid;
methyl[6-chloro-2-(4,6-dimethylpyridine-2-carbonyl)-1H-indol-3-yl]acetate;
[6-chloro-2-(4,6-dimethylpyridine-2-carbonyl)-1H-indol-3-yl]acetic acid;
methyl[5,6-dichloro-2-(4-methylpyridine-2-carbonyl)-1H-indol-3-yl]acetate;
[5,6-dichloro-2-(4-methylpyridine-2-carbonyl)-1H-indol-3-yl]acetic acid;
methyl[5-methyl-2-(4-methylpyridine-2-carbonyl)-1H-indol-3-yl]acetate;
[5-methyl-2-(4-methylpyridine-2-carbonyl)-1H-indol-3-yl]acetic acid;
methyl[5-fluoro-2-(4-methylpyridine-2-carbonyl)-1H-indol-3-yl]acetate;
[5-fluoro-2-(4-methylpyridine-2-carbonyl)-1H-indol-3-yl]acetic acid;
methyl[5-ethyl-2-(4-methylpyridine-2-carbonyl)-1H-indol-3-yl]acetate;

[5-ethyl-2-(4-methylpyridine-2-carbonyl)-1H-indol-3-yl] acetic acid;
methyl[5-isopropyl-2-(4-methylpyridine-2-carbonyl)-1H-indol-3-yl]acetate;
[5-isopropyl-2-(4-methylpyridine-2-carbonyl)-1H-indol-3-yl]acetic acid;
methyl[2-(4-methylpyridine-2-carbonyl)-6-trifluoromethyl-1H-indol-3-yl]acetate;
[2-(4-methylpyridine-2-carbonyl)-6-trifluoromethyl-1H-indol-3-yl]acetic acid;
methyl[5-tert-butyl-2-(4-methylpyridine-2-carbonyl)-1H-indol-3-yl]acetate;
[5-tert-butyl-2-(4-methylpyridine-2-carbonyl)-1H-indol-3-yl]acetic acid;
methyl[2-(4-methylpyridine-2-carbonyl)-5-trifluoromethoxy-1H-indol-3-yl]acetate;
[2-(4-methyl-2-pyridine-2-carbonyl)-5-trifluoromethoxy-1H-indol-3-yl]acetic acid;
methyl[6-methyl-2-(4-methylpyridine-2-carbonyl)-1H-indol-3-yl]acetate;
[6-methyl-2-(4-methylpyridine-2-carbonyl)-1H-indol-3-yl]acetic acid;
methyl[2-(4-methylpyridine-2-carbonyl)-5-trifluoromethyl-1H-indol-3-yl]acetate;
[2-(4-methylpyridine-2-carbonyl)-5-trifluoromethyl-1H-indol-3-yl]acetic acid;
methyl[2-(4-ethylpyridine-2-carbonyl)-5-trifluoromethyl-1H-indol-3-yl]a acetate;
[2-(4-ethylpyridine-2-carbonyl)-5-trifluoromethyl-1H-indol-3-yl]acetic acid;
[2-(4-chlorobenzoyl)-5-methyl-1H-indol-3-yl]acetic acid;
methyl[2-(4-chlorobenzoyl)-5-trifluoromethyl-1H-indol-3-yl]acetate;
[2-(4-chlorobenzoyl)-5-trifluoromethy-1H-indol-3-yl] acetic acid;
methyl[6-chloro-2-(4-trifluoromethoxybenzoyl)-1H-indol-3-yl]acetate;
[6-chloro-2-(4-trifluoromethoxybenzoyl)-1H-indol-3-yl]acetic acid;
methyl[5-chloro-2-(4-trifluoromethoxybenzoyl)-1H-indol-3-yl]acetate;
[5-chloro-2-(4-trifluoromethoxybenzoyl)-1H-indol-3-yl]acetic acid;
methyl[5-chloro-2-(4-methoxybenzoyl)-1H-indol-3-yl]acetate;
[5-chloro-2-(4-methoxybenzoyl)-1H-indol-3-yl]acetic acid;
methyl[6-chloro-2-[4-(2-furyl)benzoyl]-1H-indol-3-yl]acetate;
[6-chloro-2-[4-(2-furyl)benzoyl]-1H-indol-3-yl]acetic acid;
methyl[5-chloro-2-(isoquinoline-3-carbonyl)-1H-indol-3-yl]acetate;
[5-chloro-2-(isoquinoline-3-carbonyl)-1H-indol-3-yl]acetic acid;
methyl[6-chloro-2-(isoquinoline-3-carbonyl)-1H-indol-3-yl]acetate;
[6-chloro-2-(isoquinoline-3-carbonyl)-1H-indol-3-yl]acetic acid;
methyl[5-chloro-2-(5-methylthiazole-2-carbonyl)-1H-indol-3-yl]acetate;
[5-chloro-2-(5-methylthiazole-2-carbonyl)-1H-indol-3-yl]acetic acid;
methyl[6-chloro-2-(5-methylthiazole-2-carbonyl)-1H-indol-3-yl]acetate;
[6-chloro-2-(5-methylthiazole-2-carbonyl)-1H-indol-3-yl]acetic acid;
methyl[6-chloro-2-[3-methoxymethyl-2-furoyl]-1H-indol-3-yl]acetate;
[6-chloro-2-[3-methoxymethyl-2-furoyl]-1H-indol-3-yl] acetic acid;
methyl[5-chloro-2-(4-methylthiazole-2-carbonyl)-1H-indol-3-yl]acetate;
[5-chloro-2-(4-methylthiazole-2-carbonyl)-1H-indol-3-yl]acetic acid;
methyl[5-chloro-2-(2-methylimidazole-4-carbonyl)-1H-indol-3-yl]acetate;
[5-chloro-2-(2-methylimidazole-4-carbonyl)-1H-indol-3-yl]acetic acid;
methyl[6-chloro-2-(4-methylthiazole-2-carbonyl)-1H-indol-3-yl]acetate;
[6-chloro-2-(4-methylthiazole-2-carbonyl)-1H-indol-3-yl]acetic acid;
[6-chloro-2-(4-chlorobenzoyl)-5-fluoro-1H-indol-3-yl] acetic acid;
[6-chloro-2-(4-ethyl-3-fluoropyridine-2-carbonyl)-1H-indol-3-yl]acetic acid;
methyl[6-chloro-2-(4-chlorobenzoyl)-5-fluoro-1H-indol-3-yl]acetate, and a salt thereof.

Preferred individual compounds of this invention are:
(2-benzoyl-6-chloro-1H-indol-3-yl)acetic acid;
[6-chloro-2-(4-methylbenzoyl)-1H-indol-3-yl]acetic acid;
[6-chloro-2-(3-chlorobenzoyl)-1H-indol-3-yl]acetic acid;
methyl[6-chloro-2-(4-chlorobenzoyl)-1H-indol-3-yl]acetate;
[6-chloro-2-(4-chlorobenzoyl)-1H-indol-3-yl]acetic acid;
[6-chloro-2-(3-fluorobenzoyl)-1H-indol-3-yl]acetic acid;
[6-chloro-2-(4-fluorobenzoyl)-1H-indol-3-yl]acetic acid;
[2-(3-bromobenzoyl)-6-chloro-1H-indol-3-yl]acetic acid;
[2-(4-bromobenzoyl)-6-chloro-1H-indol-3-yl]acetic acid;
[62-chloro-2-(4-trifluoromethylbenzoyl)-1H-indol-3-yl] acetic acid;
[5-chloro-2-(3-methylbenzoyl)-1H-indol-3-yl]acetic acid;
[5-chloro-2-(4-chlorobenzoyl)-1H-indol-3-yl]acetic acid;
[5-chloro-2-(3-chlorobenzoyl)-1H-indol-3-yl]acetic acid;
[2-(4-chlorobenzoyl)-5-fluoro-1H-indol-3-yl]acetic acid;
[2-(3-chlorobenzoyl)-5-fluoro-1H-indol-3-yl]acetic acid;
(2-benzoyl-4,5-dichloro-1H-indol-3-yl)acetic acid;
(2-benzoyl-4,6-dichloro-1H-indol-3-yl)acetic acid;
(2-benzoyl-5,6-dichloro-1H-indol-3-yl)acetic acid;
[6-chloro-2-(4-methylpyridine-2-carbonyl)-1H-indol-3-yl]acetic acid;
[6-chloro-2-(5-methylpyridine-2-carbonyl)-1H-indol-3-yl]acetic acid;
methyl[6-chloro-2-(4-chloropyridine-2-carbonyl)-1H-indol-3-yl]acetate;
[6-chloro-2-(4-chloropyridine-2-carbonyl)-1H-indol-3-yl]acetic acid;
[6-chloro-2-(pyridine-2-carbonyl)-1H-indol-3-yl]acetic acid;

[5-chloro-2-(4-methylpyridine-2-carbonyl)-1H-indol-3-yl]acetic acid;
methyl[5-chloro-2-(6-methylpyridine-2-carbonyl)-1H-indol-3-yl]acetate;
[5-chloro-2-(6-methylpyridine-2-carbonyl)-1H-indol-3-yl]acetic acid;
methyl[5-chloro-2-(thiazole-2-carbonyl)-1H-indol-3-yl]acetate;
[5-chloro-2-(thiazole-2-carbonyl)-1H-indol-3-yl]acetic acid;
methyl(2-benzoyl-6-chloro-1H-indol-3-yl)acetate;
[6-chloro-2-(cyclohexanecarbonyl)-1H-indol-3-yl]acetic acid;
methyl[6-chloro-2-(4-methoxybenzoyl)-1H-indol-3-yl]acetate;
[6-chloro-2-(4-methoxybenzoyl)-1H-indol-3-yl]acetic acid;
methyl[6-chloro-2-(4-ethylpyridine-2-carbonyl)-1H-indol-3-yl]acetate;
[6-chloro-2-(4-ethylpyridine-2-carbonyl)-1H-indol-3-yl]acetic acid;
[5-chloro-2-(4-ethylpyridine-2-carbonyl)-1H-indol-3-yl]acetic acid;
[6-chloro-2-(4-isopropylpyridine-2-carbonyl)-1H-indol-3-yl]acetic acid;
[6-chloro-2-(4-propylpyridine-2-carbonyl)-1H-indol-3-yl]acetic acid;
[6-chloro-2-(6-methylpyridine-2-carbonyl)-1H-indol-3-yl]acetic acid;
[5-chloro-2-(5-methylpyridine-2-carbonyl)-1H-indol-3-yl]acetic acid;
[6-chloro-2-[5-(trifluoromethyl)pyridine-2-carbonyl]-1H-indol-3-yl]acetic acid;
[5-chloro-2-[5-(trifluoromethyl)pyridine-2-carbonyl]-1H-indol-3-yl]acetic acid;
[5-chloro-2-(5-chloropyridine-2-carbonyl)-1H-indol-3-yl]acetic acid;
[6-chloro-2-(5-chloropyridine-2-carbonyl)-1H-indol-3-yl]acetic acid;
[5-chloro-2-(4-chloropyridine-2-carbonyl)-1H-indol-3-yl]acetic acid;
[5-chloro-2-(4,5-dimethylpyridine-2-carbonyl)-1H-indol-3-yl]acetic acid;
[6-chloro-2-(4,5-dimethylpyridine-2-carbonyl)-1H-indol-3-yl]acetic acid;
[6-chloro-2-(4-methoxypyridine-2-carbonyl)-1H-indol-3-yl]acetic acid;
[5-chloro-2-(4-ethyl-3-fluoropyridine-2-carbonyl)-1H-indol-3-yl]acetic acid;
[6-chloro-2-(3-ethoxy-4-ethylpyridine-2-carbonyl)-1H-indol-3-yl]acetic acid;
[6-chloro-2-(3-chloro-4-ethylpyridine-2-carbonyl)-1H-indol-3-yl]acetic acid;
[5-chloro-2-(4,6-dimethylpyridine-2-carbonyl)-1H-indol-3-yl]acetic acid;
[6-chloro-2-(4,6-dimethylpyridine-2-carbonyl)-1H-indol-3-yl]acetic acid;
[5,6-dichloro-2-(4-methylpyridine-2-carbonyl)-1H-indol-3-yl]acetic acid;
[5-methyl-2-(4-methylpyridine-2-carbonyl)-1H-indol-3-yl]acetic acid;
[5-fluoro-2-(4-methylpyridine-2-carbonyl)-1H-indol-3-yl]acetic acid;
[5-ethyl-2-(4-methylpyridine-2-carbonyl)-1H-indol-3-yl]acetic acid;
[5-isopropyl-2-(4-methylpyridine-2-carbonyl)-1H-indol-3-yl]acetic acid;
[2-(4-methylpyridine-2-carbonyl)-6-trifluoromethyl-1H-indol-3-yl]acetic acid;
[5-tert-butyl-2-(4-methylpyridine-2-carbonyl)-1H-indol-3-yl]acetic acid;
[2-(4-methyl-2-pyridine-2-carbonyl)-5-trifluoromethoxy-1H-indol-3-yl]acetic acid;
[6-methyl-2-(4-methylpyridine-2-carbonyl)-1H-indol-3-yl]acetic acid;
[2-(4-methylpyridine-2-carbonyl)-5-trifluoromethyl-1H-indol-3-yl]acetic acid;
[2-(4-ethylpyridine-2-carbonyl)-5-trifluoromethyl-1H-indol-3-yl]acetic acid;
[2-(4-chlorobenzoyl)-5-trifluoromethyl-1H-indol-3-yl]acetic acid;
[6-chloro-2-(4-trifluoromethoxybenzoyl)-1H-indol-3-yl]acetic acid;
[5-chloro-2-(4-trifluoromethoxybenzoyl)-1H-indol-3-yl]acetic acid;
[5-chloro-2-(4-methoxybenzoyl)-1H-indol-3-yl]acetic acid;
[6-chloro-2-[4-(2-furyl)benzoyl]-1H-indol-3-yl]acetic acid;
[5-chloro-2-(isoquinoline-3-carbonyl)-1H-indol-3-yl]acetic acid;
[6-chloro-2-(isoquinoline-3-carbonyl)-1H-indol-3-yl]acetic acid;
methyl[5-chloro-2-(5-methylthiazole-2-carbonyl)-1H-indol-3-yl]acetate;
[6-chloro-2-(5-methylthiazole-2-carbonyl)-1H-indol-3-yl]acetic acid;
[6-chloro-2-[3-methoxymethyl-2-furoyl]-1H-indol-3-yl]acetic acid;
[5-chloro-2-(4-methylthiazole-2-carbonyl)-1H-indol-3-yl]acetic acid;
[5-chloro-2-(2-methylimidazole-4-carbonyl)-1H-indol-3-yl]acetic acid;
[6-chloro-2-(4-methylthiazole-2-carbonyl)-1H-indol-3-yl]acetic acid;
[6-chloro-2-(4-chlorobenzoyl)-5-fluoro-1H-indol-3-yl]acetic acid;
[6-chloro-2-(4-ethyl-3-fluoropyridine-2-carbonyl]-1H-indol-3-yl)acetic acid;
methyl[6-chloro-2-(4-chlorobenzoyl)-5-fluoro-1H-indol-3-yl]acetate;
[6-chloro-5-fluoro-2-(4-methylpyridine-2-carbonyl)-1H-indol-3-yl]acetic acid;
methyl[6-chloro-2-[4-(1-hydroxyethyl)pyridine-2-carbonyl]-1H-indol-3-yl]acetate;
[6-chloro-2-(5-chloropyridine-2-carbonyl)-1H-indol-3-yl]acetic acid, and a salt thereof.

Preferred individual compounds of this invention are:
(2-benzoyl-6-chloro-1H-indol-3-yl)acetic acid;
[6-chloro-2-(3-chlorobenzoyl)-1H-indol-3-yl]acetic acid;
[6-chloro-2-(4-chlorobenzoyl)-1H-indol-3-yl]acetic acid;
[5-chloro-2-(4-chlorobenzoyl)-1H-indol-3-yl]acetic acid;

[5-chloro-2-(3-chlorobenzoyl)-1H-indol-3-yl]acetic acid;
[2-(4-chlorobenzoyl)-5-fluoro-1H-indol-3-yl]acetic acid;
(2-benzoyl-5,6-dichloro-1H-indol-3-yl)acetic acid;
[6-chloro-2-(4-methylpyridine-2-carbonyl)-1H-indol-3-yl]acetic acid;
[6-chloro-2-(5-methylpyridine-2-carbonyl)-1H-indol-3-yl]acetic acid;
methyl[6-chloro-2-(4-chloropyridine-2-carbonyl)-1H-indol-3-yl]acetate;
[6-chloro-2-(4-chloropyridine-2-carbonyl)-1H-indol-3-yl]acetic acid;
[6-chloro-2-(pyridine-2-carbonyl)-1H-indol-3-yl]acetic acid;
[5-chloro-2-(4methylpyridine-2-carbonyl)-1H-indol-3-yl]acetic acid;
[5-chloro-2-(4-ethylpyridine-2-carbonyl)-1H-indol-3-yl]acetic acid;
methyl[5-chloro-2-(4-ethylpyridine-2-carbonyl)-1H-indol-3-yl]acetate;
[5-chloro-2-(4-ethylpyridine-2-carbonyl)-1H-indol-3-yl]acetic acid;
methyl[6-chloro-2-(4-isopropylpyridine-2-carbonyl)-1H-indol-3-yl]acetate;
[6-chloro-2-(4-isopropylpyridine-2-carbonyl)-1H-indol-3-yl]acetic acid;
methyl[6-chloro-2-(4-propylpyridine-2-carbonyl)-1H-indol-3-yl]acetate;
[6-chloro-2-(4-propylpyridine-2-carbonyl)-1H-indol-3-yl]acetic acid;
methyl[5-methyl-2-(4-methylpyridine-2-carbonyl)-1H-indol-3-yl]acetate;
[5-methyl-2-(4-methylpyridine-2-carbonyl)-1H-indol-3-yl]acetic acid;
methyl[2-(4-ethylpyridine-2-carbonyl)-5-trifluoromethyl-1H-indol-3-yl]acetate;
[2-(4-ethylpyridine-2-carbonyl)-5-trifluoromethyl-1H-indol-3-yl]acetic acid;
methyl[6-chloro-2-(4-methoxybenzoyl)-1H-indol-3-yl]acetate;
[6-chloro-2-(4-methoxybenzoyl)-1H-indol-3-yl]acetic acid;
methyl[5-chloro-2-(4-chloropyridine-2-carbonyl)-1H-indol-3-yl]acetate;
[5-chloro-2-(4-chloropyridine-2-carbonyl)-1H-indol-3-yl]acetic acid;
methyl[6-chloro-2-(4-methoxypyridine-2-carbonyl)-1H-indol-3-yl]acetate;
[6-chloro-2-(4-methoxypyridine-2-carbonyl)-1H-indol-3-yl]acetic acid;
methyl[5-chloro-2-(4-ethyl-3-fluoropyridine-2-carbonyl)-1H-indol-3-yl]acetate;
[5-chloro-2-(4-ethyl-3-fluoropyridine-2-carbonyl)-1H-indol-3-yl]acetatic acid;
methyl[5-fluoro-2-(4-methylpyridine-2-carbonyl)-1H-indol-3-yl]acetate;
[5-fluoro-2-(4-methylpyridine-2-carbonyl)-1H-indol-3-yl]acetic acid;
methyl[5-chloro-2-(4-methoxybenzoyl)-1H-indol-3-yl]acetate;
[5-chloro-2-(4-methoxybenzoyl)-1H-indol-3-yl]acetic acid;
methyl[6-chloro-2-(isoquinoline-3-carbonyl)-1H-indol-3-yl]acetate;
[6-chloro-2-(isoquinoline-3-carbonyl)-1H-indol-3-yl]acetic acid;
[6-chloro-5-fluoro-2-(4-methylpyridine-2-carbonyl)-1H-indol-3-yl]acetic acid;
methyl[6-chloro-2-[4-(1-hydroxyethyl)pyridine-2-carbonyl]-1H-indol-3-yl]acetate;
[6-chloro-2-[4-(1-hydroxyethyl)pyridine-2-carbonyl]-1H-indol-3-yl]acetic acid;
[6-chloro-2-(4-ethyl-3-fluoropyridine-2-carbonyl)-1H-indol-3-yl]acetic acid;
methyl[6-chloro-2-(5-chloropyridine-2-carbonyl)-1H-indol-3-yl]acetate;
[6-chloro-2-(5-chloropyridine-2-carbonyl)-1H-indol-3-yl]acetic acid;
methyl[6-methyl-2-(4-methylpyridine-2-carbonyl)-1H-indol-3-yl]acetate;
[6-methyl-2-(4-methylpyridine-2-carbonyl)-1H-indol-3-yl]acetic acid;
methyl[5-chloro-2-(isoquinoline-3-carbonyl)-1H-indol-3-yl]acetate;
[5-chloro-2-(isoquinoline-3-carbonyl)-1H-indol-3-yl]acetic acid;
[6-chloro-2-(4-chlorobenzoyl)-5-fluoro-1H-indol-3-yl]acetic acid (cj-020,099);
methyl[6-chloro-5-fluoro-2-(4-methylpyridine-2-carbonyl)-1H-indol-3-yl]acetate, and a salt thereof.

Most preferred individual compounds are:
(2-benzoyl-6-chloro-1H-indol-3-yl)acetic acid;
[6-chloro-2-(3-chlorobenzoyl)-1H-indol-3-yl]acetic acid;
[6-chloro-2-(4-chlorobenzoyl)-1H-indol-3-yl]acetic acid;
[5-chloro-2-(4-chlorobenzoyl)-1H-indol-3-yl]acetic acid;
[5-chloro-2-(3-chlorobenzoyl)-1H-indol-3-yl]]acetic acid;
[2-(4-chlorobenzoyl)-5-fluoro-1H-indol-3-yl]acetic acid;
(2-benzoyl-5,6-dichloro-1H-indol-3-yl)acetic acid;
[6-chloro-2-(4-methylpyridine-2-carbonyl)-1H-indol-3-yl]acetic acid;
[6-chloro-2-(5-methylpyridine-2-carbonyl)-1H-indol-3-yl]acetic acid;
[6-chloro-2-(4-chloropyridine-2-carbonyl)-1H-indol-3-yl]acetic acid;
[6-chloro-2-(pyridine-2-carbonyl)-1H-indol-3-yl]acetic acid;
[5-chloro-2-(4-methylpyridine-2-carbonyl)-1H-indol-3-yl]acetic acid;
[6-chloro-2-(4-ethylpyridine-2-carbonyl)-1H-indol-3-yl]acetic acid;
[5-chloro-2-(4-ethylpyridine-2-carbonyl)-1H-indol-3-yl]acetic acid;
[6-chloro-2-(4-isopropylpyridine-2-carbonyl)-1H-indol-3-yl]acetic acid;
[6-chloro-2-(4-propylpyridine-2-carbonyl)-1H-indol-3-yl]acetic acid;
[5-methyl-2-(4-methylpyridine-2-carbonyl)-1H-indol-3-yl]acetic acid;
[2-(4-ethylpyridine-2-carbonyl)-5-trifluoromethyl-1H-indol-3-yl]acetic acid;
[6-chloro-2-(4-methoxybenzoyl)-1H-indol-3-yl]acetic acid;

[5-chloro-2-(4-chloropyridine-2-carbonyl)-1H-indol-3-yl]acetic acid;
[6-chloro-2-(4-methoxypyridine-2-carbonyl)-1H-indol-3-yl]acetic acid;
[5-chloro-2-(4-ethyl-3-fluoropyridine-2-carbonyl)-1H-indol-3-yl]acetic acid;
[5-fluoro-2-(4-methylpyridine-2-carbonyl)-1H-indol-3-yl]acetic acid;
[5-chloro-2-(4-methoxybenzoyl)-1H-indol-3-yl]acetic acid;
[6-chloro-2-(isoquinoline-3-carbonyl)-1H-indol-3-yl]acetic acid;
[6-chloro-2-[4-(1-hydroxyethyl)pyridine-2-carbonyl]-1H-indol-3-yl]acetic acid;
[6-chloro-2-(4-ethyl-3-fluoropyridine-2-carbonyl)-1H-indol-3-yl]acetic acid;
[6-chloro-2-(5-chloropyridine-2-carbonyl)-1H-indol-3-yl]acetic acid;
[6-methyl-2-(4-methylpyridine-2-carbonyl)-1H-indol-3-yl]acetic acid;
[5-chloro-2-(isoquinoline-3-carbonyl)-1H-indol-3-yl]acetic acid;
[6-chloro-2-(4-chlorobenzoyl)-5-fluoro-1H-indol-3-yl]acetic acid, and a salt thereof.

Preferred pharmaceutical compositions of this invention comprise those compounds of the formula (I), wherein the compound is as defined above.

Most preferred individual compounds to be contained in the pharmaceutical compositions are:
(2-benzoyl-6-chloro-1H-indol-3-yl)acetic acid;
[6-chloro-2-(3-chlorobenzoyl)-1H-indol-3-yl]acetic acid;
[6-chloro-2-(4-chlorobenzoyl)-1H-indol-3-yl]acetic acid;
[5-chloro-2-(4-chlorobenzoyl)-1H-indol-3-yl]acetic acid;
[5-chloro-2-(3-chlorobenzoyl)-1H-indol-3-yl]acetic acid;
[2-(4-chlorobenzoyl)-5-fluoro-1H-indol-3-yl]acetic acid;
(2-benzoyl-5,6-dichloro-1H-indol-3-yl)acetic acid;
[6-chloro-2-(4-methylpyridine-2-carbonyl)-1H-indol-3-yl]acetic acid;
[6-chloro-2-(5-methylpyridine-2-carbonyl)-1H-indol-3-yl]acetic acid;
[6-chloro-2-(4-chloropyridine-2-carbonyl)-1H-indol-3-yl]acetic acid;
[6-chloro-2-(pyridine-2-carbonyl)-1H-indol-3-yl]acetic acid;
[5-chloro-2-(4-methylpyridine-2-carbonyl)-1H-indol-3-yl]acetic acid;
[6-chloro-2-(4-ethylpyridine-2-carbonyl)-1H-indol-3-yl]acetic acid;
[5-chloro-2-(4-ethylpyridine-2-carbonyl)-1H-indol-3-yl]acetic acid;
[6-chloro-2-(4-isopropylpyridine-2-carbonyl)-1H-indol-3-yl]acetic acid;
[6-chloro-2-(4-propylpyridine-2-carbonyl)-1H-indol-3-yl]acetic acid;
[5-methyl-2-(4-methylpyridine-2-carbonyl)-1H-indol-3-yl]acetic acid;
[2-(4-ethylpyridine-2-carbonyl)-5-trifluoromethyl-1-indol-3-yl]acetic acid;
[6-chloro-2-(4-methoxybenzoyl)-1H-indol-3-yl]acetic acid;
[5-chloro-2-(4-chloropyridine-2-carbonyl)-1H-indol-3-yl]acetic acid;
[6-chloro-2-(4-methoxypyridine-2-carbonyl)-1H-indol-3-yl]acetic acid;
[5-chloro-2-(4-ethyl-3-fluoropyridine-2-carbonyl)-1H-indol-3-yl]acetic acid;
[5-fluoro-2-(4-methylpyridine-2-carbonyl)-1H-indol-3-yl]acetic acid;
[5-chloro-2-(4-methoxybenzoyl)-1H-indol-3-yl]acetic acid;
[6-chloro-2-(isoquinoline-3-carbonyl)-1H-indol-3-yl]acetic acid;
[6-chloro-2-[4-(1-hydroxyethyl)pyridine-2-carbonyl]-1H-indol-3-yl]acetic acid;
[6-chloro-2-(4-ethyl-3-fluoropyridine-2-carbonyl)-1H-indol-3-yl]acetic acid;
[6-chloro-2-(5-chloropyridine-2-carbonyl)-1H-indol-3-yl]acetic acid;
[6-methyl-2-(4-methyl pyridine-2-carbonyl)-1H-indol-3-yl]acetic acid;
[5-chloro-2-(isoquinoline-3-carbonyl)-1H-indol-3-yl]acetic acid;
[6-chloro-2-(4-chlorobenzoyl)-5-fluoro-1H-indol-3-yl]acetic acid, and a salt thereof.

Also, the present invention provides a process for prepraing a compound of the formula:

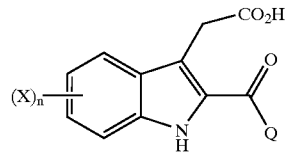

7-IV

Q is selected from the following:
(a) phenyl optionally substituted with one, two or three substituents independently selected from
(a-1) halo, $C_{1-4}$ alkyl, halo-substituted $C_{1-4}$ alkyl, OH, $C_{1-4}$ alkoxy, halo-substituted $C_{1-4}$ alkoxy, $C_{1-4}$ alkylthio, $NO_2$, $NH_2$, di-($C_{1-4}$ alkyl)amino, $C_{1-4}$ alkylamino, CN, HO—($C_{1-4}$)alkyl, $C_{1-4}$ alkoxy-$C_{1-4}$ alkyl, $C_{1-4}$ alkylsulfonyl, aminosulfonyl, —$NH_2S(O)_2NR^2R^3$, acetyl, —COOH, —C(O)O—$C_{1-4}$ alkyl, $C_{1-4}$ alkylsulfonylamino and $C_{3-7}$ cycloalkyl,
(a-2) aryl or —O—$(CH_2)_n$-aryl, and the aryl or aryl moiety being optionally substituted with one, two or three substituents independently selected from halo, $C_{1-4}$ alkyl, halo-substituted $C_{1-4}$ alkyl, OH, $C_{1-4}$ alkoxy, halo-substituted $C_{1-4}$ alkoxy, $C_{1-4}$ alkylthio, $NO_2$, $NH_2$, di-($C_{1-4}$ alkyl)amino, $C_{1-4}$ alkylamino and CN,
(a-3) 5-membered monocyclic aromatic group optionally substitued with one, two or three substituents independently selected from halo, $C_{1-4}$ alkyl, halo-substituted $C_{1-4}$ alkyl, OH, $C_{1-4}$ alkoxy, halo-substituted $C_{1-4}$ alkoxy, $C_{1-4}$ alkylthio, $NO_2$, $NH_2$, di-($C_{1-4}$ alkyl)amino, $C_{1-4}$ alkylamino and CN,
(a-4) 6-membered monocyclic aromatic group optionally substitued with one, two or three substituents independently selected from halo, $C_{1-4}$ alkyl, halo-substituted $C_{1-4}$ alkyl, OH, $C_{1-4}$ alkoxy, halo-substituted $C_{1-4}$ alkoxy, $C_{1-4}$ alkylthio, $NO_2$, $NH_2$, di-($C_{1-4}$ alkyl)amino, $C_{1-4}$ alkylamino and CN, (b) a 6-membered monocyclic aromatic group containing one, two, three or four nitrogen atom(s), and said monocyclic aromatic group being optionally substituted with one, two or three substituents independently selected from the above group (a-1), (a-2), (a-3) and (a-4), (c) a 5-membered monocyclic aromatic group containing one heteroatom selected from O, S and N and optionally containing one, two or three nitrogen atom(s) in addition to said heteroatom, and said monocyclic aromatic group being optionally substituted with one, two or three substituents independently selected from the above group (a-1), (a-2), (a-3) and (a-4);

(d) $C_{3-7}$ cycloalkyl optionally substituted with one or two substituents independently selected from OH, $C_{1-4}$ alkyl, halo and halo-substituted $C_{1-4}$ alkyl; and (e) a benzo-fuzed heterocycle optionally substituted with one, two or three substituents independently selected from the group (a-1);

$R^2$ and $R^3$ are independently H, OH, $C_{1-4}$ alkoxy, $C_{1-4}$ alkyl or $C_{1-4}$ alkyl substituted with halo, OH, $C_{1-4}$ alkoxy, $NH_2$ or CN;

X is independently selected from halo, $C_{1-4}$ alkyl, halo-substituted $C_{1-4}$ alkyl, OH, $C_{1-4}$ alkoxy, halo-substituted $C_{1-4}$ alkoxy, $C_{1-4}$ alkylthio, $NO_2$, $NH_2$, di-($C_{1-4}$ alkyl)amino, $C_{1-4}$ alkylamino, CN, HO—($C_{1-4}$)alkyl, $C_{1-4}$ alkoxy-$C_{1-4}$ alkyl, $C_{1-4}$ alkylsulfonyl, aminosulfonyl, —$NH_2S(O)_2NR^2NR^3$, acetyl, —COOH, —C(O)O—$C_{1-4}$ alkyl, $C_{1-4}$ alkylsulfonylamino and $C_{3-7}$ cycloalkyl; and n is 0, 1, 2, 3 or 4, which process comprises the steps of:

i) reacting a compound of the formula:

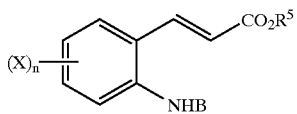

7-II wherein B is a suitable protecting group; $R^5$ is $C_{1-6}$ alkyl; X and n are as defined above, with a compound of the formula:

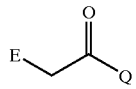

wherein E is halo and Q are as defined above, with a first base and a suitable solvent;

ii) reacting the product of step i) with a second base.

iii) reacting the product of step ii) with an acid.

Prefered process of the above mentioned process is a process, wherein said first base is potassium carbonate, potassium bicarbonate, sodium bicarbonate, sodium carbonate or cesium carbonate.

Prefered process of the above mentioned process is a process, wherein said first base is potassium carbonate.

Prefered process of the above mentioned process is a process, wherein said second base is aqueous sodium hydroxide, potassium hydroxide, sodium carbonate, potassium carbonate, sodium pentoxide (followed by water), sodium methoxide (followed by water) or potassium t-butoxide (followed by water).

Prefered process of the above mentioned process is a process, wherein said second base is sodium hydroxide.

Prefered process of the above mentioned process is a process, wherein said acid is aqueous hydrochloric acid, hydrobromic acid, sulfuric acid or ammonium chloride.

Prefered process of the above mentioned process is a process, wherein said acid is aqueous hydrochloric acid.

Prefered process of the above mentioned process is a process, wherein said solvent is N,N-dimethylacetamide, N,N-dimethylformamide, methyl ethyl ketone, acetone, or tetrahydrofuran.

Prefered process of the above mentioned process is a process, wherein said solvent is N,N-dimethylaetamide.

Also, the present invention provides a process for prepraing a compound of the formula:

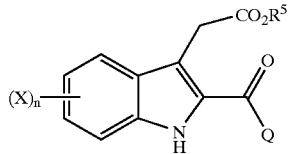

7-IV wherein

Q is selected from the following:

(a) phenyl optionally substituted with one, two or three substituents independently selected from (a-1) halo, $C_{1-4}$ alkyl, halo-substituted $C_{1-4}$ alkyl, OH, $C_{1-4}$ alkoxy, halo-substituted $C_{1-4}$ alkoxy, $C_{1-4}$ alkylthio, $NO_2$, $NH_2$, di-($C_{1-4}$ alkyl)amino, $C_{1-4}$ alkylamino, CN, HO—($C_{1-4}$)alkyl, $C_{1-4}$ alkoxy-$C_{1-4}$ alkyl, $C_{1-4}$ alkylsulfonyl, aminosulfonyl, —$NH_2S(O)_2NR^2R^3$, acetyl, —COOH, —C(O)O—$C_{1-4}$ alkyl, $C_{1-4}$ alkylsulfonylamino and $C_{3-7}$ cycloalkyl, (a-2) aryl or —O—$(CH_2)_n$-aryl, and the aryl or aryl moiety being optionally substituted with one, two or three substituents independently selected from halo, $C_{1-4}$ alkyl, halo-substituted $C_{1-4}$ alkyl, OH, $C_{1-4}$ alkoxy, halo-substituted $C_{1-4}$ alkoxy, $C_{1-4}$ alkylthio, $NO_2$, $NH_2$, di-($C_{1-4}$ alkyl)amino, $C_{1-4}$ alkylamino and CN, (a-3) 5-membered monocyclic aromatic group optionally substitued with one, two or three substituents independently selected from halo, $C_{1-4}$ alkyl, halo-substituted $C_{1-4}$ alkyl, OH, $C_{1-4}$ alkoxy, halo-substituted $C_{1-4}$ alkoxy, $C_{1-4}$ alkylthio, $NO_2$, $NH_2$, di-($C_{1-4}$ alkyl)amino, $C_{1-4}$ alkylamino and CN, (a-4) 6-membered monocyclic aromatic group optionally substitued with one, two or three substituents independently selected from halo, $C_{1-4}$ alkyl, halo-substituted $C_{1-4}$ alkyl, OH, $C_{1-4}$ alkoxy, halo-substituted $C_{1-4}$ alkoxy, $C_{1-4}$ alkylthio, $NO_2$, $NH_2$, di-($C_{1-4}$ alkyl)amino, $C_{1-4}$ alkylamino and CN, (b) a 6-membered monocyclic aromatic group containing one, two, three or four nitrogen atom(s), and said monocyclic aromatic group being optionally substituted with one, two or three substituents independently selected from the above group (a-1), (a-2), (a-3) and (a-4), (c) a 5-membered monocyclic aromatic group containing one heteroatom selected from O, S and N and optionally containing one, two or three nitrogen atom(s) in addition to said heteroatom, and said monocyclic aromatic group being optionally substituted with one, two or three substituents independently selected from the above group (a-1), (a-2), (a-3) and (a-4);
(d) $C_{3-7}$ cycloalkyl optionally substituted with one or two substituents independently selected from OH, $C_{1-4}$ alkyl, halo and halo-substituted $C_{1-4}$ alkyl; and
(e) a benzo-fuzed heterocycle optionally substituted with one, two or three substituents independently selected from the group (a-1);

$R^2$ and $R^3$ are independently H, OH, $C_{1-4}$ alkoxy, $C_{1-4}$ alkyl or $C_{1-4}$ alkyl substituted with halo, OH, $C_{1-4}$ alkoxy, $NH_2$ or CN;

X is independently selected from halo, $C_{1-4}$ alkyl, halo-substituted $C_{1-4}$ alkyl, OH, $C_{1-4}$ alkoxy, halo-substituted $C_{1-4}$ alkoxy, $C_{1-4}$ alkylthio, $NO_2$, $NH_2$, di-($C_{1-4}$ alkyl)amino, $C_{1-4}$ alkylamino, CN, HO—($C_{1-4}$)alkyl, $C_{1-4}$ alkoxy-$C_{1-4}$ alkyl, $C_{1-4}$ alkylsulfonyl, aminosulfonyl, —$NH_2S(O)_2NR^2NR^3$, acetyl, —COOH, —C(O)O—$C_{1-4}$ alkyl, $C_{1-4}$ alkylsulfonylamino and $C_{3-7}$ cycloalkyl; and n is 0, 1, 2, 3 or 4, which process comprises reacting a compound of the formula:

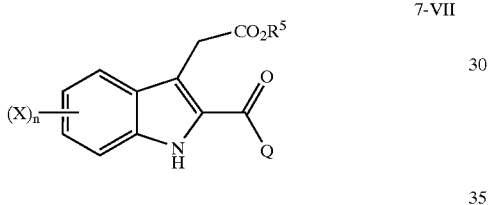

7-VII wherein $R^5$ is $C_{1-6}$ alkyl; Q, X and n are as defined as before, with a base in a suitable solvent.

Prefered process of the above mentioned process is a process, wherein said base is sodium hydroxide, potassium hydroxide, sodium carbonate, potassium carbonate, sodium bicarbonate, potassium bicarbonate, sodium t-pentoxide, sodium methoxide, sodium ethoxide or potassium t-butoxide.

Prefered process of the above mentioned process is a process, wherein said base is sodium hydroxide.

Prefered process of the above mentioned process is a process, wherein said solvent is an aqueous mixture of methanol, ethanol, isopropyl alcohol or tetrahydrofuran.

Prefered process of the above mentioned process is a process, wherein said solvent is methanol containing water.

Also, the present invention provides a process for prepraing a compound of the formula:

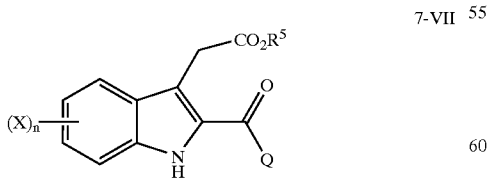

7-VII wherein

Q is selected from the following:
(a) phenyl optionally substituted with one, two or three substituents independently selected from (a-1) halo, $C_{1-4}$ alkyl, halo-substituted $C_{1-4}$ alkyl, OH, $C_{1-4}$ alkoxy, halo-substituted $C_{1-4}$ alkoxy, $C_{1-4}$ alkylthio, $NO_2$, $NH_2$, di-($C_{1-4}$ alkyl)amino, $C_{1-4}$ alkylamino, CN, HO—($C_{1-4}$)alkyl, $C_{1-4}$ alkoxy-$C_{1-4}$ alkyl, $C_{1-4}$ alkylsulfonyl, aminosulfonyl, —$NH_2S(O)_2NR^2R^3$, acetyl, —COOH, —C(O)O—$C_{1-4}$ alkyl, $C_{1-4}$ alkylsulfonylamino and $C_{3-7}$ cycloalkyl, (a-2) aryl or —O—($CH_2$)$_n$-aryl, and the aryl or aryl moiety being optionally substituted with one, two or three substituents independently selected from halo, $C_{1-4}$ alkyl, halo-substituted $C_{1-4}$ alkyl, OH, $C_{1-4}$ alkoxy, halo-substituted $C_{1-4}$ alkoxy, $C_{1-4}$ alkylthio, $NO_2$, $NH_2$, di-($C_{1-4}$ alkyl)amino, $C_{1-4}$ alkylamino and CN, (a-3) 5-membered monocyclic aromatic group optionally substitued with one, two or three substituents independently selected from halo, $C_{1-4}$ alkyl, halo-substituted $C_{1-4}$ alkyl, OH, $C_{1-4}$ alkoxy, halo-substituted $C_{1-4}$ alkoxy, $C_{1-4}$ alkylthio, $NO_2$, $NH_2$, di-($C_{1-4}$ alkyl)amino, $C_{1-4}$ alkylamino and CN, (a-4) 6-membered monocyclic aromatic group optionally substitued with one, two or three substituents independently selected from halo, $C_{1-4}$ alkyl, halo-substituted $C_{1-4}$ alkyl, OH, $C_{1-4}$ alkoxy, halo-substituted $C_{1-4}$ alkoxy, $C_{1-4}$ alkylthio, $NO_2$, $NH_2$, di-($C_{1-4}$ alkyl)amino, $C_{1-4}$ alkylamino and CN, (b) a 6-membered monocyclic aromatic group containing one, two, three or four nitrogen atom(s), and said monocyclic aromatic group being optionally substituted with one, two or three substituents independently selected from the above group (a-1), (a-2), (a-3) and (a-4), (c) a 5-membered monocyclic aromatic group containing one heteroatom selected from O, S and N and optionally containing one, two or three nitrogen atom(s) in addition to said heteroatom, and said monocyclic aromatic group being optionally substituted with one, two or three substituents independently selected from the above group (a-1), (a-2), (a-3) and (a-4);

(d) $C_{3-7}$ cycloalkyl optionally substituted with one or two substituents independently selected from OH, $C_{1-4}$ alkyl, halo and halo-substituted $C_{1-4}$ alkyl; and (e) a benzo-fuzed heterocycle optionally substituted with one, two or three substituents independently selected from the group (a-1);

$R^2$ and $R^3$ are independently H, OH, $C_{1-4}$ alkoxy, $C_{1-4}$ alkyl or $C_{1-4}$ alkyl substituted with halo, OH, $C_{1-4}$ alkoxy, $NH_2$ or CN;

X is independently selected from halo, $C_{1-4}$ alkyl, halo-substituted $C_{1-4}$ alkyl, OH, $C_{1-4}$ alkoxy, halo-substituted $C_{1-4}$ alkoxy, $C_{1-4}$ alkylthio, $NO_2$, $NH_2$, di-($C_{1-4}$ alkyl)amino, $C_{1-4}$ alkylamino, CN, HO—($C_{1-4}$)alkyl, $C_{1-4}$ alkoxy-$C_{1-4}$ alkyl, $C_{1-4}$ alkylsulfonyl, aminosulfonyl, —$NH_2S(O)_2NR^2NR^3$, acetyl, —COOH, —C(O)O—$C_{1-4}$ alkyl, $C_{1-4}$ alkylsulfonylamino and $C_{3-7}$ cycloalkyl; $R^5$ is $C_{1-6}$ alkyl; and n is 0, 1, 2, 3 or 4, which process comprises reacting a compound of the formula:

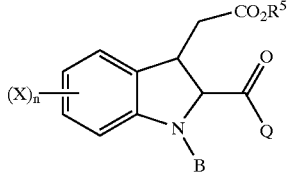

7-VI wherein B, Q, X, n and $R^5$ are as defined above with a base in a suitable solvent.

Prefered process of the above mentioned process is a process, wherein said base is 1,8-diazabicyclo[5.4.0]undec-7-ene, 1,5-diazabicyclo[4.3.0]non-5-ene, 1,1,3,3-tetramethylguanidine, sodium t-pentoxide, sodium methoxide, or potassium t-butoxide.

Prefered process of the above mentioned process is a process, wherein said base is 1,8-diazabicyclo[5.4.0]undec-7-ene or potassium t-butoxide.

Prefered process of the above mentioned process is a process, wherein said solvent is N,N-dimethylacetamide, N,N-dimethylformamide, methyl ethyl ketone, acetone, or tetrahydrofuran.

Prefered process of the above mentioned process is a process, wherein said solvent is N,N-dimethylacetamide.

Also, the present invention provides a process for prepraing a compound of the formula:

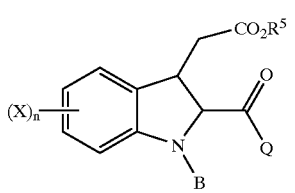

7-VI wherein B is a suitable protecting group;
Q is selected from the following:
  (a) phenyl optionally substituted with one, two or three substituents independently selected from
    (a-1) halo, $C_{1-4}$ alkyl, halo-substituted $C_{1-4}$ alkyl, OH, $C_{1-4}$ alkoxy, halo-substituted $C_{1-4}$ alkoxy, $C_{1-4}$ alkylthio, $NO_2$, $NH_2$, di-($C_{1-4}$ alkyl)amino, $C_{1-4}$ alkylamino, CN, HO—($C_{1-4}$)alkyl, $C_{1-4}$ alkoxy-$C_{1-4}$ alkyl, $C_{1-4}$ alkylsulfonyl, aminosulfonyl, —$NH_2S(O)_2NR^2R^3$, acetyl, —COOH, —C(O)O—$C_{1-4}$ alkyl, $C_{1-4}$ alkylsulfonylamino and $C_{3-7}$ cycloalkyl,
    (a-2) aryl or —O—$(CH_2)_n$-aryl, and the aryl or aryl moiety being optionally substituted with one, two or three substituents independently selected from halo, $C_{1-4}$ alkyl, halo-substituted $C_{1-4}$ alkyl, OH, $C_{1-4}$ alkoxy, halo-substituted $C_{1-4}$ alkoxy, $C_{1-4}$ alkylthio, $NO_2$, $NH_2$, di-($C_{1-4}$ alkyl)amino, $C_{1-4}$ alkylamino and CN,
    (a-3) 5-membered monocyclic aromatic group optionally substitued with one, two or three substituents independently selected from halo, $C_{1-4}$ alkyl, halo-substituted $C_{1-4}$ alkyl, OH, $C_{1-4}$ alkoxy, halo-substituted $C_{1-4}$ alkoxy, $C_{1-4}$ alkylthio, $NO_2$, $NH_2$, di-($C_{1-4}$ alkyl)amino, $C_{1-4}$ alkylamino and CN,
    (a-4) 6-membered monocyclic aromatic group optionally substitued with one, two or three substituents independently selected from halo, $C_{1-4}$ alkyl, halo-substituted $C_{1-4}$ alkyl, OH, $C_{1-4}$ alkoxy, halo-substituted $C_{1-4}$ alkoxy, $C_{1-4}$ alkylthio, $NO_2$, $NH_2$, di-($C_{1-4}$ alkyl)amino, $C_{1-4}$ alkylamino and CN,
  (b) a 6-membered monocyclic aromatic group containing one, two, three or four nitrogen atom(s), and said monocyclic aromatic group being optionally substituted with one, two or three substituents independently selected from the above group (a-1), (a-2), (a-3) and (a-4),
  (c) a 5-membered monocyclic aromatic group containing one heteroatom selected from O, S and N and optionally containing one, two or three nitrogen atom(s) in addition to said heteroatom, and said monocyclic aromatic group being optionally substituted with one, two or three substituents independently selected from the above group (a-1), (a-2), (a-3) and (a-4);
  (d) $C_{3-7}$ cycloalkyl optionally substituted with one or two substituents independently selected from OH, $C_{1-4}$ alkyl, halo and halo-substituted $C_{1-4}$ alkyl; and
  (e) a benzo-fuzed heterocycle optionally substituted with one, two or three substituents independently selected from the group (a-1);
$R^2$ and $R^3$ are independently H, OH, $C_{1-4}$ alkoxy, $C_{1-4}$ alkyl or $C_{1-4}$ alkyl substituted with halo, OH, $C_{1-4}$ alkoxy, $NH_2$ or CN;
X is independently selected from halo, $C_{1-4}$ alkyl, halo-substituted $C_{1-4}$ alkyl, OH, $C_{1-4}$ alkoxy, halo-substituted $C_{1-4}$ alkoxy, $C_{1-4}$ alkylthio, $NO_2$, $NH_2$, di-($C_4$ alkyl)amino, $C_{1-4}$ alkylamino, CN, HO—($C_{1-4}$) alkyl, $C_{1-4}$ alkoxy-$C_{1-4}$ alkyl, $C_{1-4}$ alkylsulfonyl, aminosulfonyl, —$NH_2S(O)_2NR^2NR^3$, acetyl, —COOH, —C(O)O—$C_{1-4}$ alkyl, $C_{1-4}$ alkylsulfonylamino and $C_{3-7}$ cycloalkyl; $R^5$ is $C_{1-6}$ alkyl; and
n is 0, 1, 2, 3 or 4,
which process comprises reacting a compound of the formula:

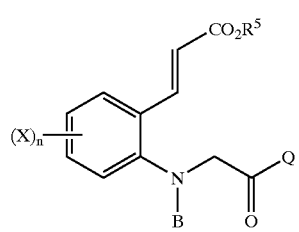

7-V wherein B, Q, X, n and $R^5$ are as defined above, with a base in the presence of a solvent.

Prefered process of the above mentioned process is a process, wherein said base is potassium carbonate, potassium bicarbonate, sodium bicarbonate, sodium carbonate, or cesium carbonate.

Prefered process of the above mentioned process is a process, wherein said base is potassium carbonate.

Prefered process of the above mentioned process is a process, wherein said solvent is N,N-dimethylacetamide, N,N-dimethylformamide, methyl ethyl ketone, acetone, or tetrahydrofuran.

Prefered process of the above mentioned process is a process, wherein said solvent is N,N-dimethylacetamide.

Also, the present invention provides a process for prepraing a compound of the formula:

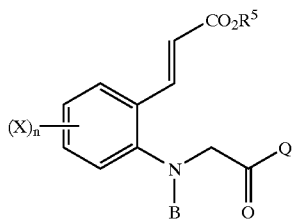

wherein B is a suitable protecting group;

Q is selected from the following:
(a) phenyl optionally substituted with one, two or three substituents independently selected from
  (a-1) halo, $C_{1-4}$ alkyl, halo-substituted $C_{1-4}$ alkyl, OH, $C_{1-4}$ alkoxy, halo-substituted $C_{1-4}$ alkoxy, $C_{1-4}$ alkylthio, $NO_2$, $NH_2$, di-($C_{1-4}$ alkyl)amino, $C_{1-4}$ alkylamino, CN, HO—($C_{1-4}$)alkyl, $C_{1-4}$ alkoxy-$C_{1-4}$ alkyl, $C_{1-4}$ alkylsulfonyl, aminosulfonyl, —$NH_2S(O)_2NR^2R^3$, acetyl, —COOH, —C(O)O—$C_{1-4}$ alkyl, $C_{1-4}$ alkylsulfonylamino and $C_{3-7}$ cycloalkyl,
  (a-2) aryl or —O—$(CH_2)_n$-aryl, and the aryl or aryl moiety being optionally substituted with one, two or three substituents independently selected from halo, $C_{1-4}$ alkyl, halo-substituted $C_{1-4}$ alkyl, OH, $C_{1-4}$ alkoxy, halo-substituted $C_{1-4}$ alkoxy, $C_{1-4}$ alkylthio, $NO_2$, $NH_2$, di-($C_{1-4}$ alkyl)amino, $C_{1-4}$ alkylamino and CN,
  (a-3) 5-membered monocyclic aromatic group optionally substitued with one, two or three substituents independently selected from halo, $C_{1-4}$ alkyl, halo-substituted $C_{1-4}$ alkyl, OH, $C_{1-4}$ alkoxy, halo-substituted $C_{1-4}$ alkoxy, $C_{1-4}$ alkylthio, $NO_2$, $NH_2$, di-($C_{1-4}$ alkyl)amino, $C_{1-4}$ alkylamino and CN,
  (a-4) 6-membered monocyclic aromatic group optionally substituted with one, two or three substituents independently selected from halo, $C_{1-4}$ alkyl, halo-substituted $C_{1-4}$ alkyl, OH, $C_{1-4}$ alkoxy, halo-substituted $C_{1-4}$ alkoxy, $C_{1-4}$ alkylthio, $NO_2$, $NH_2$, di-($C_{1-4}$ alkyl)amino, $C_{1-4}$ alkylamino and CN,
(b) a 6-membered monocyclic aromatic group containing one, two, three or four nitrogen atom(s), and said monocyclic aromatic group being optionally substituted with one, two or three substituents independently selected from the above group (a-1), (a-2), (a-3) and (a-4),
(c) a 5-membered monocyclic aromatic group containing one heteroatom selected from O, S and N and optionally containing one, two or three nitrogen atom(s) in addition to said heteroatom, and said monocyclic aromatic group being optionally substituted with one, two or three substituents independently selected from the above group (a-1), (a-2), (a-3) and (a-4);
(d) $C_{3-7}$ cycloalkyl optionally substituted with one or two substituents independently selected from OH, $C_{1-4}$ alkyl, halo and halo-substituted $C_{1-4}$ alkyl; and
(e) a benzo-fuzed heterocycle optionally substituted with one, two or three substituents independently selected from the group (a-1);

$R^2$ and $R^3$ are independently H, OH, $C_{1-4}$ alkoxy, $C_{1-4}$ alkyl or $C_{1-4}$ alkyl substituted with halo, OH, $C_{1-4}$ alkoxy, $NH_2$ or CN;

X is independently selected from halo, $C_{1-4}$ alkyl, halo-substituted $C_{1-4}$ alkyl, OH, $C_{1-4}$ alkoxy, halo-substituted $C_{1-4}$ alkoxy, $C_{1-4}$ alkylthio, $NO_2$, $NH_2$, di-($C_{1-4}$ alkyl)amino, $C_{1-4}$ alkylamino, CN, HO—($C_{1-4}$)alkyl, $C_{1-4}$ alkoxy-$C_{1-4}$ alkyl, $C_{1-4}$ alkylsulfonyl, aminosulfonyl, —$NH_2S(O)_2NR^2NR^3$, acetyl, —COOH, —C(O)O—$C_{1-4}$ alkyl, $C_{1-4}$ alkylsulfonylamino and $C_{3-7}$ cycloalkyl; $R^5$ is $C_{1-6}$ alkyl; and n is 0, 1, 2, 3 or 4, which comprises reacting a compound of the formula:

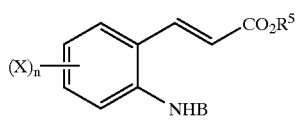

wherein B, X, n and $R^5$ are as defined above, with a compound of the formula:

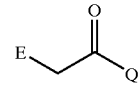

wherein E is halo and Q are as defined above, with a base in the presence of a solvent.

Prefered process of the above mentioned process is a process, wherein said base is potassium carbonate, potassium bicarbonate, sodium bicarbonate, sodium carbonate, or cesium carbonate.

Prefered process of the above mentioned process is a process, wherein said base is potassium carbonate.

Prefered process of the above mentioned process is a process, wherein said solvent is N,N-dimethylacetamide, N,N-dimethylformamide, methyl ethyl ketone, acetone or tetrahydrofuran.

Prefered process of the above mentioned process is a process, wherein said solvent is N,N-dimethylacetamide.

Also, the present invention provides a process for prepraing a compound of the formula:

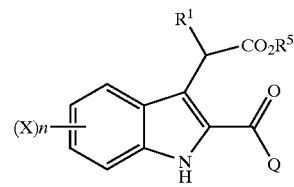

wherein
Q is selected from the following:
(a) phenyl optionally substituted with one, two or three substituents independently selected from
  (a-1) halo, $C_{1-4}$ alkyl, halo-substituted $C_{1-4}$ alkyl, OH, $C_{1-4}$ alkoxy, halo-substituted $C_{1-4}$ alkoxy, $C_{1-4}$ alkylthio, $NO_2$, $NH_2$, di-($C_{1-4}$ alkyl)amino, $C_{1-4}$ alkylamino, CN, HO—($C_{1-4}$)alkyl, $C_{1-4}$ alkoxy-$C_{1-4}$ alkyl, $C_{1-4}$ alkylsulfonyl, aminosulfonyl, —$NH_2S(O)_2NR^2R^3$, acetyl, —COOH, —C(O)O—$C_{1-4}$ alkyl, $C_{1-4}$ alkylsulfonylamino and $C_{3-7}$ cycloalkyl,
  (a-2) aryl or —O—$(CH_2)_n$-aryl, and the aryl or aryl moiety being optionally substituted with one, two or three substituents independently selected from halo, $C_{1-4}$ alkyl, halo-substituted $C_{1-4}$ alkyl, OH, $C_{1-4}$ alkoxy, halo-substituted $C_{1-4}$ alkoxy, $C_{1-4}$ alkylthio, $NO_2$, $NH_2$, di-($C_{1-4}$ alkyl)amino, $C_{1-4}$ alkylamino and CN, (a-3) 5-membered monocyclic aromatic group optionally substitued with one, two or three substituents independently selected from halo, $C_{1-4}$ alkyl, halo-substituted $C_{1-4}$ alkyl, OH, $C_{1-4}$ alkoxy, halo-substituted $C_{1-4}$ alkoxy, $C_{1-4}$ alkylthio, $NO_2$, $NH_2$, di-($C_{1-4}$ alkyl)amino, $C_{1-4}$ alkylamino and CN, (a-4) 6-membered monocyclic aromatic group optionally substitued with one, two or three substituents independently selected from halo, $C_{1-4}$ alkyl, halo-substituted $C_{1-4}$ alkyl, OH, $C_{1-4}$ alkoxy, halo-substituted $C_{1-4}$ alkoxy, $C_{1-4}$ alkylthio, $NO_2$, $NH_2$, di-($C_{1-4}$ alkyl)amino, $C_{1-4}$ alkylamino and CN, (b) a 6-membered monocyclic aromatic group containing one, two, three or four nitrogen atom(s), and said monocyclic aromatic group being optionally substituted with one, two or three substituents independently selected from the above group (a-1), (a-2), (a-3) and (a-4), (c) a 5-membered monocyclic aromatic group containing one heteroatom selected from O, S and N and optionally containing one, two or three nitrogen atom(s) in addition to said heteroatom, and said monocyclic aromatic group being optionally substituted with one, two or three substituents independently selected from the above group (a-1), (a-2), (a-3) and (a-4);

(d) $C_{3-7}$ cycloalkyl optionally substituted with one or two substituents independently selected from OH, $C_{1-4}$ alkyl, halo and halo-substituted $C_{1-4}$ alkyl; and (e) a benzo-fuzed heterocycle optionally substituted with one, two or three substituents independently selected from the group (a-1);

$R^1$ is hydrogen, $C_{1-4}$ alkyl or halo;

$R^2$ and $R^3$ are independently H, OH, $C_{1-4}$ alkoxy, $C_{1-4}$ alkyl or $C_{1-4}$ alkyl substituted with halo, OH, $C_{1-4}$ alkoxy, $NH_2$ or CN;

$R^5$ is $C_{1-6}$ alkyl;

X is independently selected from halo, $C_{1-4}$ alkyl, halo-substituted $C_{1-4}$ alkyl, OH, $C_{1-4}$ alkoxy, halo-substituted $C_{1-4}$ alkoxy, $C_{1-4}$ alkylthio, $NO_2$, $NH_2$, di-($C_{1-4}$ alkyl)amino, $C_{1-4}$ alkylamino, CN, HO—($C_{1-4}$)alkyl, $C_{1-4}$ alkoxy-$C_{1-4}$ alkyl, $C_{1-4}$ alkylsulfonyl, aminosulfonyl, —$NH_2S(O)_2NR^2NR^3$, acetyl, —COOH, —C(O)O—$C_{1-4}$ alkyl, $C_{1-4}$ alkylsulfonylamino and $C_{3-7}$ cycloalkyl; and n is 0, 1, 2, 3 or 4, which process comprises treating a compound of the formula (X):

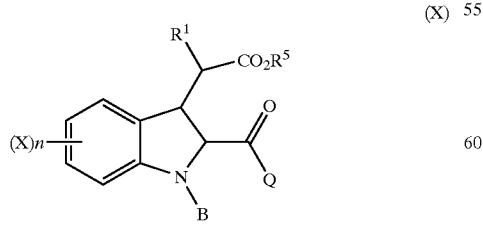

(X)

wherein $R^1$, $R^5$, X, Q and n are as defined herein before, and B is a suitable protecting group, in the presence of a suitable base to obtain a compound of the formula (XII).

Also, the present invention provides a process for prepraing a compound of the formula:

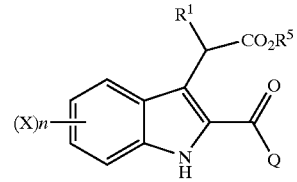

(XII)

wherein

Q is selected from the following:
(a) phenyl optionally substituted with one, two or three substituents independently selected from
(a-1) halo, $C_{1-4}$ alkyl, halo-substituted $C_{1-4}$ alkyl, OH, $C_{1-4}$ alkoxy, halo-substituted $C_{1-4}$ alkoxy, $C_{1-4}$ alkylthio, $NO_2$, $NH_2$, di-($C_{1-4}$ alkyl)amino, $C_{1-4}$ alkylamino, CN, HO—($C_{1-4}$)alkyl, $C_{1-4}$ alkoxy-$C_{1-4}$ alkyl, $C_{1-4}$ alkylsulfonyl, aminosulfonyl, —$NH_2S(O)_2NR^2R^3$, acetyl, —COOH, —C(O)O—$C_{1-4}$ alkyl, $C_{1-4}$ alkylsulfonylamino and $C_{3-7}$ cycloalkyl, (a-2) aryl or —O—$(CH_2)_n$-aryl, and the aryl or aryl moiety being optionally substituted with one, two or three substituents independently selected from halo, $C_{1-4}$ alkyl, halo-substituted $C_{1-4}$ alkyl, OH, $C_{1-4}$ alkoxy, halo-substituted $C_{1-4}$ alkoxy, $C_{1-4}$ alkylthio, $NO_2$, $NH_2$, di-($C_{1-4}$ alkyl)amino, $C_{1-4}$ alkylamino and CN, (a-3) 5-membered monocyclic aromatic group optionally substitued with one, two or three substituents independently selected from halo, $C_{1-4}$ alkyl, halo-substituted $C_{1-4}$ alkyl, OH, $C_{1-4}$ alkoxy, halo-substituted $C_{1-4}$ alkoxy, $C_{1-4}$ alkylthio, $NO_2$, $NH_2$, di-($C_{1-4}$ alkyl)amino, $C_{1-4}$ alkylamino and CN, (a-4) 6-membered monocyclic aromatic group optionally substitued with one, two or three substituents independently selected from halo, $C_{1-4}$ alkyl, halo-substituted $C_{1-4}$ alkyl, OH, $C_{1-4}$ alkoxy, halo-substituted $C_{1-4}$ alkoxy, $C_{1-4}$ alkylthio, $NO_2$, $NH_2$, di-($C_{1-4}$ alkyl)amino, $C_{1-4}$ alkylamino and CN, (b) a 6-membered monocyclic aromatic group containing one, two, three or four nitrogen atom(s), and said monocyclic aromatic group being optionally substituted with one, two or three substituents independently selected from the above group (a-1), (a-2), (a-3) and (a-4), (c) a 5-membered monocyclic aromatic group containing one heteroatom selected from O, S and N and optionally containing one, two or three nitrogen atom(s) in addition to said heteroatom, and said monocyclic aromatic group being optionally substituted with one, two or three substituents independently selected from the above group (a-1), (a-2), (a-3) and (a-4);

(d) $C_{3-7}$ cycloalkyl optionally substituted with one or two substituents independently selected from OH, $C_{1-4}$ alkyl, halo and halo-substituted $C_{1-4}$ alkyl; and (e) a benzo-fuzed heterocycle optionally substituted with one, two or three substituents independently selected from the group (a-1);

$R^1$ is hydrogen, $C_{1-4}$ alkyl or halo;

$R^2$ and $R^3$ are independently H, OH, $C_{1-4}$ alkoxy, $C_{1-4}$ alkyl or $C_{1-4}$ alkyl substituted with halo, OH, $C_{1-4}$ alkoxy, $NH_2$ or CN;

$R^5$ is $C_{1-6}$ alkyl;

X is independently selected from halo, $C_{1-4}$ alkyl, halo-substituted $C_{1-4}$ alkyl, OH, $C_{1-4}$ alkoxy, halo-substituted $C_{1-4}$ alkoxy, $C_{1-4}$ alkylthio, $NO_2$, $NH_2$, di-($C_{1-4}$ alkyl)amino, $C_{1-4}$ alkylamino, CN, HO—($C_{1-4}$)alkyl, $C_{1-4}$ alkoxy-$C_{1-4}$ alkyl, $C_{1-4}$ alkylsulfonyl, aminosulfonyl, —$NH_2S(O)_2NR^2NR^3$, acetyl, —COOH, —C(O)O—$C_{1-4}$ alkyl, $C_{1-4}$ alkylsulfonylamino and $C_{3-7}$ cycloalkyl; and n is 0, 1, 2, 3 or 4, which process comprises reacting a compound of the formula (IX):

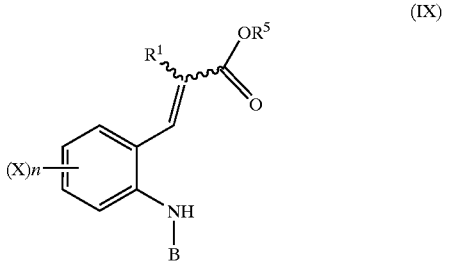

(IX)

wherein $R^1$, $R^5$, X, and n are as defined above, and B is a suitable protecting group, with a compound of the formula (XI):

(XI)

in the presence of a suitable base at a temperature of –40° C. to 200° C. to obtain a compound of the formula (XII).

Prefered process of the above mentioned process is a process, wherein the reaction is carried out at a temperature of 0° C. to 100° C.

Prefered process of the above mentioned process is a process, wherein the suitable base is potassium carbonate, cesium carbonate, sodium carbonate, sodium tert-butoxide, potassium tert-butoxide, sodium hydride, potassium hydride or potassium fluoride.

Prefered process of the above mentioned process is a process, wherein the reaction is firstly carried out in the presence of a base for 2 minutes to a day; and then, another base is added to the reaction mixture.

Prefered process of the above mentioned process is a process, wherein the reaction is firstly carried out for 30 minutes to 8 hours.

Prefered process of the above mentioned process is a process, wherein the suitable protecting group is methoxycarbonyl, ethoxycarbonyl, tert-butoxycarbonyl, benzyloxycarbonyl, phenylsulfonyl, p-toluenesulfonyl, methanesulfonyl or trifluoromethanesulfonyl.

Prefered process of the above mentioned process is a process, wherein the suitable protecting group is phenylsulfonyl, p-toluenesulfonyl, methanesulfonyl or trifluoromethanesulfonyl.

Prefered process of the above mentioned process is a process, wherein the first base is selected from sodium tert-butoxide, potassium tert-butoxide, sodium carbonate, potassium carbonate, cesium carbonate, sodium hydride, potassium hydride, sodium carbonate, potassium carbonate, cesium carbonate, potassium fluoride, 1,8-diazabicyclo[5.4.0]undec-7-ene, 1,5-diazabicyclo[4.3.0]non-5-ene, 1,4-diazabicyclo[2.2.2]octane, pyridine, pyrrolidine, triethylamine, diisopropylamine, diisopropylethylamine and diethylisopropylamine; and the second base is selected from sodium tert-butoxide, potassium tert-butoxide, sodium carbonate, potassium carbonate, cesium carbonate, sodium hydride, potassium hydride, sodium carbonate, potassium carbonate, cesium carbonate, potassium fluoride, 1,8-diazabicyclo[5.4.0]undec-7-ene, 1,5-diazabicyclo[4.3.0]non-5-ene, 1,4-diazabicyclo[2.2.2]octane, pyridine, pyrrolidine, triethylamine, diisopropylamine, diisopropylethylamine and diethylisopropylamine.

Prefered process of the above mentioned process is a process, wherein the first base is selected from potassium carbonate, cesium carbonate, sodium hydride and potassium fluoride; and the second base is selected from 1,8-diazabicyclo[5.4.0]undec-7-ene, cesium carbonate, pyrrolidine, diisopropylamine, triethylamine, diethylisopropylamine and diisopropylethylamine.

Prefered process of the above mentioned process is a process, wherein the first base is potassium carbonate, cesium carbonate or potassium fluoride; and the second base is 1,8-diazabicyclo[5.4.0]undec-7-ene, potassium tert-butoxide or cesium carbonate.

Prefered process of the above mentioned process is a process, wherein the combination of the first base and the second base (first base/second base) is selected from potassium carbonate/1,8-diazabicyclo[5.4.0]undec-7-ene, potassium carbonate/cesium carbonate, cesium carbonate/potassium tert-butoxide, cesium carbonate/1,8-diazabicyclo[5.4.0]undec-7-ene and potassium fluoride/1,8-diazabicyclo[5.4.0]undec-7-ene and potassium fluoride/cesium carbonate.

Prefered process of the above mentioned process is a process, wherein the combination of the first base and the second base (first base/second basse) is selected from potassium carbonate/1,8-diazabicyclo[5.4.0]undec-7-ene, potassium carbonate/cesium carbonate and cesium carbonate/potassium tert-butoxide.

Also, the present invention provides a process for prepraing a compound of the formula:

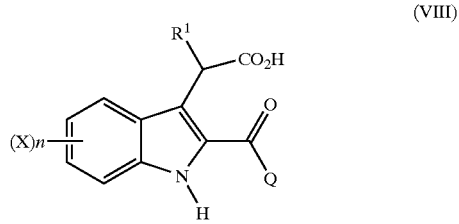

(VIII)

wherein

Q is selected from the following:
(a) phenyl optionally substituted with one, two or three substituents independently selected from
(a-1) halo, $C_{1-4}$ alkyl, halo-substituted $C_{1-4}$ alkyl, OH, $C_{1-4}$ alkoxy, halo-substituted $C_{1-4}$ alkoxy, $C_{1-4}$ alkylthio, $NO_2$, $NH_2$, di-($C_{1-4}$ alkyl)amino, $C_{1-4}$ alkylamino, CN, HO—($C_{1-4}$)alkyl, $C_{1-4}$ alkoxy-$C_{1-4}$ alkyl, $C_{1-4}$ alkylsulfonyl, aminosulfonyl, —$NH_2S(O)_2NR^2R^3$, acetyl, —COOH, —C(O)O—$C_{1-4}$ alkyl, $C_{1-4}$ alkylsulfonylamino and $C_{3-7}$ cycloalkyl,
(a-2) aryl or —O—($CH_2$)$_n$-aryl, and the aryl or aryl moiety being optionally substituted with one, two or three substituents independently selected from halo, $C_{1-4}$ alkyl, halo-substituted $C_{1-4}$ alkyl, OH, $C_{1-4}$ alkoxy, halo-substituted $C_{1-4}$ alkoxy, $C_{1-4}$ alkylthio, $NO_2$, $NH_2$, di-($C_{1-4}$ alkyl)amino, $C_{1-4}$ alkylamino and CN, (a-3) 5-membered monocyclic aromatic group optionally substitued with one, two or three substituents independently selected from halo, $C_{1-4}$ alkyl, halo-substituted $C_{1-4}$ alkyl, OH, $C_{1-4}$ alkoxy, halo-substituted $C_{1-4}$ alkoxy, $C_{1-4}$ alkylthio, $NO_2$, $NH_2$, di-($C_{1-4}$ alkyl)amino, $C_{1-4}$ alkylamino and CN, (a-4) 6-membered monocyclic aromatic group optionally substitued with one, two or three substituents independently selected from halo, $C_{1-4}$ alkyl, halo-substituted $C_{1-4}$ alkyl, OH, $C_{1-4}$ alkoxy, halo-substituted $C_{1-4}$ alkoxy, $C_{1-4}$ alkylthio, $NO_2$, $NO_2$, di-($C_{1-4}$ alkyl)amino, $C_{1-4}$ alkylamino and CN, (b) a 6-membered monocyclic aromatic group containing one, two, three or four nitrogen atom(s), and said monocyclic aromatic group being optionally substituted with one, two or three substituents independently selected from the above group (a-1), (a-2), (a-3) and (a-4), (c) a 5-membered monocyclic aromatic group containing one heteroatom selected from O, S and N and optionally containing one, two or three nitrogen atom(s) in addition to said heteroatom, and said monocyclic aromatic group being optionally substituted with one, two or three substituents independently selected from the above group (a-1), (a-2), (a-3) and (a-4);

(d) $C_{3-7}$ cycloalkyl optionally substituted with one or two substituents independently selected from OH, $C_{1-4}$ alkyl, halo and halo-substituted $C_{1-4}$ alkyl; and (e) a benzo-fuzed heterocycle optionally substituted with one, two or three substituents independently selected from the group (a-1);

$R^1$ is hydrogen, $C_{1-4}$ alkyl or halo;

$R^2$ and $R^3$ are independently H, OH, $C_{1-4}$ alkoxy, $C_{1-4}$ alkyl or $C_{1-4}$ alkyl substituted with halo, OH, $C_{1-4}$ alkoxy, $NH_2$ or CN;

X is independently selected from halo, $C_{1-4}$ alkyl, halo-substituted $C_{1-4}$ alkyl, OH, $C_{1-4}$ alkoxy, halo-substituted $C_{1-4}$ alkoxy, $C_{1-4}$ alkylthio, $NO_2$, $NH_2$, di-($C_{1-4}$ alkyl)amino, $C_{1-4}$ alkylamino, CN, HO—($C_{1-4}$)alkyl, $C_{1-4}$ alkoxy-$C_{1-4}$ alkyl, $C_{1-4}$ alkylsulfonyl, aminosulfonyl, —$NH_2S(O)_2NR^2NR^3$, acetyl, —COOH, —C(O)O—$C_{1-4}$ alkyl, $C_{1-4}$ alkylsulfonylamino and $C_{3-7}$ cycloalkyl; and n is 0, 1, 2, 3 or 4, which process comprises treating a compound of the formula (X):

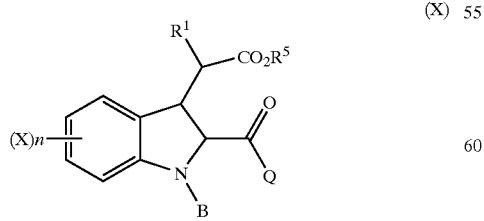

wherein $R^1$, $R^5$, X, Q and n are as defined here before, with a suitable base under hydrolyzing conditions to obtain the compound of formula (VIII).

This invention also provides a process for preparing a compound of the formula (VIII):

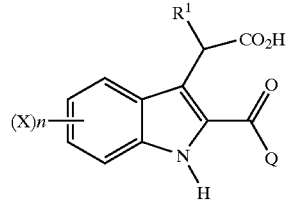

wherein

Q is selected from the following:
(a) phenyl optionally substituted with one, two or three substituents independently selected from
(a-1) halo, $C_{1-4}$ alkyl, halo-substituted $C_{1-4}$ alkyl, OH, $C_{1-4}$ alkoxy, halo-substituted $C_{1-4}$ alkoxy, $C_{1-4}$ alkylthio, $NO_2$, $NH_2$, di-($C_{1-4}$ alkyl)amino, $C_{1-4}$ alkylamino, CN, HO—($C_{1-4}$)alkyl, $C_{1-4}$ alkoxy-$C_{1-4}$ alkyl, $C_{1-4}$ alkylsulfonyl, aminosulfonyl, —$NH_2S(O)_2NR^2R^3$, acetyl, —COOH, —C(O)O—$C_{1-4}$ alkyl, $C_{1-4}$ alkylsulfonylamino and $C_{3-7}$ cycloalkyl, (a-2) aryl or —O—($CH_2$)$_n$-aryl, and the aryl or aryl moiety being optionally substituted with one, two or three substituents independently selected from halo, $C_{1-4}$ alkyl, halo-substituted $C_{1-4}$ alkyl, OH, $C_{1-4}$ alkoxy, halo-substituted $C_{1-4}$ alkoxy, $C_{1-4}$ alkylthio, $NO_2$, $NH_2$, di-($C_{1-4}$ alkyl)amino, $C_{1-4}$ alkylamino and CN, (a-3) 5-membered monocyclic aromatic group optionally substitued with one, two or three substituents independently selected from halo, $C_{1-4}$ alkyl, halo-substituted $C_{1-4}$ alkyl, OH, $C_{1-4}$ alkoxy, halo-substituted $C_{1-4}$ alkoxy, $C_{1-4}$ alkylthio, $NO_2$, $NH_2$, di-($C_{1-4}$ alkyl)amino, $C_{1-4}$ alkylamino and CN, (a-4) 6-membered monocyclic aromatic group optionally substitued with one, two or three substituents independently selected from halo, $C_{1-4}$ alkyl, halo-substituted $C_{1-4}$ alkyl, OH, $C_{1-4}$ alkoxy, halo-substituted $C_{1-4}$ alkoxy, $C_{1-4}$ alkylthio, $NO_2$, $NH_2$, di-($C_{1-4}$ alkyl)amino, $C_{1-4}$ alkylamino and CN, (b) a 6-membered monocyclic aromatic group containing one, two, three or four nitrogen atom(s), and said monocyclic aromatic group being optionally substituted with one, two or three substituents independently selected from the above group (a-1), (a-2), (a-3) and (a-4), (c) a 5-membered monocyclic aromatic group containing one heteroatom selected from O, S and N and optionally containing one, two or three nitrogen atom(s) in addition to said heteroatom, and said monocyclic aromatic group being optionally substituted with one, two or three substituents independently selected from the above group (a-1), (a-2), (a-3) and (a-4);

(d) $C_{3-7}$ cycloalkyl optionally substituted with one or two substituents independently selected from OH, $C_{1-4}$ alkyl, halo and halo-substituted $C_{1-4}$ alkyl; and (e) a benzo-fuzed heterocycle optionally substituted with one, two or three substituents independently selected from the group (a-1);

$R^1$ is hydrogen, $C_{1-4}$ alkyl or halo;

$R^2$ and $R^3$ are independently H, OH, $C_{1-4}$ alkoxy, $C_{1-4}$ alkyl or $C_{1-4}$ alkyl substituted with halo, OH, $C_{1-4}$ alkoxy, $NH_2$ or CN;

X is independently selected from halo, $C_{1-4}$ alkyl, halo-substituted $C_{1-4}$ alkyl, OH, $C_{1-4}$ alkoxy, halo-substituted $C_{1-4}$ alkoxy, $C_{1-4}$ alkylthio, $NO_2$, $NH_2$, di-($C_{1-4}$ alkyl)amino, $C_{1-4}$ alkylamino, CN, HO—($C_{1-4}$)alkyl, $C_{1-4}$ alkoxy-$C_{1-4}$ alkyl, $C_{1-4}$ alkylsulfonyl, aminosulfonyl, —$NH_2S(O)_2NR^2NR^3$, acetyl, —COOH, —C(O)O—$C_{1-4}$ alkyl, $C_{1-4}$ alkylsulfonylamino and $C_{3-7}$ cycloalkyl; and n is 0, 1, 2, 3 or 4, which process comprises hydrolyzing a compound of the formula (XII):

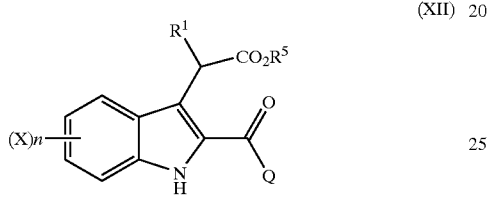

(XII)

wherein $R^5$ is $C_{1-6}$ alkyl, $R^1$, X, Q and n are as defined herein before.

General Synthesis

A compound of general formula (I) may be prepared by any synthetic procedure applicable to structure-related compounds known to those skilled in the art. The following representative examples as described hereinafter are illustrative and are not meant to limit the scope of the invention in anyway. Unless otherwise stated, Q, X, Z, $R^1$, and n are as defined above.

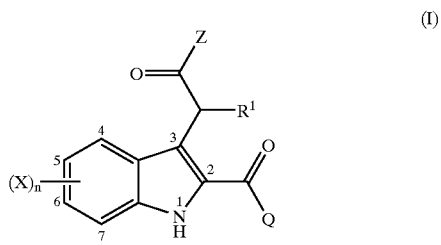

(I)

Scheme 1:

In one embodiment, for example, a compound of the formula (VI) may be prepared according to the reaction sequences depicted in Scheme 1. (Compound (VI) corresponds to a compound (I) wherein $R^1$ is H, and Z is OH.)

Scheme 1

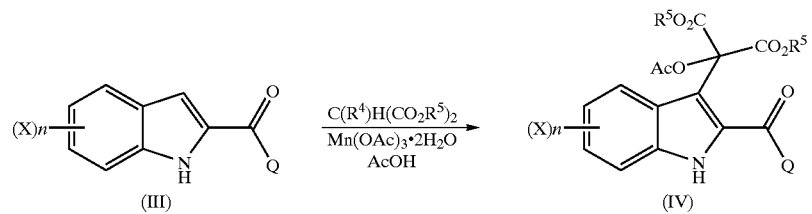

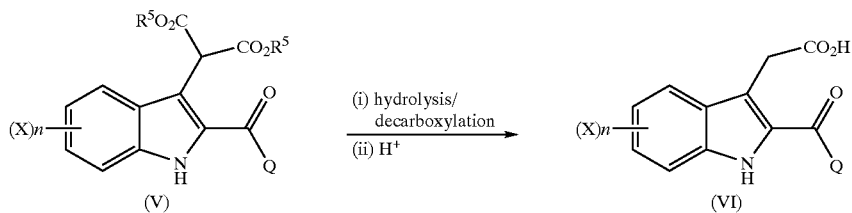

[$R^4$ = H or halo]   [$R^5$ = $C_{1-6}$alkyl]

In brief, a compound of formula (III) is subjected to oxidative homolytic malonylation (for leading references see J. M. Muchowski et al; Can. J. Chem., 70, 1838, 1992 and E. Baciocchi et al; J. Org. Chem., 58, 7610, 1993). In one example, a compound of the formula (III) is reacted with a suitable malonyl radical generated from a compound of formula $C(R^4)H(CO_2R^5)_2$, wherein $R^4$ is hydrogen or halogen, preferably chloro, and $R^5$ is $C_{1-6}$ alkyl, and a manganese(III) agent, preferably manganese(III) triacetate. The manganese(III) agent is usually used in stoichiometric amounts but, alternatively, may be made catalytic by use of a suitable reoxidizing agent such as sodium persulfate, usually in the presence of a co-catalyst such as, a silver(I) salt such as silver nitrate. A preferred reaction solvent is acetic acid; however, acetic acid-acetic anhydride or other protic solvents such as propionic acid can be used. The reaction is preferably conducted in the presence of sodium acetate or potassium acetate, but, may be conducted in solvent alone. Reaction temperatures are generally in the range of room temperature (e.g., 25° C.) to reflux temperature of solvent, preferably 60 to 100° C., but if necessary, lower or higher temperature can be employed. Reaction times are, in general, from one hour to a day, preferably from 4 to 16 hours, however shorter or longer reaction times, if necessary, can be employed. In the immediate instance, the α-acetoxy compounds of formula (IV) is usually obtained as the major product. Compounds of formula (IV) can readily be transformed to compounds of formula (V) by reduction with a suitable reducing agent, for example, a trialkylsilane, sodium α-(dimethylamino)naphtalenide, lithium in liquid ammonia, sodium naphtalenide, preferably triethylsilane in a suitable protic solvent, notably, trifluoroacetic acid. Alternatively, the reaction can be conducted in a reaction inert co-solvent such as dichloromethane or 1,2-dichloroethane. Reaction temperatures are generally in the range of room temperature to reflux temperature of solvent, preferably 15 to 100° C., but if necessary, lower or higher temperature can be employed. Reaction times are, in general, from several minutes to a day, preferably from 20 minutes to 5 hours, however shorter or longer reaction times, if necessary, can be employed. Alternatively, a compound of formula (V) may be obtained directly from a compound of formula (III) from a malonyl radical generated from (i) a suitable monohalomalonate, preferably, bromomalonate, mediated by aerial oxidation of a trialkylborane such as triethylborane (see B. Giese; In Radicals in organic synthesis: formation of carbon-carbon bonds. Pergamon Press, Oxford. pp. 86–89, 1986, and P. G. Allies and P. B. Brindley; J. Chem. Soc. (B), 1126, 1960) or, (ii) a malonic ester in the presence of a cerium(IV) salt such as cerium(IV) ammonium nitrate (for example, see E. Baciocchi et al; Tetrahedron Lett, 2763, 1986). A compound of formula (V) may be readily transformed to a compound of formula (VI) by subjection to standard saponification/decarboxylation conditions.

Scheme 2:

Alternatively, as depicted in Scheme 2, a compound of the formula (VIII) (a compound (I) wherein Z is OH), wherein $R^1$ is $C_{1-4}$ alkyl, may be prepared in an analogous manner to that of a compound of formula (VI) employing appropriate reaction conditions as described by illustration herein above from a suitable monoalkylmalonate, wherein $R^1$ is $C_{1-4}$ alkyl, W is hydrogen or a halogen, preferably bromide, and $R^5$ is $C_{1-6}$ alkyl, from a compound of formula (III).

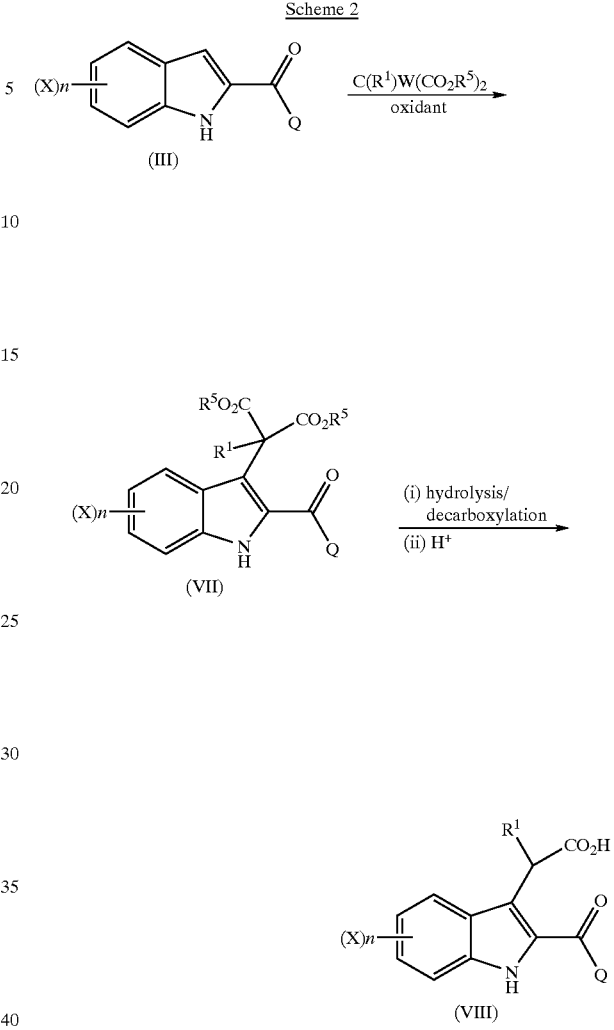

In Scheme 2, for example, the oxidant is manganese(III) agent such as manganese(III) triacetate, or Cerium(IV) agent such as ammonium Cerium(IV) nitrate and Cerium(IV) sulfate.

Scheme 3:

In another embodiment, a compound of formula (VIII) is readily accessible from the appropriate 2-aminocinnamic acid ester (IX) wherein B is a suitable protecting group, for example, methoxycarbonyl, ethoxycarbonyl, tert-butoxycarbonyl (Boc), benzyloxycarbonyl, phenylsulfonyl, p-toluenesulfonyl, methanesulfonyl, trifluoromethanesulfonyl, methanesulfonyl or trifluoromethanesulfonyl (preferably phenylsulfonyl, p-toluenesulfonyl, methanesulfonyl or trifluoromethanesulfonyl).

Scheme 3

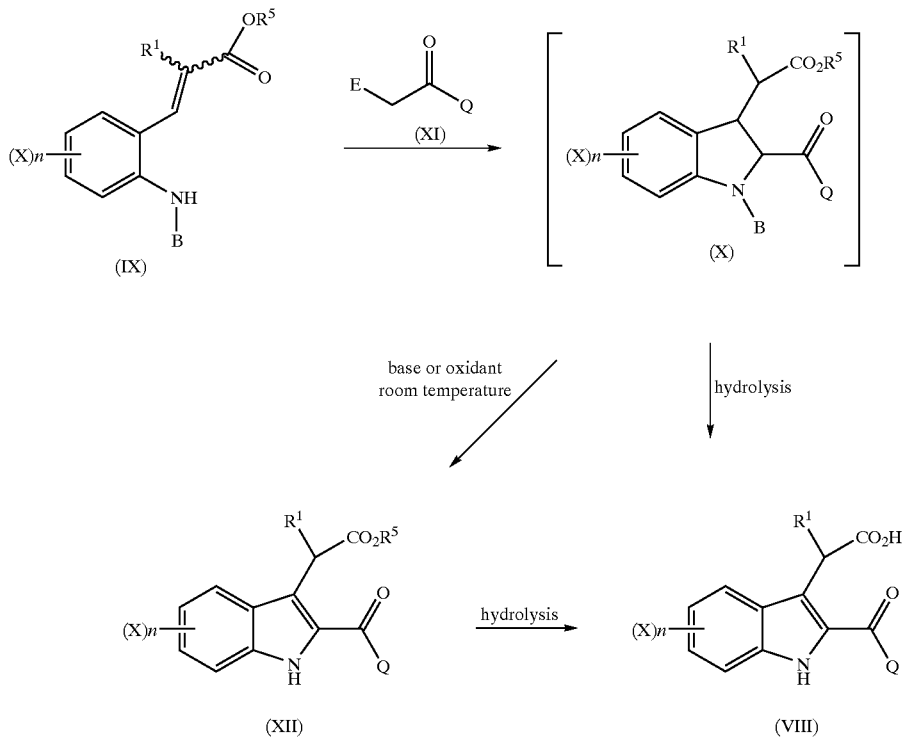

[$R^5$ = $C_{1-6}$alkyl]
[B = a suitable protecting group]
[E = halogen]

In Scheme 3, the requisite 2-aminocinnamic acid ester (IX) is reacted with a compound of formula (XI), wherein Q is as defined above and E is halogen, preferably, iodo, bromo or chloro, in the presence of a suitable base. A suitable base is, for example, an alkali or alkaline earth metal alkoxide, carbonate, fluoride or hydride, such as sodium tert-butoxide, potassium tert-butoxide, sodium carbonate, potassium carbonate, cesium carbonate, sodium hydride, potassium fluoride or potassium hydride. Preferred reaction inert solvents include, but are not limited to, acetone, methyl ethyl ketone, acetonitrile, N,N-dimethylformamide (DMF), N,N-dimethylacetamide (DMA), dimethylsulfoxide (DMSO), dioxane or tetrahydrofuran (THF). Reaction temperatures are preferably in the range of −40° C. to reflux temperature of solvent (for example 200° C.), usually in the range of 0° C. to 100° C., but if necessary, lower or higher temperature can be employed. Reaction time is in general from 2 minutes to a day, preferably from 30 minutes to 8 hours, however shorter or longer reaction times, if necessary, can be employed. When the reaction is, for example, conducted at room temperature (e.g., 25° C.) the intermediate indoline (X) can be isolated. Reaction at higher temperatures (e.g., 40 to 100° C.) can result in formation of indole (XII). Usually the intermediate indoline (X) is not isolated but either (i) hydrolyzed with commitant formation of the indole ring directly to a compound of formula (VIII) under standard conditions known to those skilled in the art, or (ii) transformed to a compound of formula (XII) by using a suitable base, for example, an alkali or alkaline earth metal carbonate such as sodium carbonate, potassium carbonate or cesium carbonate, or an organic base such as 1,8-diazabicyclo[5.4.0]undec-7-ene (DBU), 1,5-diazabicyclo[4.3.0]non-5-ene (DBN), 1,4-diazabicyclo[2.2.2]octane (DABCO), pyridine, pyrrolidine, triethylamine, diisopropylamine, diisopropylethylamine, diethylisopropylamine, Hunig's base, potassium tert-butoxide, sodium tert-butoxide, or the like, or a suitable oxidant such as cerium(IV) ammonium nitrate (CAN), manganese(IV) oxide, manganese(III) triacetate, copper(II) acetate/air, chloranil, 2,3-dichloro-5,6-dicyano-1,4-benzoquinone (DDQ), N-methylmorpholine-N-oxide, or the like (for example, see H. Dumoulin et al; J. Heterocycl. Chem., 32, 1703, 1995; H. Rapoport et al; Tetrahedron Lett., 5053, 1991; P. Martin et al; Helv. Chim. Acta, 77, 111, 1994; Y. Kikugawa et al, J. Chem. Soc. Perkins Trans 1, 7, 1401, 1984; A. Goti et al; Tetrahedron Lett., 6567, 1996; L. S. Liebeskind et al; J. Org. Chem, 61, 2594, 1996). Preferred reaction inert solvents include, but are not limited to, acetone, methyl ethyl ketone, acetonitrile, dioxane or tetrahydrofuran (THF). Reaction temperatures are preferably in the range of 0° C. to reflux temperature of solvent, usually in the range of 15 to 60° C., but if necessary, lower or higher temperature can be employed. Reaction time is in general from several minutes to a day, preferably from 30 minutes to 8 hours, however shorter or longer reaction times, if necessary, can be employed. A compound of formula (XII) may be readily hydrolyzed to a compound of formula (VIII) under standard conditions.

Scheme 4:

In another embodiment, a compound of formula (VIII), wherein Q, X, $R^1$ and n are as defined above, may be prepared as illustrated in Scheme 4.

Scheme 4

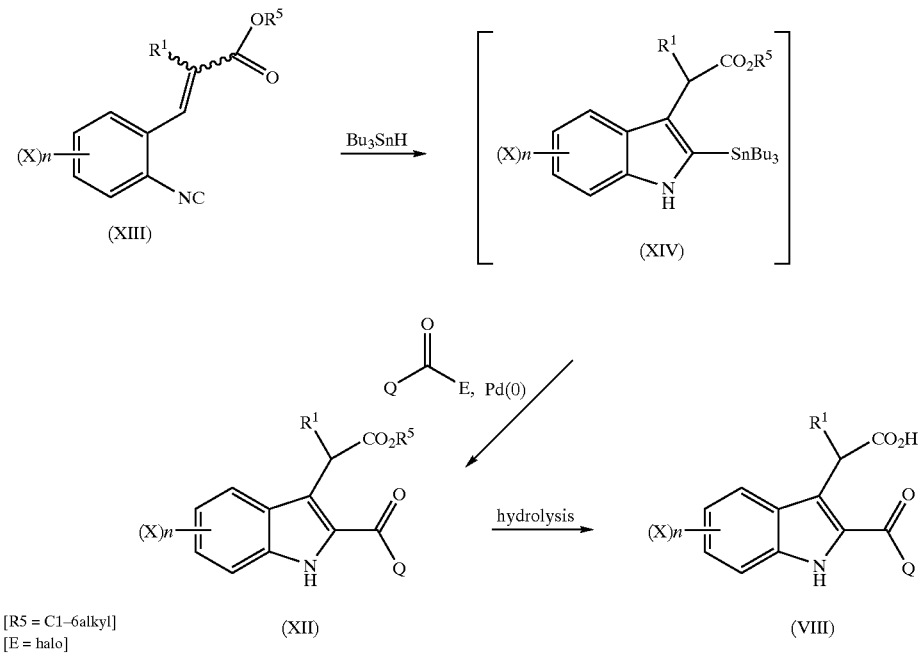

[R5 = C1–6alkyl]
[E = halo]

For example, treatment of a compound of formula (XIII), wherein $R^1$, $R^5$, X and n are as defined above, with a trialkyltin hydride, e.g., tributyltin hydride usually in the presence of a radical initiator such as, 2,2'-azabisisobutyronitrile (AIBN), affords the intermediate 2-stannylindole (XIV) via an intramolecular radical cyclization as described in J. Am. Chem. Soc., 116, 3127, (1994); T. Fukuyama et al. The intermediate (XIV) generated in situ is subsequently treated with an acyl halide, wherein Q and E are as defined above, in the presence of a suitable palladium catalyst according to Stille's procedure (for example see. J. K. Stille et al; J. Am. Chem. Soc., 109, 813, 5478, (1987) and J. Am. Chem. Soc., 106, 4833, (1984)) to afford indole (XII) which may be hydrolyzed to a compound of formula (VIII) by conventional procedure.

Examples of the palladium catalyst are
tetrakis(triphenylphosphine)palladium(0),
dichlorobis(triphenylphosphine)palladium(II),
bis(dibenzylideneacetone)palladium(0),
benzyl(chloro)bis(triphenylphosphine)palladium(II),
bis(acetonitrile)dichloropalladium(II).

Scheme 5:

In another embodiment, a compound of formula (VIII), wherein Q, X, $R^1$ and n are as defined above, may be prepared as illustrated in Scheme 5.

Scheme 5

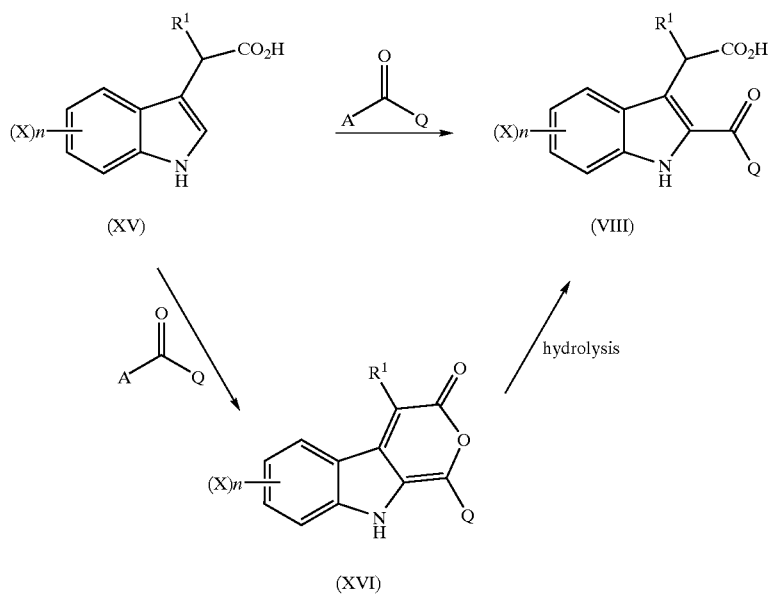

For example, treatment of a compound (XV), wherein $R^1$, X and n are as defined above, is reacted with a compound of formula Q—C(O)—A affords a compound of formula (VIII), or a compound of formula (XVI) (for example see U. Pindur et al., *Liebigs Ann. Chem.*, 601 (1991) and C. J. Moody et al., *J. Chem. Soc. Perkin Trans. I*, 3249 (1988)) which may be hydrolyzed to a compound of formula (VIII) by conventional procedure (for example see E. B. Fray et al., *Tetrahedron*, 49, 439 (1993) and U. Pindur et al., *J. Heterocycl. Chem.*, 29, 145 (1992)). In a compound of formula A—C(O)—Q, A is defined such that the compound of A—C(O)—Q is, for example, an acyl halide, carboxylic acid, carboxylic acid anhydride, a mixed carboxylic sulfonic anhydride, or the like. The reaction may be conducted in the presence or absence of catalyst, preferably in the presence of catalyst such as, boron trifluoride-diethyl ether, tin(IV) chloride, aluminum chloride, ferric chloride, zinc chloride, iodine, iron, or the like. Preferred reaction inert solvents include, but are not limited to, diethyl ether, dichloromethane, 1,2-dichloroethane, carbon disulfide, nitrobenzene or nitromethane. Reaction temperatures are preferably in the range of −78 to 210° C., usually in the range of −10° C. to reflux temperature of solvent, but if necessary, lower or higher temperature can be employed. Reaction time is in general from several minutes to a day, preferably from 30 minutes to 8 hours, however shorter or longer reaction times, if necessary, can be employed.

Scheme 6:

Acetic acid compounds of formulae (VI) and (VIII) as described in the aforementioned schemes may be readily transformed to the corresponding amide, compounds of formulae (XVII) and (XVIII), or ester, compound of formula (XII), by any conventional method known to those skilled in the art.

Scheme 6

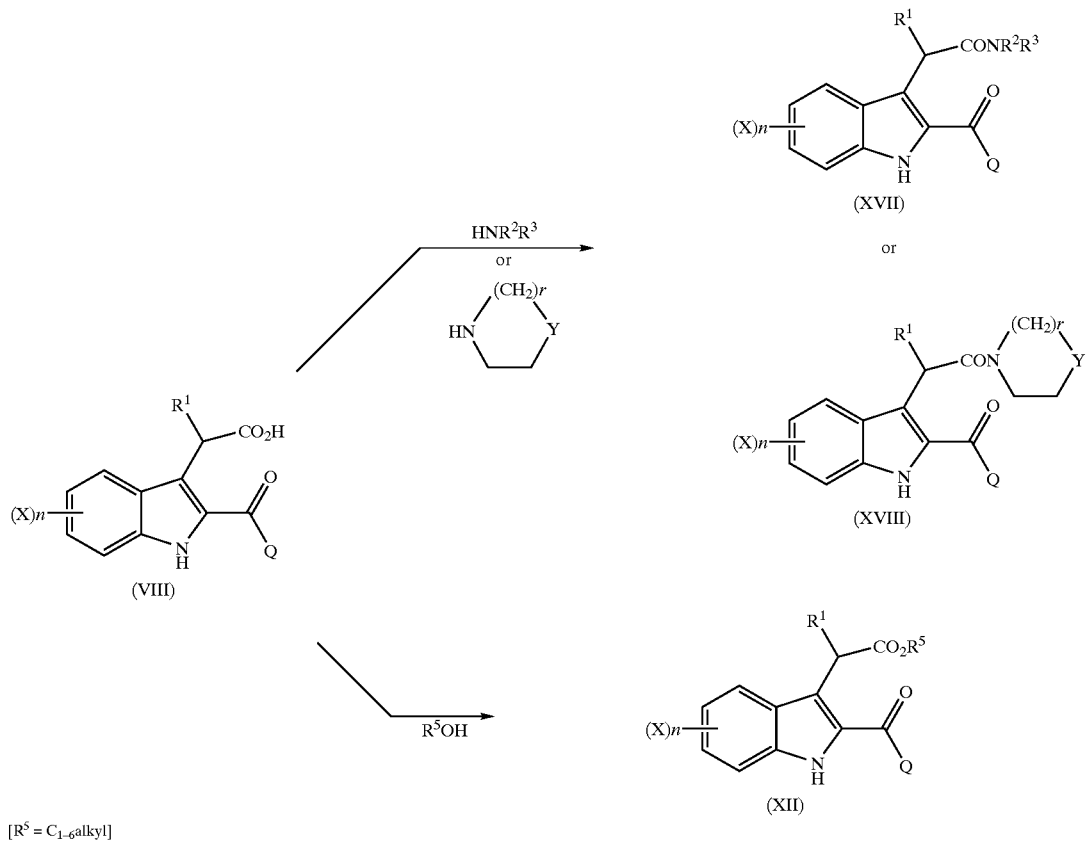

As depicted in Scheme 6, compounds of formulae (XVII) and (XVIII) can be readily prepared by treating the requisite acetic acid compounds of formulae (VI) and (VIII) with an appropriate amine, wherein $R^2$, $R^3$, Y and r are as described herein before, in the presence of a suitable coupling reagent such as, but not limited to, 1-(dimethylaminopropyl)-3-ethylcarbodiimide (WSC), N,N'-dicyclohexylcarbodiimidazole (DCC), carbonyldiimidazole, diethylphosphorocyanidate (DEPC), or the like. Preferred reaction inert solvents include, but are not limited to, acetone, acetonitrile, dichloromethane, 1,2-dichloroethane, N,N-dimethylformamide (DMF), N,N-dimethylacetamide (DMA), dimethylsulfoxide (DMSO), dioxane, tetrahydrofuran (THF) or pyridine. Reaction temperatures are preferably in the range of 40 to 150° C., usually in the range of 15° C. to reflux temperature of solvent, but if necessary, lower or higher temperature can be employed. Reaction time is in general from several minutes to a day, preferably from 30 minutes to 8 hours, however shorter or longer reaction times, if necessary, can be employed. The compounds of formulae (VI) and (VIII) can also be readily transformed to the corresponding ester by conventional methods.

Scheme 7

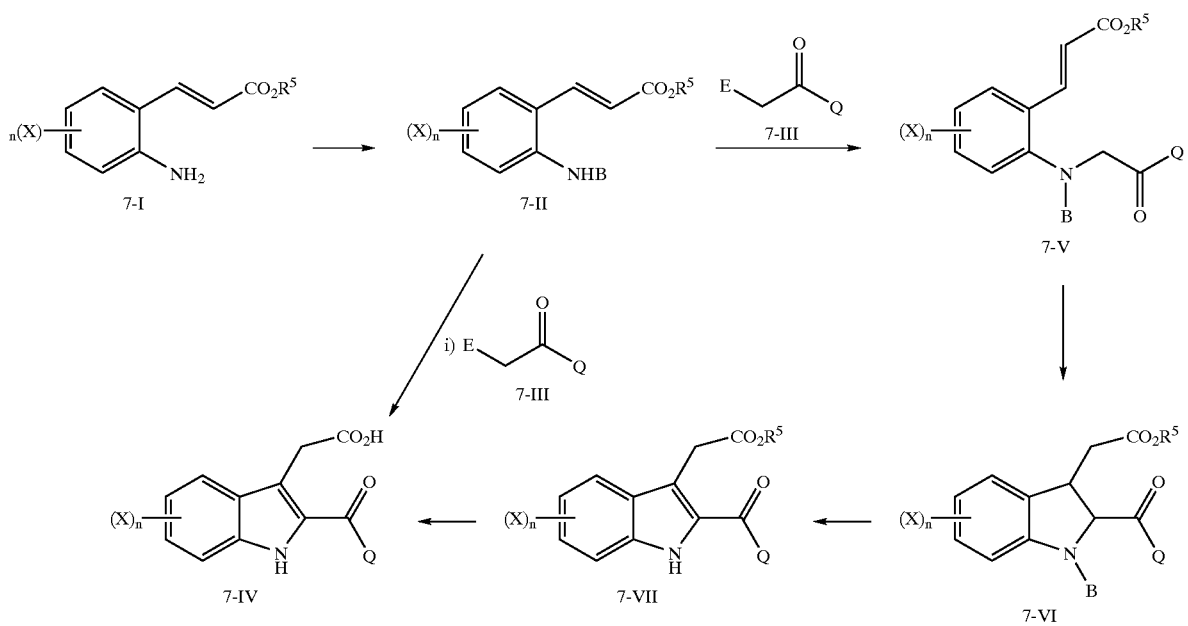

(wherein B is a suitable protecting group, $R^5$ is $C_{1-6}$ alkyl, E is halo, Q, X and n is as defined above.)

In Scheme 7, the starting material of formula 7-I may be prepared according to methods familiar to those of ordinary skill in the art, including one or more synthetic procedures described in R. W. Carling, P. D. Leeson, K. Moore, J. D. Smith, C. R. Moyes, J. Med. Chem., 1993, pages 3397–3408.

The compound of formula 7-II is prepared from a compound of formula 7-I by treatment with a base and an electrophile in a suitable solvent. Suitable bases include such as triethylamine, diisopropylethylamine, or pyridine optionally substituted by 1 to 3 ($C_1$–$C_4$)alkyl groups, preferably pyridine. Suitable electrophiles include methanesulfonyl chloride or anhydride, or phenylsulfonyl chloride wherein the phenyl moiety of said phenylsulfonyl optionally includes 1 or 2 substituents selected from halo, nitro, and ($C_1$–$C_4$)alkyl. Suitable solvents include dichloromethane, dichloroethane, methyl t-butyl ether, disopropyl ether or toluene, preferably dichloromethane. The temperature of the aforesaid reaction may range from about 0° C. to about 50° C., preferably about room temperature (20–25° C.) for a period of about 1 to 30 hours, preferably about 18 hours.

The compound of formula 7-IV is prepared from a compound of formula 7-II by treatment with a first base and an alkylating agent of the formula 7-III in the presence of a solvent followed by reaction with a second base followed by reaction with an acid. Suitable first bases include potassium carbonate, potassium bicarbonate, sodium bicarbonate, sodium carbonate or cesium carbonate, preferably potassium carbonate. Suitable solvents include N,N-dimethylacetamide, N,N-dimethylformamide, methyl ethyl ketone, acetone or tetrahydrofuran, preferably N,N-dimethylaetamide. The aforesaid reaction is performed at a temperature ranging from about 0° C. to about 100° C., preferably room temperature (20–25° C.), for a period of time of about 10 minutes to 5 hours, typically 15 minutes. Suitable second bases include an aqueous solution of a base such as sodium hydroxide, potassium hydroxide, sodium carbonate, potassium carbonate, sodium t-pentoxide (followed by water), sodium methoxide (followed by water) or potassium t-butoxide (followed by water), preferably sodium hydroxide. The reaction with the second base is performed at a temperature ranging from about 20° C. to about 120° C., preferably 100° C., for a period of time of about 1 hour to 24 hours, typically 8 hours. Suitable acids include aqueous hydrochloric acid, hydrobromic acid, sulfuric acid or ammonium chloride, preferably hydrochloric acid. The reaction with the acid is performed at a temperature ranging from about 0° C. to about 50° C., preferably about 20° C. to about 25° C., for a period of time of about ½ hour to about 6 hours, typically about 1 hour.

Alternatively, the conversion of the compound of formula 7-II to a compound of formula 7-IV can be accomplished stepwise. The compound of formula 7-V may be prepared from a compound of formula 7-II by treatment with a base and an alkylating agent of formula 7-III in the presence of a solvent. Suitable bases include potassium carbonate, potassium bicarbonate, sodium bicarbonate, sodium carbonate, or cesium carbonate, preferably potassium carbonate. Suitable solvents include N,N-dimethylacetamide, N,N-dimethylformamide, methyl ethyl ketone, acetone or tetrahydrofuran, preferably N,N-dimethylacetamide. The temperature for the aforesaid reaction may range from about 0° C. to about 50° C., preferably room temperature (20–25° C.), for a period of time of about 10 minutes to 40 minutes, typically 30 minutes.

The compound of formula 7-VI is prepared from a compound of formula 7-V by reaction with a base in the presence of a solvent. Suitable bases include potassium carbonate, potassium bicarbonate, sodium bicarbonate, sodium carbonate or cesium carbonate, preferably potassium carbonate. Suitable solvents include N,N-dimethylacetamide, N,N-dimethylformamide, methyl ethyl ketone, acetone or tetrahydrofuran, preferably N,N-dimethylacetamide. The temperature for the aforesaid reaction may range from about 0° C. to about 50° C., preferably room temperature (20–25° C.), for a period of about 1 hour to 6 hours, preferably 4 hours.

The compound of formula 7-VII is prepared from a compound of formula 7-VI by reaction with a base in a suitable solvent. Suitable bases include 1,8-diazabicyclo[5.4.0]undec-7-ene, 1,5-diazabicyclo[4.3.0]non-5-ene, 1,1,3,3-tetramethylguanidine, sodium t-pentoxide, sodium methoxide or potassium t-butoxide, preferably 1,8-diazabicyclo[5.4.0]undec-7-ene methoxide or potassium t-butoxide. Suitable solvents include N,N-dimethylacetamide, N,N-dimethylformamide, methyl ethyl ketone, acetone or tetrahydrofuran, preferably N,N-dimethylacetamide. The temperature for the aforesaid reaction may range from about 0° C. to 100° C., preferably room temperature (20–25° C.), for a period of 30 minutes to 5 hours, preferably 1 hour.

The compound of formula 7-IV is prepared from a compound of formula 7-VII by treatment with a base in a suitable solvent. Suitable bases include sodium hydroxide, potassium hydroxide, sodium carbonate, potassium carbonate, sodium bicarbonate, potassium bicarbonate, sodium t-pentoxide, sodium methoxide, sodium ethoxide or potassium t-butoxide, preferably sodium hydroxide. Suitable solvents include an aqueous mixture of methanol, ethanol, isopropyl alcohol or tetrahydrofuran, preferably methanol, containing water. The temperature of the aforesaid reaction may range from about 10° C. to 100° C., preferably room temperature (20–25° C.), for a period of 12 to 48 hours, preferably 24 hours, to provide the carboxylate salt of compound of formula 7-IV which can then be treated with an acid to provide the compound of formula 7-IV.

The compound of formula 7-VI has asymmetric atoms and therefore exist in different enantiomeric and diastereomeric forms. Diastereomeric mixtures can be separated into their individual diastereomers on the basis of their physical chemical differences by methods known to those skilled in the art, for example, by chromatography or fractional crystallization. The use of all such isomers, including diastereoisomer mixtures and pure enantiomers, are considered to be part of the present invention.

The starting materials in the aforementioned general syntheses may be obtained by conventional methods known to those skilled in the art. The preparation of such starting materials is described within the accompanying non-limiting examples which are provided for the purpose of illustration only. Alternatively, requisite starting materials may be obtained by analogous procedures, or modifications thereof, to those described hereinafter.

The products which are addressed in the aforementioned general syntheses and illustrated in the experimental examples described herein after may be isolated by standard methods and purification can be achieved by conventional means known to those skilled in the art, such as distillation, crystallization or chromatography techniques.

Certain compounds described herein contain one or more asymmetric centers and are capable of existing in various stereoisomeric forms. The present invention contemplates all such possible stereoisomers as well as their racemic and resolved, enantiomerically pure forms and pharmaceutically acceptable salts thereof Certain compounds of the present invention are capable of forming addition salts with inorganic or organic acids. The pharmaceutically acceptable acid salts of the compounds of formula (I) are those which form non-toxic addition salts, such as, but not limited to, the hydrochloride, hydrobromide, sulfate or bisulfate, acetate, benzoate, besylate, citrate, fumarate, glucuronate, hippurate, lactate, tartrate, saccharate, succinate, maleate, methanesulfonate, p-toluenesulfonate, phosphate and pamoate (i.e., 4,4'-methylene-bis-(3-hydroxy-2-naphthoate)) salts. The pharmaceutically acceptable acid salts may be prepared by conventional techniques.

Certain compounds of the present invention are capable of forming pharmaceutically acceptable non-toxic cations. Pharmaceutically acceptable non-toxic cations of compounds of formula (I) may be prepared by conventional techniques by, for example, contacting said compound with a stoichiometric amount of an appropriate alkali or alkaline earth metal (sodium, potassium, calcium and magnesium) hydroxide or alkoxide in water or an appropriate organic solvent such as ethanol, isopropanol, mixtures thereof, or the like.

Also included within the scope of this invention are bioprecursors (also called pro-drugs) of the compounds of the formula (I). A bioprecursor of a compound of the formula (I) is a chemical derivative thereof which is readily converted back into the parent compound of the formula (I) in biological systems. In particular, a bioprecursor of a compound of the formula (I) is converted back to the parent compound of the formula (I) after the bioprecursor has been administered to, and absorbed by, a mammalian subject, e.g., a human subject. When the compounds of the formula (I) of this invention may form solvates such as hydrates, such solvates are included within the scope of this invention.

An example of prodrug of the compound of formula (I) is a compound of the formula (I), wherein the 1st position of indole ring is substituted with a group selected from hydroxymethyl, —C(O)—$C_{1-4}$ alkyl, —C(O)—(NH$_2$)CH—($C_{1-4}$ alkyl), —C(O)-phenyl, —CH$_2$NHC(O)-aryl, —CH$_2$—$C_{1-4}$ alkyl-O—C(O)—$C_{1-4}$ alkyl, —$C_{1-4}$ alkyl-pyridyl, —C(O)CH$_2$NR$_2$ and —CH$_2$N($C_{1-4}$ alkyl)$_2$.

Another example of prodrug of the compound of formula (I) is a compound of the formula (I), wherein the carboxyl group is substituted with a group selected from $C_{1-4}$ alkyl, —CH$_2$—$C_{1-4}$ alkyl-O—C(O)—$C_{1-4}$ alkyl, —CH$_2$—$C_{1-4}$ alkyl-O—C(O)—N($C_{1-4}$ alkyl)$_2$, —CH$_2$C(O)—N($C_{1-4}$ alkyl)$_2$, —CH$_2$—$C_{1-4}$ alkyl-O—C(O)—O—$C_{1-4}$alkyl, ethyl-OH and —CH$_2$CO$_2$H.

The compounds of the formula (I) of this invention can be administered via either the oral, parenteral or topical routes to mammals. In general, these compounds are most desirably administered to humans in doses ranging from 0.01 mg to 100 mg per kg of body weight per day, although variations will necessarily occur depending upon the weight, sex and condition of the subject being treated, the disease state being treated and the particular route of administration chosen. However, a dosage level that is in the range of from 0.01 mg to 10 mg per kg of body weight per day, single or divided dosage is most desirably employed in humans for the treatment of abovementioned diseases.

The compounds of the present invention may be administered alone or in combination with pharmaceutically acceptable carriers or diluents by either of the above routes previously indicated, and such administration can be carried out in single or multiple doses. More particularly, the novel therapeutic agents of the invention can be administered in a wide variety of different dosage forms, i.e., they may be combined with various pharmaceutically acceptable inert carriers in the form of tablets, capsules, lozenges, trochees, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various nontoxic organic solvents, etc. Moreover, oral pharmaceutical compositions can be suitably sweetened and/or flavored. In general, the therapeutically-effective compounds of this invention are present in such dosage forms at concentration levels ranging 5% to 70% by weight, preferably 10% to 50% by weight.

For oral administration, tablets containing various excipients such as microcrystalline cellulose, sodium citrate, calcium carbonate, dipotassium phosphate and glycine may be employed along with various disintegrants such as starch and preferably corn, potato or tapioca starch, alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatine capsules; preferred materials in this connection also include lactose or milk sugar as well as high molecular weight polyethylene grycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various combinations thereof.

For parenteral administration, solutions of a compound of the present invention in either sesame or peanut oil or in aqueous propylene glycol may be employed. The aqueous solutions should be suitably buffered (preferably pH>8) if necessary and the liquid diluent first rendered isotonic. These aqueous solutions are suitable for intravenous injection purposes. The oily solutions are suitable for intra-articular, intra-muscular and subcutaneous injection purposes. The preparation of all these solutions under sterile conditions is readily accomplished by standard pharmaceutical techniques well-known to those skilled in the art. Additionally, it is also possible to administer the compounds of the present invention topically when treating inflammatory conditions of the skin and this may preferably be done by way of creams, jellies, gels, pastes, ointments and the like, in accordance with standard pharmaceutical practice.

The compounds of formula (I) may also be administered in the form of suppositories for rectal or vaginal administration of the active ingredient. These compositions can be prepared by mixing the active ingredient with a suitable non-irritating excipient which is solid at room temperature (for example, 10° C. to 32° C.) but liquid at the rectal temperature and will melt in the rectum or vagina to release the active ingredient. Such materials are polyethylene glycols, cocoa butter, suppository and wax.

For buccal administration, the composition may take the form of tablets or lozenges formulated in conventional manner.

Combination With Other Drugs:

Compounds of Formula I would be useful for, but not limited to, the treatment of inflammation in a subject, and for treatment of other inflammation-associated disorders, such as, as an analgesic in the treatment of pain and headaches, or as an antipyretic for the treatment of fever. For example, combinations of the invention would be useful to treat arthritis, including but not limited to rheumatoid arthritis, spondyloarthopathies, gouty arthritis, osteoarthritis, systemic lupus erythematosus and juvenile arthritis. Such combinations of the invention would be useful in the treatment of asthma, bronchitis, in menstrual cramps, tendinitis, bursitis, and skin related conditions such as psoriasis, eczema, burns and dermatitis. Combinations of the invention also would be useful to treat gastrointestinal conditions such as inflammatory bowel disease. Crohn's disease, gastritis, irritable bowel syndrome and ulcerative colitis and for the prevention of colorectal cancer. Combinations of the invention would be useful in creating inflammation in such diseases as vascular diseases, migraine headaches, periarteritis nodosa, thyroiditis, aplastic anemia, Hodgkin's disease, sclerodoma, rheumatic fever, type I diabetes, myasthenia gravis, multiple sclerosis, sarcoidosis, nephrotic syndrome, Behcet's syndrome, polymyositis, gingivitis, hypersensitivity, Conjunctivitis, swelling occurring after injury, myocardial ischemia, and the like. The combinations would also be useful for the treatment of certain central nervous system disorders such as Alzheimer's disease and dimentia. The combinations of the invention are useful as anti-inflammatory agents, such as for the treatment of arthritis, with the additional benefit of having significantly less harmful side effects. These compositions would also be useful in the treatment of allergic rhinitis, respiratory distress syndrome, endotoxin shock syndrome, atherosclerosis and central nervous system damage resulting from stroke, ischemia and trauma.

Compounds of formula (I) will be useful as a partial or complete substitute for conventional NSAID's in preparations wherein they are presently co-administered with other agents or ingredients. Thus, the invention encompasses pharmaceutical compositions for treating COX-2 mediated diseases as defined above comprising a non-toxic therapeutically effective amount of the compound of formula (I) and one or more ingredients such as another pain reliever including acetaminophen or phenacetin; a potentiator including caffeine; an $H_2$-antagonist, aluminom or magnesium hydroxide, simethicone, a decongestant including phenylephrine, phenylproanolamine, psuedophedrine, oxymetazoline, ephinephrine, naphazoline, xylometazoline, propylhexedrine, or levodesoxyephedrine; an antiitussive including codeine, hydrocodone, caramiphen, carbetapentane, or dextramethorphan; a prostaglandin including misoprostol, enprostil, rioprostil, ornoprotol or rosaprostol; a diuretic; a sedating or non-sedating antihistamine; anticancer agents such as angiostatin and endostatin; anti-Alzheimers such as Doepezil and Tacrine hydrochloride; and TNF alpha inhibitors such as Etanercept.

These cyclooxygenase inhibitors can further be used in combination with a nitric oxide inhibitors disclosed in WO 96/28145.

Also, the invention encompasses pharmaceutical compositions for treating COX-2 mediated diseases as defined above comprising a non-toxic therapeutically effective amount of the compound of formula (I) and one or more anti-ulcer agent and/or prostaglandins, which are disclosed in WO 97/11701.

The useful prostaglandins include misoprostol, plus-minus methyl 11α,16-dihydroxy-16-methyl-9-oxoprost 13E-en-1-oate; enisoprost and methyl-7-[2B-[6-(1-cyclopenten-1-yl)-4-hydroxy-4-methyl-1E, 5E-hexadienyl]-3α-hydroxy-5-oxo 1R,1α-cyclopentyl]-4Z-heptenoate. Prostaglandins within the scope of the invention also include arbaprostil, enprostil, rioprostol, nocloprost, mexiprostil, ornoprostol, dimoxaprost, tiprostanide and rosaprostol.

The present compounds may also be used in co-therapies, partially or completely, in place of other conventional antiinflammatories, such as together with steroids, 5-lipoxygenase inhibitors, $LTB_4$ antagonists and $LTA_4$ hydrolase inhibitor's.

An example of $LTB_4$ is disclosed in WO97/29774. Suitable $LTB_4$ inhibitors include, among others, ebselen, Bayer Bay-x-1005, Ciba Geigy compound CGS-25019C, Leo Denmark compound ETH-615, Lilly compound LY-293111, Ono compound ONO4057, Terumo compound TMK-688, Lilly compounds LY-213024, 264086 and 292728, Ono compound ONO-LB457, Searle compound SC-S3228, calcitrol, Lilly compounds LY-210073, LY223982, LY233469, and LY255283, Ono compound ONO-LB-448, Searle compounds SC-41930, SC-50605 and SC-51146, and SK&F compound SKF-104493. Preferably, the $LTB_4$ inhibitors are selected from ebselen, Bayer Bay-x-1005, Ciba Geigy compound CGS-25019C, Leo Denmark compound ETH-61S, Lilly compound LY-293111, Ono compound ONO-4057 and Terumo compound TMK-688.

An example of 5-LO inhibitors is disclosed in WO97/29776. Suitable 5-LO inhibitors include, among others, masoprocol, tenidap, zileuton, pranlukast, tepoxalin, rilopirox, flezelastine hydrochloride, enazadrem phosphate and bunaprolast.

An example of $LTA_4$ hydrolase inhibitors is disclosed in WO97/29774. Suitable $LTA_4$ hydrolase inhibitors include, among others, Rhone-Poulenc Rorer RP-64966.

The administration of the present invention may be for either prevention or treatment purposes. The methods and compositions used herein may be used alone or in conjunction with additional therapies known to those skilled in the art in the prevention or treatment of angiogenesis. Alternatively, the methods and compositions described herein may be used as adjunct therapy. By way of example, the cyclooxygenase-2 inhibitor may be administered alone or in conjunction with other antineoplastic agents or other growth inhibiting agents or other drugs or nutrients.

There are large numbers of antineoplastic agents available in commercial use, in clinical evaluation and in pre-clinical development, which could be selected for treatment of angiogenesis by combination drug chemotherapy. Such antineoplastic agents fall into several major categories, namely, antibiotic-type agents, alkylating agents, antimetabolite agents, hormonal agents, immunological agents, interferon-type agents and a category of miscellaneous agents. Alternatively, other anti-neoplalstic agents, such as metallomatrix proteases inhibitors (MMP), such as MMP-13 inhibitors including batiastat, marimastat. Agouron Pharmaceuticals AG-3340, and Roche R0-32-3555, or alpha,beta, inhibitors may be used.

A first family of antineoplastic agents which may be used in combination with a selective cyclooxygenase-2 inhibitor consists of antimetabolite-type antineoplastic agents. Suitable antimetabolite antineoplastic agents may be selected from the group consisting of 5-FU-fibrinogen, acanthifolic acid, aminothiadiazole, brequinar sodium, carmoftir, Ciba-Geigy CGP-30694, cyclopentyl cytosine, cytarabine phosphate stearate, cytarabine conjugates, Lilly DATHF, Merrel Dow DDFC, dezaguanine, dideoxycytidine, dideoxyguanosine, didox, Yoshitomi DMDC, doxifluridine, Wellcome EHNA, Merck & Co. EX-015, fazarabine, floxuridine, fludarabine phosphate, 5-fluorouracil, N-(2'-furanidyl)-5-fluorouracil, Daiichi Seiyaku F0-152, isopropyl pyrrolizine, Lilly LY-188011, Lilly LY-264618, methobenzaprim, methotrexate, Wellcome MZPES. norspermidine, NCI NSC-127716, NCI NSC-264880, NCI NSC-39661, NCI NSC-612567, Warner-Lambert PALA, pentostatin, piritrexim, plicamycin, Asahi Chemical PL-AC, Takeda TAC-788, thioguanine, tiazofurin, Erbamont TIF, trimetrexate, tyrosine kinase inhibitors, tyrosine protein kinase inhibitors, Taiho UFT and uricytin.

A second family of antineoplastic agents which may be used in combination with a selective cyclooxygenase-2 inhibitor consists of alkylating-type antineoplastic agents. Suitable alkylating-type antineoplastic agents may be selected from the group consisting of Shionogi 254-S, aldo-phosphamide analogues, altretamine, anaxirone, Boehringer Mannheim BBR-2207, bestrabucil, budotitane, Wakunaga CA-102, carboplatin, carmustine, Chinoin-139, Chinoin-153, chlorambucil, cisplatin, cyclophosphamide, American Cyanamid CL-286558, Sanofi CY-233, cyplatate, Degussa D-19-384, Sumimoto DACHP(Myr)2, diphenylspiromustine, diplatinum cytostatic. Erba distamycin derivatives, Chugai DWA-2114R, ITI E09, elmustine, Erbamont FCE-24517, estramustine phosphate sodium, fotemustine, Unimed G-6-M, Chinoin GYKI-17230, hepsulfam, ifosfamide, iproplatin, lomustine, mafosfamnide, mitolactol, Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, Yakult Honsha SN-22, spiromus-tine, Tanabe Seiyaku TA-077, tauromustine, temozolomide, teroxirone, tetraplatin and trimelamol.

A third family of antineoplastic agents which may be used in combination with a selective cyclooxygenase-2 inhibitor consists of antibiotic-type antineoplastic agents. Suitable antibiotic-type antineoplastic agents may be selected from the group consisting of Taiho 4181-A, aclarubicin, actinomycin D, actinoplanone, Erbamont ADR-456, aeroplysinin derivative, Ajinomoto AN-201-II. Ajinomoto AN-3, Nippon Soda anisomycins, anthracycline, azino-mycin-A, bisucaberin, Bristol-Myers BL-6859, Bristol-Myers BMY-25067. Bristol-Myers BMY-25551, Bristol-Myers BMY-26605, Bristol-Myers BMY-27557, Bristol-Myers BMY-28438, bleomycin sulfate, bryostatin-1, Taiho C-1027, calichemycin, chromoximycin, dactinomycin, daunorubicin, Kyowa Hakko DC-102, Kyowa Hakko DC-79, Kyowa Hakko DC-88A, Kyowa Hakko DC89-A1, Kyowa Hakcko DC92-B, ditrisarubicin B, Shionogi DOB-41, doxorubicin, doxorubicin-fibrinogen, elsamicin-A, epirubicin, erbstatin, esorubicin, esperamicin-A1, esperamicin-A1b. Erbamont FCE-21954, Fujisawa FK-973, fostriecin, Fujisawa FR-900482, glidobactin, gregatin-A, grincamycin, herbimycin, idarubicin, illudins, kazusamycin, kesarirhodins, Kyowa Hakko KM-5539, Kirin Brewery KRN-8602, Kyowa Hakko KT-5432, Kyowa Hakko KT-5594, Kyowa Hakko KT-6149, American Cyanamid LL-D49194, Meiji Seika ME 2303, menogaril, mitomycin, mitoxantrone, SmithKline M-TAG, neoenactin, Nippon Kayaku NK-313, Nippon Kayaku NKT-O1, SRI International NSC-357704, oxalysine, oxaunomycin, peplomycin, pilatin, pirarubicin, porothramycin, pyrindamycin A, Tobishi RA-I, rapamycin, rhizoxin, rodorubicin, sibanomicin, siwenmycin, Sumitomo SM-5887, Snow Brand SN-706, Snow Brand SN-07, sorangicin-A, sparsomycin, SS Pharmaceutical SS-21020, SS Pharmaceutical SS-7313B, SS Pharmaceutical SS-9816B, steffimycin B, Taiho 4181-2, talisomycin, Takeda TAN-868A, terpentecin, thrazine, tricrozarin A, Upjohn U-73975, Kyowa Hakko UCN-10028A, Fujisawa WF-3405, Yoshitomi Y-2S024 and zorubicin.

A fourth family of antineoplastic agents which may be used in combination with the selective cyclooxygenase-2 inhibitor consists of a miscellaneous family of antineoplastic agents selected from the group consisting of alpha-carotene, alpha-difluoromethyl-arginine, acitretin, Biotec AD-5, Kyorin AHC-52, alstonine, amonafide, amphethinile. arnsacrine, Angiostat, ankinomycin, anti-neoplaston AIO, antineoplaston A2, antineoplaston A3, antineoplaston A5, antineoplaston AS2-1, Henkel APD, aphidicolin glycinate, asparaginase, Avarol, baccharin, batracylin, benfluron, benzotript, Ipsen-Beaufour BIM-23015, bisantrene. Bristo-Myers BMY-40481, Vestar boron-1O, bromofosfamide, Wellcome BW-502, Wellcome BW-773, caracemide, carmethizole hydrochloride, Ajinomoto CDAF, chlorsulfaquinoxalone, Chemes CHX-2053, Chemex CHX-1OO, Warner-Lambert CI-921, Warner-Lambert CI-937, Warner-Lambert CI-941, Warner-Lambert CI-958, clanfenur, claviridenone, ICN compound 1259, ICN compound 4711, Contracan, Yakult Honsha CPT-11, crisnatol, curaderm, cytochalasin B, cytarabine, cytocytin, Merz D-609, DABIS maleate, dacarbazine, datelliptinium, didemnin-B, dihaematoporphyrin ether, dihydrolenperone, dinaline, distamycin, Toyo Pharmnar DM-341, Toyo Pharmar DM-75, Daiichi Seiyaku DN-9693, elliprabin, elliptinium acetate, Tsumura EPMTC, ergotamine, etoposide, etretinate, fenretinide, Fujisawa FR-57704, gallium nitrate, genkwadaphnin, Chugai GLA43, Glaxo GR-63178, grifolan NMF-5N, hexadecylphosphocholine, Green Cross HO-221, homoharringtonine, hydroxyurea, BTG ICRF-187, ilmofosine, isoglutamine, isotretinoin. Otsuka JI-36, Ramot K-477, Otsuak K-76COONa, Kureha Chemical K-AM, MECT Corp KI-8110, American Cyanamid L-623, leukoregulin, lonidamine, Lundbeck LU-23-112, Lilly LY-186641, NCI (US) MAP, marycin, Merrel Dow MDL-27048, Medco MEDR-340, merbarone, merocyanine derivatives, methylanilinoacridine, Molecular Genetics MGI-136, minactivin, mitonafide, mitoquidone, mopidamol, motretinide, Zenyaku Kogyo MST-16, N-(retinoyl)amino acids, Nisshin Flour Milling N-021, N-acylated-dehydroalanines, nafazatrom, Taisho NCU-190, nocodazole derivative, Normosang, NCI NSC-145813, NCI NSC-361456, NCI NSC-604782, NCI NSC-95580, octreotide, Ono ON0-112, oquizanocine, Akzo Org-10172, pancratistatin, pazelliptine, Warner-Lambert PD-111707, Warner-Lambert PD-115934, Warner-Lambert PD-131141, Pierre Fabre PE-1OO1, ICRT peptide D, piroxantrone, polyhaematoporphyrin, polypreic acid, Efamol porphyrin, probimane, procarbazine, proglurnide, Invitron protease nexin I, Tobishi RA-700, razoxane, Sapporo Breweries RBS, restrictin-P, retelliptine, retinoic acid, Rhone-Poulenc RP-49532, Rhone-Poulenc RP-56976, SmithKline SK&F-104864, Sumitomo SM-108, Kuraray SMANCS, SeaPharm SP-10094, spatol, spirocyclopropane derivatives, spirogermanium, Unimed, SS Pharmaceutical SS-554, strypoldinone, Stypoldione, Suntory SUN 0237, Suntory SUN 2071, superoxide dismutase, Toyama T-506, Toyama T-680, taxol, Teijin TEI-0303, teniposide, thaliblastine, Eastman Kodak TJB-29, tocotrienol, Topostin, Teijin TT-82, kyowa Hakko UCN-O1, Kyowa Hakko UCN-1028, ukrain, Eastman Kodak USB-006, vinblastine sulfate, vincristine, vindesine, vinestramide, vinorelbine, vintriptol, vinzolidine, withanolides and Yamanouchi YM-534.

Examples of radioprotective agents which may be used in the combination chemotherapy of this invention are AD-5, adchnon, amifostine analogues, detox, dimesna, 1-102, MN-159, N-acylated-dehydroalanines, TGF-Genentech, tiprotimod, amifostine, WR-1511327, FUT-187, ketoprofen transdermal, naburnetone, superoxide dismutase (Chiron) and superoxide disrrtutase Enzon.

Methods for preparation of the antineoplastic agents described above may be found in the literature. Methods for preparation of doxorubicin, for example, are described in U.S. Pat. Nos. 3,590,028 and No. 4,012,448. Methods for preparing metallomatrix protease inhibitors are described in EP 780386, WO97/20824. WO96/15096. Methods for preparing SOD mimics are described in EP 524,101. Methods for preparing alpha,beta, inhibitors are described in WO97/08174.

In addition, the selective COX-2 inhibitor may be administered in conjunction with other antiinflammatory agents for maximum safety and efficacy, including NSAID's, selective COX-1 inhibitors and inhibitors of the leukotriene pathway, including 5-lipoxygenase inhibitors. Examples of NSAID's include indomethacin, naproxen, ibruprofen, salicylic acid derivatives such as aspirin, diclofenac, ketorolac, piroxicam, meloxicam, mefenamic acid, sulindac, tolmetin sodium, zomepirac, fenoprofen, phenylbutazone, oxyphenbutazone, nimesulide, zaltoprofen and letodolac.

Method for Assessing Biological Activities

The activity of the compounds of the formula (I) of the present invention was demonstrated by the following assays.

In Vitro Assays

Human Cell Based COX-1 Assay

Human peripheral blood obtained from healthy volunteers was diluted to 1/10 volume with 3.8% sodium citrate solution. The platelet-rich plasma immediately obtained was washed with 0.14 M sodium chloride containing 12 mM Tris-HCl (pH 7.4) and 1.2 mM EDTA. Platelets were then washed with platelet buffer (Hanks buffer (Ca free) containing 0.2% BSA and 20 mM Hepes). Finally, the human washed platelets (HWP) were suspended in platelet buffer at the concentration of $2.85 \times 10^8$ cells/ml and stored at room temperature until use. The HWP suspension (70 µl aliquots, final $2.0 \times 10^7$ cells/ml) was placed in a 96-well U bottom plate and 10 µl aliquots of 12.6 mM $CaCl_2$ added. Platelets were incubated with A23187 (final 10 µM, Sigma) with test compound (0.1–100 µM) dissolved in DMSO (final concentration; less than 0.01%) at 37° C. for 15 min. The reaction was stopped by addition of EDTA (final 7.7 mM) and $TxB_2$ in the supernatant quantitated by using a radioimmunoassay kit (Amersham) according to the manufacturer's procedure.

Human Cell Based COX-2 Assay

Inhibition of COX-2 Activity After Induction of COX-2 by hIL-1β

The human cell based COX-2 assay was carried out as previously described (Moore et al., Inflam. Res., 45, 54, 1996). Confluent human umbilical vein endothelial cells (HUVECs, Morinaga) in a 96-well U bottom plate were washed with 100 µl of RPMI1640 containing 2% FCS and incubated with hIL-1β (final concentration 300 U/ml, R & D Systems) at 37° C. for 24 hr. After washing, the activated HUVECs were stimulated with A23187 (final concentration 30 µM) in Hanks buffer containing 0.2% BSA, 20 mM Hepes and test compound (0.1 nM–100 µM) dissolved in DMSO (final concentration; less than 0.01%) at 37° C. for 15 min. 6-Keto-$PGF_{1\alpha}$, stable metabolite of $PGI_2$, in the supernatant was quantitated after adequate dilution by using a radioimmunoassay kit (Amersham) according to the manufacturer's procedure.

Inhibition of COX-2 During the Induction Phase

Confluent human umbilical vein endothelial cells (HUVECs, Morinaga) in a 96-well U bottom plate were washed with 100 µl of RPMI1640 containing 2% FCS and test compound (0.1 nM–100 µM) dissolved in DMSO (final concentration; less than 0.01%), and incubated with hIL-1β (final concentration 300 U/ml, R & D Systems) at 37° C. for 24 hr. After washing, the HUVECs were stimulated with A23187 (final concentration 30 µM) in Hanks buffer containing 0.2% BSA and 20 mM Hepes at 37° C. for 15 min. 6-Keto-$PGF_{1\alpha}$, a stable metabolite of $PGI_2$, in the supernatant was quantitated after adequate dilution by using a radioimmunoassay kit (Amersham) according to the manufacturer's procedure.

In Vivo Assays
Carrageenan Induced Foot Edema in Rats

Male Sprague-Dawley rats (5 weeks old, Charles River Japan) were fasted overnight. A line was drawn using a marker above the ankle on the right hind paw and the paw volume (V0) was measured by water displacement using a plethysmometer (Muromachi). Animals were given orally either vehicle (0.1% methyl cellulose or 5% Tween 80) or a test compound (2.5 ml per 100 g body weight). One hour later, the animals were then injected intradermally with λ-carrageenan (0.1 ml of 1% w/v suspension in saline, Zushikagaku) into right hind paw (Winter et al., *Proc. Soc. Exp. Biol. Med.*, 111, 544, 1962; Lombardino et al., *Arzneim. Forsch.*, 25, 1629, 1975) and three hours later, the paw volume (V3) was measured and the increase in volume (V3–V0) calculated. Since maximum inhibition attainable with classical NSAIDs is 60–70%, ED30 values were calculated.

Gastric Ulceration in Rats

The gastric ulcerogenicity of test compound was assessed by a modification of the conventional method (Ezer et al., *J. Pharm. Pharmacol.*, 28, 655, 1976; Cashin et al., *J. Pharm. Pharmacol.*, 29, 330–336, 1977). Male Sprague-Dawley rats (5 weeks old, Charles River Japan), fasted overnight, were given orally either vehicle (0.1% methyl cellulose or 5% Tween 80) or a test compound (1 ml per 100 g body weight). Six hours after, the animals were sacrificed by cervical dislocation. The stomachs were removed and inflated with 1% formalin solution (10 ml). Stomachs were opened by cutting along the greater curvature. From the number of rats that showed at least one gastric ulcer or haemorrhaging erosion (including ecchymosis), the incidence of ulceration was calculated. Animals did not have access to either food or water during the experiment.

Data Analysis

Statistical program packages, SYSTAT (SYSTAT, INC.) and StatView (Abacus Cencepts, Inc.) for Macintosh were used. Differences between test compound treated group and control group were tested for using ANOVA. The $IC_{50}$ ($ED_{30}$) values were calculated from the equation for the log-linear regression line of concentration (dose) versus percent inhibition.

Some compounds prepared in the Working Examples as described herein after were tested by these methods, and showed $IC_{50}$ values of 0.001 µM to 10 µM with respect to inhibition of COX-2.

Also, the above-mentioned most preferred compounds were tested by these methods, and showed $IC_{50}$ values of 0.001 µM to 0.5 µM with respect to inhibition of COX-2.

COX-2 selectivity can be determined by ratio in terms of $IC_{50}$ value of COX-1 inhibition to COX-2 inhibition. In general, it can be said that a compound showing a COX-1/COX-2 inhibition ratio of more than 2 has good COX-2 selectivity.

Some compounds prepared in Examples showed COX-1/COX-2 inhibition ratio of more than 10.

The following examples contain detailed descriptions of the methods of the preparation of compounds of formula (I). These detailed descriptions fall within the scope of the invention and serve to exemplify the above described general synthetic procedures which form part of the invention. These detailed descriptions are presented for illustrative purposes only and are not intended to restrict the scope of the present invention.

EXAMPLES

The invention is illustrated in the following non-limiting examples in which, unless stated otherwise: all operations were carried out at room or ambient temperature, that is, in the range of 18–25° C.; evaporation of solvent was carried out using a rotary evaporator under reduced pressure with a bath of up to 60° C.; reactions were monitored by thin layer chromatography (tlc) and reaction times are given for illustration only; melting points (m.p.) given are uncorrected (polymorphism may result in different melting points); structure and purity of all isolated compounds were assured by at least one of the following techniques: tlc (Merck silica gel 60 F-254 precoated plates), mass spectrometry, nuclear magnetic resonance (NMR) or microanalysis. Yields are given for illustrative purposes only. Flash column chromatography was carried out using Merck silica gel 60 (230–400 mesh ASTM). Low-resolution mass spectral data (EI) were obtained on a Automass 120 (JEOL) mass spectrometer. Low-resolution mass spectral data (ESI) were obtained on a Quattro II (Micromass) mass spectrometer. NMR data was determined at 270 MHz (JEOL JNM-LA 270 spectrometer) using deuterated chloroform (99.8% D) or dimethylsulfoxide (99.9% D) as solvent unless indicated otherwise, relative to tetramethylsilane (TMS) as internal standard in parts per million (ppm); conventional abbreviations used are: s=singlet, d=doublet, t=triplet, q=quartet, m=multiplet, br=broad, etc.

Example 1

Ethyl(2-benzoyl-6-chloro-1H-indol-3-yl)acetate

Step 1. Ethyl trans-4-Chloro-2-nitrocinnamate

To a suspension of sodium hydride (60% w/w dispersion in mineral oil, 4.4 g, 0.11 mol) in THF (150 ml) was added dropwise a solution of triethyl phosphonoacetate (25.0 g, 0.11 mol) in THF (50 ml) at room temperature. After stirring for 1 h. a solution of 4-chloro-2-nitrobenzaldehyde (19.0 g, 0.10 mol) in THF (50 ml) was added. After stirring for an additional 1 h, saturated aqueous ammonium chloride (50 ml) was added and the resulting mixture was extracted with ethyl acetate (300 ml×2). The combined organic extracts were dried (MgSO$_4$) and concentrated to gave 27 g (quant.) of the title compound as brown solids.

$^1$H-NMR (CDCl$_3$) δ: 8.04 (1H, d, J=15.8 Hz), 8.03 (1H, d, J=1.8 Hz), 7.64–7.58 (2H, m), 6.36 (1H, d, J=15.8 Hz), 4.30 (2H, q, J=7.0 Hz), 1.35 (3H, t, J=7.0 Hz).

Step 2. Ethyl trans-2-Amino-4-chlorocinnamate

A mixture of ethyl trans-4-chloro-2-nitrocinnamate (step 1, 27.0 g, 0.11 mol) and sodium hydrosulfite (92 g, 0;53 mol) in THF-H$_2$O (1:1, 500 ml) was stirred at room temperature for 1 h. Saturated aqueous sodium bicarbonate (300 ml) was then added and the mixture was extracted with ethyl acetate (300 ml×2). The combined organic extracts were dried (MgSO$_4$) and concentrated to gave 16.7 g (67%) of the title compound as yellow solids.

$^1$H-NMR (CDCl$_3$) δ: 7.72 (1H, d, J=15.8 Hz), 7.27 (1H, d, J=8.4 Hz), 6.78–6.68 (2H, m), 6.31 (1H, d, J=15.8 Hz), 4.27 (2H, q, J=7.0 Hz), 1.33 (3H, t, J=7.0 Hz).

Step 3. Ethyl trans-4-Chloro-2-formamidocinnamate

A mixture of acetic anhydride (20 ml) and formic acid (10 ml) was heated at 60° C. for 2 h. After cooling to 0° C., a solution of ethyl trans-2-amino-4-chlorocinnamate (step 2, 15.5 g, 0.069 mol) in THF (80 ml) was carefully added. The resulting mixture was allowed to warm to room temperature. After stirring overnight, the mixture was concentrated and the precipitates were collected by filtration. The solids were washed with hexane to give 9.6 g (55%) of the title compound.

$^1$H-NMR (CDCl$_3$) δ: 9.40–9.15 (1H, m), 8.51–8.40 (1H, m), 8.10–7.80 (2H, m), 7.60–7.47 (1H, m), 7.28–7.12 (1H, m), 6.40 (1H, d, J=15.8 Hz), 4.25 (2H, q, J=7.3 Hz), 1.34 (3H, t, J=7.3 Hz).

Step 4. Ethyl trans-4-Chloro-2-isocyanocinnamate

To a solution of triphenylphosphine (5.3 g, 20 mmol) in dichloromethane (80 ml) cooled to 0° C. was added dropwise a solution of triphosgene (2.0 g, 6.7 mmol) in dichloromethane (20 ml). The ice-bath was removed and the resulting mixture stirred at room temperature for 10 min. The mixture was then cooled to 0° C. and a solution of ethyl trans-4-chloro-2-formamidocinnamate (step 3, 5.2 g, 0.020 mol) in dichloromethane (80 ml) was added. The mixture was allowed to warm to room temperature overnight, and then concentrated. The residue was partitioned between water (80 ml) and ethyl acetate (100 ml), the aqueous layer separated and extracted with ethyl acetate (100 ml). The combined organic extracts were dried ($MgSO_4$), solvent removed by evaporation and the crude product was purified by flash column chromatography eluting with ethyl acetate/hexane (1:6) to afford 3.9 g (83%) of the title compound as white solids.

$^1$H-NMR (CDCl$_3$) δ: 7.89 (1H, d, J=16.1 Hz), 7.60 (1H, d, J=8.8 Hz), 7.45 (1H, d, J=1.8 Hz), 7.42 (1H, dd, J=1.8, 8.8 Hz), 6.52 (1H, d, J=16.1 Hz), 4.30 (2H, q, J=7.0 Hz), 1.35 (3H, t, J=7.0 Hz).

Step 5. Ethyl(2-benzoyl-6-chloro-1H-indol-3-yl)acetate

A mixture of ethyl trans-4-chloro-2-isocyanocinnamate (step 4, 1.2 g, 5.1 mmol), tributyltin hydride (1.6 g, 5.6 mmol) and AIBN (43 mg, 0.26 mmol) in acetonitrile (30 ml) was heated at 100° C. After 1 h, tetrakis(triphenylphosphine)palladium (580 mg, 0.50 mmol) and benzoyl chloride (0.65 ml, 5.6 mmol) were added and the mixture was heated for a further 17 h. The mixture was cooled and poured into 2N aqueous HCl (50 ml) and extracted with diethyl ether (80 ml×2). The combined organic extracts were washed with saturated aqueous potassium fluoride (50 ml) and dried ($MgSO_4$). After removal of solvent, the crude product was purified by flash column chromatography eluting with ethyl acetate/hexane (1:5) to afford 0.43 g (25%) of the title compound as white solids.

m.p.: 160–163° C. $^1$H-NMR (CDCl$_3$) δ: 8.94 (1H, br s), 7.82–7.75 (2H, m), 7.67–7.47 (4H, m), 7.37 (1H, d, J=1.8 Hz), 7.13 (1H, dd, J=1.8, 8.4 Hz), 4.11 (2H, q, J=7.3 Hz), 3.78 (2H, s), 1.22 (3H, t, J=7.3 Hz).

Example 2

(2-Benzoyl-6-chloro-1H-indol-3-yl)acetic Acid

Method A

To a solution of ethyl(2-benzoyl-6-chloro-1H-indol-3-yl)acetate (Example 1, 380 mg, 0.11 mmol) in ethanol (15 ml) was added 2N aqueous KOH (5 ml). After heating at 80° C. for 1 h, the mixture was cooled and concentrated, and then 2N aqueous HCl (15 ml) added carefully. The mixture was extracted with diethyl ether (50 ml×2), the combined organic extracts dried ($MgSO_4$) and concentrated. The residual solids were recrystallized from ethyl acetate/hexane to afford 60 mg (17%) of the title compound as pale yellow solids.

m.p.: 183–186° C. IR (KBr) ν: 1700, 1610, 1520, 1425, 1330, 1000 cm$^{-1}$. $^1$H-NMR (DMSO-d$_6$) δ: 12.26 (1H, br s), 11.76 (1H, s), 7.77–7.66 (4H, m), 7.62–7.54 (2H, m), 7.48 (1H, d, J=1.8 Hz), 7.13 (1H, dd, J=1.8, 8.7 Hz), 3.80 (2H, s).

Method B

Step 1. 6-Chloro-1-(phenylsulfonyl)indole

A mixture of 6-chloroindole (Y. Watanabe et al., *J. Org. Chem.*, 1990, 55, 580, 36.2 g, 0.24 mol), tetrabutylammmonium hydrogen sulfate (8.1 g, 0.024 mol) and 50% aqueous KOH (160 ml) in benzene (500 ml) was stirred at room temperature for 10 min. The mixture was then cooled to 0° C. and a solution of benzenesulfonyl chloride in benzene (20 ml) was added. After stirring at room temperature for 3 h, the mixture was poured into water (200 ml), the organic layer separated and the aqueous layer extracted with diethyl ether (200 ml×2). The combined organic extracts were washed with brine (200 ml), dried ($MgSO_4$) and concentrated. The residual solids were washed with ethanol (100 ml×3) to give 58 g (83%) of the title compound as off-white solids.

$^1$H-NMR (CDCl$_3$) δ: 8.02 (1H, s), 7.92–7.85 (2H, m), 7.60–7.40 (5H, m), 7.21 (1H, dd, J=1.8, 8.4 Hz), 6.62 (1H, d, J=3.6 Hz).

Step 2. 6-Chloro-2-benzoyl-1-(phenylsulfonyl)indole

To a stirred solution of 6-chloro-1-(phenylsulfonyl)indole (Step 1, 12.58 g, 43.0 mmol) in THF (270 ml) cooled to −78° C. was added dropwise tert-butyllithium. (32 ml, 52.0 mmol, 1.64 M in n-pentane) with keeping the internal temperature below −65° C. After stirring for 30 min. at −78° C., this solution was transferred via cannula to a solution of benzoyl chloride (6.0 ml, 52.0 mmol) in THF (30 ml) cooled to −78° C. The mixture was stirred for 1.5 h and then quenched with saturated ammonium chloride (200 ml) at −78° C. and allowed to warm to room temperature. The aqueous layer was separated and neutralized with aqueous sodium carbonate, and then extracted with ethyl acetate (50 ml×2). The combined organic extracts were washed with brine (50 ml), dried ($MgSO_4$), and concentrated. Crystallization of the residue from diethyl ether/hexane (1:3) afforded the title compound as white solids (1 4.4 g, 85%).

$^1$H-NMR(CDCl$_3$) δ: 8.20–8.16 (1H, m), 8.14–8.06 (2H, m), 8.01–7.93 (2H, m), 7.66–7.47 (7H, m), 7.29 (1H, dd, J=1.7, 8.5 Hz), 6.89 (1H, J=0.7 Hz).

Step 3. 2-Benzoyl-6-chloroindole

A mixture of 2-benzoyl-6-chloro-1-(phenylsulfonyl)indole (step 2, 48 g, 0.12 mol) and potassium carbonate (80 g, 0.58 mol) in THF-MeOH—H$_2$O (4:2:1, 1100 ml) was heated at reflux temperature overnight. After removal of solvent, the residue was extracted with diethyl ether (300 ml×2) and dried ($MgSO_4$). Removal of solvent gave the crude product as pale brown solids. Recrystallization from ethyl acetate afforded 20 g (65%) of the title compound as white solids.

m.p.: 206–207° C. $^1$H-NMR (CDCl$_3$) δ: 9.31 (1H, br s), 8.01–7.95 (2H m), 7.68–7.47 (5H, m), 7.17–7.12 (2H, m).

Step 4. Diethyl α-Acetoxy-(2-benzoyl-6-chloro-1H-indol-3-yl)malonate

A mixture of 2-benzoyl-6-chloroindole (step 3, 4.0 g, 16 mmol), manganese(III) acetate dihydrate (13 g, 48 mmol), diethyl malonate (14 g, 80 mmol) and sodium acetate (6.6 g, 80 mmol) in acetic acid (150 ml) was heated at 80° C. with stirring for 2h. Manganese(III) acetate dihydrate (3 g, 11 mmol) was added and heating was continued for an additional 2 h. The mixture was cooled and brine (200 ml) was added. The resulting mixture was extracted with diethyl ether (200 ml×2) and the combined organic extracts dried ($MgSO_4$) and concentrated. The residue was purified by flash column chromatography eluting with ethyl acetate/hexane (1:3) to afford 5.2 g (69%) of the title compound as yellow solids.

m.p.: 141–144° C. $^1$H-NMR (CDCl$_3$) δ: 8.84 (1H, br s), 7.90–7.81 (3H, m), 7.66–7.58 (1H, m), 7.51–7.42 (2H, m), 7.38 (1H, d, J=1.3 Hz), 7.15 (1H, dd, J=2.0, 8.7 Hz), 4.30–4.06 (4H, m), 1.70 (3H, s), 1.30–1.58 (6H, m).

Step 5. Diethyl(2-benzoyl-6-chloro-1H-indol-3-yl)malonate

A mixture of diethyl α-acetoxy-(2-benzoyl-6-chloro-1H-indol-3-yl)malonate (step 4. 5.0 g, 11 mmol), trifluoroacetic acid (3.3 ml, 44 mmol) and triethylsilane (2.1 ml, 13 mmol)

in dichloromethane (80 ml) was heated at reflux temperature for 12 h and then cooled and concentrated. The resulting residue was partitioned between saturated sodium bicarbonate (50 ml) and dichloromethane (80 ml). The aqueous layer was separated and extracted with dichloromethane (80 ml). The combined organic extracts were dried (MgSO$_4$) and solvent removed. Crude product was purified by flush column chromatography eluting with ethyl acetate/hexane (1:4) to 10 afford 4.0 g (87%) of the title compound as white solids.

$^1$H-NMR (CDCl$_3$) δ: 8.93 (1H, br s), 7.81–7.70 (3H, m), 7.68–7.60 (1H, m), 7.55–7.48 (2H, m), 7.32 (1H, s), 7.12 (1H, dd, J=1.8, 8.8 Hz), 5.29 (1H, s), 4.26–4.09 (4H, m), 1.21 (6H, t, J=7.1 Hz).

Step 6. (2-Benzoyl-6-chloro-1H-indol-3-yl)acetic Acid

Diethyl(2-benzoyl-6-chloro-1H-indol-3-yl)malonate (step 5, 4.4 g, 11 mmol) in a mixture of ethanol (120 ml) and 2N aqueous NaOH (15 ml) was heated at reflux temperature for 1 h. The mixture was cooled and concentrated, and the residue carefully acidified with 2N aqueous HCl (30 ml). The mixture was extracted with diethyl ether (150 ml×3), and the combined extracts were dried (MgSO$_4$) and concentrated. The residual solids were recrystallized from ethyl acetate/hexane to afford 1.1 g (30%) of the title compound as pale yellow solids.

m.p.: 183–186° C. IR (KBr) ν: 1700, 1610, 1520, 1425, 1330, 1000 cm$^{-1}$. $^1$H-NMR (DMSO-d$_6$) δ: 12.26 (1H, br s), 11.76 (1H, s), 7.77–7.66 (4H, m), 7.62–7.54 (2H, m), 7.48 (1H, d, J=1.8 Hz), 7.13 (1H, dd, J=1.8, 8.7 Hz), 3.80 (2H, s).

Example 3

(2-Benzoyl-6-chloro-1H-indol-3-yl)acetic Acid, Sodium Salt (2-Benzoyl-6-chloro-1H-indol-3-yl)acetic acid (Example 2, 480 mg, 1.5 mmol) in ethanol (10 ml) was treated with 2N aqueous NaOH (0.7 ml, 1.4 mmol) at room temperature for 30 min. and then concentrated. The residue was dissolved in water (10 ml) and washed with diethyl ether (15 ml×2). The aqueous layer was concentrated to afford 350 mg (68%) of the title compound as pale brown solids.

m.p.: 185–189° C. IR (KBr) ν: 1523, 1380, 1230, 1060, 1004, 918 cm$^{-1}$. $^1$H-NMR (DMSO-d$_6$) δ: 11.46 (1H, br s), 7.88–7.84 (21H, m), 7.66 (1H, d, J=8.4 Hz), 7.64–7.46 (3H, m), 7.39 (1H, d, J=1.8 Hz), 7.00 (1H, dd, J=1.8, 8.4 Hz), 3.32 (2H, s).

Example 4

[6-Chloro-2-(2-methylbenzoyl)-1H-indol-3-yl]acetic Acid

Step 2. 6-Chloro-2-(2-methylbenzoyl)-1-(phenylsulfonyl)indole

The title compound was prepared according to the procedure described in step 2 of Example 2 (Method B) from 6-chloro-1-(phenylsulfonyl)indole (step 1 of Example 2, Method B) and o-toluoyl chloride.

tlc: Rf=0.3 (ethyl acetate/hexane=1:10).

Step 2. 6-Chloro-2-(2-methylbenzoyl)indole

The title compound was prepared according to the procedure described in step 3 of Example 2 (Method B) from 6-chloro-2-(2-methylbenzoyl)-1-(phenylsulfonyl)indole (step 1).

$^1$H-NMR (CDCl$_3$) δ: 9.37 (1H, br s), 7.58 (2H, d, J=8.91 Hz), 7.48 (1H, s), 7.42 (1H, dd, J=1.49, 7.75 Hz), 7.34–7.27 (2H, m), 7.12 (2H, dd, J=1.81, 8.56 Hz), 2.44 (3H, s).

Step 3. Diethyl α-Acetoxy-[6-chloro-2-(2-methylbenzoyl)-1H-indol-3-yl]malonate

The title compound was prepared according to the procedure described in step 4 of Example 2 (Method B) from 6-chloro-2-(2-methylbenzoyl)indole (step 2).

$^1$H-NMR (CDCl$_3$) δ: 8.52 (1H, br s), 7.78 (1H, d, J=8.88 Hz), 7.48–7.13 (6H, m), 4.31–4.16 (4H, m), 2.52 (3H, s), 1.96 (3H, s), 1.22 (6H, t, 7.26 Hz).

Step 4. Diethyl[6-chloro-2-(2-methylbenzoyl)-1H-indol-3-yl]malonate

The title compound was prepared according to the procedure described in step 5 of Example 2 (Method B) from diethyl(α-acetoxy-[6-chloro-2-(2-methylbenzoyl)-1H-indol-3-yl]malonate (step 3).

$^1$H-NMR (CDCl$_3$) δ: 9.0 (1H, br s), 7.73 (1H, d, J=8.88 Hz), 7.73–7.09 (5H, m), 7.11 (1H, dd, J=1.97, 8.75 Hz), 4.89 (1H, s), 4.20–4.08 (4H, m), 2.35 (3H, s), 1.19 (6H, t, J=7.1 Hz).

Step 5. [6-Chloro-2-(2-methylbenzoyl)-1H-indol-3-yl]acetic Acid

The title compound was prepared according to the procedure described in step 6 of Example 2 (Method B) from diethyl[6-chloro-2-(2-methylbenzoyl)-1H-indol-3-yl]malonate (step 4).

m.p.: 150–152° C. IR (KBr) ν: 3321, 1717, 1624, 1602, 1568, 1531, 1431, 1319, 1249, 1230 cm$^{-1}$. $^1$H-NMR (DMSO-d$_6$) δ: 11.70 (1H, s), 7.69 (2H, d, 8.72 Hz), 7.51–7.31 (3H, m), 7.10 (2H, dd, J=1.97, 8.56 Hz), 3.57 (2H, s), 2.24 (3H, s).

Example 5

[6-Chloro-2-(3-methylbenzoyl)-1H-indol-3-yl]acetic Acid

Step 1. 6-Chloro-2-(3-methylbenzoyl)-1-(phenylsulfonyl)indole

The title compound was prepared according to the procedure described in step 2 of Example 2 (Method B) from 6-chloro-1-(phenylsulfonyl)indole (step 1 of Example 2, Method B) and m-toluoyl chloride.

tlc: Rf=0.3 (ethyl acetate/hexane=1:10).

Step 2. 6-Chloro-2-(3-methylbenzoyl)indole

The title compound was prepared according to the procedure described in step 3 of Example 2 (Method B) from 6-chloro-2-(3-methylbenzoyl)-1-(phenylsulfonyl)indole (step 1).

$^1$H-NMR (CDCl$_3$) δ: 9.37 (1H, s), 7.77 (2H, br s), 7.64 (1H, d, J=8.56 Hz), 7.47–7.12 (5H, m), 2.47 (3H, s).

Step 3. Diethyl α-Acetoxy-[6-chloro-2-(3-methylbenzoyl)-1H-indol-3-yl]malonate

The title compound was prepared according to the procedure described in step 4 of Example 2 (Method B) from 6-chloro-2-(3-methylbenzoyl)indole (step 2).

$^1$H-NMR (CDCl$_3$) δ: 8.80 (1H, br s), 7.83 (1H, d, J=8.88 Hz), 7.67–7.32 (5H, m), 7.16 (1H, dd, J=1.81, 8.88 Hz), 4.27–4.15 (4H, m), 2.39 (3H, s), 1.72 (3H, s), 1.29 (6H, t, J=7.26 Hz).

Step 4. Diethyl[6-chloro-2-(3-methylbenzoyl)-1H-indol-3-yl]malonate

The title compound was prepared according to the procedure described in step 5 of Example 2 (Method B) from diethyl ac-acetoxy-[6-chloro-2-(3-methylbenzoyl)-1H-indol-3-yl]malonate (step 3).

$^1$H-NMR (CDCl$_3$) δ: 9.21 (1H, br s), 7.71 (1H, d, J=8.51 Hz), 7.59–7.28 (5H, m), 7.10 (1H, dd, J=1.97, 8.72 Hz), 5.27 (1H, s), 4.23–4.07 (4H, m), 2.40 (3H, s), 1.21 (6H, t, J=7.1 Hz).

Step 5. [6-Chloro-2-(3-methylbenzoyl)-1H-indol-3-yl]acetic Acid

The title compound was prepared according to the procedure described in step 6 of Example 2 (Method B) from diethyl[6-chloro-2-(3-methylbenzoyl)-1H-indol-3-yl] malonate (step 4).

m.p.: 182–184° C. IR (KBr) ν: 3313, 1699, 1616, 1568, 1533, 1408, 1325, 1265, 1203 cm$^{-1}$. $^1$H-NMR (DMSO-d$_6$) δ: 11.75 (1H, s), 7.70 (1H, d,J=8.75), 7.55–7.46 (5H, m), 7.12 (1H, dd, J=1.97, 8.72 Hz), 3.75 (2H, s), 2.39 (3H, s).

Example 6

[6-Chloro-2-(4-methylbenzoyl)-1H-indol-3-yl]acetic Acid

Step 1. 6-Chloro-2-(4-methylbenzoyl)-1-(phenylsulfonyl) indole

The title compound was prepared according to the procedure described in step 2 of Example 2 (Method B) from 6-chloro-1-(phenylsulfonyl)indole (step 1 of Example 2, Method B) and p-toluoyl chloride.

tlc: Rf=0.3 (ethyl acetate/hexane=1:10).

Step 2. 6-Chloro-2-(4-methylbenzoyl)indole

The title compound was prepared according to the procedure described in step 3 of Example 2 (Method B) from 6-chloro-2-(4-methylbenzoyl)-1-(phenylsulfonyl)indole (step 1).

$^1$H-NMR (CDCl$_3$) δ: 9.37 (1H, br s), 7.90 (2H, d, J=8.6 Hz), 7.63 (1H, d, J=8.9 Hz), 7.48 (1H, s), 7.34 (2H, d, J=8.6 Hz), 7.16–7.10 (2H, m), 2.47 (3H, s).

Step 3. Diethyl α-Acetoxy-[6-chloro-2-(4-methylbenzoyl)-1H-indol-3-yl]malonate

The title compound was prepared according to the procedure described in step 4 of Example 2 (Method B) from 6-chloro-2-(4-methylbenzoyl)indole (step 2).

$^1$H-NMR (CDCl$_3$) δ: 8.65 (1H, br s), 7.84 (1H, d, J=8.9 Hz), 7.76 (2H, d, J=8.2 Hz), 7.39–7.37 (1H, m), 7.27 (2H, d, J=8.2 Hz), 7.16 (1H, dd, J=1.8, 8.2 Hz), 4.36–4.16 (4H, m), 2.44 (3H, s), 1.72 (3H, s), 1.34–1.22 (6H, m).

Step 4. Diethyl[6-chloro-2-(4-methylbenzoyl)-1H-indol-3-yl]malonate

The title compound was prepared according to the procedure described in step 5 of Example 2 (Method B) from diethyl α-acetoxy-[6-chloro-2-(4-methylbenzoyl)-1H-indol-3-yl]malonate (step 3).

$^1$H-NMR (CDCl$_3$) δ: 8.83 (1H, br s), 7.76 (1H, d, J=8.7 Hz), 7.71 (2H, d, J=8.2 Hz), 7.39–7.36 (1H, m), 7.32 (2H, d, J=8.2 Hz), 7.14 (1H, dd, J=2.0, 8.7 Hz), 5.30 (1H, s), 4.26–4.14 (4H, m), 2.47 (3H, s), 1.22 (6H, t, J=7.1 Hz).

Step 5. [6-Chloro-2-(4-methylbenzoyl)-1H-indol-3-yl] acetic Acid

The title compound was prepared according to the procedure described in step 6 of Example 2 (Method B) from diethyl[6-chloro-2-(4-methylbenzoyl)-1H-indol-3-yl] malonate (step 4).

m.p.: 182–184° C. IR (KBr) ν: 3321, 1705, 1616, 1602, 1566, 1529, 1431, 1323, 1257, 1230 cm$^{-1}$. $^1$H-NMR (DMSO-d$_6$) δ: 11.72 (1H, s), 7.74–7.64 (3H, m), 7.49–7.45 (1H, m), 7.39 (2H, d, J=8.1 Hz), 7.16–7.09 (1H, m), 3.81 (2H, s), 2.43 (3H, s).

Example 7

[6-Chloro-2-(3-chlorobenzoyl)-1H-indol-3-yl]acetic Acid

Step 1. 6-Chloro-2-[(N-methoxy-N-methylamino)carbonyl] indole

To a stirred suspension of 6-chloroindole-2-carboxylic acid (H. N. Rydon and J. C. Tweddle, *J. Chem. Soc.*, 1955, 3499., 7.0 g, 36 mmol) in thionyl chloride (30 ml) was added dropwise DMF (1 ml). After stirring for 30 min., the mixture was concentrated, and the residue was dissolved in dichloromethane (100 ml) and cooled to 0° C. To the mixture was added N,O-dimethylhydroxylamine hydrochloride (7.0 g, 72 mmol) and pyridine (15 ml). After stirring 2 h, the mixture was quenched with water (100 ml), and extracted with dichloromethane (150 ml×2). The combined organic extracts were washed with 2N aqueous HCl (100 ml), saturated sodium bicarbonate (100 ml), brine (100 ml), and dried (MgSO$_4$). Removal of solvent afforded 8.2 g (96%) of the title compound as yellow solids.

$^1$H-NMR (CDCl$_3$) δ: 9.48 (1H, br s), 7.60 (1H, d, J=8.6 Hz), 7.46–7.41 (1H, m), 7.22–7.18 (1H, m), 7.11 (1H, dd, J=8.6, 1.8 Hz), 3.85 (3H, s), 3.44 (3H, s).

Step 2. 6-Chloro-2-(3-chlorobenzoyl)indole

To a stirred solution of 6-chloro-2-[(N-methoxy-N-methylamino)carbonyl]indole (step 1, 610 mg, 2.56 mmol) and 3-bromochlorobenzene (1.47 g, 7.67 mmol) in THF (20 ml) at −78° C. was added dropwise n-butyllithium (1.54M in hexane, 4.90 ml, 7.67 mmol). After stirring for 1 h, the mixture was quenched with saturated ammonium chloride (20 ml), and extracted with ethyl acetate (50 ml×2). The combined organic extracts were washed with 2N aqueous HCl (50 ml), saturated sodium bicarbonate (50 ml), brine (50 ml), and dried (MgSO$_4$). After removal of solvent, the crude product was purified by flash column chromatography eluting with ethyl acetate/hexane (1:10) to afford 565 mg (76%) of the title compound as pale brown solids.

$^1$H-NMR (CDCl$_3$) δ: 9.31 (1H, br s), 7.94 (1H, t, J=1.9 Hz), 7.85 (1H, dt, J=1.9, 7.6 Hz), 7.65 (1H, d, J=8.4 Hz), 7.63–7.58 (1H, m), 7.52–7.45 (2H, m), 7.18–7.12 (2H, m).

Step 3. Diethyl α-Acetoxy-[6-chloro-2-(3-chlorobenzoyl)-1H-indol-3-yl]malonate

The title compound was prepared according to the procedure described in step 4 of Example 2 (Method B) from 6-chloro-2-(3-chlorobenzoyl)indole (step 2).

$^1$H-NMR (CDCl$_3$) δ: 8.88 (1H, br s), 7.87–7.74 (3H, m), 7.61–7.56 (1H, m), 7.43 (1H, d, J=7.6 Hz), 7.41–7.38 (1H, m), 7.20–7.14 (1H, m), 4.30–4.14 (4H, m), 1.74 (3H, s), 1.20 (6H, t, J=8.2 Hz).

Step 4. Diethyl[6-chloro-2-(3-chlorobenzoyl)-1H-indol-3-yl]malonate

The title compound was prepared according to the procedure described in step 5 of Example 2 (Method B) from diethyl α-acetoxy-[6-chloro-2-(3-chlorobenzoyl)-1H-indol-3-yl]malonate (step 3).

$^1$H-NMR (CDCl$_3$) δ: 8.87 (1H, br s), 7.79–7.74 (2H, m), 7.70–7.58 (2H, m), 7.47 (1H, t, J=8.1 Hz), 7.39–7.37 (1H, m), 7.15 (1H, dd, J=1.8, 8.7 Hz), 5.19 (1H, s), 4.27–4.10 (4H, m), 1.22 (6H, t, J=7.1 Hz).

Step 5. [6-Chloro-2-(3-chlorobenzoyl)-1H-indol-3-yl]acetic Acid

The title compound was prepared according to the procedure described in step 6 of Example 2 (Method B) from diethyl[6-chloro-2-(3-chlorobenzoyl)-1H-indol-3-yl] malonate (step 4).

m.p.: 199–201° C. $^1$H-NMR (DMSO-d$_6$) δ: 12.25 (1H, br s), 11.81 (1H, s), 7.79–7.57 (5H, m), 7.48 (1H, d, J=1.8 Hz), 7.14 (1H, dd, J=1.8, 8.7 Hz), 3.81 (2H, s).

Example 8

Methyl[6-chloro-2-(4-chlorobenzoyl)-1H-indol-3-yl] acetate

Method A

Step 1. Methyl trans 4-Chloro-2-(phenylsulfonylamino) cinnamate

To a solution of methyl trans-2-amino-4-chlorocinnamate (R. W. Carling et al., *J. Med. Chem.*, 1993, 36, 3397., 30.7 g, 0.15 mol) and pyridine (36 ml, 0.45 mol) in dichloromethane (500 ml) was added benzenesulfonyl chloride (20 ml, 0.16 mol). After stirring for 20 h, methanol (50 ml) was added and the mixture was concentrated. The residual solids were dissolved in dichloromethane (700 ml) and washed with 2N aqueous HCl (150 ml), brine (150 ml) and dried (MgSO$_4$). After removal of solvent, the residual solids were recrystallized from ethanol to give 40 g (76%) of the title compound as pale yellow solids.

$^1$H-NMR (CDCl$_3$) δ: 7.77–7.71 (2H, m), 7.59–7.52 (1H, m), 7.48–7.35 (5H, m), 7.20 (1H, dd, J=2.0, 8.4 Hz), 6.85 (1H, br s), 6.15 (1H, d, J=15.8 Hz), 3.78 (3H, s).

Step 2. Methyl[6-chloro-2-(4-chlorobenzoyl)-1-(phenylsulfonyl)indolin-3-yl]acetate A mixture of methyl trans-4-chloro-2-(phenylsulfonylamino)cinnamate (step 1, 1.1 g, 3.1 mmol), 4-chlorophenacylbromide (1.1 g, 4.6 mmol) and potassium carbonate (2.1 g, 15.4 mmol) in acetone (10 ml) was stirred at room temperature for 1.5 h. The mixture was filtered and the filtrate concentrated. The residual solids were recrystallized from ethyl acetate/hexane to afford 0.91 g (59%) of the title compound as pale yellow solids.

$^1$H-NMR (CDCl$_3$) δ: 7.97–7.94 (2H, m), 7.86–7.81 (2H, m), 7.65–7.58 (1H, m), 7.55–7.46 (5H, m), 7.02 (1H, dd, J=2.0, 8.2 Hz), 6.90 (1H, d, J=8.2 Hz), 5.99 (1H, d, J=9.7 Hz), 4.00–3.87 (1H, m), 3.41 (3H, s), 2.63 (1H, dd, J=6.3, 17.6 Hz), 2.51 (1H, dd, J=6.3, 17.6 Hz).

Step 3. Methyl[6-chloro-2-(4-chlorobenzoyl)-1H-indol-3-yl]acetate

To a stirred solution of methyl[6-chloro-2-(4-chlorobenzoyl)-1-(phenylsulfonyl)indolin-3-yl]acetate (step 2, 50 mg, 0.10 mmol) in THF was added 1,8-diazabicyclo[5.4.0]undec-7-ene (DBU, 30 μl, 0.20 mmol). After stirring for 15 h, the mixture was quenched with water (30 ml), and extracted with ethyl acetate (50 ml). The extract was washed with 2N aqueous HCl (30 ml), saturated sodium bicarbonate (30 ml), brine (30 ml), and dried (MgSO$_4$). Removal of solvent afforded 34 mg (93%) of the title compound as yellow solids.

MS (EI) m/z: 361 (M$^+$). $^1$H-NMR (CDCl$_3$) δ: 8.90 (1H, br s), 7.74 (2H, d, J=8.6 Hz), 7.56 (1H, d, J=8.6 Hz), 7.49 (2H, d, J=8.6 Hz), 7.36 (1H, d, J=1.6 Hz), 7.16 (1H, dd, J=1.6, 8.6 Hz), 3.81 (2H, s), 3.66 (3H, s).

Method B

A mixture of methyl trans-4-chloro-2-(phenylsulfonylamino)cinnamate (step 1 of Method A, 0.70 g, 2.0 mmol), 4-chlorophenacyl bromide (0.51 g, 2.2 mmol), and potassium carbonate (0.83 g, 6.0 mmol) in acetone (20 ml) was stirred at room temperature. After stirring for 2h, cesium carbonate (2.0 g, 6.0 mmol) was added and the stirring was continued for an additional 4 h. The mixture was concentrated and the residue was diluted in water (100 ml). The aqueous mixture was extracted with ethyl acetate (100 ml×2). The combined organic extracts were washed with 2N aqueous HCl (100 ml), saturated sodium bicarbonate (100 ml), brine (100 ml), and dried (MgSO$_4$). After removal of solvent, the solids were recrystalized from ethanol to afford 0.44 g (61%) of the title compound.

MS and NMR spectra were identical with those of the compound prepared in step 3.

Example 9

[6-Chloro-2-(4-chlorobenzoyl)-1H-indol-3-yl]acetic Acid

Method A

Step 1. 6-Chloro-2-(4-chlorobenzoyl)indole

The title compound was prepared according to the procedure described in step 2 of Example 7 from 6-chloro-2-[(N-methoxy-N-methylamino)carbonyl]indole (Example 7, step 1) and 4-bromochlorobenzene.

$^1$H-NMR (DMSO-d$_6$) δ: 12.14 (1H, br s), 7.97 (2H, d, J=8.41 Hz), 7.76 (1H, d, J=8.6 Hz), 7.66 (2H, d, J=8.4 Hz), 7.54–7.50 (1H, m), 7.20 (1H, s), 7.14 (1H, dd, J=2.0, 8.6 Hz).

Step 2. Diethyl α-Acetoxy-[6-chloro-2-(4-chlorobenzoyl)-1H-indol-3-yl]malonate

The title compound was prepared according to the procedure described in step 4 of Example 2 (Method B) from 6-chloro-2-(4-chlorobenzoyl)indole (step 1).

$^1$H-NMR (CDCl$_3$) δ: 8.83 (1H, br s), 7.87–7.77 (3H, m), 7.48–7.36 (3H, m), 7.17 (1H, dd, J=2.0, 8.9 Hz), 4.28–4.14 (4H, m), 1.73 (3H, s), 1.20 (6H, t, J=7.1 Hz).

Step 3. Diethyl[6-chloro-2-(4-chlorobenzoyl)-1H-indol-3-yl]malonate

The title compound was prepared according to the procedure described in step 5 of Example 2 (Method B) from diethyl α-acetoxy-[6-chloro-2-(4-chlorobenzoyl)-1H-indol-3-yl]malonate (step 2).

$^1$H-NMR (CDCl$_3$) δ: 8.91 (1H, br s), 7.75 (2H, d, J=8.6 Hz), 7.75–7.69 (1H, m), 7.50 (2H, d, J=8.6 Hz), 7.29 (1H, d, J=1.8Hz), 7.13 (1H, dd, J=1.8, 8.7 Hz). 5.23 (1H, s), 4.28–4.07 (4H, m), 1.23 (6H, t, J=7.2 Hz).

Step 4. [6-Chloro-2-(4-chlorobenzoyl)-1H-indol-3-yl]acetic Acid

The title compound was prepared according to the procedure described in step 6 of Example 2 (Method B) from diethyl[6-chloro-2-(4-chlorobenzoyl)-1H-indol-3-yl]malonate (step 3).

m.p.: 189–190° C. IR (KBr) ν: 3309, 1699, 1616, 1525, 1431, 1325, 1255, 1226, 1091 cm$^{-1}$. $^1$H-NMR (DMSO-d$_6$) δ: 11.78 (1H, s), 7.80–7.72 (3H, m), 7.65 (2H, d, J=8.6 Hz), 7.47 (1H, d, J=1.8 Hz), 7.13 (1H, dd, J=1.8, 8.7 Hz), 3.83 (2H, s).

Method B

[6-Chloro-2-(4-chlorobenzoyl)-1H-indol-3-yl]acetic Acid

A mixture of methyl[6-chloro-2-(4-chlorobenzoyl)-1H-indol-3-yl]acetate (Example 8, 1.80 g) and 2N aqueous NaOH (7.5 ml) in MeOH-THF (10 ml-10 ml) was stirred at 80° C. for 1 h. The mixture was cooled and concentrated. The residue was dissolved in water (150 ml) and washed with diethyl ether (50 ml). The aqueous layer was acidified with 2N aqueous HCl (10 ml), and extracted with ethyl acetate (100 ml×2). The combined organic extracts were washed with brine (50 ml), dried (MgSO$_4$), and concentrated. The residual solids were recrystalized from toluene to afford 1.58 g (91%) of the title compound.

IR and NMR spectra were identical with those of the compound prepared by Method A.

Example 10

[6-Chloro-2-(3-fluorobenzoyl)-1H-indol-3-yl]acetic Acid

Step 1. 6-Chloro-2-(3-fluorobenzoyl)indole

The title compound was prepared according to the procedure described in step 2 of Example 7 from 6-chloro-2-[(N-methoxy-N-methylamino)carbonyl]indole (Example 7, step 1) and 3-bromofluorobenzene.

$^1$H-NMR (CDCl$_3$) δ: 9.28 (1H, br s), 7.79–7.75 (1H, m), 7.68–7.63 (2H, m), 7.56–7.48 (2H, m), 7.36–7.30 (1H, m), 7.17–7.14 (2H, m).

Step 2. Diethyl α-Acetoxy-[6-chloro-2-(3-fluorobenzoyl)-1H-indol-3-yl]malonate

The title compound was prepared according to the procedure described in step 4 of Example 2 (Method B) from 6-chloro-2-(3-fluorobenzoyl)indole (step 1).

$^1$H-NMR (CDCl$_3$) δ: 9.15 (1H, br s), 8.83 (1H, d, J=8.72 Hz), 7.66–7.27 (5H, m), 7.17 (1H, dd, J=2.00, 8.72 Hz), 4.254.13 (4H, m), 1.75 (3H, s), 1.19 (6H, t, J=7.07 Hz).

Step 3. Diethyl[6-chloro-2-(3-fluorobenzoyl)-1H-indol-3-yl]malonate

The title compound was prepared according to the procedure described in step 5 of Example 2 (Method B) from diethyl α-acetoxy-[6-chloro-2-(3-fluorobenzoyl)-1H-indol-3-yl]malonate (step 2).

$^1$H-NMR (CDCl$_3$) δ: 8.91 (1H, br s), 7.77–7.12 (7H, m), 5.21 (1H, s), 4.25–4.11 (4H, m), 1.22 (6H, t, J=7.07 Hz).

Step 4. [6-Chloro-2-(3-fluorobenzoyl)-1H-indol-3-yl]acetic Acid

The title compound was prepared according to the procedure described in step 6 of Example 2 (Method B) from diethyl[6-chloro-2-(3-fluorobenzoyl)-1H-indol-3-yl]malonate (step 3).

m.p.: 278–281° C. IR (KBr) ν: 3385, 1697, 1638, 1583, 1541, 1508, 1420, 1400, 1315, 1261, 1236 cm$^{-1}$. $^1$H-NMR (DMSO-d$_6$) δ: 11.79 (1H, s), 7.76–7.48 (7H, m), 7.13 (1H, dd, J=1.97, 8.56 Hz), 3.80 (2H, s).

Example 11

[6-Chloro-2-(4-fluorobenzoyl)-1H-indol-3-yl]acetic Acid

Step 1. 6-Chloro-2-(4-fluorobenzoyl)indole

The title compound was prepared according to the procedure described in step 2 of Example 7 from 6-chloro-2-[(N-methoxy-N-methylamino)carbonyl]indole (Example 7, step 1) and 4-bromofluorobenzene.

$^1$H-NMR (CDCl$_3$) δ: 9.29 (1H, br s), 8.05–8.00 (2H, m), 7.64 (1H, d, 8.72 Hz), 7.48–7.11 (5H, m).

Step 2. Diethyl α-Acetoxy-[6-chloro-2-(4-fluorobenzoyl)-1H-indol-3-yl]malonate

The title compound was prepared according to the procedure described in step 4 of Example 2 (Method B) from 6-chloro-2-(4-fluorobenzoyl)indole (step 1).

$^1$H-NMR (CDCl$_3$) δ: 9.20 (1H, br s), 7.92–7.11 (7H, m), 4.25–4.14 (4H, m), 1.73 (3H, s), 1.20 (6H, t, J=7.10 Hz).

Step 3. Diethyl[6-chloro-2-(4-fluorobenzoyl)-1H-indol-3-yl]malonate

The title compound was prepared according to the procedure described in step 5 of Example 2 (Method B) from diethyl α-acetoxy-[6-chloro-2-(4-fluorobenzoyl)-1H-indol-3-yl]malonate (step 2).

$^1$H-NMR (CDCl$_3$) δ: 9.01 (1H, br s), 7.87–7.69 (2H, m), 7.71 (2H, d , J=8.91 Hz), 7.27–7.10 (4H, m), 5.25 (1H, s), 4.26–4.11 (4H, m), 1.22 (6H, t, J=7.07 Hz).

Step 4. [6-Chloro-2-(4-fluorobenzoyl)-1H-indol-3-yl]acetic Acid

The title compound was prepared according to the procedure described in step 6 of Example 2 (Method B) from diethyl[6-chloro-2-(4-fluorobenzoyl)-1H-indol-3-yl]malonate (step 3).

m.p.: 181–183° C. IR (KBr) ν: 3309, 1701, 1616, 1601, 1566, 1527, 1508, 1419, 1323, 1257, 1229 cm$^{-1}$. $^1$H-NMR (DMSO-d$_6$) δ: 11.75 (1H, s), 7.87–7.82 (2H, m), 7.73 (1H, d, J=8.72), 7.47–7.36 (3H, m), 7.12 (1H, dd, J=1.84, 8.72 Hz), 3.78 (2H, s).

Example 12

[2-(3-Bromobenzoyl)-6-chloro-1H-indol-3-yl]acetic Acid

Step 1. 2-(3-Bromobenzoyl)-6-chloroindole

The title compound was prepared according to the procedure described in step 2 of Example 7 from 6-chloro-2-[(N-methoxy-N-methylamino)carbonyl]indole (Example 7, step 1) and 3-bromoiodobenzene.

$^1$H-NMR (CDCl$_3$) δ: 9.28 (1H, br s), 8.11–8.08 (1H, m), 7.93–7.87 (1H, m), 7.79–7.73 (1H, m), 7.65 (1H, d, J=8.6 Hz), 7.50–7.38 (2H, m), 7.19–7.01 (2H, m).

Step 2. Diethyl α-Acetoxy-[2-(3-bromobenzoyl)-6-chloro-1H-indol-3-yl]malonate

The title compound was prepared according to the procedure described in step 4 of Example 2 (Method B) from 2-(3-bromobenzoyl)-6-chloroindole (step 1).

$^1$H-NMR (CDCl$_3$) δ: 8.73 (1H, br s), 7.93 (1H, t, J=1.8 Hz), 7.85 (1H, d, J=8.6 Hz), 7.82–7.72 (2H, m), 7.42–7.32 (2H, m), 7.18 (1H, dd, J=2.0, 8.6 Hz), 4.32–4.16 (4H, m), 1.75 (3H, s), 1.20 (6H, t, J=7.1 Hz).

Step 3. Diethyl[2-(3-bromobenzoyl)-6-chloro-1H-indol-3-yl]malonate

The title compound was prepared according to the procedure described in step 5 of Example 2 (Method B) from diethyl α-acetoxy-[2-(3-bromobenzoyl)-6-chloro-1H-indol-3-yl]malonate (step 2).

$^1$H-NMR (CDCl$_3$) δ: 8.88 (1H, br s), 7.92–7.90 (1H, m), 7.80–7.68 (3H, m), 7.45–7.36 (2H, m), 7.15 (1H, dd, J=1.8, 8.7 Hz). 5.20 (1H, s), 4.304.10 (4H, m), 1.23 (6H, t, J=7.2 Hz).

Step 4. [2-(3-Bromobenzoyl)-6-chloro-1H-indol-3-yl]acetic Acid

The title compound was prepared according to the procedure described in step 6 of Example 2 (Method B) from diethyl[2-(3-bromobenzoyl)-6-chloro-1H-indol-3-yl]malonate (step 3).

m.p.: 215–218° C. IR (KBr) ν: 3369, 1710, 1604, 1558, 1533, 1423, 1319, 1253, 1228 cm$^{-1}$. $^1$H-NMR (DMSO-d$_6$) δ: 11.81 (11H, s), 7.92–7.83 (2H, m), 7.78–7.70 (2H, m), 7.54 (1H, t, J=7.8 Hz), 7.48 (1H, d, J=2.0 Hz), 7.13 (1H, dd, J=2.0, 8.7 Hz), 3.80 (2H, s).

Example 13

[2-(4-Bromobenzoyl)-6-chloro-1H-indol-3-yl]acetic Acid

Step 1. 2-(4-Bromobenzoyl)-6-chloroindole

The title compound was prepared according to the procedure described in step 2 of Example 7 from 6-chloro-2-[(N-methoxy-N-methylamino)carbonyl]indole (Example 7, step 1) and 4-bromoiodobenzene.

$^1$H-NMR (DMSO-d$_6$) δ: 12.28 (1H, br s), 7.88 (2H, d, J=8.7 Hz), 7.80 (2H, d, J=8.7 Hz), 7.76 (1H, d, J=8.7 Hz), 7.53–7.50 (1H, m), 7.22–7.19 (1H, m), 7.13 (1H, dd, J=2.0, 8.7 Hz).

Step 2. Diethyl α-Acetoxy-[2-(4-bromobenzoyl)-6-chloro-1H-indol-3-yl]malonate

The title compound was prepared according to the procedure described in step 4 of Example 2 (Method B) from 2-(4-bromobenzoyl)-6-chloroindole (step 1).

$^1$H-NMR (CDCl$_3$) δ: 8.72 (1H, br s), 7.84 (1H, d, J=8.7 Hz), 7.73 (2H, d, J=8.4 Hz), 7.62 (2H, d, J=8.4 Hz), 7.38 (1H, d, J=1.8 Hz), 7.18 (1H, dd, J=1.8, 8.7 Hz), 4.28–4.14 (4H, m), 1.73 (3H, s), 1.20 (6H, t, J=7.1 Hz).

Step 3. Diethyl[2-(4-bromobenzoyl)-6-chloro-1H-indol-3-yl]malonate

The title compound was prepared according to the procedure described in step 5 of Example 2 (Method B) from diethyl α-acetoxy-[2-(4-bromobenzoyl)-6-chloro-1H-indol-3-yl]malonate (step 2).

¹H-NMR (CDCl₃) δ: 8.86 (1H, br s), 7.75 (1H, d, J=8.4 Hz), 7.67 (4H, s), 7.37–7.32 (1H, m), 7.18–7.12 (1H, m), 5.22 (1H, s), 4.26–4.10 (4H, m), 1.23 (6H, t, J=7.1 Hz).

Step 4. [2-(4-Bromobenzoyl)-6-chloro-1H-indol-3-yl]acetic Acid

The title compound was prepared according to the procedure described in step 6 of Example 2 (Method B) from diethyl[2-(4-bromobenzoyl)-6-chloro-1H-indol-3-yl]malonate (step 3).

m.p.: 199–201° C. IR (KBr) ν: 3300, 1699, 1618, 1587, 1525, 1433, 1406, 1325, 1255, 1226 cm⁻¹. ¹H-NMR (DMSO-d₆) δ: 11.78 (1H, s), 7.80 (2H, d, J=8.4 Hz), 7.75 (1H, d, J=8.6 Hz), 7.69 (2H, d, J=8.4 Hz), 7.47 (1H, d, J=1.8 Hz), 7.13 (1H, dd, J=1.8, 8.6 Hz), 3.84 (2H, s).

Example 14

[6-Chloro-2-(3-trifluoromethylbenzoyl-1H-indol-3-yl)acetic Acid

Step 1. 6-Chloro-2-(3-trifluoromethylbenzoyl)indole

The title compound was prepared according to the procedure described in step 2 of Example 7 from 6-chloro-2-[(N-methoxy-N-methylamino)carbonyl]indole (Example 7, step 1) and 3-bromobenzotrifluoride.

¹H-NMR (DMSO-d₆) δ: 12.23 (1H, br s). 8.28–8.04 (3H, m), 7.89–7.75 (2H, m), 7.55–7.51 (1H, m), 7.22–7.12 (2H, m).

Step 2. Diethyl α-Acetoxy-[6-chloro-2-(3-trifluoromethylbenzoyl)-1H-indol-3-yl]malonate The title compound was prepared according to the procedure described in step 4 of Example 2 (Method B) from 6-chloro-2-(3-trifluoromethylbenzoyl)indole (step 1).

¹H-NMR (CDCl₃) δ: 8.82 (11H, br s), 8.25–7.80 (4H, m), 7.68–7.57 (1H, m), 7.43–7.41 (1H, m), 7.22–7.16 (1H, m), 4.36–4.20 (4H, m), 1.67 (3H, s), 1.20 (6H, t, J=7.1 Hz).

Step 3. Diethyl[6-chloro-2-(3-trifluoromethylbenzoyl)-1H-indol-3-yl]malonate

The title compound was prepared according to the procedure described in step 5 of Example 2 (Method B) from diethyl α-acetoxy-[6-chloro-2-(3-trifluoromethylbenzoyl)-1H-indol-3-yl]malonate (step 2).

¹H-NMR (CDCl₃) δ: 8.91 (11H, br s), 8.08–8.03 (1H, m), 8.02–7.87 (2H, m), 7.76 (1H, d, J=9.0 Hz), 7.73–7.64 (1H, m), 7.39–7.36 (1H, m), 7.15 (1H, dd, J=1.8, 9.0 Hz). 5.15 (1H, s), 4.26–4.10 (4H, m), 1.22 (6H, t, J=7.2 Hz).

Step 4. [6-Chloro-2-(3-trifluoromethylbenzoyl)-1H-indol-3-yl]acetic Acid

The title compound was prepared according to the procedure described in step 6 of Example 2 (Method B) from diethyl[6-chloro-2-(3-trifluoromethylbenzoyl)-1H-indol-3-yl]malonate (step 3).

m.p.: 194–196° C. IR (KBr) ν: 3371, 1705, 1631, 1421, 1307, 1228, 1168, 1122, 1072 cm⁻¹. ¹H-NMR (DMSO-d₆) δ: 11.86 (1H, s), 8.10–7.98 (3H, m), 7.83 (1H, t, J=7.7 Hz), 7.75 (1H, d, J=8.6 Hz), 7.49 (1H, d, J=2.0 Hz), 7.15 (11H, dd, J=2.0, 8.6 Hz), 3.80 (2H, s).

Example 15

[6-Chloro-2-(4-trifluoromethylbenzoyl)-1H-indol-3-yl]acetic Acid

Step 1. 6-Chloro-1-(phenylsulfonyl)-2-(4-trifluoromethylbenzoyl)indole

The title compound was prepared according to the procedure described in step 2 of Example 2 (Method B) from 6-chloro-1-(phenylsulfonyl)indole (step 1 of Example 2, Method B) and 4-trifluoromethylbenzoyl chloride.

tlc: Rf=0.2 (ethyl acetate/hexane=1:4).

Step 2. 6-Chloro-2-(4-trifluoromethylbenzoyl)indole

The title compound was prepared according to the procedure described in step 3 of Example 2 (Method B) from 6-chloro-1-phenylsulfonyl-2-(4-trifluoromethylbenzoyl) indole (step 1).

¹H-NMR (CDCl₃) δ: 9.53 (1H, br s), 7.94 (4H, dd, J=8.24, 69.1 Hz), 7.63 (1H, d, J=8.56 Hz), 7.49–7.11 (3H, m).

Step 3. Diethyl α-Acetoxy-[6-chloro-2-(4-trifluoromethylbenzoyl)-1H-indol-3-yl]malonate The title compound was prepared according to the procedure described in step 4 of Example 2 (Method B) from 6-chloro-2-(4-trifluoromethylbenzoyl)indole (step 2).

¹H-NMR (CDCl₃) δ: 8.66 (1H, br s), 7.98 (2H, d, J=8.24 Hz), 7.87 (1H, d, J=8.91 Hz), 7.75 (2H, d, J=8.07 Hz), 7.39 (1H, d, J=1.81 Hz), 7.19 (1H, dd, J=1.81, 7.10 Hz), 4.36–4.16 (4H, m), 1.70 (3H, s), 1.34–1.22 (6H, m).

Step 4. Diethyl[6-chloro-2-(4-trifluoromethylbenzoyl)-1H-indol-3-yl]malonate

The title compound was prepared according to the procedure described in step 5 of Example 2 (Method B) from diethyl α-acetoxy-[6-chloro-2-(4-trifluoromethylbenzoyl)-1H-indol-3-yl]malonate (step 3).

¹H-NMR (CDCl₃) δ: 9.24 (1H, br s), 7.84 (4H, dd, J=7.91, 25.7 Hz), 7.69–7.09 (3H, m), 5.24 (1H, s), 4.21 4.06 (4H, m), 1.21 (6H, t, J=7.07 Hz).

Step 5. [6-Chloro-2-(4-trifluoromethylbenzoyl)-1H-indol-3-yl]acetic Acid

The title compound was prepared according to the procedure described in step 6 of Example 2 (Method B) from diethyl[6-chloro-2-(4-trifluoromethylbenzoyl)-1H-indol-3-yl]malonate (step 4).

¹H-NMR (DMSO-d₆) δ: 11.78 (1H, s), 7.94 (4H, s), 7.76 (1H, d, J=8.72 Hz), 7.47 (1H, m), 7.14 (1H, d, J=1.81, 8.72), 3.81 (2H, s).

Example 16

[6-Chloro-2-(3,4-dichlorobenzoyl)-1H-indol-3-yl] acetic Acid

Step 1. 6-Chloro-2-(3,4-dichlorobenzoyl)indole

The title compound was prepared according to the procedure described in step 2 of Example 7 from 6-chloro-2-[(N-methoxy-N-methylamino)carbonyl]indole (Example 7, step 1) and 1-bromo-3,4-dichlorobenzene.

tlc: Rf=0.7 (ethyl acetate/hexane=1:3).

Step 2. Diethyl α-Acetoxy-[6-chloro-2-(3,4-dichlorobenzoyl)-1H-indol-3-yl]malonate The title compound was prepared according to the procedure described in step 4 of Example 2 (Method B) from 6-chloro-2-(3,4-dichlorobenzoyl)indole (step 1).

¹H-NMR (CDCl₃) δ: 8.80 (1H, br s), 7.90–7.79 (2H, m), 7.71 (1H, dd, J=2.0, 8.4 Hz), 7.57 (1H, d, J=8.4 Hz), 7.40–7.35 (1H, m), 7.18 (1H, dd, J=1.8, 8.8 Hz), 4.30–4.14 (4H, m), 1.77 (3H, s), 1.20 (6H, t, J=7.1 Hz).

Step 3. Diethyl[6-chloro-2-(3,4-dichlorobenzoyl)-1H-indol-3-yl]malonate

The title compound was prepared according to the procedure described in step 5 of Example 2 (Method B) from diethyl α-acetoxy-[6-chloro-2-(3,4-dichlorobenzoyl)-1H-indol-3-yl]malonate (step 2).

¹H-NMR (CDCl₃) δ: 8.95 (1H, br s), 7.88 (1H, d, J=1.6 Hz), 7.72 (1H, d, J=8.7 Hz), 7.68–7.58 (2H, m), 7.28 (1H, d, J=1.6 Hz), 7.14 (1H, dd, J=1.6, 8.7 Hz). 5.18 (1H, s), 4.28–4.10 (4H, m), 1.23 (6H, t, J=7.1 Hz).

Step 4. [6-Chloro-2-(3,4-dichlorobenzoyl)-1H-indol-3-yl] acetic Acid

The title compound was prepared according to the procedure described in step 6 of Example 2 (Method B) from diethyl[6-chloro-2-(3,4-dichlorobenzoyl)-1H-indol-3-yl]malonate (step 3).

m.p.: 206–209° C. IR (KBr) v: 3435, 1708, 1620, 1583, 1525, 1423, 1384, 1301, 1263, 1228 cm$^{-1}$. $^1$H-NMR (DMSO-d$_6$) δ: 11.62 (1H, br s), 7.95–7.75 (3H, m), 7.68 (1H, d, J=8.7 Hz), 7.42 (1H, d, J=2.0 Hz), 7.02 (1H, dd, J=2.0, 8.7 Hz), 3.50 (2H, s).

Example 17

(2-Benzoyl-4-chloro-1H-indol-3-yl)acetic Acid

Step 1. 4-Chloro-2-[(N-methoxy-N-methylamino)carbonyl]indole

The title compound was prepared according to the procedure described in step 1 of Example 7 employing 4-chloroindole-2-carboxylic acid (F. C. Uhle, *J. Amer. Chem. Soc.*, 1949, 71, 761).

$^1$H-NMR (CDCl$_3$) δ: 9.56 (1H, br s), 7.36–7.29 (2H, m), 7.24–7.12 (2H, m), 3.88 (3H, s), 3.45 (3H, s).

Step 2. 2-Benzoyl-4-chloroindole

To a solution of 4-chloro-2-[(N-methoxy-N-methylamino)carbonyl]indole (step 1, 3.4 g, 0.014 mol) in THF (60 ml) cooled to −78° C. was added dropwise phenyllithium (1.8 M in cyclohexane/ether (7:3), 30 ml, 0.070 mol). After stirring for 1 h, the mixture was poured into water (80 ml) and extracted with ethyl acetate (80 ml×2). After drying (MgSO$_4$) and removal of solvent, the crude product was purified by flash column chromatography eluting with ethyl acetate/hexane (1:10) to afford 3.6 g (100%) of the title compound as white solids.

$^1$H-NMR (CDCl$_3$) δ: 9.46 (1H, br s), 8.05–8.00 (2H, m), 7.73–7.51 (3H, m), 7.40 (1H, dd, J=1.0, 8.3 Hz), 7.33–7.24 (2H, m), 7.18 (1H, d, J=7.6 Hz).

Step 3. Diethyl α-Acetoxy-(2-benzoyl-4-chloro-1H-indol-3-yl malonate

The title compound was prepared according to the procedure described in step 4 of Example 2 (Method B) from 2-benzoyl-4-chloroindole (step 2).

$^1$H-NMR (CDCl$_3$) δ: 9.49 (1H, br s), 7.98–7.92 (2H, m), 7.66–7.57 (11H, m), 7.53–7.44 (2H, m), 7.34 (1H, dd, J=2.0, 7.1 Hz), 7.21–7.15 (2H, m), 4.30–3.90 (4H, m), 2.08 (3H, s), 1.15 (6H, t, J=7.3 Hz).

Step 4. Diethyl(2-benzoyl-4-chloro-1H-indol-3-yl)malonate

The title compound was prepared according to the procedure described in step 5 of Example 2 from diethyl α-acetoxy-(2-benzoyl-4-chloro-1H-indol-3-yl)malonate (step 3).

$^1$H-NMR (CDCl$_3$) δ: 8.88 (1H, br s), 7.83–7.77 (2H, m), 7.64–7.58 (1H, m), 7.55–7.46 (2H, m), 7.25–7.05 (3H, m), 5.86 (1H, s), 4.25–4.08 (4H, m), 1.23 (6H, t, J=7.3 Hz).

Step 5. (2-Benzoyl-4-chloro-1H-indol-3-yl)acetic Acid

The title compound was prepared according to the procedure described in step 6 of Example 2 (Method B) from diethyl(2-benzoyl-4-chloro-1H-indol-3-yl)malonate.

m.p.: 206–209° C. (recrystallized from ethyl acetate/hexane). IR (KBr) v: 1700, 1575, 1245 cm$^{-1}$. $^1$H-NMR (DMSO-d$_6$) δ: 12.20 (1H, br s), 11.98 (1H, s), 7.85–7.67 (3H, m), 7.63–7.55 (2H, m), 7.45 (1H, d, J=8.2 Hz), 7.25 (1H, t, J=8.2 Hz), 7.12 (1H, d, J=7.6 Hz), 4.02 (2H, s).

Example 18

[5-Chloro-2-(3-methylbenzoyl)-1H-indol-3-yl]acetic Acid

Step 1. 5-Chloro-2-[(N-method-N-methylamino)carbonyl]indole

The title compound was prepared according to the procedure described in step 1 of Example 7 from 5-chloroindole-2-carboxylic acid.

$^1$H-NMR (CDCl$_3$) δ: 9.68 (1H, br s), 7.68–7.65 (1H, m), 7.37 (1H, d, J=8.7 Hz), 7.23 (1H, d, J=1.6 Hz), 7.18–7.15 (1H, m), 3.85 (3H, s), 2.05 (3H, s).

Step 2. 5-Chloro-2-(3-methylbenzoyl)indole

The title compound was prepared according to the procedure described in step 2 of Example 17 from 5-chloro-2-[(N-methoxy-N-methylamino)carbonyl]indole (step 1) and 3-methylphenyllithium.

m.p.: 197.5–198° C. (recrystallized from ethyl acetate/hexane). IR (KBr) v: 3310, 1626, 1603, 1583, 1516, 1406, 1377, 1337, 1269, 1178, 1134 cm$^{-1}$. $^1$H-NMR (CDCl$_3$) δ: 9.39 (1H, br s), 7.28–7.76 (2H, m), 7.71–7.68 (1H, m), 7.46–7.38 (3H, m), 7.32 (1H, dd, J=8.7, 2.0 Hz), 7.08 (1H, dd, J=2.0, 0.8 Hz), 2.47 (3H, s).

Step 3. Diethyl α-Acetoxy-[5-chloro-2-(3-methylbenzoyl)-1H-indol-3-yl]malonate

The title compound was prepared according to the procedure described in step 4 of Example 2 (Method B) from 5-chloro-2-(3-methylbenzoyl)indole (step 2).

m.p.: 173–174° C. (recrystallized from ethyl acetate/hexane). $^1$H-NMR (CDCl$_3$) δ: 8.64 (1H, br s), 7.91 (1H, br s), 7.69–7.61 (2H, m), 7.46–7.22 (4H, m), 4.30 4.16 (4H, m), 2.39 (3H, s), 1.72 (3H, s), 1.23 (3H, t, J=7.2 Hz).

Step 4. Diethyl[5-chloro-2-(3-methylbenzoyl)-1H-indol-3-yl]malonate

The title compound was prepared according to the procedure described in step 5 of Example 2 (Method B) from diethyl α-acetoxy-[5-chloro-2-(3-methylbenzoyl)-1H-indol-3-yl] malonate (step 3).

m.p.: 143–144° C. (recrystallized from ethyl acetate/hexane). $^1$H-NMR (CDCl$_3$) δ: 8.88 (1H, br s), 7.84–7.80 (1H, m), 7.62–7.55 (2H, m), 7.48–7.36 (2H, m), 7.32–7.28 (2H, m), 5.27 (1H, s), 4.30–4.10 (4H, m), 2.42 (3H, s), 1.24 (3H, t, J=7.1 Hz).

Step 5. [5-Chloro-2-(3-methylbenzoyl)-1H-indol-3-yl]acetic Acid

The title compound was prepared according to the procedure described in step 6 of Example 2 (Method B) from diethyl[5-chloro-2-(3-methylbenzoyl)-1H-indol-3-yl]malonate.

m.p.: 241–242° C. (recrystallized from ethyl acetate/hexane). IR (KBr) v: 3321, 1703, 1618, 1535, 1431, 1335, 1232, 1016, 808, 758 cm$^{-1}$. $^1$H-NMR (DMSO-d$_6$) δ: 11.7 (1H, br s), 7.62 (1H, d, J=1.8 Hz), 7.45–7.30 (6H, m), 7.19 (11H, dd, J=8.6, 1.8 Hz), 3.63 (2H, s), 2.27 (3H, s).

Example 19

[5-Chloro-2-(4-chlorobenzoyl)-1H-indol-3-yl]acetic Acid

Step 1. 5-Chloro-2-(4-chlorobenzoyl)indole

The title compound was prepared according to the procedure described in step 2 of Example 7 from 5-chloro-2-[(N-methoxy-N-methylamino)carbonyl]indole (Example 18, step 1) and 4-bromochlorobenzene.

$^1$H-NMR (CDCl$_3$) δ: 9.32 (1H, br s), 7.94 (2H, d, J=8.4 Hz), 7.70 (1H, s), 7.53 (2H, d, J=8,4 Hz), 7.42 (1H, d, J=8.9 Hz), 7.34 (1H, dd, J=2.0, 8.9 Hz), 7.07 (1H, s).

Step 2. Diethyl α-Acetoxy-[5-chloro-2-(4-chlorobenzoyl)-1H-indol-3-yl]malonate

The title compound was prepared according to the procedure described in step 4 of Example 2 (Method B) from 5-chloro-2-(4-chlorobenzoyl)indole (step 1).

$^1$H-NMR (CDCl$_3$) δ: 9.11 (1H, br s), 7.87 (1H, s), 7.76 (2H, d, J=8.6 Hz), 7.41 (2H, d, J=8.6 Hz), 7.27 (1H, d, J=8.7 Hz), 7.22 (1H, dd, J=1.8, 8.7 Hz), 4.25–4.14 (4H, m), 1.72 (3H, s), 1.24–1.19 (6H, m).

Step 3. Diethyl[5-chloro-2-(4-chlorobenzoyl)-1H-indol-3-yl]malonate

The title compound was prepared according to the procedure described in step 5 of Example 2 (Method B) from diethyl α-acetoxy-[5-chloro-2-(4-chlorobenzoyl)-1H-indol-3-yl]malonate (step 2).

$^1$H-NMR (CDCl$_3$) δ: 9.13 (1H, br s), 7.73 (2H, d, J=8.4 Hz), 7.68 (1H, d, J=2.0 Hz), 7.48 (2H, d, J=8.4 Hz), 7.11 (1H, dd, J=2.0, 8.9 Hz), 7.02 (1H, d, J=8.9 Hz), 5.28 (1H, s), 4.24–4.03 (4H, m), 1.27–1.21 (6H, m).

Step 4. [5-Chloro-2-(4-chlorobenzoyl)-1H-indol-3-yl]acetic Acid

The title compound was prepared according to the procedure described in step 6 of Example 2 (Method B) from diethyl[5-chloro-2-(4-chlorobenzoyl)-1H-indol-3-yl]malonate (step 3).

m.p.: 220–224° C. (recrystallized from ethyl acetate/hexane). IR (KBr) ν: 3321, 1618, 1535, 1379, 1339, 1263, 1130, 1090, 1057, 1007 cm$^{-1}$. $^1$H-NMR (DMSO-d$_6$) δ: 11.83 (1H, s), 7.80–7.75 (3H, m), 7.67–7.62 (2H, m), 7.48 (1H, d, J=8.7 Hz), 7.31 (1H, dd, J=2.0, 8.7 Hz), 3.84 (2H, s).

Example 20

[5-Chloro-2-(3-Chlorobenzoyl)-1H-indol-3-yl]acetic Acid

Step 1. 5-Chloro-2-(3-chlorobenzoyl)indole

The title compound was prepared according to the procedure described in step 2 of Example 7 from 5-chloro-2-[(N-methoxy-N-methylamino)carbonyl]indole (Example 18, step 1) and 3-bromochlorobenzene.

$^1$H-NMR (CDCl$_3$) δ: 9.28 (1H, br s), 7.95 (1H, t, J=1.7 Hz), 7.88–7.84 (1H, m), 7.71 (1H, d, J=2.0 Hz), 7.63–7.59 (1H, m), 7.49 (1H, t, J=7.7 Hz), 7.42 (1H, d, J=8.7 Hz), 7.34 (1H, dd, J=2.0, 8.7 Hz), 7.10–7.09 (1H, m).

Step 2. Diethyl α-Acetoxy-[5-chloro-2-(3-chlorobenzoyl)-1H-indol-3-yl]malonate

The title compound was prepared according to the procedure described in step 4 of Example 2 (Method B) from 5-chloro-2-(3-chlorobenzoyl)indole (step 1).

$^1$H-NMR (CDCl$_3$) δ: 8.94 (1H, br s), 7.91 (1H, d, J=1.8 Hz), 7.79–7.76 (1H, m), 7.74 (1H, d, J=7.7 Hz), 7.60–7.56 (1H, m), 7.42 (1H, t, J=7.7 Hz), 7.33 (1H, d, J=8.7 Hz), 7.27 (1H, dd, J=1.8, 8.7 Hz), 4.37–4.19 (4H, m), 1.75 (3H, s), 1.26–1.20 (6H, m).

Step 3. Diethyl[5-chloro-2-(3-chlorobenzoyl)-1H-indol-3-yl]malonate

The title compound was prepared according to the procedure described in step 5 of Example 2 (Method B) from diethyl α-acetoxy-[5-chloro-2-(3-chlorobenzoyl)-1H-indol-3-yl]malonate (step 2).

$^1$H-NMR (CDCl$_3$) δ: 9.04 (1H, br.s), 7.77–7.75 (2H, m), 7.68–7.58 (2H, m), 7.46 (1H, t, J=7.7 Hz), 7.24–7.20 (2H, m), 5.23 (1H, s), 4.27–4.14 (4H, m), 1.27–1.22 (6H, m).

Step 4. [5-Chloro-2-(3-chlorobenzoyl)-1H-indol-3-yl]acetic Acid

The title compound was prepared according to the procedure described in step 6 of Example 2 (Method B) from diethyl[5-chloro-2-(3-chlorobenzoyl)-1H-indol-3-yl]malonate (step 3).

m.p.: 243–247° C. (recrystallized from ethyl acetate/hexane). IR (KBr) ν: 3329,1707, 1618, 1535, 1431, 1406, 1375, 1333, 1279, 1232, 1053 cm$^{-1}$. $^1$H-NMR (DMSO-d$_6$) δ: 11.87 (1H, s), 7.81–7.68 (4H, m), 7.64–7.58 (1H, m), 7.49 (1H, d, J=8.9 Hz), 7.32 (1H, dd, J=2.0, 8.9 Hz), 3.82 (2H, s).

Example 21

[2-(4-Chlorobenzoyl)-5-fluoro-1H-indol-3-yl]acetic Acid

Step 1. 5-Fluoro-2-[(N-methoxy-N-methylamino)carbonyl]indole

The title compound was prepared according to the procedure described in step 1 of Example 7 from 5-fluoroindole-2-carboxylic acid.

$^1$H-NMR (CDCl$_3$) δ: 10.15 (1H, br s), 7.41–7.36 (1H, m), 7.32 (1H, dd, J=2.5, 9.1 Hz), 7.20–7.19 (1H, m), 7.09–7.01 (1H, m), 3.84 (3H, s), 3.47 (3H, s).

Step 2. 2-(4-Chlorobenzoyl)-5-fluoro-indole

The title compound was prepared according to the procedure described in step 2 of Example 7 from 5-fluoro-2-[(N-methoxy-N-methylamino)carbonyl]indole (step 1) and 4-bromochlorobenzene.

$^1$H-NMR (CDCl$_3$) δ: 9.27 (1H, br s), 7.94 (2H, d, J=8.4 Hz), 7.52 (2H, d, J=8.4 Hz), 7.45–7.40 (1H, m), 7.37–7.33 (1H, m), 7.21–7.12 (1H, m), 7.10–7.09 (1H, m).

Step 3. Diethyl α-Acetoxy-[2-(4-chlorobenzoyl)-5-fluoro-1H-indol-3-yl]malonate

The title compound was prepared according to the procedure described in step 4 of Example 2 (Method B) from 2-(4-chlorobenzoyl)-5-fluoroindole (step 2).

$^1$H-NMR (CDCl$_3$) δ: 9.01 (1H, br s), 7.80–7.77 (2H, m), 7.58–7.54 (1H ,m), 7.45–7.41 (2H, m), 7.36–7.27 (1H, m), 7.12–7.01 (1H, m), 4.29–4.15 (4H, m), 1.74 (3H, s), 1.28–1.17 (6H, m).

Step 4. Diethyl[2-(4-chlorobenzoyl)-5-fluoro-1H-indol-3-yl]malonate

The title compound was prepared according to the procedure described in step 5 of Example 2 (Method B) from diethyl α-acetoxy-[2-(4-chlorobenzoyl)-5-fluoro-1H-indol-3-yl]malonate (step 3).

$^1$H-NMR (CDCl$_3$) δ: 8.98 (1H, br s), 7.77–7.72 (2H, m), 7.51–7.46 (2H, m), 7.40 (1H, dd, J=2.5, 9.7 Hz), 7.18–7.13 (1H, m), 7.04–6.96 (1H, m), 5.28 (1H, s), 4.26–4.07 (4H, m), 1.30–1.18 (6H, m).

Step 5. [2-(4-Chlorobenzoyl)-5-fluoro-1H-indol-3-yl]acetic Acid

The title compound was prepared according to the procedure described in step 6 of Example 2 (Method B) from diethyl[2-(4-chlorobenzoyl)-5-fluoro-1H-indol-3-yl]malonate (step 4).

m.p.: 233–238° C. (recrystallized from ethyl acetate/hexane). IR (KBr) ν: 3317, 1707, 1624, 1609, 1587, 1526, 1458, 1408, 1344, 1263, 1242 cm$^{-1}$. $^1$H-NMR (DMSO-d$_6$) δ: 11.73 (1H, s), 7.77 (2H, d, J=8.6 Hz), 7.65 (2H, d, J=8.6 Hz), 7.52–7.44 (2H, m), 7.22–7.15 (1H, m), 3.84 (2H, s).

Example 22

[2-(3-Chlorobenzoyl)-5-fluoro-1H-indol-3-yl]acetic Acid

Step 1. 2-(3-Chlorobenzoyl)-5-fluoroindole

The title compound was prepared according to the procedure described in step 2 of Example 7 from 5-fluoro-2-[(N-methoxy-N-methylamino)carbonyl]indole (Example 21, step 1) and 3-bromochlorobenzene.

$^1$H-NMR (CDCl$_3$) δ: 9.29 (1H, m), 7.96–7.94 (1H, m), 7.88–7.84 (1H, m), 7.63–7,59 (1H, m), 7.48 (1H, t, J=8.0 Hz), 7.45–7.40 (1H, m), 7.36 (1H, dd, J=2.6, 8.6 Hz), 7.20–7.11 (2H, m).

Step 2. Diethyl α-Acetoxy-[2-(3-chlorobenzoyl)-5-fluoro-1H-indol-3-yl]malonate

The title compound was prepared according to the procedure described in step 4 of Example 2 (Method B) from 2-(3-chlorobenzoyl)-5-fluoroindole (step 1).

¹H-NMR (CDCl₃) δ: 8.73 (1H, br s), 7.79–7.74 (2H, m), 7.61–7.56 (2H, m), 7.43 (1H, t, J=7.6 Hz), 7.37–7.32 (1H, m), 7.13–7.06 (1H, m), 4.34–4.20 (4H, m), 1.76 (3H, s), 1.33–1.20 (6H, m).

Step 3. Diethyl[2-(3-chlorobenzoyl)-5-fluoro-1H-indol-3-yl]malonate

The title compound was prepared according to the procedure described in step 5 of Example 2 (Method B) from diethyl o:-acetoxy-[2-(3-chlorobenzoyl)-5-fluoro-1H-indol-3-yl]malonate (step 2).

¹H-NMR (CDCl₃) δ: 9.05 (1H, br s), 7.76–7.75 (1H, m), 7.68–7.64 (1H, m), 7.61–7.56 (1H, m), 7.48–7.40 (2H, m), 7.24–7.19 (1H, m), 7.08–7.00 (1H, m), 5.25 (1H, s), 4.28–4.07 (4H, m), 1.33–1.21 (6H, m).

Step 4. [2-(3-Chlorobenzoyl)-5-fluoro-1H-indol-3-yl]acetic Acid

The title compound was prepared according to the procedure described in step 6 of Example 2 (Method B) from diethyl[2-(3-chlorobenzoyl)-5-fluoro-1H-indol-3-yl]malonate (step 3).

m.p.: 208–212° C. (recrystallized from ethyl acetate/hexane). IR (KBr) v: 3337, 1709, 1618, 1560, 1529, 1477, 1458, 1427, 1408, 1335, 1304 cm⁻¹. ¹H-NMR (DMSO-d₆) δ: 11.78 (1H, s), 7.77–7.58 (4H, m), 7.52–7.46 (2H, m), 7.24–7.16 (1H, m), 3.82 (2H, s).

Example 23

[5-Methoxy-2-(3-methylbenzoyl)-1H-indol-3-yl]acetic Acid

Step 1. 5-Methoxy-2-[(N-methoxy-N-methylamino)carbonyl]indole

The title compound was prepared according to the procedure described in step 1 of Example 7 from 5-methoxyindole-2-carboxylic acid.

¹H-NMR (CDCl₃) δ: 9.29–9.13 (1H, br), 7.33 (1H, d, J=8.9 Hz), 7.19–7.14 (1H, m), 7.10 (1H, d, J=2.3 Hz), 6.98 (1H, dd, J=8.9, 2.3 Hz), 3.86 (3H, s), 3.84 (3H, s), 3.42 (3H, s).

Step 2. 5-Methoxy-2-(3-methylbenzoyl)indole

The title compound was prepared according to the procedure described in step 2 of Example 17 from 5-methoxy-2-[(N-methoxy-N-methylamino)carbonyl]indole (step 1) and 3-methylphenyllithium.

¹H-NMR (CDCl₃) δ: 9.65–9.45 (1H, br), 7.84–7.75 (2H, m), 7.46–7.35 (3H, m), 7.12–7.01 (3H, m), 3.85 (3H, s), 2.46 (3H, s).

Step 3. Diethyl α-Acetoxy-[5-methoxy-2-(3-methylbenzoyl)-1H-indol-3-yl]malonate

The title compound was prepared according to the procedure described in step 4 of Example 2 (Method B) from 5-methoxy-2-(3-methylbenzoyl)indole (step 2).

tlc: Rf=0.45 (ethyl acetate/hexane=1:3).

Step 4. Diethyl[5-methoxy-2-(3-methylbenzoyl)-1H-indol-3-yl]malonate

The title compound was prepared according to the procedure described in step 5 of Example 2 (Method B) from diethyl α-acetoxy-[5-methoxy-2-(3-methylbenzoyl)-1H-indol-3-yl]malonate (step 3).

¹H-NMR (CDCl₃) δ: 9.52–9.13 (0.5H, m), 8.81–8.71 (0.5H, m), 7.80–7.72 (1H, m), 7.63–7.55 (1H, m), 7.47–7.00 (5H, m), 5.41 (0.5H, s), 5.37 (0.5H, s), 4.27–4.15 (4H, m), 3.89 (1.5H, s), 3.84 (1.5H, s), 2.45 (1.5H, s), 2.43 (1.5H, s), 1.29–1.19 (6H, m).

Step 5. [5-Methoxy-2-(3-methylbenzoyl-1H-indol-3-yl]acetic Acid

The title compound was prepared according to the procedure described in step 6 of Example 2 (Method B) from diethyl[5-methoxy-2-(3-methylbenzoyl)-1H-indol-3-yl]malonate (step 4).

m.p.: 230.4–232.0° C. (decomposed) (recyrstallized from ethyl acetate). IR (KBr) v: 3310, 1705, 1614, 1583 cm⁻¹. ¹H-NMR (DMSO-d₆) δ: 11.47 (1H, br s), 7.60–7.34 (5H, m), 7.16–7.09 (1H, m), 6.98 (1H, dd, J=9.0, 2.4 Hz), 3.78 (5H, s), 2.40 (3H, s). ¹³C-NMR (DMSO-d₆) δ: 188.1, 172.1, 153.8, 138.9, 137.9, 132.7, 132.3, 132.0, 129.2, 128.5, 128.0, 125.8, 117.0, 115.6, 113.6, 100.7, 55.3, 30.6, 20.8.

Example 24

(2-Benzoyl-7-chloro-1H-indol-3-yl)acetic Acid

Step 1. 7-Chloro-2-[N-methoxy-N-methylamino)carbonyl]indole

The title compound was prepared according to the procedure described in step 1 of Example 7 from 7-chloroindole-2-carboxylic acid (H. N. Rydon and J. C. Tweddle, *J. Chem. Soc.*, 1955, 3499).

¹H-NMR (CDCl₃) δ: 9.40 (1H, br s), 7.59 (1H, d, J=8.1 Hz), 7.32–7.25 (2H, m), 7.08 (1H, t, J=8.1 Hz), 3.85 (3H, s), 3.43 (3H, s).

Step 2. 2-Benzoyl-7-chloroindole

The title compound was prepared according to the procedure described in step 2 of Example 17 from 7-chloro-2-[(N-methoxy-N-methylamino)carbonyl]indole (step 1) and phenyllithium.

¹H-NMR (CDCl₃) δ: 9.40 (1H, br s), 8.01–7.96 (2H, m), 7.70–7.50 (4H, m), 7.38 (1H, d, J=7.6 Hz), 7.18 (1H, d, J=2.0 Hz), 7.11 (1H, t, J=7.6 Hz).

Step 3. Diethyl α-Acetoxy-(2-benzoyl-7-chloro-1H-indol-3-yl)malonate

The title compound was prepared according to the procedure described in step 4 of Example 2 (Method B) from 2-benzoyl-7-chloroindole (step 2).

¹H-NMR (CDCl₃) δ: 8.76 (1H, br s), 7.92–7.81 (3H, m), 7.68–7.60 (1H, m), 7.53–7.45 (2H, m), 7.33 (1H, d, J=7.6 Hz), 7.15 (1H, t, J=8.2 Hz), 4.60–4.20 (4H, m), 1.71 (3H, s), 1.98 (6H, t, J=7.1 Hz).

Step 4. Diethyl(2-benzoyl-7-chloro-1H-indol-3-yl)malonate

The title compound was prepared according to the procedure described in step 5 of Example 2 (Method B) from diethyl α-acetoxy-(2-benzoyl-7-chloro-1H-indol-3-yl)malonate (step 3).

¹H-NMR (CDCl₃) δ: 8.94 (1H, br s), 7.86–7.80 (2H, m), 7.75 (1H, d, J=8.1 Hz), 7.70–7.62 (1H, m), 7.55–7.50 (2H, m), 7.36 (1H, d, J=7.6 Hz), 7.13 (1H, t, J=7.6 Hz), 5.29 (1H, s), 4.25–4.11 (4H, m), 1.22 (6H, t, J=7.3 Hz).

Step 5. (2-Benzoyl-7-chloro-1H-indol-3-yl)acetic Acid

The title compound was prepared according to the procedure described in step 6 of Example 2 (Method B) from diethyl(2-benzoyl-7-chloro-1H-indol-3-yl)malonate (step 4).

m.p.: 190–193° C. (recrystallized from ethyl acetate/hexane) IR (KBr) v: 1691, 1627, 1598, 1323, 1260 1199, 1010 cm⁻¹. ¹H-NMR (DMSO-d₆) δ: 11.90 (1H, br s), 7.82 (2H, m), 7.74–7.65 (2H, m), 7.62–7.38 (2H, m), 7.40 (1H, d, J=7.6 Hz), 7.13 (1H, t, J=7.6 Hz), 3.75 (2H, s).

Example 25

(2-Benzoyl-4,5-dichloro-1H-indol-3-yl)acetic Acid

Step 1. 4,5-Dichloroindolyl-2-carboxylic Acid

To a suspension of ethyl 4,5-dichloroindole-2-carboxylate (Ishii et al., *Chem. Pharm. Bull.*, 1974, 22, 1981., 1.8 g, 7.0 mmol) in ethanol (40 ml) was added 2N aqueous NaOH (10 ml) and the mixture was heated at reflux temperature for 2 h. The mixture was cooled to room temperature and concentrated. The residual solid was acidified with 2N aqueous HCl (30 ml) and extracted with diethyl ether (80 ml×2). The organic extracts were dried (MgSO$_4$) and concentrated to give 1.5 g (94%) of the title compound as yellow solids.

$^1$H-NMR (DMSO-d$_6$) δ: 12.34 (1H, br s), 7.47–7.39 (2H, m), 7.08 (1H, d, J=1.8 Hz).

Step 2. 4,5-Dichloro-2-[N-methoxy-N-methylamino) carbonyl]indole

The title compound was prepared according to the procedure described in step 1 of Example 7 from 4,5-dichloroindole-2-carboxylic acid (step 1).

$^1$H-NMR (CDCl$_3$) δ: 9.62 (1H, br s), 7.40–7.05 (3H, m), 3.88 (3H, s), 3.45 (3H, s).

Step 3. 2-Benzoyl-4,5-dichloroindole

The titled compound was prepared according to the procedure described in step 2 of Example 17 from 4,5-dichloro-2-[(N-methoxy-N-methylamino)carbonyl]indole (step 2) and phenyllithium.

m.p.: 206–210° C. (recrysallized from ethyl acetate/hexane). $^1$H-NMR (CDCl$_3$) δ: 9.58 (1H, br s), 8.05–7.98 (2H, m), 7.71–7.53 (3H, m), 7.42 (1H, d, J=8.9 Hz), 7.35 (1H, d, J=8.9 Hz), 7.22 (1H, s).

Step 4. Diethyl α-Acetoxy-(2-benzoyl-4,5-dichloro-1H-indol-3-yl)malonate

The title compound was prepared according to the procedure described in step 4 of Example 2 (Method B) from 2-benzoyl-4,5-dichloroindole (step 3).

$^1$H-NMR (CDCl$_3$) δ: 8.85 (1H, br s), 7.91–7.86 (2H, m), 7.66–7.58 (1H, m), 7.52–7.44 (2H, m), 7.36 (1H, d, J=8.7 Hz), 7.21 (1H, d, J=8.7 Hz), 4.20–3.98 (4H, m), 2.07 (3H, s), 1.15 (6H, t, J=7.3 Hz).

Step 5. Diethyl(2-benzoyl-4,5-dichloro-1H-indol-3-yl)malonate

The title compound was prepared according to the procedure described in step 5 of Example 2 (Method B) from diethyl α-acetoxy-(2-benzoyl-4,5-dichloro-1H-indol-3-yl)malonate (step 4).

$^1$H-NMR (CDCl$_3$) δ: 9.24 (1H, br s), 7.82–7.76 (2H, m), 7.65–7.58 (1H, m), 7.55–7.44 (2H, m), 7.20 (1H, d, J=8.7 Hz), 7.03 (1H, d, J=8.7 Hz), 5.89 (1H, s), 4.16–4.02 (4H, m), 1.20 (6H, t, J=7.3 Hz).

Step 6. (2-Benzoyl-4,5-dichloro-1H-indol-3-yl)acetic Acid

The title compound was prepared according to the procedure described in step 6 of Example 2 (Method B) from diethyl(2-benzoyl-4,5-dichloro-1H-indol-3-yl)malonate (step 5).

m.p.: 249–252° C. (recrystallized from ethyl acetate/hexane). IR (KBr) ν: 1701, 1625, 1523, 1450, 1330, 1257, 1012 cm$^{-1}$. $^1$H-NMR (CDCl$_3$) δ: 9.92 (1H, br s), 7.85–7.81 (2H, m), 7.66–7.42 (3H, m), 7.36 (1H, d, J=8.8 Hz), 7.29 (1H, d, J=8.8 Hz), 4.09 (2H, s).

Example 26

(2-Benzoyl-4,6-dichloro-1H-indol-3-yl)acetic Acid

Step 1. 4,6-Dichloro-2-(N-methoxy-N-methylamino)carbonyl]indole

The title compound was prepared according to the procedure described in step 1 of Example 7 from 4,6-dichloroindole-2-carboxylic acid (Salituro, Francesco G. et al., *J. Med. Chem.*, 1990, 33, 2944).

$^1$H-NMR (DMSO-d$_6$) δ: 12.09 (1H, br s), 7.48 (1H, dd, J=1.0, 1.6 Hz), 7.25 (1H, d, J=1.6 Hz), 7.11 (1H, s), 3.82 (3H, s), 3.63 (3H, s).

Step 2. 2-Benzoyl-4,6-dichloroindole

The titled compound was prepared according to the procedure described in step 2 of Example 17 from 4,6-dichloro-2-[(N-methoxy-N-methylamino)carbonyl]indole (step 1) and phenyllithium.

m.p.: 214–218° C. $^1$H-NMR (CDCl$_3$) δ: 9.45 (1H, br s), 8.02–7.95 (2H, m), 7.70–7.52 (3H, m), 7.40 (1H, d, J=1.6 Hz), 7.25 (1H, s), 7.20 (1H, d, J=1.6 Hz).

Step 3. Diethyl α-Acetoxy-(2-benzoyl-4,6-dichloro-1H-indol-3-yl)malonate

The title compound was prepared according to the procedure described in step 4 of Example 2 (Method B) from 2-benzoyl-4,6-dichloroindole (step 2).

$^1$H-NMR (CDCl$_3$) δ: 8.92 (1H, br s), 7.95–7.86 (2H, m), 7.68–7.43 (3H, m), 7.29 (1H, d, J=1.8 Hz), 7.23 (1H, d, J=1.8 Hz), 4.60–4.00 (4H, m), 2.04 (3H, s), 1.30–1.10 (6H, m).

Step 4. Diethyl(2-benzoyl-4,6-dichloro-1H-indol-3-yl)malonate

The title compound was prepared according to the procedure described in step 5 of Example 2 (Method B) from diethyl α-acetoxy-(2-benzoyl-4,6-dichloro-1H-indol-3-yl)malonate (step 3).

m.p.: 170–172° C. $^1$H-NMR (CDCl$_3$) δ: 9.15 (1H, br s), 7.84–7.75 (2H, m), 7.66–7.45 (3H, m), 7.26 (1H, s), 7.12 (1H, s), 5.79 (1H, s), 4.20–4.00 (4H, m), 1.20 (6H, t, J=7.3 Hz).

Step 5. (2-Benzoyl-4,6-dichloro-1H-indol-3-yl)acetic Acid

The title compound was prepared according to the procedure described in step 6 of Example 2 (Method B) from diethyl[2-benzoyl-4,5-dichloro-1H-indol-3-yl]malonate (step 4).

m.p.: 239–243° C. (recrystallized from ethyl acetate/hexane). IR (KBr) ν: 1725, 1555, 1525, 1330, 1287, 1250, 1005 cm$^{-1}$. $^1$H-NMR (DMSO-d$_6$) δ: 12.40 (1H, br s), 12.12 (1H, br s), 7.80–7.67 (3H, m), 7.64–7.54 (2H, m), 7.48 (1H, d, J=1.8 Hz), 7.23 (1H, d, J=1.8 Hz), 3.99 (2H, s).

Example 27

(2-Benzoyl-5,6-dichloro-1H-indol-3-yl)acetic Acid

Step 1. 5,6-Dichloroindole-2-carboxylic Acid

The title compound was prepared according to the procedure described in step 1 of Example 25 from ethyl 5,6-dichloroindole-2-carboxylate (Ishii et al., *Chem. Pharm. Bull.*, 1974, 22, 1981).

$^1$H-NMR (DMSO-d$_6$) δ: 12.06 (1H, br s), 7.95 (1H, s), 7.62 (1H, s), 7.09 (1H, s).

Step 2. 5,6-Dichloro-2-[N-methoxy-N-methylamino) carbonyl]indole

The title compound was prepared according to the procedure described in step 1 of Example 7 from 5,6-dichloroindole-2-carboxylic acid (step 1).

$^1$H-NMR (CDCl$_3$) δ: 11.86 (1H, br s), 7.96 (1H, s), 7.66 (1H, s), 7.16 (1H, s), 3.80 (3H, s), 3.34 (3H, s).

Step 3. 2-Benzoyl-5,6-dichloroindole

The titled compound was prepared according to the procedure described in step 2 of Example 17 from 5,6-dichloro-2-[(N-methoxy-N-methylamino)carbonyl]indole (step 2) and phenyllithium.

m.p.: 206–210° C. (recyrstallized from ethyl acetate/hexane). $^1$H-NMR (CDCl$_3$) δ: 9.35 (1H, br s), 8.00–7.93 (2H, m), 7.81 (1H, s), 7.69–7.51 (3H, m), 7.26 (1H, s), 7.08 (1H, s).

Step 4. Diethyl α-Acetoxy-(2-benzoyl-5,6-dichloro-1H-indol-3-yl)malonate

The title compound was prepared according to the procedure described in step 4 of Example 2 (Method B) from 2-benzoyl-5,6-dichloroindole (step 3).

$^1$H-NMR (CDCl$_3$) δ: 8.76 (1H, br s), 8.05 (1H, s), 7.90–7.82 (2H, m), 7.67–7.59 (1H, m), 7.54–7.44 (3H, m), 4.30–4.10 (4H, m), 1.69 (3H, s), 1.35–1.20 (6H, m).

Step 5. Diethyl(2-benzoyl-5,6-dichloro-1H-indol-3-yl)malonate

The title compound was prepared according to the procedure described in step 5 of Example 2 (Method B) from diethyl α-acetoxy-(2-benzoyl-5,6-dichloro-1H-indol-3-yl)malonate (step 4).

$^1$H-NMR (CDCl$_3$) δ: 8.90 (1H, br s), 7.95 (1H, s), 7.82–7.76 (2H, m), 7.70–7.61 (1H, m), 7.58–7.46 (3H, m), 5.26 (1H, s), 4.30–4.05 (4H, m), 1.24 (6H, t, J=7.1 Hz).

Step 6. (2-Benzoyl-5,6-dichloro-1H-indol-3-yl)acetic Acid

The title compound was prepared according to the procedure described in step 6 of Example 2 (Method B) from diethyl(2-benzoyl-4,5-dichloro-1H-indol-3-yl)malonate (step 5).

m.p.: 208–210° C. (recrystallized from ethyl acetate/hexane). $^1$H-NMR (DMSO-d$_6$) δ: 11.91 (1H, br s), 8.04 (1H, s), 7.77–7.50 (6H, m), 3.81 (2H, s).

Example 28 dl-2-(2-Benzoyl-6-chloro-1H-indol-3-yl)propanic Acid

Step 1. Diethyl α-Methyl-(2-benzoyl-6-chloro-1H-indol-3-yl)malonate

The title compound was prepared according to the procedure described in step 4 of Example 2 (Method B) from 2-benzoyl-6-chloroindole (step 3 of Example 2, Method B) and diethyl methylmalonate.

m.p.: 193–196° C. $^1$H-NMR (CDCl$_3$) δ: 8.42 (1H, br s), 7.87 (2H, m), 7.66–7.48 (3H, m), 7.42 (1H, d, J=8.8 Hz), 7.35 (1H, d, J=1.8 Hz), 7.11 (1H, dd, J=1.8, 8.8 Hz), 4.30–4.02 (4H, m), 1.98 (3H, s), 1.15 (6H, t, J=7.1 Hz).

Step 2. dl-2-(2-Benzoyl-6-chloro-1H-indol-3-yl)propanoic Acid

The title compound was prepared according to the procedure described in step 6 of Example 2 (Method B) from diethyl α-methyl-(2-benzoyl-6-chloro-1H-indol-3-yl)malonate (step 1).

m.p.: 204–208° C. (recrystallized from dichloromethane/hexane). IR (KBr)ν: 1720, 1620, 1475, 1260, 1230 cm$^{-1}$. $^1$H-NMR (DMSO-d$_6$) δ: 12.29 (1H, br s), 11.72 (1H, br s), 7.82–7.76 (2H, m), 7.75–7.68 (2H, m), 7.65–7.57 (2H, m), 7.48 (1H, d, J=1.8 Hz), 7.12 (1H, dd, J=1.8, 8.4 Hz), 4.15 (1H, q, J=7.1 Hz), 1.44 (3H, d, J=7.1 Hz).

Example 29 and Example 30

Less Polar Antipode, 2-(2-Benzoyl-6-chloro-1H-indol-3-yl)propanic Acid (Example 29) and More Polar Antipode, 2-(2-Benzoyl-6-chloro-1H-indol-3-yl)propanic Acid (Example 30)

Chiral separation of dl-2-(2-Benzoyl-6-chloro-1H-indol-3-yl)propanoic acid (Example 28) was performed by DAICEL CHIRALCEL OJ (4.6×250 mm, eluent: hexane/isopropanol/trifluoroacetic acid=85:15:0.1, flow rate: 1.0 ml/min) to afford; less polar compound (retention time: 17 mm.) and more polar compound (retention time: 27 min.).

Example 31

[6-Chloro-2-(4-methylpyridine-2-Carbonyl)-1H-indol-3-yl]acetic Acid

Step 1. Methyl trans-4-Chloro-2-(ethoxycarbonylamino)cinnamate

To a stirred solution of methyl trans-2-amino-4-chlorocinnamate (R. W. Carling et al., *J. Med. Chem.* 1993, 36, 3397., 32.6 g, 0.15 mol), pyridine (14.9 ml, 0.17 mol) and 4-dimethylaminopridine (0.5 g) in dichloromethane (500 ml) was added dropwise ethyl chloroformate (16.2 ml, 0.17 mol) at room temperature. After stirring for 2h, the mixture was concentrated. The residue was diluted in ethyl acetate (1000 ml) and washed with 10% aqueous citric acid (500 ml). The organic layer was successively washed with water (500 ml), saturated sodium bicarbonate (500 ml), water (500 ml), brine (500 ml). After drying (MgSO$_4$) and removal of solvent, the residual solids were recrystallized from ethyl acetate/hexane to give 39.13 g (92%) of the title compound.

$^1$H-NMR (CDCl$_3$) δ: 7.95 (1H, br s), 7.76 (1H, d, J=15.8 Hz), 7.42 (1H, d, J=8.6 Hz), 7.22 (1H, dd, J=2.1, 8.5 Hz), 6.69 (1H, br), 6.37 (1H, d, J=15.7 Hz), 4.26 (2H, q, J=7.3 Hz), 3.82 (3H, s), 1.34 (3H, t, J=7.25 Hz).

Step 2. Methyl[6-chloro-1-ethoxycarbonyl-2-(4-methylpyridine-2-carbonyl)indolin-3-yl]acetate A mixture of methyl trans-4-chloro-2-(ethoxycarbonylamino)cinnamate (step 1, 1.5 g, 5.3 mmol), 2-bromoacetyl-4-methylpyridine hydrobromide*, potassium carbonate (7.3 g, 53 mmol) and acetonitrile (50 ml) was heated at reflux temperature for 17 h. The mixture was then cooled and concentrated. The residue was diluted in ethyl acetate (200 ml) and washed with water (200 ml) and brine (200 ml). After drying (MgSO$_4$) and removal of solvent, the crude product was purified by flash column chromatography eluting with ethyl acetate/hexane (1:5) to afford 433 mg (20%) of the title compound.

* 2-bromoacetyl-4-methylpyridine hydrobromide was prepared as follows;

MS (EI) m/z: 416 (M+).

To a stirred solution of 2-acetyl-4-methylpyridine (F. H. Case et al, *J. Am. Chem. Soc.*, 1956, 78, 5842., 7.8 g, 57.7 mmol) in 25% HBr—AcOH (40 ml) was added dropwise a solution of bromine (10.1 g, 63.5 mmol) in AcOH (10 ml) with ice-cooling. After stirring for 1 h, diethyl ether (100 m) was added and the precipitates were collected by filtration to give 10.8 g (63%) of the title compound.

$^1$H-NMR (DMSO-d$_6$) δ: 8.71 (1H, d, J=5.1 Hz), 8.14 (1H, s), 7.75 (1H, d, J=5.1 Hz), 5.07 (2H, s), 2.52 (3H, s).

Step 3. [6-Chloro-2-(4-methylpyridine-2-carbonyl)-1H-indol-3-yl]acetic Acid

A stirred solution of methyl[6-chloro-1-ethoxycarbonyl-2-(4-methylpyridine-2-carbonyl)indolin-3-yl]acetate (step 2, 930 mg, 2.2 mmol) in ethanol (20 ml) and 2N aqueous NaOH (10 ml) was heated at reflux temperature for 72 h. After cooling to room temperature, the resulting mixture was neutralized with 2N aqueous HCl (10 ml) and concentrated. The residue was diluted in dichloromethane/mehanol (10:1, 300 ml) and dried (MgSO$_4$). After removal of solvent, the crude product was purified by flash column chromatography eluting with dichloromethane/methanol (20:1) and then washed with i-PrOH (ca.20 ml) to give 120 mg (17%) of the title compound as a yellow powder.

m.p.: 223° C. (decomposed). IR (KBr) ν: 1707, 1647, 1595, 1533, 1487, 1429, 1276, 1289, 1196 cm$^{-1}$. $^1$H-NMR (DMSO-d$_6$) δ: 12.30 (1H, s), 8.70 (1H, d, J=4.9 Hz), 7.96 (1H, br s), 7.85–7.70 (2H, m), 7.65–7.55 (1H, m), 7.17–7.07 (1H, m), 4.08 (2H, s), 2.47 (3H, s).

Example 32

[6-Chloro-2-(5-methylpyridine-2-carbonyl)-1H-indol-3-yl]acetic Acid

Step 1. Methyl[6-chloro-1-ethoxycarbonyl-2-(5-methylpyridine-2-carbonyl)indolin-3-yl]acetate Two diastreomers of the title compound were prepared according the procedure described in step 2 of Example 31 from methyl trans-4-chloro-2-(ethoxycarbonylamino)

cinnamate (Example 31, step 1) and 2-bromoacetyl-5-methylpyridine.*

* 2-Bromoacetyl-5-methylpyridine was prepared as follows;

Less polar product; tlc: Rf=0.30 (ethyl acetate/hexane=1/2), MS (EI) m/z: 416 (M$^+$).

More polar product; tlc: Rf=0.25 (ethyl acetate/hexane=1/2), MS (EI) m/z: 416 (M$^+$).

A mixture of 2-bromo-5-methylpyridine (5.00 g, 29.06 mmol), tributyl(1-ethoxyvinyl)tin (10.49 g, 29.07 mmol), and tetrakis(triphenylphosphine)palladium (3.36 g, 2.91 mmol) in toluene (40 ml) was heated at reflux temperature for 18 h. The mixture was cooled, filtered through a pad of Celite and then concentrated. The residue (10 g) was dissolved in a mixture of THF (100 ml) and water (20 ml), cooled to 0° C. and N-bromosuccinimide (5.43 g, 30.52 mmol) was added over 20 min. The resulting mixture was stirred for 0.5 h at the same temperature and then concentrated to ca. 20 ml. The mixture was diluted in ethyl acetate (300 ml), washed with water (100 ml×3), and dried (MgSO$_4$). After removal of solvent, the crude product was purified by flash column chromatography eluting with ethyl acetate/hexane (1:15 to 1:10) to afford 2.30 g (37%) of the title compound as an oil.

$^1$H-NMR (CDCl$_3$) δ: 8.49 (1H, br s), 8.01 (1H, d, J=8.1 Hz), 7.68–7.64 (1H, m), 4.84 (2H, s), 2.44 (3H, s).

Step 2. [6-Chloro-2-(5-methylpyridine-2-carbonyl)-1H-indol-3-yl]acetic Acid

Both of the diastereoisomers of methyl[6-chloro-1-ethoxycarbonyl-2-(5-methylpyridine-2-carbonyl)indolin-3-yl]acetate (step 2) were converted to the title compound, respectively, according to the procedure described in step 3 of Example 31.

MS (EI) m/z: 328 (M$^+$). m.p.: 235–238° C. (recrystallized from ethyl acetate). IR (KBr) ν: 3281, 1699, 1638, 1529, 1310, 1150, 797, 702 cm$^{-1}$. $^1$H-NMR (DMSO-d$_6$) δ: 12.26 (1H, br s), 8.68 (1H, br s), 8.04 (1H, d, J=8.1 Hz), 7.94 (1H, br d, J=9.1 Hz), 7.79 (1H, d, J=8.7 Hz), 7.74 (1H, br s), 7.11 (1H, br d, J=8.6 Hz), 4.10 (2H, s), 2.47 (3H, s). One signal due to NH or COOH was not observed.

Example 33

Methyl[6-chloro-2-(4-chloropyridine-2-carbonyl)-1H-indol-3-yl]acetate

A mixture of methyl trans-4-chloro-2-(phenylsulfonylamino)cinnamate (step 1 of Example 8, Method A, 675 mg, 1.92 mmol), 2-bromoacetyl-4-chloropyridine hydrobromide* (907 mg, 2.88 mmol), and potassium carbonate (2.65 g, 19.18 mmol) in acetone (20 ml) was heated at reflux temperature for 4 h. The mixture was cooled and concentrated. The residue was diluted with ethyl acetate (150 ml) and washed with water (70 ml×6). After drying (MgSO$_4$) and removal of solvent, the crude product was purified by flash column chromatography eluting with ethyl acetate/hexane (1:6–1:3) to afford 195 mg (28%) of the title compound (yellow solids) along with 264 mg (27%) of methyl[6-chloro-2-(4-chloropyridine-2-carbonyl)-1-(phenylsulfonyl)indolin-3-yl]acetate (brown crystals).

* 2-Bromoacetyl-4-chloropyridine hydrobromide was prepared as follows;

Methyl[6-chloro-2-(4-chloropyridine-2-carbonyl)-1H-indol-3-yl]acetate:

MS (EI) m/z: 362 (M$^+$). $^1$H-NMR (CDCl$_3$) δ: 12.09 (1H, br s), 8.62 (1H, d, J=5.3 Hz), 8.28 (1H, d, J=2.1 Hz), 7.57 (1H, d, J=8.6 Hz), 7.52 (1H, dd, J=2.0 and 5.3 Hz), 7.45 (1H, d, J=1.8 Hz), 7.08 (1H, dd, J=1.8 and 8.7 Hz), 4.27 (2H, s), 3.75 (3H, s).

Methyl[6-chloro-2-(4-chloropyridine-2-carbonyl)-1-(phenylsulfonyl)indolin-3-yl]acetate:

tlc: Rf=0.35 (ethyl acetate/hexane=1:2). MS (EI) m/z (intensity): 504 (M$^+$, 0.1), 363 (90), 335 (30), 304 (100), 275 (10), 223 (15). 4-Chloro-2-pyridinecarbonitrile: To a mixture of 4-chloropyridine-N-oxide (5.00 g, 38.6 mmol) and trimethylsilyl cycanide (4.84 g, 46.3 mmol) in dichloromethane (60 ml) cooled to 0° C. was added dropwise N,N-dimethylcarbamoyl chloride (3.8 ml, 40.5 mmol). The mixture was allowed to warm to ambient temperature and stirred for 16 h. The mixture was cooled to 0° C. and a 30% aqueous solution of potassium carbonate (100 ml) was added. The crude product was extracted with dichloromethane (100 ml×2), the organic extracts dried (MgSO$_4$) and evaporated to give 4-chloro-2-pyridinecarbonitrile (5.35 g, 100%).

$^1$H-NMR (CDCl$_3$) δ: 8.63 (1H, d, J=4.8 Hz), 7.72 (1H, d, J=2.6 Hz), 7.55 (1H, dd, J=1.8, 5.1 Hz).

2-Acetyl-4-chloropyridine: To a solution of 4-chloro-2-pyridinecarbonitrile (5.35 g, 38.6 mmol) in benzene (50 ml) and ether (50 ml) cooled to 0° C. was added dropwise over 20 min a 2M solution of MeMgI in ether (23 ml, 46.3 mmol). After 0.5 h, the mixture was allowed to warm to ambient temperature, and stirring continued for 2 h. The mixture was cooled to 0° C. and 2M aqueous HCl (100 ml) added. The mixture was made basic with saturated aqueous sodium bicarbonate (~80 ml) and the organic layer separated and dried (MgSO$_4$). After removal of solvent, the residue was purified by flash chromatography eluting with ethyl acetate/hexane (1:5) to afford 3.60 g (60%) of 2-acetyl-4-chloropyridine.

$^1$H-NMR (DMSO-d$_6$) δ: 8.59 (1H, d, J=5.1 Hz), 8.04 (1H, d, J=1.8 Hz), 7.47 (1H, dd, J=1.8, 5.1 Hz), 2.72 (3H, s).

2-Bromoacetyl-4-chloropyridine hydrobromide: 2-(Bromoacetyl)-4-chloropyridine hydrobromide was prepared from 2-acetyl-4-chloropyridine according to the method of H. McKennis, Jr., L. B. Turnbull, E. R. Bowman, and E. Tamaki (in J. Org. Chem., 1963, 28, 383–387).

$^1$H-NMR (DMSO-d$_6$) δ: 8.74 (1H, d, J=5.5 Hz), 8.05 (1H, d, J=1.8 Hz), 7.88 (1H, dd, J=2.2 and 5.5 Hz), 5.02 (2H, s).

Example 34

[6-Chloro-2-(4-chloropyridine-2-carbonyl)-1H-indol-3-yl]acetic Acid

A suspension of methyl[6-chloro-2-[4-chloropyridine-2-carbonyl]-1H-indol-3-yl]acetate (Example 33, 195 mg, 0.537 mmol) in ethanol (20 ml) and 2N sodium hydroxide (4 ml) was heated for 1 h at 50° C. After cooling to room temperature, 2N hydrochloric acid (4 ml) was added and the mixture was concentrated. The residue was diluted in ethyl acetate (100 ml), washed with water (50 ml×2), and dried (MgSO$_4$). After removal of solvent, the crystalline residue was recrystallized from ethyl acetate to afford 175 mg (94%) of the title compound.

m.p.: 233–234° C. IR (KBr) ν: 3306, 1709, 1641, 1531, 1254, 1236, 741 cm$^{-1}$. $^1$H-NMR (DMSO-d$_6$) δ: 12.20 (1H, br s), 12.16 (1H, br s), 8.80 (1H, d, J=5.4 Hz), 8.12 (1H, d, J=2.1 Hz), 7.90 (1H, dd, J=2.1, 5.3 Hz), 7.81 (1H, d, J=8.7 Hz), 7.70 (1H, d, J=1.8 Hz), 7.13 (1H, dd, J=2.0, 8.7 Hz), 4.07 (2H, s).

Example 35

[6-Chloro-2-(pyridine-2-carbonyl)-1H-indol-3-yl]acetic Acid

Step 1. Methyl[6-chloro-1-ethoxycarbonyl-2-(pyridine-2-carbonyl)indolin-3-yl]acetate The title compound were prepared according the procedure described in step 2 of Example 31 from methyl trans- 4-chloro-2-(ethoxycarbonylamino)cinnamate (Example 31, step 1) and 2-bromoacetylpyridine hydrobromide (H. McKennis et al., *J. Org. Chem.*, 1963, 387.).

tlc: Rf=0.3 (ethyl acetate/hexane=1:3).

Step 2. [6-Chloro-2-(pyridine-2-carbonyl)-1H-indol-3-yl] acetic Acid

The title compound were prepared according the procedure described in step 3 of Example 31 from methyl[6-chloro-1-ethoxycarbonyl-2-(pyidine-2-carbonyl)indolin-3-yl]acetate (step 1).

m.p.: 210° C. (decomposed). IR (KBr) ν: 3280, 1697, 1643, 1531, 1234, 1150 cm$^{-1}$. $^1$H-NMR (DMSO-d$_6$) δ: 12.22 (1H, s), 8.84 (1H, d, J=4.9 Hz), 8.15–8.05 (2H, m), 7.85–7.65 (3H, m), 7.11 (1H, dd, J=1.9, 8.7 Hz), 4.04 (2H, s).

Example 36

[5-Chloro-2-(4-methylpyridine-2-carbonyl)-1H-indol-3-yl]acetic Acid

Step 1. Methyl trans-5-Chloro-2-nitrocinnamate

A mixture of the 5-chloro-2-nitrobenzaldehyde (9.68 g, 52.16 mmol) and methyl(triphenylphophoranylidene) acetate (18.31 g, 54.77 mmol) in toluene (200 ml) was heated at reflux temperature for 2 h. The mixture was concentrated and the crystalline residue was purified by flash column chromatography eluting with ethyl acetate/hexane (1:5) to afford crystals. Recrystallizaion from ethyl acetate/hexane gave 7.54 g (60%) of the title compound as pale yellow solids.

$^1$H-NMR (CDCl$_3$) δ: 8.09 (1H, d, J=15.8 Hz), 8.04 (1H, d, J=8.7 Hz), 7.60 (1H, d, J=2.1 Hz), 7.51 (1H, dd, J=2.1, 8.7 Hz), 6.36 (1H, d, J=15.8 Hz), 3.84 (3H, s).

Step 2. Methyl trans-2-Amino-5-chlorocinnamate

A mixture of methyl trans-5-chloro-2-nitrocinnamate (step 1, 3.00 g, 12.42 mmol), iron powder (3.65 g, 62.08 mmol), ammonium chloride (332 mg, 6.21 mmol), ethanol (60 ml) and water (10 ml) was heated at reflux temperature for 2 h. The mixture was cooled and filtered through a pad of Celite. The filtrate was concentrated. The residue was diluted with ethyl acetate (200 ml) and washed with water (100 ml×2). After drying (MgSO$_4$), removal of solvent gave 2.57 g (98%) of the title compound as crystals.

$^1$H-NMR (CDCl$_3$) δ: 7.73 (1H, d, J=15.8 Hz), 7.34 (1H, d, J=2.5 Hz), 7.12 (1H, dd, J=2.3, 8.6 Hz), 6.64 (1H, d, J=8.6 Hz), 6.35 (1H, d, J=15.8 Hz), 3.95 (2H, br s), 3.81 (3H, s).

Step 3. Methyl trans-5-Chloro-2-(phenylsulfonylamino) cinnamate

The title compound was prepared according to the procedure described in step 1 of Example 8 (Method A) from methyl trans-2-amino-5-chlorocinnamate (step 2).

$^1$H-NMR (CDCl$_3$) δ: 7.72–7.67 (2H, m), 7.58–7.51 (1H, m), 7.47–7.40 (4H, m), 7.36 (1H, d, J=8.6 Hz), 7.31 (1H, dd, J=2.1, 8.6 Hz), 6.14 (1H, d, J=15.8 Hz), 3.78 (3H, s). One signal due to NH was not observed.

Step 4. Methyl[5-chloro-2-(4-methylpyridine-2-carbonyl)-1-(phenylsulfonyl)indolin-3-yl]acetate The title compound was prepared according to the procedure described in step 2 of Example 8 (Method A) from methyl trans-5-chloro-2-(phenylsulfonylamino)cinnamate (step 3) and 2-bromoacetyl-4-methylpyridine hydrobromide (F. H. Case et al., *J. Am. Chem. Soc.*, 1956, 78, 5842).

tlc: Rf=0.32 (ethyl acetate/hexane=1:2)

Step 5. [5-Chloro-2-(4-methylpyridine-2-carbonyl)-1H-indol-3-yl]acetic Acid

The title compound was prepared according to the procedure described in step 3 of Example 31 from methyl[5-chloro-2-(4-methylpyridine-2-carbonyl)-1-(phenylsulfonyl) indolin-3-yl]acetate (step 4).

MS (EI) m/z: 328 (M$^+$). m.p.: 230–231° C. (recrystallized from ethyl acetate). IR (KBr) ν: 3292, 1699, 1597, 1533, 1282, 1198, 1059, 802, 704 cm$^{-1}$. $^1$H-NMR (DMSO-d$_6$) δ: 12.26 (1H, br s), 8.69 (1H, d, J=5.1 Hz), 7.93 (1H, br s), 7.82 (1H, d, J=2.0 Hz), 7.66 (1H, d, J=8.7 Hz), 7.56 (1H, br d, J=4.9 Hz), 7.31 (1H, dd, J=2.0, 8.7 Hz), 4.02 (2H, s), 2.46 (3H, s). One signal due to NH or COOH was not observed.

Example 37

Methyl[5-chloro-2-(6-methylpyridine-2-carbonyl)-1H-indol-3-yl]acetate

Step 1. Methyl[5-chloro-2-(6-methylpyridine-2-carbonyl)-1-(phenylsulfonyl)indolin-3-yl]acetate The title compound was prepared according to the procedure described in step 2 of Example 8 (Method A) from methyl trans-5-chloro-2-(phenylsulfonylamino)cinnamate (Example 36, step 3) and 2-bromoacetyl-6-methylpyridine hydrobromide (H. Erlenmeyer, J. Jenni, and B. Prijs, *J. Med. Pharm. Chem.*, 1961, 3, 561–566).

tlc: Rf=0.39 (ethyl acetate/hexane=2:3).

Step 2. Methyl[5-chloro-2-(6-methylpyridine-2-carbonyl)-1H-indol-3-yl]acetate

The title compound was prepared according to the procedure described in step 3 of Example 8 (Method A) from methyl[5-chloro-2-(6-methylpyridine-2-carbonyl)-1-(phenylsulfonyl)indolin-3-yl]acetate (step 1).

$^1$H-NMR (CDCl$_3$) δ: 12.62 (1H, br s), 8.15 (1H, d, J=7.9 Hz), 7.84 (1H, t, J=7.7 Hz), 7.67 (1H, d, J=1.8 Hz), 7.43 (1H, d, J=8.9 Hz), 7.40 (1H, d, J=7.7 Hz), 7.32 (1H, dd, J=2.0, 8.7 Hz), 4.28 (2H, s), 3.73 (3H, s), 2.76 (3H, s).

Example 38

[5-Chloro-2-(6-methylpyridine-2-carbonyl)-1H-indol-3-yl]acetic Acid

The title compound was prepared according to the procedure described in Example 34 from methyl[5-chloro-2-(6-methylpyridine-2-carbonyl)-1H-indol-3-yl]acetate.

MS (EI) m/z: 328 (M$^+$). m.p.: 225–226° C. (recrystallized from ethyl acetate). IR (KBr) ν: 1705, 1636, 1529, 1333, 1236, 1180, 1061, 669 cm$^1$. $^1$H-NMR (DMSO-d$_6$) δ: 12.13 (1H, br s), 12.09 (1H, br s), 7.99 (1H, t, J=7.7 Hz), 7.87 (1H, d, J=7.7 Hz), 7.84 (1H, d, J=2.0 Hz), 7.66 (1H, d, J=8.9 Hz), 7.59 (1H, d, J=7.6 Hz), 7.33 (1H, dd, J=2.0, 8.9 Hz), 4.03 (2H, s), 2.69 (3H, s).

Example 39

[6-Chloro-2-(1-methylimidazole-2-carbonyl)-1H-indol-3-yl]acetic Acid

Step 1. Methyl[6-chloro-1-ethoxycarbonyl-2-(1-methylimidazole-2-carbonyl)indolin-3-yl]acetate The title compound was prepared according to the procedure described in step 2 of Example 31 from methyl trans-4-chloro-2-(ethoxycarbonylamino)cinnamate (Example 31, step 1) and 2-bromoacetyl-1-methylimidazole hydrobromide.*

* 2-Bromoacetyl-1-methylimidazole hydrobromide was prepared as follows;

MS (EI) m/z: 405 (M$^+$).

To a stirred suspension of 2-acetyl-1-methylimidazole (D. H. Davis, J. Hall, and E. H. Smith, *J. Chem. Soc. Perkin trans.* 1, 1991, 2691., 3.0 g, 26.8 mmol) in 25% HBr—AcOH was added dropwise a solution of bromine (4.7 g, 29.5 mmol) with ice-cooling. After stirring for 0.5 h, the mixture was allowed to warm to room temperature and the stirring was continued for an additional 1 h. To the mixture was added diethyl ether (150 ml) and the mixture was cooled with ice-bath. The precipitates were collected by filtration to give 5.2 g (66%) of the title compound as a pale yellow powder.

$^1$H-NMR (DMSO-$d_6$) d: 7.61 (1H, s), 7.27 (1H, s), 4.68 (2H, s), 3.81 (3H, s).

Step 2. [6-Chloro-2-(1-methylimidazole-2-carbonyl)-1H-indol-3-yl]acetic Acid

The title compound was prepared according to the procedure described in step 3 of Example 31 from [6-chloro-1-ethoxycarbonyl-2-(1-methylimidazole-2-carbonyl)indolin-3-yl]acetate (step 1).

m.p.: 236° C. (decomposed). MS (EI) m/z: 317 (M$^+$). IR (KBr) ν: 3238, 1695, 1630, 1537, 1402, 1229, 1146 cm$^{-1}$. $^1$H-NMR (CDCl$_3$+DMSO-$d_6$) δ: 12.30 (1H, s), 7.65 (1H, d, J=8.7 Hz), 7.50 (1H, d, J=1.8 Hz), 7.42 (1H, s), 7.28–7.23 (1H, m), 7.16 (1H, s), 7.09 (1H, dd, J=1.8, 8.6 Hz), 4.25 (2H, s), 4.13 (3H, s).

Example 40

Methyl[5-chloro-2-(thiazole-2-carbonyl)-1H-indol-3-yl]acetate

Step 1. Methyl[5-chloro-1-phenylsulfonyl-2-(thiazole-2-carbonyl)indolin-3-yl]acetate The title compound was prepared according to the procedure described in step 2 of Example 8 (Method A) from methyl trans-5-chloro-2-(phenylsulfonylamino)cinnamate (Example 36, step 3) and 2-bromoacetylthiazole hydrobromide (A. Dondoni, A. Marra, and P. Merino, *J. Am. Chem. Soc.*, 1994, 116, 3324).

tlc: Rf=0.07 (ethyl acetate/hexane=1:2).

Step 2. Methyl[5-chloro-2-(thiazole-2-carbonyl)-1H-indol-3-yl]acetate

The title compound was prepared according to the procedure described in step 3 of Example 8 (Method A) from methyl[5-chloro-1-phenylsulfonyl-2-(thiazole-2-carbonyl)indolin-3-yl]acetate (step 1).

$^1$H-NMR (CDCl$_3$) δ: 11.78 (1H, br s), 8.12 (1H, d, J=3.1 Hz), 7.75 (1H, d, J=3.1 Hz), 7.68 (1H, d, J=1.8 Hz), 7.44 (1H, d, J=8.7 Hz), 7.34 (1H, dd, J=2.0, 8.9 Hz), 4.29 (2H, s), 3.74 (3H, s).

Example 41

[5-Chloro-2-(thiazole-2-carbonyl)-1H-indol-3-yl]acetic Acid

The title compound was prepared according to the procedure described in Example 9 (Method B) from methyl[5-chloro-1-phenylsulfonyl-2-(thiazole-2-carbonyl)-1H-indol-3-yl)acetate (step 2).

MS (EI) m/z: 320 (M$^+$). m.p.; 230–231lC (recrystallized from ethyl acetate). IR (KBr) ν: 3302, 1703, 1636, 1541, 1387, 1335, 1267, 1232, 1186, 1003, 766 cm$^{-1}$. $^1$H-NMR (DMSO-$d_6$) δ: 12.23 (1H, br s), 12.10 (1H, br s), 8.33 (1H, d, J=3.1 Hz), 8.31 (1H, d, J=3.1 Hz), 7.89 (1H, d, J=2.0 Hz), 7.77 (1H, d, J=8.9 Hz), 7.36 (1H, dd, J=2.0, 8.7 Hz), 4.17 (2H, s).

Example 42

Methyl(2-benzoyl-6-chloro-1H-indol-3-yl)acetate

A mixture of (2-benzoyl-6-chloro-1H-indol-3-yl)acetic acid (Example 2, 50 mg, 0.16 mmol) and 10% HCl in methanol (3 ml) was stirred for 3 h at room temperature. The mixture was concentrated and the residue was purified by flash column chromatography eluting with ethyl acetate/hexane (1:5) to afford 23 mg (44%) of the title compound as white solids.

m.p.: 134–137° C. IR (KBr) ν: 1735, 1620, 1529, 1434, 1325, 1147, 1013, 945 cm$^{-1}$. $^1$H-NMR (CDCl$_3$) δ: 8.96 (1H, br s), 7.85–7.74 (2H, m), 7.66–7.47 (4H, m), 7.38 (1H, d, J=1.8 Hz), 7.15 (1H, dd, J=1.8, 8.6 Hz), 3.18 (2H, s), 3.65 (3H, s).

Example 43

(2-Benzoyl-6-chloro-1H-indol-3-yl)-N,N-dimethylacetamide

To a solution of (2-benzoyl-6-chloro-1H-indol-3-yl)acetic acid (Example 2, 140 mg, 0.45 mmol), dimethylamine hydrochloride (45 mg, 0.54 mmol) and triethylamine (0.1 ml, 0.54 mmol) in DMF (2 ml) at 0° C. was added diethyl phosphorocyanidate (DEPC, 0.1 ml, 0.54 mmol). The mixture was then stirred at room temperature for 1 h. The mixture was poured into water (20 ml) and extracted with diethyl ether (50 ml×2). The organic extracts were washed with water (30 ml×2), dried (MgSO$_4$) and concentraied. The residual solids were recrystallized from ethyl acetate/hexane to afford 50 mg (33%) of the title compound.

m.p.: 190–193° C. (recrystallized from ethyl acetate/hexane). IR (KBr) ν: 1631, 1232, 1007, 908 cm$^{-1}$. $^1$H-NMR (CDCl$_3$) δ: 11.72 (1H, br s), 7.72–7.64 (4H, m), 7.60–7.52 (2H, m), 7.45 (1H, d, J=1.2 Hz), 7.08 (1H, d, J=8.6 Hz), 3.32 (2H, s), 2.80 (3H, s), 2.76 (3H, s).

Example 44

(2-Benzoyl-6-chloro-1H-indol-3-yl)-N-methylacetamide

The title compound was prepared according to the procedure described in Example 43 from (2-benzoyl-6-chloro-1H-indol-3-yl)acetic acid (Example 2) and methylamine hydrochloride.

m.p.: 242–246° C. (recrystallized from ethyl acetate/hexane). IR (KBr) ν: 1618, 1527, 1409, 1325 cm$^{-1}$. $^1$H-NMR (CDCl$_3$) δ: 11.71 (1H, br s), 7.82–7.75 (2H, m), 7.62–7.52 (5H, m), 7.49–7.46 (1H, m), 7.15–7.08 (1H, m), 3.64 (2H, s), 3.31 (3H, s).

Example 45

(2-Benzoyl-6-chloro-1H-indol-3-yl)acetamide

The title compound was prepared according to the procedure described in Example 43 from (2-benzoyl-6-chloro-1H-indol-3-yl)acetic acid (Example 2) and a solution of ammonia in THF.

m.p.: 234–237° C. IR (KBr) ν: 1665, 1618, 1566, 1523, 1325, 1259, 943 cm$^{-1}$. $^1$H-NMR (CDCl$_3$) δ: 11.66 (1H, br s), 7.82–7.75 (2H, m), 7.74–7.65 (2H, m), 7.62–7.53 (2H, m), 7.46 (1H, d, J=1.8 Hz), 7.27 (1H, br s), 7.12 (1H, dd, J=1.8, 8.6 Hz), 6.85 (1H, br s), 3.63 (2H, s).

Example 46

(2-Benzoyl-6-chloro-1H-indol-3-yl)-N-methoxy-N-methylacetamide

The title compound was prepared according to the procedure described in Example 43 from (2-benzoyl-6-chloro-1H-indol-3-yl)acetic acid (Example 2) and N,O-dimethylhydroxylamine hydrochloride.

m.p.: 109.9–112.2° C. (decomposed). IR (KBr) ν: 3179, 2970, 2937, 1634, 1599, 1570 cm$^{-1}$. $^1$H-NMR (CDCl$_3$) δ: 9.20–8.90 (1H, m), 7.84–7.75 (2H, m), 7.66–7.45 (4H, m), 7.33 (1H, d, J=1.3 Hz), 7.12 (1H, dd, J=8.6, 1.8 Hz), 3.94 (2H, s), 3.51 (3H, s), 3.13 (3H, s).

Example 47

2-(2-Benzoyl-6-chloro-1H-indol-3-yl)-1-piperidino-1-ethanone

Step 1. 7-Chloro-1-phenyl-9H-pyrano[3,4-b]indole-3-one

A solution of (2-benzoyl-6-chloro-1H-indol-3-yl)acetic acid (Example 2, 200 mg, 0.64 mmol), diethyl phosphorocyanidate (DEPC, 0.12 ml, 0.76 mmol) and triethylamine (0.11 ml, 0.76 mmol) in DMF (3.0 ml) was stirred at room temperature for 5 min. The mixture was then poured into water (20 ml) and the orange precipitates were collected by filtration to give 20 mg (11%) of the title compound as orange solids.

$^1$H-NMR (CDCl$_3$) δ: 10.79 (1H, br s), 8.10 (1H, d, J=8.4 Hz), 7.93–7.84 (2H, m), 7.67–7.50 (3H, m), 7.29 (1H, s), 7.13 (1H, d, J=8.4 Hz), 6.87 (1H, s).

Step 2. 2-(2-Benzoyl-6-chloro-1H-indol-3-yl)-1-piperidino-1-ethanone

A mixture of 7-chloro-1-phenyl-9H-pyrano[3,4-b]indole-3-one (step 1, 0.30 g, 1.0 mmol), and piperidine (1.0 ml, 10 mmol) in methanol (20 ml) was heated under reflux temperature for 2 h. After cooling down to rt, the yellow mixture was concentrated and the residual solids were recrystallized from methanol/hexane to give 0.12 g (32%) of the title compound.

m.p.: 223–224° C. IR (KBr) ν: 3310, 2928, 1655, 1570, 1533, 1447, 1323, 1256, 1225, 1059, 945, 858, 737, 700 cm$^{-1}$. $^1$H-NMR (DMSO-d$_6$) δ: 11.7 (1H, br s), 7.74–7.63 (4H, m), 7.55 (2H, t, J=8.7 Hz), 7.46 (1H, d, J=1.8 Hz), 7.09 (1H, dd, J=8.7, 1.8 Hz), 3.80 (2H, s), 3.45–3.20 (4H, m), 1.55–1.20 (6H, m).

Example 48

2-(2-Benzoyl-6-chloro-1H-indol-3-yl)-N-(4-methyl-1-piperazinyl)-1-ethanone

The title compound was prepared according to the procedure described in Example 43 from (2-benzoyl-6-chloro-1H-indol-3-yl)acetic acid (Example 2) and 1-methylpiperazine.

m.p.: 184–185° C. (recrystallized from methanol/hexane). IR (KBr) ν: 2939, 2795, 1634, 1531, 1435, 1325, 1229, 1144, 1001, 737, 700 cm$^{-1}$. $^1$H-NMR (CDCl$_3$) δ: 9.37 (1H, br s), 7.78–7.75 (1H, m), 7.73 (1H, d, J=1.5 Hz), 7.62–7.52 (2H, m), 7.52–7.43 (2H, m), 7.18–7.10 (1H, m), 7.10–7.02 (1H, m), 3.81 (2H, s), 3.54 (2H, br s), 3.36 (2H, t, J=4.8 Hz), 2.36–2.22 (4H, m), 2.28 (3H, s).

Example 49

(2-Benzoyl-6-chloro-1H-indol-3-yl)-N-(2-cyanoethyl)acetamide

The title compound was prepared according to the procedure described in Example 43 from (2-benzoyl-6-chloro-1H-indol-3-yl)acetic acid (Example 2) and aminopropionitrile.

m.p.: 233–233.5° C. (recrystallized from methanol/hexane). $^1$H-NMR (DMSO-d$_6$) δ: 11.7 (1H, br s), 8.16 (1H, t, J=6.3 Hz), 7.81–7.75 (2H, m), 7.72–7.64 (2H, m), 7.62–7.53 (2H, m), 7.47 (1H, d, J=1.9 Hz), 7.10 (1H, dd, J=8.7, 1.9 Hz), 3.67 (2H, s), 3.23 (2H, q, J=6.3 Hz), 2.58 (2H, t, J=6.3 Hz).

Example 50

(2-Benzoyl-6-chloro-1H-indol-3-yl)-N-(2-hydroxyethyl)acetamide

The title compound was prepared according to the procedure described in Example 43 from (2-benzoyl-6-chloro-1H-indol-3-yl)acetic acid (Example 2) and 2-aminoethanol.

m.p.: 178–179.5° C. (recrystallized from methanol/hexane). $^1$H-NMR (DMSO-d$_6$) δ: 11.7 (1H, br s), 7.84–7.75 (3H, m), 7.72–7.64 (2H, m), 7.61–7.52 (2H, m), 7.46 (1H, d, J=2.0 Hz), 7.11 (1H, dd, J=8.6, 2.0 Hz), 3.64 (2H, s), 3.38–3.30 (3H, m), 3.06 (2H, q, J=5.9 Hz).

Example 51

2-(2-Benzoyl-6-chloro-1H-indol-3-yl)-1-morpholino-1-ethanone

The title compound was prepared according to the procedure described in Example 43 from (2-benzoyl-6-chloro-1H-indol-3-yl)acetic acid (Example 2) and morpholine.

m.p.: 187.7–189.5° C. IR (KBr) ν: 3339, 2964, 2849, 1653, 1612, 1568 cm$^{-1}$. $^1$H-NMR (CDCl$_3$) δ: 9.08–8.92 (1H, m), 7.81–7.72 (2H, m), 7.69–7.58 (2H, m), 7.56–7.47 (2H, m), 7.29 (1H, d, J=1.8 Hz), 7.12 (1H, dd, J=8.6, 1.8 Hz), 3.87 (2H, s), 3.67–3.46 (6H, m), 3.41–3.31 (2H, m).

Example 52

[2-(4-Chlorobenzoyl)-1H-indol-3-yl]acetic Acid

Step 1. 2-(4-Chlorobenzoyl)-1-(phenylsulfonyl)indole

To a solution of 1-(phenylsulfonyl)indole (500 mg, 1.94 mmol) in THF (5 ml) was added dropwise tert-butyllithium (1.4 ml, 2.33 mmol) under nitrogen atmosphere at −78° C. The yellow solution was cannulated directly into a solution of p-chlorobenzoyl chloride (0.3 ml, 2.33 mmol) in THF (3 ml) cooled to −78° C. The reaction mixture was stirred at −78° C. for 2 h. The mixture was quenched with saurated ammonium chloride and extracted with ethyl acetate (100 ml). The organic layer was washed with water (50 ml), brine (50 ml) and dried (MgSO$_4$). After removal of solvent, the crude product was purified by flash column chromatography eluting with hexane/ethyl acetate (10:1) to afford 339 mg (44.1%) of the title compound as yellow amorphous solids.

$^1$H-NMR (CDCl$_3$) δ: 8.13 (1H, d, J=8.4 Hz), 8.04–8.00 (2H, m), 7.93–7.90 (2H, m), 7.58–7.44 (7H, m), 7.30 (1H, t, J=7.4 Hz), 6.95 (1H, s).

Step 2. 2-(4-Chlorobenzoyl)indole

A mixture of 2-(4-chlorobenzoyl)-1-(phenylsulfonyl)indole (step 1, 334 mg, 0.84 mmol) and 2N sodium hydroxide (1.5 ml, 2.78 mmol) in ethanol (5 ml) was heated at reflux temperature for 15 min. The mixture was concentrated and the residue was diluted with ethyl acetate (100 ml). The organic layer was washed with water and dried (MgSO$_4$), and concentrated to afford 211 mg (98.2%) of the title compound as yellow solids.

$^1$H-NMR (CDCl$_3$) δ: 9.45 (1H, br.s), 7.97–7.92 (2H, m), 7.74–7.70 (1H, m), 7.54–7.47 (3H, m), 7.42–7.36 (1H, m), 7.21–7.13 (2H, m).

Step 3. Diethyl α-Acetoxy-[2-(4-chlorobenzoyl)-1H-indol-3-yl)]malonate

The title compound was prepared according to the procedure described in step 4 of Example 2 (Method B) employing 2-(4-chlorobenzoyl)indole (step 2).

$^1$H-NMR (CDCl$_3$) δ: 8.94 (1H, br.s), 7.90 (1H, d, J=8.4 Hz), 7.81–7.77 (2H, m), 7.43–7.36 (3H, m), 7.32–7.26 (1H, m), 7.22–7.16 (1H, m), 4.27–4.14 (4H, m), 1.75 (3H, s), 1.29–1.16 (6H, m).

Step 4. Diethyl[2-(4-chlorobenzoyl)-1H-indol-3-yl]malonate

The title compound was prepared according to the procedure described in step 5 of Example 2 (Method B) employing diethyl α-acetoxy-[2-(4-chlorobenzoyl)-1H-indol-3-yl)]malonate (step 3).

$^1$H-NMR (CDCl$_3$) δ: 8.73 (1H, br.s), 7.85–7.82 (1H, m), 7.79–7.76 (2H, m), 7.52–7.46 (2H, m), 7.39–7.37 (1H, m), 7.26–7.19 (2H, m), 5.27 (1H, s), 4.26–4.16 (4H, m), 1.26–1.21 (6H, m).

Step 5. [2-(4-Chlorobenzoyl)-1H-indol-3-yl]acetic Acid

The title compound was prepared according to the procedure described in step 6 of Example 2 (Method B) employing diethyl[2-(4-chlorobenzoyl)-1H-indol-3-yl]malonate (step 4).

m.p.: 221–224° C. (recrystallized from ethyl acetate/hexane). IR (KBr) ν: 3321, 1697, 1607, 1576, 1529, 1433, 1408, 1339, 1263, 1223, 1202 cm$^{-1}$. $^1$H-NMR (DMSO-d$_6$) δ: 11.62 (1H, s), 7.79–7.75 (2H, m), 7.71–7.63 (3H, m), 7.46 (1H, d, J=8.2 Hz), 7.35–7.29 (1H, m), 7.14–7.08 (1H, m), 3.84 (2H, s).

Example 53

[6-Chloro-2-(2-furylcarbonyl)-1H-indol-3-yl]acetic Acid

Step 1. 6-Chloro-2-(2-furylcarbonyl)-1-(phenylsulfonyl)indole

The title compound was prepared according the procedure described in step 2 of Example 2 (Method B) from 6-chloro-1-(phenylsulfonyl)indole (step 1 of Example 2, Method B) and 2-furoyl chloride.

$^1$H-NMR (CDCl$_3$) δ: 8.11–8.19 (3H, m), 7.73–7.74 (1H, m), 7.51–7.65 (4H, m), 7.27–7.31 (2H, m), 7.10 (1H, s), 6.62–6.64 (1H, m).

Step 2. 6-Chloro-2-(2-furylcarbonyl)indole

The title compound was prepared according to the procedure described in step 3 of Example 2 (Method B) from 6-chloro-2-(2-furylcarbonyl)-1-(phenylsulfonyl)indole (step 1).

$^1$H-NMR (CDCl$_3$) δ: 9.33 (1H, br s), 7.65–7.73 (3H, m), 7.46–7.48 (2H, m), 7.12–7.16 (1H, m), 6.64–6.66 (1H, m).

Step 3. Diethyl α-Acetoxy[6-chloro-2-(2-furylcarbonyl)indol-3-yl]malonate

The title compound was prepared according to the procedure described in step 4 of Example 2 (Method B) from 6-chloro-2-(2-furylcarbonyl)indole (step 2).

$^1$H-NMR (CDCl$_3$) δ: 9.60 (1H, br s), 7.76 (1H, d, J=8.9 Hz), 7.62–7.63 (1H, m), 7.43 (1H, d, J=1.3 Hz), 7.28–7.29 (1H, m), 7.13 (1H, dd, J=1.8 Hz, 8.7 Hz), 6.59 (1H, dd, J=1.6 Hz, 3.5 Hz), 4.18–4.32 (4H, m), 1.88 (3H, s), 1.18–1.28 (6H, m).

Step 4. Diethyl[6-chloro-2-(2-furylcarbonyl)indol-3-yl]malonate

The title compound was prepared according to the procedure described in step 5 of Example 2 (Method B) from diethyl α-acetoxy-[6-chloro-2-(2-furylcarbonyl)indol-3-yl]malonate (step 3).

$^1$H-NMR (CDCl$_3$) δ: 9.83 (1H, br s), 7.67 (1H, t, J=0.8 Hz), 7.63 (1H, d, J=8.9 Hz), 7.40 (1H, d, J=3.6 Hz), 7.30 (1H, d, J=1.8 Hz), 7.01 (1H, dd, J=1.8 Hz, 8.9 Hz), 6.62 (1H, dd, J=1.6 Hz. 2.1 Hz), 6.19 (1H, s), 4.20–4.32 (4H, m), 1.27 (6H, t, J=7.3 Hz).

Step 5. [6-Chloro-2-(2-furylcarbonyl)indol-3-yl]acetic Acid.

The title compound was prepared according to the procedure described in step 6 of Example 2 (Method B) from diethyl[6-chloro-2-(2-furylcarbonyl)indol-3-yl]malonate (step 4).

$^1$H-NMR (DMSO-d$_6$) δ: 12.22 (1H, br s), 11.76 (1H, br s), 8.13 (1H, d, J=1.0 Hz), 7.75 (1H, d, J=8.6 Hz), 7.56 (1H, d, J=1.8 Hz), 7.48 (1H, d, J=3.6 Hz), 7.14 (1H, dd, J=1.8 Hz, 8.6 Hz), 6.85 (1H, dd, J=1.8 Hz, 3.6 Hz), 4.02 (2H, s).

Example 54

[6-Chloro-2-(cyclohexanecarbonyl)-1H-indol-3-yl]acetic Acid

Step 1. 6-Chloro-2-cyclohexanecarbonyl-1-(phenylsulfonyl)indole

The title compound was prepared according to the procedure described in step 2 of Example 2 (Method B) from 6-chloro-1-(phenylsulfonyl)indole (step 1 of Example 2, Method B) and cyclohexanecarbonyl chloride.

tlc: Rf=0.4 (ethyl acetate/hexane=1:4).

Step 2. 6-Chloro-2-(cyclohexanecarbonyl)indole

The title compound was prepared according to the procedure described in step 3 of Example 2 (Method B) from 6-chloro-2-cyclohexanecarbonyl-1-(phenylsulfonyl)indole (step 1).

$^1$H-NMR (CDCl$_3$) δ: 10.08 (1H, br s), 8.08–7.04 (4H, m), 2.28–1.20 (1H, m).

Step 3. Diethyl α-Acetoxy-[6-chloro-2-(cyclohexanecarbonyl)-1H-indol-3-yl]malonate The title compound was prepared according to the procedure described in step 4 of Example 2 (Method B) from 6-chloro-2-(cyclohexanecarbonyl)indole (step 2).

$^1$H-NMR (CDCl$_3$) δ: 8.94 (1H, br s), 8.12–7.09 (3H, m), 4.34–4.21 (4H, m), 2.20 (3H, s), 1.81–1.20 (17H, m).

Step 4. Diethyl[6-chloro-2-(cyclohexanecarbonyl)-1H-indol-3-yl]malonate

The title compound was prepared according to the procedure described in step 5 of Example 2 (Method B) from diethyl α-acetoxy-[6-chloro-2-(cyclohexanecarbony)-1H-indol-3-yl]malonate (step 3).

$^1$H-NMR (CDCl$_3$) δ: 8.90 (1H, br s), 7.72 (1H, d, J=8.72 Hz), 7.36–7.09 (2H, m), 5.70 (1H, s), 4.28–4.19 (4H, m), 1.91–1.22 (17H, m).

Step 5. [6-Chloro-2-(cyclohexanecarbonyl)-1H-indol-3-yl]acetic Acid

The title compound was prepared according to the procedure described in step 6 of Example 2 (Method B) from diethyl[6-chloro-2-(cyclohexanecarbonyl)-1H-indol-3-yl]malonate (step 4).

m.p.: 206–209° C. IR (KBr) ν: 3314, 2924, 2856, 1734, 1650, 1537, 1396, 1248, cm$^{-1}$. $^1$H-NMR (DMSO-d$_6$) δ: 11.78 (1H, s), 7.71 (1H, d, J=8.64 Hz), 7.46–7.07 (2H, m), 4.01 (2H, s), 1.78–1.16 (11H).

Example 55

Methyl[6-chloro-2-(4-methoxybenzoyl-1H-indol-3-yl]acetate

The title compound was prepared according to the procedure described in Example 8 from methyl trans-4-chloro-2-(phenylsulfonylamino)cinnamate (step 1 of Example 8) and 4-methoxyphenacyl bromide.

$^1$H-NMR (CDCl$_3$) δ: 8.85 (1H, s), 7.82 (2H, d, J=8.9 Hz), 7.56 (1H, d, J=8.6 Hz), 7.40 (1H, d, J=1.8 Hz), 7.15 (1H, dd, J=1.8, 8.6 Hz), 6.99 (2H, d, J=8.6 Hz), 3.90 (3H, s), 3.86 (2H, s), 3.67 (3H, s).

Example 56

[6-Chloro-2-(4-methoxybenzoyl)-1H-indol-3-yl]acetic Acid

The title compound was prepared according to the procedure described in Example 9 (Method B) from methyl[6-chloro-2-(4-methoxybenzoyl)-1H-indol-3-yl]acetate (step 1).

m.p.: 187–190° C. $^1$H-NMR (DMSO-d$_6$) δ: 11.72 (1H, s), 7.78 (2H, d, J=8.7 Hz), 7.70 (1H, d, J=8.6 Hz), 7.49–7.45 (1H, m), 7.15–7.07 (3H, m), 3.87 (3H, s), 3.81 (2H, s).

Example 57

Methyl[6-chloro-2-(4-ethylpyridine-2-carbonyl)-1H-indol-3-yl]acetate

A mixture of methyl trans-4-chloro-2-(phenylsulfonylamino)cinnamate (step 1 of Example 8, Method A, 700 mg, 1.99 mmol), 2-bromoacetyl-4-ethylpyridine* (545 mg, 2.39 mmol), potassium carbonate (1.37 g, 13.9 mmol) and acetone (20 ml) was stirred at room temperature. After stirring for 3 h, 1,8-diazabicyclo[5.4.0]undec-7-ene (DBU, 0.6 ml, 3.98 mmol) was added. The resulting mixture was stirred for an additional 19 h and then concentrated. The residue was diluted with dichloromethane (200 ml) and washed with water (100 ml×2). The organic layer was dried (MgSO$_4$) and concentrated. The residue was purified by flash column chromatography eluting with ethyl acetate/hexane/dichloromethane (1:4:1) to give the title compound including impurity. The crude product was washed with ethyl acetate to give 297 mg (42%) of the title compound as yellow solids.

* 2-Bromoacetyl-4-ethylpyridine was prepared as follows;

$^1$H-NMR (CDCl$_3$) δ: 12.52 (1H, br s), 8.64 (1H, d, J=4.9 Hz), 8.21 (1H, br s), 7.62 (1H, d, J=8.7 Hz), 7.52 (1H, d, J=1.8 Hz), 7.39–7.35 (1H, m), 7.13 (1H, dd, J=1.8, 8.6 Hz), 4.31 (2H, s), 3.73 (3H, s), 2.78 (2H, q, J=7.6 Hz), 1.32 (3H, t, J=7.6 Hz).

To a solution of 2-acetyl-4-ethylpyridine (E. C. Constable et al., *J. Am. Chem. Soc.*, 1997, 119, 5606, 8.37 g, 56.1 mmol) in 25% hydrobromic acid-acetic acid (150 ml) was added dropwise a solution of bromine (9.86 g, 61.7 mmol) in acetic acid (30 ml) with ice-cooling. The mixture was allowed to warm to room temperature and stirred for 2 h. Diethyl ether (500 ml) was added to the mixture and the resulting mixture was cooled with an ice-bath. A brown oil, separated out from the solution, was collected by decantation. The oil was treated with saturated aqueous sodium bicarbonate (50 ml) and extracted with diethyl ether (300 ml). The organic layer was dried (MgSO$_4$) and concentrated to give 15.3 g (88%) of the title compound.

$^1$H-NMR (CDCl$_3$) δ: 8.56 (1H, d, J=5.1 Hz), 7.95 (1H, br s), 7.36–7.34 (1H, m), 4.86 (2H, s), 2.74 (2H, q, J=7.7 Hz), 1.29 (3H, t, J=7.6 Hz).

Example 58

[6-Chloro-2-(4-ethylpyridine-2-carbonyl)-1H-indol-3-yl]acetic Acid

A yellow suspension of methyl[6-chloro-2-(4-ethylpyridine-2-carbonyl)-1H-indol-3-yl]acetate (Example 57, 297 mg, 0.83 mmol) in 2N aqueous sodium hydroxide (2.5 ml) and ethanol (20 ml) was heated at reflux temperature for 3 h. After cooling to room temperature, the mixture was neutralized with 2N aqueous hydrochloric acid (2.5 ml) and concentrated. The residue was diluted with THF (150 ml), dried (MgSO$_4$) and concentrated. The residual solids were recrystallization from ethyl acetate to give 251 mg (88%) of the title compound as yellow solids.

MS (EI) m/z: 342 (M$^+$). m.p.: 215–216° C. (decomposition). IR (KBr) ν: 3206, 1707, 1643, 1595, 1535, 1421, 1227, 1192, 1140, 912, 777 cm$^{-1}$. $^1$H-NMR (DMSO-d$_6$) δ: 12.30 (1H, br s), 12.18 (1H, br s), 8.73 (1H, d, J=4.9 Hz), 7.98 (1H, br s), 7.79 (1H, d, J=8.7 Hz), 7.74 (1H, d, J=1.8 Hz), 7.62 (1H, br d, J=5.1 Hz), 7.12 (1H, dd, J=1.8, 8.6 Hz), 4.08 (2H, s), 2.78 (2H, q, J=7.7 Hz), 1.26 (3H, t, J=7.7 Hz).

Example 59

Methyl[5-chloro-2-(4-ethylpyridine-2-carbonyl)-1H-indol-3-yl]acetate

The title compound was prepared according to the procedure described in Example 57 from methyl trans-5-chloro-2-(phenylsulfonylamino)cinnamate (Example 36, step 3) and 2-bromoacetyl-4-ethylpyridine (Preparation is described in Example 57).

$^1$H-NMR (CDCl$_3$) δ: 12.57 (1H, br s), 8.65 (1H, d, J=5.1 Hz), 8.21 (1H, br s), 7.68 (1H, br s), 7.45 (1H, d, J=8.9 Hz), 7.40–7.36 (1H, m), 7.31 (1H, dd, J=2.0, 8.7 Hz), 4.28 (2H, s), 3.74 (3H, s), 2.78 (2H, q, J=7.7 Hz), 1.32 (3H, t, J=7.7 Hz).

Example 60

[5-Chloro-2-(4-ethylpyridine-2-carbonyl)-1H-indol-3-yl]acetic Acid

The title compound was prepared according to the procedure described in Example 58 from methyl[5-chloro-2-(4-ethylpyridine-2-carbonyl)-1H-indol-3-yl]acetate (Example 59).

MS (EI) m/z: 342 (M$^+$). m.p.: 217–218° C. IR (KBr) ν: 3269, 1705, 1643, 1595, 1533, 1418, 1335, 1225, 1200, 1059, 779 cm$^{-1}$. $^1$H-NMR (DMSO-d$_6$) δ: 12.33 (1H, br s), 8.73 (1H, d, J=4.9 Hz), 7.98 (1H, br s), 7.86 (1H, d, J=2.0 Hz), 7.69 (1H, d, J=8.9 Hz), 7.61 (1N, dd, J=4.8, 1.6 Hz), 7.33 (1H, dd, J=2.0, 8.7 Hz), 4.07 (2H, s), 2.78 (2H, q, J=7.6 Hz), 1.26 (3H, t, J=7.6 Hz).

Example 61

Methyl[6-chloro-2-(4-isopropylpyridine-2-carbonyl)-1H-indol-3-yl]acetate

The title compound was prepared according to the procedure described in Example 57 from methyl trans-4-chloro-2-(phenylsulfonylamino)cinnamate (step 1 of Example 8, Method A) and 2-bromoacetyl-4-isopropylpyridine*.

* 2-Bromoacetyl-4-isopropylpyridine was prepared from 2-acetyl-4-isopropylpyridine (K. Ishihama et al., *J. Agric. Food Chem.*, 1992, 40, 1647) according to the procedure for preparing 2-bromoacetyl-4-ethylpyridine described in Example 57.

$^1$H-NMR (CDCl$_3$) δ: 12.53 (1H, br s), 8.65 (1H, d, J=4.9 Hz), 8.24 (1H, d, J=1.6 Hz), 7.62 (1H, d, J=8.7 Hz), 7.52 (1H, d, J=1.6 Hz), 7.40 (1H, dd, J=1.8, 4.9 Hz), 7.13 (1H, dd, J=1.8, 8.7 Hz), 4.30 (2H, s), 3.73 (3H, s), 2.97–3.07 (1H, m), 1.32 (6H, d, J=6.9 Hz). $^1$H-NMR (CDCl$_3$) δ: 8.57 (1H, d, J=5.8 Hz), 7.97–7.98 (1H, m), 7.36–7.38 (1H, m), 4.86 (2H, s), 2.94–3.04 (1H, m), 1.27–1.32 (6H, m).

Example 62

[6-Chloro-2-(4-isopropylpyridine-2-carbonyl)-1H-indol-3-yl]acetic Acid

The title compound was prepared according to the procedure described in Example 58 from methyl[6-chloro-2-(4-isopropylpyridine-2-carbonyl)-1H-indol-3-yl]acetate (Example 61).

m.p.: 194–196° C. IR (KBr) ν: 3244, 2965, 1692, 1647, 1597, 1537, 1254, 1200, 1178, 1150, 764 cm$^{-1}$. $^1$H-NMR (DMSO-d$_6$) δ: 12.28 (1H, br s), 8.74 (1H, d, J=5.3 Hz), 8.01 (1H, s), 7.80 (1H, d, J=8.9 Hz), 7.74 (1H, d, J=1.6 Hz), 7.64–7.66 (1H, m), 7.12 (1H, dd, J=1.8, 8.6 Hz), 4.08 (2H, s), 3.02–3.13 (1H, m), 1.28 (6H, d, J=6.9 Hz).

Example 63

Methyl[5-chloro-2-(4-isopropylpyridine-2-carbonyl)-1H-indol-3-yl]acetate

The title compound was prepared according to the procedure described in Example 57 from methyl trans-5-chloro-2-(penylsulfonylamino)cinnamate (Example 36, step 3) and 2-bromoacetyl-4-isopropylpyridine (Preparation is described in Example 61).

¹H-NMR (CDCl₃) δ: 12.57 (1H, br s), 8.65 (1H, d, J=5.1 Hz), 8.24 (1H, d, J=1.6 Hz), 7.67 (1H, d, J=2.0 Hz), 7.44 (1H, d, J=8.2 Hz), 7.40 (1H, dd, J=1.8, 4.9 Hz), 7.31 (1H, dd, J=2.0, 8.7 Hz), 4.28 (2H, s), 3.74 (3H, s), 2.97–3.07 (1H, m), 1.32 (6H, d, J=6.9 Hz).

Example 64

[5-Chloro-2-(4-isopropylpyridine-2-carbonyl)-1H-indol-3-yl]acetic Acid

The title compound was prepared according to the procedure described in Example 58 from methyl[5-chloro-2-(4-isopropylpyridine-2-carbonyl)-1H-indol-3-yl]acetate (Example 63).

MS (EI) m/z: 356 (M⁺). m.p.: 227–228° C. IR (KBr) ν: 2964, 1703, 1643, 1595, 1537, 1202, 1059, 768 cm⁻¹. ¹H-NMR (DMSO-d₆) δ: 12.32 (1H, br s), 12.15 (1H, br s), 8.74 (1H, d, J=4.9 Hz), 8.00 (1H, s), 7.86 (1H, s), 7.64–7.71 (2H, m), 7.31–7.35 (1H, m), 4.08 (2H, s), 3.03–3.13 (1H, m), 1.28 (6H, d, J=6.9 Hz).

Example 65

Methyl[6-chloro-2-(4-propylpyridine-2-carbonyl)-1H-indol-3-yl]acetate

The title compound was prepared according to the procedure described in Example 57 from methyl trans-4-chloro-2-(penylsulfonylamino)cinnamate (step 1 of Example 8, Method A) and 2-bromoacetyl-4-propylpyridine hydrobromide*.

* 2-Bromoacetyl-4-propylpyridine hydrobromide was prepared as follows;

¹H-NMR (CDCl₃) δ: 12.53 (1H, br s), 8.64 (1H, d, J=4.9 Hz), 8.19 (1H, s), 7.62 (1H, d, J=8.7 Hz), 7.53 (1H, d, J=1.6 Hz), 7.35–7.37 (1H, m), 7.13 (1H, dd, J=1.8, 8.7 Hz), 4.31 (2H, s), 3.73 (3H, s), 2.71 (2H, t, J=7.3 Hz), 1.69–1.77 (2H, m), 0.98 (3H, t, J=7.3 Hz).

4-Propyl-2-pyridinecarbonitrile:

The title compound was prepared from 4-propylpyrinine-N-oxide (S. Ghersetti et al., *J. Heterocycl. Chem.*, 1969, 6, 859) according to the procedure for preparing 4-chloro-2-pyridinecarbonitrile described in Example 33.

¹H-NMR (CDCl₃) δ: 8.59 (1H, d, J=5.1 Hz), 7.53 (1H, s), 7.32–7.34 (1H, m), 2.66 (2H, t, J=7.3 Hz), 1.62–1.76 (2H, m), 0.97 (3H, t, J=7.3 Hz).

2-Acetyl-4-propylpyridine:

The title compound was prepared from 4-propyl-2-pyridinecarbonitrile according to the procedure for preparing 2-acetyl-4-chloropyridine described in Example 33.

¹H-NMR (CDCl₃) δ: 8.56 (1H, d, J=4.9 Hz), 7.88 (1H, s), 7.27–7.30 (1H, m), 2.72 (3H, s), 2.66 (2H, t, J=7.4 Hz), 1.62–1.76 (2H, m), 0.95 (3H, t, J=7.4 Hz).

2-Bromoacetyl-4-propylpyridine hydrobromide:

The title compound was prepared from 2-acetyl-4-propylpyridine according to the procedure for preparing 2-bromoacetyl-4-methylpyridine hydrobromide described in step 2 of Example 31.

¹H-NMR (DMSO-d₆) δ: 8.64 (1H, d, J=4.9 Hz), 7.90 (1H, d, J=1.0 Hz), 7.59 (1H, dd, J=1.6, 4.9 Hz), 5.02 (2H, s), 2.70 (2H, t, J=7.4 Hz), 1.57–1.71 (2H, m), 0.89 (3H, t, J=7.3 Hz).

Example 66

[6-Chloro-2-(4-propylpyridine-2-carbonyl)-1H-indol-3-yl]acetic Acid

The title compound was prepared according to the procedure described in Example 58 from methyl 2-[6-chloro-2-(4-propylpyridine-2-carbonyl)-1H-indol-3-yl]acetate (Example 65).

m.p.: 189–191° C. IR (KBr) ν: 2964, 2928, 1711, 1645, 1595, 1533, 1281, 1225, 1192, 799 cm⁻¹. ¹H-NMR (DMSO-d₆) δ: 12.28 (1H, br s), 8.73 (1H, d, J=5.1 Hz), 7.96 (1H, s), 7.73–7.81 (2H, m), 7.59 (1H, d, J=4.9 Hz), 7.10–7.13 (1H, m), 4.08 (2H, s), 2.73 (2H, t, J=7.1 Hz), 1.63–1.72 (2H, m), 0.92 (3H, t, J=7.3 Hz).

Example 67

Methyl[5-chloro-2-(4-propylpyridine-2-carbonyl)-1H-indol-3-yl]acetate

The title compound was prepared according to the procedure described in Example 57 from methyl trans-5-chloro-2-(penylsulfonylamino)cinnamate (Example 36, step 3) and 2-bromoacetyl-4-propylpyridine hydrobromide (Preparation is described in Example 65).

¹H-NMR (CDCl₃) δ: 12.56 (1H, br s), 8.64 (1H, d, J=4.9 Hz), 8.18 (1H, s), 7.67 (1H, d, J=2.0 Hz), 7.45 (1H, d, J=8.7 Hz), 7.29–7.37 (2H, m), 4.28 (2H, s), 3.74 (3H, s), 2.71 (2H, t, J=7.4 Hz), 1.80–1.66 (2H, m), 0.97 (3H, t, J=7.3 Hz).

Example 68

[5-Chloro-2-(4-propylpyridine-2-carbonyl)-1H-indol-3-yl]acetic Acid

The title compound was prepared according to the procedure described in Example 58 from methyl[5-chloro-2-(4-propylpyridine-2-carbonyl)-1H-indol-3-yl]acetate (Example 67).

m.p.: 208–209° C. IR (KBr) ν: 3296, 2957, 1705, 1645, 1595, 1535, 1329, 1273, 1204, 1057, 795 cm⁻¹. ¹H-NMR (DMSO-d₆) δ: 12.33 (1H, br s), 12.15 (1H, br s), 8.73 (1H, d, J=4.9 Hz), 7.95 (1H, s), 7.86 (1H, s), 7.69 (1H, d, J=8.7 Hz), 7.58–7.61 (1H, m), 7.31–7.35 (1H, m), 4.08 (2H, s), 2.73 (2H, t, J=7.4 Hz), 1.64–1.72 (2H, m), 0.92 (3H, t, J=7.4 Hz).

Example 69

Methyl[2-(4-tert-butylpyridine-2-carbonyl)-6-chloro-1H-indol-3-yl]acetate

The title compound was prepared according to the procedure described in Example 57 from methyl trans-4-chloro-2-(penylsulfonylamino)cinnamate (step 1 of Example 8, Method A) and 2-bromoacetyl-4-tert-butylpyridine*.

* 2-Bromoacetyl-4-tert-butylpyridine was prepared from 2-acetyl-4-tert-butylpyridine (E. C. Constable et al., *J. Am. Chem. Soc.*, 1997, 119, 5606) according to the procedure for preparing 2-bromoacetyl-4-ethylpyridine described in Example 57.

¹H-NMR (CDCl₃) δ: 12.55 (1H, br s), 8.67 (1H, d, J=5.3 Hz), 8.39 (1H, d, J=2.1 Hz), 7.63 (1H, d, J=8.7 Hz), 7.53–7.55 (2H, m), 7.13 (1H, dd, J=1.8, 8.7 Hz), 4.31 (2H, s), 3.73 (3H, s), 1.38 (9H, s). ¹H-NMR (CDCl₃) δ: 8.58 (1H, d, J=4.8 Hz), 8.11 (1H, d, J=1.6 Hz), 7.51 (1H, dd, J=1.8, 5.1 Hz), 4.86 (2H, s), 1.35 (9H, s).

Example 70

[2-(4-tert-Butylpyridine-2-carbonyl)-6-chloro-1H-indol-3-yl]acetic Acid

The title compound was prepared according to the procedure described in Example 58 from methyl[2-(4-tert-butylpyridine-2-carbonyl)-6-chloro-1H-indol-3-yl]acetate (Example 69).

MS (EI) m/z: 370 (M⁺). m.p.: 203–205° C. IR (KBr) ν: 2966, 1699, 1647, 1591, 1535, 1229 cm⁻¹. ¹H-NMR (DMSO-d$_6$) δ: 12.29 (1H, br s), 8.76 (1H, d, J=5.3 Hz), 8.10 (1H, d, J=2.0 Hz), 7.74–7.81 (3H, m), 7.12 (1H, dd, J=1.8, 8.6 Hz), 4.08 (2H, s), 1.36 (9H, s).

Example 71

Methyl[2-(4-tert-butylpyridine-2-carbonyl)-5-chloro-1H-indol-3-yl]acetate

The title compound was prepared according to the procedure described in Example 57 from methyl trans-5-chloro-2-(penylsulfonylamino)cinnamate (Example 36, step 3) and 2-bromoacetyl-4-tert-butylpyridine (Preparation is described in Example 69).

$^1$H-NMR (CDCl$_3$) δ: 12.59 (1H, br s), 8.67 (1H, d, J=5.3 Hz), 8.38 (1H, d, J=2.0 Hz), 7.68 (1H, d, J=2.0 Hz), 7.54 (2H, dd, 2.0, 5.3 Hz), 7.45 (1H, d, J=8.9 Hz), 7.32 (1H, dd, J=2.0, 8.9 Hz), 4.29 (2H, s), 3.74 (3H, s), 1.38 (9H, s).

Example 72

[2-(4-tert-Butylpyridine-2-carbonyl)-5-chloro-1H-indol-3-yl]acetic Acid

The title compound was prepared according to the procedure described in Example 58 from methyl[2-(4-tert-butylpyridine-2-carbonyl)-5-chloro-1H-indol-3-yl]acetate (Example 71).

MS (EI) m/z: 370 (M$^+$). m.p.: 209–211° C. IR (KBr) ν: 3269, 2968, 1746, 1705, 1589, 1531, 1236, 1207, 1177, 1150, 1059, 737 cm$^{-1}$. $^1$H-NMR (DMSO-d$_6$) δ: 12.33 (1H, br s), 8.76 (1H, d, J=5.3 Hz), 8.10 (1H, d, J=2.0 Hz), 7.86 (1H, d, J=2.0 Hz), 7.78 (1H, dd, J=2.0, 5.1 Hz), 7.69 (1H, d, J=8.7 Hz), 7.33 (1H, dd, J=2.0, 8.7 Hz), 4.08 (2H, s), 1.36 (9H, s).

Example 73

Methyl[6-chloro-2-(3-methylpyridine-2-carbonyl)-1H-indol-3-yl]acetate

The title compound was prepared according to the procedure described in Example 57 from methyl trans-4-chloro-2-(penylsulfonylamino)cinnamate (step 1 of Example 8, Method A) and 2-bromoacetyl-3-methylpyridine hydrobromide*.

* 2-Bromoacetyl-3-methylpyridine hydrobromide was prepared from 2-acetyl-3-methylpyridine (T. A. Crabb et al., Org. Magn. Reson., 1982, 20, 242) according to the procedure for preparing 2-bromoacetyl-4-methylpyridine hydrobromide described in step 2 of Example 31.

$^1$H-NMR (CDCl$_3$) δ: 11.19 (1H, br s), 8.54 (1H, d, J=4.6 Hz), 7.65 (1H, d, J=7.7 Hz), 7.55 (1H, d, J=8.6 Hz), 7.33–7.38 (2H, m), 7.06 (1H, dd, J=1.8, 8.7 Hz), 4.15 (2H, s), 3.69 (3H, s), 2.59 (3H, s).

$^1$H-NMR (DMSO-d$_6$) δ: 8.56 (1H, d, J=3.6 Hz), 7.84 (1H, d, J=7.7 Hz), 7.56–7.60 (1H, m), 5.01 (2H, s), 4.01 (3H, s).

Example 74

[6-Chloro-2-(3-methylpyridine-2-carbonyl)-1H-indol-3-yl]acetic Acid

The title compound was prepared according to the procedure described in Example 58 from methyl[6-chloro-2-(3-methylpyridine-2-carbonyl)-1H-indol-3-yl]acetate (Example 73).

MS (EI) m/z: 328 (M$^+$). m.p.: 195–196° C. IR (KBr) ν: 3314, 1703, 1636, 1526, 1418, 1396, 1231, 1196, 1150, 1109 cm$^{-1}$. $^1$H-NMR (DMSO-d$_6$) δ: 12.14 (1H, br s), 11.76 (1H, br s), 8.53 (1H, d, J=3.8 Hz), 7.85 (1H, d, J=7.9 Hz), 7.74 (1H, d, J=8.6 Hz), 7.52–7.56 (2H, m), 7.10 (1H, dd, J=1.8, 8.6 Hz), 3.66 (2H, s), 2.33 (3H, s).

Example 75

Methyl[5-chloro-2-(3-methylpyridine-2-carbonyl)-1H-indol-3-yl]acetate

The title compound was prepared according to the procedure described in Example 57 from methyl trans-5-chloro-2-(penylsulfonylamino)cinnamate (Example 36, step 3) and 2-bromoacetyl-3-methylpyridine hydrobromide (Preparation is described in Example 73).

$^1$H-NMR (CDCl$_3$) δ: 11.28 (1H, br s), 8.56 (1H, d, J=3.1 Hz), 7.61–7.69 (2H, m), 7.23–7.41 (3H, m), 4.15 (2H, s), 3.70 (3H, s), 2.61 (3H, s).

Example 76

[5-Chloro-2-(3-methylpyridine-2-carbonyl)-1H-indol-3-yl]acetic Acid

The title compound was prepared according to the procedure described in Example 58 from methyl[5-chloro-2-(3-methylpyridine-2-carbonyl)-1H-indol-3-yl]acetate (Example 75).

m.p.: 209–211° C. (decomposed). IR (KBr) ν: 3379, 3271, 1728, 1649, 1638, 1528, 1231, 1195, 1182, 1165, 1015 cm$^{-1}$. $^1$H-NMR (DMSO-d$_6$) δ: 11.81 (1H, br s), 8.53 (1H, d, J=4.4 Hz), 7.85 (1H, d, J=7.7 Hz), 7.80 (1H, d, J=2.0 Hz), 7.49–7.56 (2H, m), 7.31 (1H, dd, J=2.1, 8.7 Hz), 3.66 (2H, s), 2.33 (3H, s).

Example 77

Methyl[6-chloro-2-(6-methylpyridine-2-carbonyl)-1H-indol-3-yl]acetate

The title compound was prepared according to the procedure described in Example 57 from methyl trans-4-chloro-2-(phenylsulfonylamino)cinnamate (step 1 of Example 8, Method A) and 2-bromoacetyl-6-methylpyridine hydrobromide (H. Erlenmeyer, J. Jenni, and B. Prijs, J. Med. Pharm. Chem., 1961, 3, 561–566).

$^1$H-NMR (CDCl$_3$) δ: 12.58 (1H, br s), 8.15 (1H, d, J=7.9 Hz), 7.83 (1H, t, J=7.7 Hz), 7.62 (1H, d, J=8.7 Hz), 7.51 (1H, d, J=1.8 Hz), 7.40 (1H, d, J=7.7 Hz), 7.13 (1H, dd, J=1.8, 8.7 Hz), 4.31 (2H, s), 3.72 (3H, s), 2.76 (3H, s).

Example 78

[6-Chloro-2-(6-methylpyridine-2-carbonyl)-1H-indol-3-yl]acetic Acid

The title compound was prepared according to the procedure described in Example 58 from methyl[6-chloro-2-(6-methylpyridine-2-carbonyl)-1H-indol-3-yl]acetate (Example 77).

MS (EI) m/z: 328 (M$^+$). m.p.: 230–231° C. IR (KBr) ν: 3273, 1697, 1643, 1535, 1308, 1227, 1183, 1150, 797, 760, 671 cm$^{-1}$. $^1$H-NMR (DMSO-d$_6$) δ: 12.06 (1H, br s), 7.99 (1H, t, J=7.7 Hz), 7.87 (1H, d, J=7.6 Hz), 7.78 (1H, d, J=8.9 Hz), 7.74 (1H, d, J=2.0 Hz), 7.59 (1H, d, J=7.6 Hz), 7.13 (1H, dd, J=2.0, 8.7 Hz), 4.04 (2H, s), 2.69 (3H, s).

Example 79

Methyl[5-chloro-2-(5-methylpyridine-2-carbonyl)-1H-indol-3-yl]acetate

The title compound was prepared according to the procedure described in Example 57 from methyl trans-5-chloro- 2-(phenylsulfonylamino)cinnamate (Example 36, step 3) and 2-bromoacetyl-5-methylpyridine (Preparation is described in step 1 of Example 32).

$^1$H-NMR (CDCl$_3$) δ: 12.48 (1H, br s), 8.59 (1H, d, J=2.1 Hz), 8.24 (1H, d, J=8.1 Hz), 7.75 (1H, dd, J=2.1, 8.1 Hz), 7.67 (1H, d, J=2.0 Hz), 7.44 (1H, d, J=8.7 Hz), 7.31 (1H, dd, J=2.0, 8.9 Hz), 4.29 (2H, s), 3.74 (3H, s), 2.48 (3H, s).

Example 80

[5-Chloro-2-(5-methylpyridine-2-carbonyl)-1H-indol-3-yl]acetic Acid

The title compound was prepared according to the procedure described in Example 58 from methyl[5-chloro-2-(5-methylpyridine-2-carbonyl)-1H-indol-3-yl]acetate (Example 79).

MS (EI) m/z: 328 (M$^+$). m.p.: 247–248° C. IR (KBr) ν: 3288, 1699, 1638, 1531, 1427, 1329, 1285, 1246, 1209, 1177, 1059, 1016, 800, 700 cm$^{-1}$. $^1$H-NMR (DMSO-d$_6$) δ: 12.30 (1H, br s), 12.15 (1H, br s), 8.68 (1H, br s), 8.04 (1H, d, J=7.9 Hz), 7.93 (1H, br d, J=8.9 Hz), 7.84 (1H, br s), 7.69 (1H, d, J=8.9 Hz), 7.33 (1H, dd, J=2.0, 8.9 Hz), 4.09 (2H, s), 2.46 (3H, s).

Example 81

Methyl[6-chloro-2-[5-(trifluoromethyl)pyridine-2-carbonyl]-1H-indol-3-yl]acetate The title compound was prepared according to the procedure described in Example 57 from methyl trans-4-chloro-2-(phenylsulfonylamino)cinnamate (step 1 of Example 8, Method A) and 2-bromoacetyl-5-(trifluoromethyl)pyridine*.
* 2-Bromoacetyl-5-(trifluoromethyl)pyridine was prepared from 2-chloro-5-(trifluoromethyl)pyridine according to the procedure for preparing 2-bromoacetyl-5-methylpyridine described in step 1 of Example 32.

$^1$H-NMR (CDCl$_3$) δ: 11.97 (1H, br s), 9.07 (1H, br s), 8.48 (1H, d, J=8.4 Hz), 8.23 (1H, dd, J=2.1, 8.4 Hz), 7.63 (1H, d, J=8.6 Hz), 7.52 (1H, d, J=1.8 Hz), 7.15 (1H, dd, J=1.8, 8.6 Hz), 4.31 (2H, s), 3.74 (3H, s). $^1$H-NMR (CDCl$_3$) δ: 8.96 (1H, br s), 8.23 (1H, br d, J=8.2 Hz), 8.13 (1H, dd, J=2.1, 8.1 Hz), 4.83 (2H, s).

Example 82

[6-Chloro-2-[5-(trifluoromethyl)pyridine-2-carbonyl]-1H-indol-3-yl]acetic Acid

The title compound was prepared according to the procedure described in Example 58 from methyl[6-chloro-2-(5-trifluoromethylpyridine-2-carbonyl)-1H-indol-3-yl]acetate (Example 81).

MS (EI) m/z: 382 (M$^+$). m.p.: 228–229° C. IR (KBr) ν: 3325, 1707, 1636, 1529, 1333, 1310, 1138, 1078, 1020 cm$^{-1}$. $^1$H-NMR (DMSO-d$_6$) δ: 12.05 (1H, br s), 9.17 (1H, br s), 8.54 (1H, dd, J=2.0, 8.4 Hz), 8.24 (1H, d, J=8.2 Hz), 7.82 (1H, d, J=8.6 Hz), 7.64 (1H, d, J=1.8 Hz), 7.14 (1H, dd, J=2.0, 8.7 Hz), 4.06 (2H, s).

Example 83

Methyl[5-chloro-2-[5-(trifluoromethyl)pyridine-2-carbonyl]-1H-indol-3-yl]acetate The title compound was prepared according to the procedure described in Example 57 from methyl trans-5-chloro-2-(phenylsulfonylamino)cinnamate (Example 36, step 3) and 2-bromoacetyl-5-(trifluoromethyl)pyridine (Preparation is described in Example 81).

$^1$H-NMR (CDCl$_3$) δ: 12.01 (1H, br s), 9.05 (1H, br s), 8.45 (1H, d, J=8.2 Hz), 8.21 (1H, dd, J=2.3, 8.4 Hz), 7.65 (1H, br s), 7.43 (1H, d, J=8.7 Hz), 7.32 (1H, dd, J=2.0, 8.7 Hz), 4.27 (2H, s), 3.76 (3H, s).

Example 84

[5-Chloro-2-[5-(trifluoromethyl)pyridine-2-carbonyl]-1H-indol-3-yl]acetic Acid

The title compound was prepared according to the procedure described in Example 58 from methyl[5-chloro-2-[5-(trifluoromethyl)pyridine-2-carbonyl]-1H-indol-3-yl]acetate (Example 83).

MS (EI) m/z: 382 (M$^+$). m.p.: 230–231° C. IR (KBr) ν: 3300, 1720, 1701, 1641, 1531, 1327, 1235, 1163, 1130, 1078, 1020, 864 cm$^{-1}$. $^1$H-NMR (DMSO-d$_6$) δ: 12.09 (1H, br s), 9.17 (1H, br s), 8.54 (1H, dd, J=2.0, 8.2 Hz), 8.23 (1H, d, J=8.2 Hz), 7.89 (1H, d, J=1.8 Hz), 7.62 (1H, d, J=8.9 Hz), 7.36 (1H, dd, J=1.8, 8.9 Hz), 4.06 (2H, s).

Example 85

Methyl[5-chloro-2-(5-chloropyridine-2-carbonyl)-1H-indol-3-yl]acetate

The title compound was prepared according to the procedure described in Example 57 from methyl trans-5-chloro-2-(phenylsulfonylamino)cinnamate (Example 36, step 3) and 2-bromoacetyl-5-chloropyridine*.
* 2-Bromoacetyl-5-chloropyridine was prepared from 2-bromo-5-chloropyridine (Case, J. Am. Chem. Soc., 1946, 68, 2574) according to the procedure for preparing 2-bromoacetyl-5-methylpyridine described in step 1 of Example 32.

$^1$H-NMR (CDCl$_3$) δ: 12.01 (1H, br s), 8.72 (1H, d, J=2.5 Hz), 8.29 (1H, d, J=8.6 Hz), 7.93 (1H, dd, J=2.5, 8.6 Hz), 7.65 (1H, d, J=2.0 Hz), 7.43 (1H, d, J=8.7 Hz), 7.31 (1H, dd, J=2.0, 8.7 Hz), 4.27 (2H, s), 3.75 (3H, s). $^1$H-NMR (CDCl$_3$) δ: 8.63 (1H, dd, J=0.6, 2.5 Hz), 8.06 (1H, dd, J=0.6, 8.4 Hz), 7.85 (1H, dd, J=2.3, 8.4 Hz), 4.79 (2H, s).

Example 86

[5-Chloro-2-(5-chloropyridine-2-carbonyl)-1H-indol-3-yl]acetic Acid

The title compound was prepared according to the procedure described in Example 58 from methyl[5-chloro-2-(5-chloropyridine-2-carbonyl)-1H-indol-3-yl]acetate (Example 85).

MS (EI) m/z: 348 (M$^+$). m.p.: 259–260° C. IR (KBr) ν: 3314, 1703, 1632, 1528, 1331, 1236, 1178, 1111, 1059, 1015, 806, 698 cm$^{-1}$. $^1$H-NMR (DMSO-d$_6$) δ: 12.18 (1H, br s), 12.08 (1H, br s), 8.84 (1H, d, J=2.5 Hz), 8.25 (1H, dd, J=2.5, 8.4 Hz), 8.10 (1H, d, J=8.6 Hz), 7.87 (1H, d, J=2.0 Hz), 7.63 (1H, d, J=8.7 Hz), 7.34 (1H, dd, J=2.1, 8.9 Hz), 4.06 (2H, s).

Example 87

Methyl[6-chloro-2-(5-chloropyridine-2-carbonyl)-1H-indol-3-yl]acetate

The title compound was prepared according to the procedure described in Example 57 from methyl trans-4-chloro-2-(phenylsulfonylamino)cinnamate (step 1 of Example 8, Method A) and 2-bromoacetyl-5-chloropyridine (Preparation is described in Example 85).

$^1$H-NMR (CDCl$_3$) δ: 11.98 (1H, br s), 8.74 (1H, dd, J=0.7 and 2.3 Hz), 8.31 (1H, dd, J=0.7, 8.6 Hz), 7.94 (1H, dd, J=2.3, 8.4 Hz), 7.63 (1H, d, J=8.7 Hz), 7.52 (1H, d, J=1.6 Hz), 7.14 (1H, dd, J=1.8, 8.7 Hz), 4.30 (2H, s), 3.73 (3H, s).

Example 88

[6-Chloro-2-(5-chloropyridine-2-carbonyl)-1H-indol-3-yl]acetic Acid

The title compound was prepared according to the procedure described in Example 58 from methyl[6-chloro-2-(5-chloropyridine-2-carbonyl)-1H-indol-3-yl]acetate (Example 87).

MS (EI) m/z: 348 (M$^+$). m.p.: 242–244° C. IR (KBr) v: 3306, 1703, 1636, 1529, 1308, 1234, 1151, 1109, 698 cm$^{-1}$. $^1$H-NMR (DMSO-d$_6$) δ: 12.05 (1H, br s), 8.84 (1H, d, J=2.3 Hz), 8.26 (1H, dd, J=2.3, 8.4 Hz), 8.10 (1H, d, J=8.4 Hz), 7.80 (1H, d, J=8.7 Hz), 7.67 (1H, d, J=1.8 Hz), 7.13 (1H, dd, J=1.8, 8.7 Hz), 4.06 (2H, s).

Example 89

Methyl[5-chloro-2-(4-chloropyridine-2-carbonyl)-1H-indol-3-yl]acetate

The title compound was prepared according to the procedure described in Example 57 from methyl trans-5-chloro-2-(phenylsulfonylamino)cinnamate (Example 36, step 3) and 2-bromoacetyl-4-chloropyridine hydrobromide (Preparation is described in Example 33).

$^1$H-NMR (CDCl$_3$) δ: 12.20 (1H, br s), 8.67 (1H, d, J=5.3 Hz), 8.33 (1H, d, J=2.1 Hz), 7.66 (1H, d, J=2.0 Hz), 7.56 (1H, dd, J=2.1, 5.3 Hz), 7.43 (1H, d, J=8.7 Hz), 7.32 (1H, dd, J=2.0, 8.9 Hz), 4.27 (2H, s), 3.75 (3H, s).

Example 90

[5-Chloro-2-(4-chloropyridine-2-carbonyl)-1H-indol-3-yl]acetic Acid

The title compound was prepared according to the procedure described in Example 58 from methyl[5-chloro-2-(5-chloropyridine-2-carbonyl)-1H-indol-3-yl]acetate (Example 89).

MS (EI) m/z: 348 (M$^+$). m.p.: 243–244° C. IR (KBr) v: 3000, 1719, 1643, 1528, 1242, 1202, 741 cm$^{-1}$. $^1$H-NMR (DMSO-d$_6$) δ: 12.20 (1H, br s), 8.80 (1H, d, J=5.3 Hz), 8.12 (1H, d, J=2.1 Hz), 7.90 (1H, dd, J=2.1, 5.4 Hz), 7.66 (1H, d, J=8.9 Hz), 7.34 (1H, d, J=2.0, 8.7 Hz), 4.06 (2H, s).

Example 91

Methyl[6-chloro-2-(pyridine-3-carbonyl)-1H-indol-3-yl]acetate

The title compound was prepared according to the procedure described in Example 57 from methyl trans-4-chloro-2-(phenylsulfonylamino)cinnamate (step 1 of Example 8, Method A) and 3-bromoacetylpyridine hydrobromide (G. B. Barlin, L. P. Davies, S. J. Ireland, M. M. L. Ngu, Aust. J. Chem., 1989, 42, 1735).

$^1$H-NMR (CDCl$_3$) δ: 9.26 (1H, br s), 9.00 (1H, dd, J=0.8, 2.1 Hz), 8.80 (1H, dd, J=1.6, 4.8 Hz), 8.10 (1H, dt, J=2.0, 2.0, 7.9 Hz), 7.58 (1H, d, J=8.7 Hz), 7.47 (1H, ddd, J=0.8, 4.9, 7.9 Hz), 7.37 (1H, d, J=1.8 Hz), 7.16 (1H, dd, J=1.8, 8.6 Hz), 3.84 (2H, s), 3.65 (3H, s).

Example 92

[6-Chloro-2-(pyridine-3-carbonyl)-1H-indol-3-yl]acetic Acid

The title compound was prepared according to the procedure described in Example 58 from methyl[6-chloro-2-(pyridine-3-carbonyl)-1H-indol-3-yl]acetate (Example 91).

MS (EI) m/z: 314 (M$^+$). m.p.: 267–268° C. IR (KBr) v: 3346, 1705, 1609, 1566, 1528, 1433, 1418, 1327, 1267, 1215, 943, 761 cm$^{-1}$. $^1$H-NMR (DMSO-d$_6$) δ: 12.28 (1H, br s), 11.86 (1H, br s), 8.90 (1H, br s), 8.85 (1H, br d, J=4.9 Hz), 8.12 (1H, dt, J=2.0, 2.0, 7.9 Hz), 7.77 (1H, t, J=8.6 Hz), 7.62 (1H, dd, J=4.9, 8.0 Hz), 7.49 (1H, d, J=2.0 Hz), 7.15 (1H, dd, J=1.6, 8.4 Hz), 3.85 (2H, s).

Example 93

Methyl[6-chloro-2-(pyridine-4-carbonyl)-1H-indol-3-yl]acetate

The title compound was prepared according to the procedure described in Example 57 from methyl trans-4-chloro-2-(phenylsulfonylamino)cinnamate (step 1 of Example 8, Method A) and 4-bromoacetylpyridine hydrobromide (L. W. Deady, M. S. Stanborough, Aust. J. Chem., 1981, 34, 1295).

$^1$H-NMR (CDCl$_3$) δ: 9.21 (1H, br s), 8.82–8.79 (2H, m), 7.59–7.57 (2H, m), 7.56 (1H, d, J=8.7 Hz), 7.33 (1H, d, J=1.8 Hz), 7.16 (1H, dd, J=1.8, 8.7 Hz), 3.80 (2H, s), 3.65 (3H, s).

Example 94

[6-Chloro-2-(pyridine-4-carbonyl)-1H-indol-3-yl]acetic Acid

The title compound was prepared according to the procedure described in Example 58 from methyl[6-chloro-2-(pyridine-4-carbonyl)-1H-indol-3-yl]acetate (Example 93).

MS (EI) m/z: 314 (M$^+$). m.p.: 256–257° C. IR (KBr) v: 3352, 1709, 1607, 1528, 1431, 1329, 1259, 1202, 772, 687 cm$^{-1}$. $^1$H-NMR (DMSO-d$_6$) δ: 11.82 (1H, br s), 8.82 (2H, d, J=5.8 Hz), 7.77 (1H, d, J=8.6 Hz), 7.64–7.62 (2H, m), 7.48 (1H, d, J=1.8Hz), 7.15 (1H, dd, J=2.0, 8.7 Hz), 3.83 (2H, s).

Example 95

Methyl[6-chloro-2-[4-(hydroxymethyl)pyridine-2-carbonyl]-1H-indol-3-yl]acetate

Step 1. Methyl[6-chloro-2-[4-(tert-buthyldimethylsilyloxymethyl)pyridine-2-carbonyl]-1H-indol-3-yl]acetate The title compound was prepared according to the procedure described in Example 57 from methyl trans-4-chloro-2-(penylsulfonylamino)cinnamate (step 1 of Example 8, Method A) and 2-bromoacetyl-4-(tert-butyldimethylsilyloxymethyl)pyridine*.

* 2-Bromoacetyl-4-(tert-butyldimethylsilyloxymethyl)pyridine was prepared as follows;

$^1$-NMR (CDCl$_3$) δ: 12.47 (1H, br s), 8.70 (1H, d, J=4.9 Hz), 8.21–8.22 (1H, m), 7.55–7.58 (2H, m), 7.50–7.51 (1H, m), 7.10 (1H, dd, J=1.8, 8.7 Hz), 4.83 (2H, s), 4.31 (2H, s), 3.72 (3H, s), 0.98 (9H, s), 0.15 (6H, s).

2-Acetyl-4-(tert-butyldimethylsilyloxymethyl)pyridine:

The title compound was prepared from 4-(tert-butyldimethylsilyloxymethyl)pyridinecarbonitrile (A. Hadri et al., J. Heterocycl. Chem., 1993, 30, 631) according to the procedure for preparing 2-acetyl-4-chloropyridine described in Example 33.

$^1$H-NMR (CDCl$_3$) δ: 8.64 (1H, d, J=4.8 Hz), 7.96 (1H, s), 7.50 (1H, d, J=4.8 Hz), 4.80 (2H, s), 2.73 (3H, s), 0.96 (9H, s), 0.12 (6H, s).

2-Bromoacetyl-4-(tert-butyldimethylsilyloxymethyl)pyridine:

To a solution of 2-acetyl-4-(tert-butyldimethylsilyloxymethyl)pyridine (1.84 g, 6.932 mmol) in THF (50 ml) was added dropwise a solution of lithium bis(trimethylsilyl)a- mide (1M in THF, 8.3 ml, 8.3 mmol) at −78° C. After stirring for 1 h, chlorotriethylsilane (1.7 ml, 10.4 mmol) was added to the mixture at −78° C. The mixture was stirred at the same temperature for 1 h, then allowed to warm to 0° C. After stirring for 1 h, saturated aqueous ammonium chloride (50 ml) was added. The mixture was extracted with diethyl ether (100 ml). The organic layer was washed with water (50 ml), dried (MgSO$_4$) and concentrated. The residue was dissolved in THF (20 ml), and then water (4 ml) and NBS were added at 0° C. After stirring for 1 h, the mixture was diluted with diethyl ether (200 ml), washed with water (50 ml) and dried (MgSO$_4$). Removal of solvent gave the crude product. Purification by flash column chromatography eluting with ethyl acetate/hexane (1:20) to afford 0.74 g (31%) of the title compound as crystals.

$^1$H-NMR (CDCl$_3$) δ: 8.63 (1H, d, J=4.8 Hz), 8.02 (1H, q, J=0.8 Hz), 7.53 (1H, dt, J=0.8, 4.9 Hz), 4.87 (2H, s), 4.81 (2H, s), 0.96 (9H, s), 0.13 (3H, s).

Step 2. Methyl[6-chloro-2-[4-(hydroxymethyl)pyridine-2-carbonyl]-1H-indol-3-yl]acetate To a solution of methyl[6-chloro-2-[4-(tert-buthyldimethylsilyloxymethyl)pyridine-2-carbonyl]-1H-indol-3-yl]acetate (step 1, 171.5 mg, 0.3625 mmol) in THF (5 ml) was added a solution of tetrabutylammonium fluoride (1M in THF, 0.54 ml, 0.54 mmol) at room temperature. After stirring for 1 h, the mixture was concentrated. The residue was diluted with ethyl acetate (100 ml), washed with water (20 ml×2) and dried (MgSO$_4$). Removal of solvent gave the crude product. Purification by flash column chromatography eluting with ethyl acetate/hexane/dichloromethane (1:1:1) to afford 69.6 mg (54%) of the title compound as crystals.

$^1$H-NMR (CDCl$_3$) δ: 12.43 (1H, br s), 8.74 (1H, d, J=5.1 Hz), 8.29 (1H, s), 7.59–7.64 (2H, m), 7.52 (1H, d, J=1.5 Hz), 7.13 (1H, dd, J=1.6, 8.6 Hz), 4.86 (2H, d, J=5.1 Hz), 4.31 (2H, s), 3.73 (3H, s).

Example 96

[6-Chloro-2-[4-(hydroxymethyl)pyridine-2-carbonyl]-1H-indol-3-yl]acetic Acid

The title compound was prepared according to the procedure described in Example 58 from methyl[6-chloro-2-[4-(hydroxymethyl)pyridine-2-carbonyl]-1H-indol-3-yl]acetate (Example 95).

MS (EI) m/z: 344 (M$^+$). m.p.: 210–212° C. IR (KBr) ν: 3304, 1728, 1713, 1622, 1583, 1526, 1194 cm$^{-1}$. $^1$H-NMR (DMSO-d$_6$) δ: 12.31 (1H, br s), 8.78 (1H, d, J=4.8 Hz), 8.08 (1H, s), 7.80 (1H, d, J=8.6 Hz), 7.74 (1H, d, J==1.8 Hz), 7.67 (1H, d, J=4.9 Hz), 7.12 (1H, dd, J=1.8, 8.7Hz), 4.69 (2H, s), 4.09 (2H, s).

Example 97

Methyl[5-chloro-2-[4-(hydroxymethyl)pyridine-2-carbonyl]-1H-indol-3-yl]acetate

Step 1. Methyl[5-chloro-2-[4-(tert-buthyldimethylsilyloxymethyl)pyridine-2-carbonyl]-1H-indol-3-yl]acetate The title compound was prepared according to the procedure described in Example 57 from methyl trans-5-chloro-2-(penylsulfonylamino)cinnamate (Example 36, step 3) and 2-bromoacetyl-4-(tert-butyldimethylsilyloxymethyl)pyridine (Preparation is described in step 1 of Example 95).

$^1$H-NMR (CDCl$_3$) δ: 12.47 (1H, br s), 8.66 (1H, d, J=4.9 Hz), 8.18 (1H, s), 7.60–7.61 (1H, m), 7.54–7.57 (1H, m), 7.39 (1H, d, J=8.9 Hz), 7.25 (1H, dd, J=2.0, 8.9 Hz), 4.82 (2H, s), 4.27 (2H, s), 3.74 (3H, s), 0.98 (9H, s), 0.14 (6H, s).

Step 2. Methyl[5-chloro-2-[4-(hydroxymethyl)pyridine-2-carbonyl]-1H-indol-3-yl]acetate The title compound was prepared according to the procedure described in step 2 of Example 95 from methyl[5-chloro-2-[4-(4-tert-buthyldimethylsilyloxymethyl)pyridine-2-carbonyl]-1H-indol-3-yl]acetate (step 1).

$^1$H-NMR (CDCl$_3$) δ: 12.48 (1H, br s), 8.75 (1H, d, J=4.9 Hz), 8.31 (1H, s), 7.68 (1H, s), 7.60–7.62 (1H, m), 7.45 (1H, d, J=8.9 Hz), 7.32 (1H, dd, J=2.0, 8.9 Hz), 4.87 (2H, d, J=5.4 Hz), 4.28 (2H, s), 3.74 (3H, s).

Example 98

[5-Chloro-2-[4-(hydroxymethyl)pyridine-2-carbonyl]-1H-indol-3-yl]acetic Acid

The title compound was prepared according to the procedure described in Example 58 from methyl[5-chloro-2-[4-(hydroxymethyl)pyridine-2-carbonyl]-1H-indol-3-yl]acetate (Example 97).

MS (EI) m/z: 344 (M$^+$). m.p.: 218–219° C. IR (KBr) ν: 3263, 1705, 1641, 1595, 1528, 1327, 1198, 1061 cm$^{-1}$. $^1$H-NMR (DMSO-d$_6$) δ: 12.34 (1H, br s), 8.77 (1H, d, J=4.9 Hz), 8.08 (1H, s), 7.85 (1H, s), 7.66–7.71 (2H, m), 7.33 (1H, dd, J=1.8, 8.9 Hz), 5.63 (1H, br s), 4.68 (2H, s), 4.09 (2H, s).

Example 99

Methyl[5-chloro-2-(3,4-dimethylpyridine-2-carbonyl)-1H-indol-3-yl]acetate

The title compound was prepared according to the procedure described in Example 57 from methyl trans-5-chloro-2-(phenylsulfonylamino)cinnamate (Example 36, step 3) and 2-bromoacetyl-3,4-dimethylpyridine hydrobromide*.

* 2-Bromoacetyl-3,4-dimethylpyridine hydrobromide was prepared as follows;

$^1$H-NMR (CDCl$_3$) δ: 12.20 (1H, br s), 8.67 (1H, d, J=5.3 Hz), 8.33 (1H, d, J=2.1 Hz), 7.66 (1H, d, J=2.0 Hz), 7.56 (1H, dd, J=2.1, 5.3 Hz), 7.43 (1H, d, J=8.7 Hz), 7.32 (1H, dd, J=2.0, 8.9 Hz). 4.27 (2H, s), 3.75 (3H, s).

3,4-Dimethylpyridine-2-carbonitrile:

The title compound including 4,5-dimethylpyridine-2-carbonitrile in the ratio of 5.5 to 1 was prepared from 3,4-dimethylpyridine-N-oxide (Abramovitch et al., *J. Org. Chem.*, 1972, 37, 1690) according to the procedure for preparing 4-chloro-2-pyridinecarbonitrile described in Example 33.

2-Acetyl-3,4-dimethylpyridine:

The title compound was prepared along with 2-acetyl-4,5-dimethylpyridine from 3,4-dimethylpyridine-2-carbonitrile including 4,5-dimethylpyridine-2-carbonitrile in the ratio of 5.5 to 1 according to the procedure for preparing 2-acetyl-4-chloropyridine described in Example 33.

2-acetyl-3,4-dimethylpyridine: $^1$H-NMR (CDCl$_3$) δ: 8.34 (1H, d, J=4.6 Hz), 7.19 (1H, d, J=4.8 Hz), 2.69 (3H, s), 2.43 (3H, s), 2.34 (3H, s).

2-acetyl-4,5-dimethylpyridine: $^1$H-NMR (CDCl$_3$) δ: 8.39 (1H, s), 7.83 (1H, s), 2.70 (3H, s), 2.33 (3H, s), 2.32 (3H, s).

2-Bromoacetyl-3,4-dimethylpyridine Hydrobromide:

The title compound was prepared from 2-acetyl-3,4-dimethylpyridine according to the method of H. McKennis, Jr., L. B. Turnbull, E, R. Bowman, and E. Tamaki (in *J. Org. Chem.*, 1963, 23, 383–387).

$^1$H-NMR (DMSO-d$_6$) δ: 8.39 (1H, d, J=4.8 Hz), 7.46 (1H, d, J=4.8 Hz), 4.96 (2H, s), 2.38 (3H, s), 2.35 (3H, s).

Example 100

[5-Chloro-2-(3,4-dimethylpyridine-2-carbonyl)-1H-indol-3-yl]acetic Acid

The title compound was prepared according to the procedure described in Example 58 from methyl[5-chloro-2-(3,4-dimethylpyridine-2-carbonyl)-1H-indol-3-yl]acetate (Example 99).

MS (EI) m/z: 342 (M+). m.p.: 236–237° C. IR (KBr) ν: 3395, 1710, 1641, 1526, 1339, 1281, 1196, 1053, 1007 cm$^{-1}$. $^1$H-NMR (DMSO-d$_6$) δ: 11.76 (1H, br s), 8.37 (1H, d, J=4.9 Hz), 7.79 (1H, d, J=2.0 Hz), 7.48 (1H, d, J=8.7 Hz), 7.41 (1H, d, J=4.9 Hz), 7.31 (1H, dd, J=2.0, 8.7 Hz), 3.56 (2H, s), 2.35 (3H, s), 2.16 (3H, s).

Example 101

Methyl[5-chloro-2-(4,5-dimethylpyridine-2-carbonyl)-1H-indol-3-yl]acetate

The title compound was prepared according to the procedure described in Example 57 from methyl trans-5-chloro-2-(phenylsulfonylamino)cinnamate (Example 36, step 3) and 2-bromoacetyl-4,5-dimethylpyridine*.

* 2-Bromoacetyl-3,4-dimethylpyridine was prepared from 2-acetyl-4,5-dimethylpyridine (Preparation is described in Example 99) according to the procedure for preparing 2-bromoacetyl-4-ethylpyridine described in Example 57.

$^1$H-NMR (CDCl$_3$) δ: 12.59 (1H, br s), 8.47 (1H, s), 8.12 (1H, s), 7.67 (1H, d, J=1.8 Hz), 7.44 (1H, d, J=9.4 Hz), 7.30 (1H, dd, J=2.0, 8.7 Hz), 4.28 (2H, s), 3.73 (3H, s), 2.38 (6H, s). $^1$H-NMR (CDCl$_3$) δ: 8.39 (1H, s), 7.87 (1H, s), 4.83 (2H, s), 2.35 (3H, s), 2.34 (3H, s).

Example 102

[5-Chloro-2-(4,5-dimethylpyridine-2-carbonyl)-1H-indol-3-yl]acetic Acid

The title compound was prepared according to the procedure described in Example 58 from methyl[5-chloro-2-(4,5-dimethylpyridine-2-carbonyl)-1H-indol-3-yl]acetate (Example 101).

MS (EI) m/z: 342 (M+). m.p.: 245–246° C. IR (KBr) ν: 3281, 1697, 1638, 1589, 1535, 1254, 1232, 1188, 1060, 802 cm$^{-1}$. $^1$H-NMR (DMSO-d$_6$) δ: 12.34 (1H, br s), 12.15 (1H, br s), 8.57 (1H, s), 7.93 (1H, s), 7.84 (1H, d, J=1.8 Hz), 7.69 (1H, d, J=8.7 Hz), 7.32 (1H, dd, J=2.0, 8.7 Hz), 4.09 (2H, s), 2.39 (3H, s), 2.38 (3H, s).

Example 103

Methyl[6-chloro-2-(4,5-dimethylpyridine-2-carbonyl)-1H-indol-3-yl]acetate

The title compound was prepared according to the procedure described in Example 57 from methyl trans-4-chloro-2-(phenylsulfonylamino)cinnamate (step 1 of Example 8, Method A) and 2-bromoacetyl-4,5-dimethylpyridine (Preparation is described in Example 99).

$^1$H-NMR (CDCl$_3$) δ: 12.55 (1H, br s), 8.47 (1H, s), 8.12 (1H, s), 7.62 (1H, d, J=8.6 Hz), 7.52 (1H, d, J=1.8 Hz), 7.13 (1H, dd, J=1.8, 8.6 Hz), 4.31 (2H, s), 3.72 (3H, s), 2.39 (6H, s).

Example 104

[6-Chloro-2-(4,5-dimethylpyridine-2-carbonyl)-1H-indol-3-yl]acetic Acid

The title compound was prepared according to the procedure described in Example 58 from methyl[6-chloro-2-(4,5-dimethylpyridine-2-carbonyl)-1H-indol-3-yl]acetate (Example 103).

MS (EI) m/z: 342 (M+). m.p.: 226–228° C. IR (KBr) ν: 3275, 1697, 1638, 1537,1258, 1188, 799 cm$^{-1}$. $^1$H-NMR (DMSO-d$_6$) δ: 12.30 (1H, br s), 8.57 (1H, s), 7.94 (1H, s), 7.78 (1H, d, J=8.7 Hz), 7.74 (1H, d, J=1.8 Hz), 7.11 (1H, dd, J=2.0, 8.6 Hz), 4.09 (2H, s), 2.39 (3H, s), 2.38 (3H, s).

Example 105

Methyl[6-chloro-2-(4-methoxypyridine-2-carbonyl)-1H-indol-3-yl]acetate

The title compound was prepared according to the procedure described in Example 57 from methyl trans-4-chloro-2-(penylsulfonylamino)cinnamate (step 1 of Example 8, Method A) and 2-bromoacetyl-4-methoxypyridine hydrobromide*.

* 2-Bromoacetyl-4-methoxypyridine hydrobromide was prepared from 2-acetyl-4-methoxypyridine (B. Case et al., *J. Org. Chem.*, 1961, 26, 4415) according to the procedure for preparing 2-bromoacetyl-4-methylpyridine hydrobromide described in step 2 of Example 31.

$^1$H-NMR (CDCl$_3$) δ: 12.61 (1H, br s), 8.57 (1H, d, J=5.9 Hz), 7.89 (1H, d, J=2.6 Hz), 7.63 (1H, d, J=8.6 Hz), 7.52 (1H, d, J=1.8 Hz), 7.13 (2H, dd, J=1.8, 8.7 Hz), 7.04 (1H, dd, J=2.6, 5.8 Hz), 4.30 (2H, s), 3.96 (3H, s), 3.73 (3H, s). $^1$H-NMR (DMSO-d$_6$) δ: 8.59–8.62 (1H, m), 7.63–7.65 (1H, m), 7.33–7.37 (1H, m), 5.03 (2H, s), 3.96 (3H, s).

Example 106

[6-Chloro-2-(4-methoxypyridine-2-carbonyl)-1H-indol-3-yl]acetic Acid

The title compound was prepared according to the procedure described in Example 58 from methyl[6-chloro-2-(4-methoxypyridine-2-carbonyl)-1H-indol-3-yl]acetate (Example 105).

MS (EI) m/z: 344 (M+). m.p.: 213° C.(decomposed). IR (KBr) ν: 3200, 1709, 1645, 1589, 1533, 1225, 1207 cm$^{-1}$. $^1$H-NMR (DMSO-d$_6$) δ: 12.35 (1H, br s), 12.18 (1H, br s), 8.66 (1H, d, J=5.6 Hz), 7.80 (1H, d, J=8.9 Hz), 7.74 (1H, d, J=1.8 Hz), 7.63 (1H, d, J=2.6 Hz), 7.31 (1H, dd, J=2.9, 5.1 Hz), 7.12 (1H, dd, J=1.3, 8.7 Hz), 4.09 (2H, s), 3.96 (3H, s).

Example 107

Methyl[5-chloro-2-(4-methoxypyridine-2-carbonyl)-1H-indol-3-yl]acetate

The title compound was prepared according to the procedure described in Example 57 from methyl trans-5-chloro-2-(penylsulfonylamino)cinnamate (Example 36, step 3) and 2-bromoacetyl-4-methoxypyridine hydrobromide (Preparation is described in Example 105).

$^1$H-NMR (CDCl$_3$) δ: 12.65 (1H, br s), 8.57 (1H, d, J=5.8 Hz), 7.88 (1H, d, J=2.5 Hz), 7.68 (1H, d, J=2.0 Hz), 7.45 (1H, dd, J=0.5, 8.7 Hz), 7.32 (1H, dd, J=1.8, 8.7 Hz), 7.05 (1H, dd, J=2.8, 5.8 Hz), 4.28 (2H, s), 3.96 (3H, s), 3.74 (3H, s).

Example 108

[5-Chloro-2-(4-methoxypyridine-2-carbonyl)-1H-indol-3-yl]acetic Acid

The title compound was prepared according to the procedure described in Example 58 from methyl[5-chloro-2-(4-methoxypyridine-2-carbonyl)-1H-indol-3-yl]acetate (Example 107).

m.p.: 228° C. (decomposed). IR (KBr) ν: 3230, 1707, 1647, 1595, 1566, 1533, 1477, 1331, 1300, 1219, 1180, 1038, 1013 cm$^{-1}$. $^1$H-NMR (DMSO-d$_6$) δ: 12.39 (1H, br s), 12.16 (1H, br s), 8.66 (1H, d, J=5.8 Hz), 7.86 (1H, d, J=1.5 Hz), 7.70 (1H, d, J=8.7 Hz), 7.63 (1H, d, J=2.5 Hz), 7.29–7.35 (2H, m), 4.09 (2H, s), 3.96 (3H, s).

Example 109

Methyl[6-chloro-2-(3.5-dimethylpyridine-2-carbonyl)-1H-indol-3-yl]acetate

The title compound was prepared according to the procedure described in Example 57 from methyl trans-4-chloro- 2-(penylsulfonylamino)cinnamate (step 1 of Example 8, Method A) and 2-bromoacetyl-3,5-dimethylpyridine hydrobromide*.

* 2-Bromoacetyl-3,5-dimethylpyridine hydrobromide was prepared as follows;
$^1$H-NMR (CDCl$_3$) δ: 11.43 (1H, br s), 8.43 (1H, s), 7.60 (1H, d, J=8.7 Hz), 7.51 (1H, s), 7.45 (1H, d, J=1.8 Hz), 7.12 (1H, dd, J=1.8, 8.7 Hz), 4.22 (2H, s), 3.69 (3H, s), 2.62 (3H, s), 2.43 (3H, s).

2-Acetyl-3,5-dimethylpyridine:

The title compound was prepared from 3,5-dimethylpyridinecarbonitrile (K. Takahashi et al., *J. Heterocycl. Chem.*, 1978, 15, 893) according to the procedure for preparing 2-acetyl-4-chloropyridine described in Example 33.
$^1$H-NMR (CDCl$_3$) δ: 8.32 (1H, s), 7.37 (1H, s), 2.69 (3H, s), 2.56 (3H, s), 2.36 (3H, s). 2-Bromoacetyl-3,5-dimethylpyridine hydrobromide:

The title compound was prepared from 2-acetyl-3,5-dimethylpyridine according to the method of H. McKennis, Jr., L. B. Tumbull, E, R. Bowman, and E. Tamaki (in *J. Org. Chem.*, 1963, 23, 383–387).
$^1$H-NMR (DMSO-d$_6$) δ: 8.43 (1H, s), 7.69 (1H, s), 5.00 (2H, s), 2.52 (3H, s), 2.39 (3H, s).

Example 110

[6-Chloro-2-(3,5-dimethylpyridine-2-carbonyl)-1H-indol-3-yl]acetic Acid

The title compound was prepared according to the procedure described in Example 58 from methyl[6-chloro-2-(3,5-dimethylpyridine-2-carbonyl)-1H-indol-3-yl]acetate (Example 109).

MS (EI) m/z: 342 (M$^+$). m.p.: 199–200° C. IR (KBr) v: 3279, 1705, 1639, 1526, 1238, 1177, 827, 797 cm$^{-1}$. $^1$H-NMR (DMSO-d$_6$) δ: 12.12 (1H, br s), 11.72 (1H, br s), 8.38 (1H, s), 7.74 (1H, d, J=8.6 Hz), 7.68 (1H, s), 7.52 (1H, d, J=2.0 Hz), 7.10 (1H, dd, J=1.8, 8.6 Hz), 3.72 (2H, s), 2.38 (3H, s), 2.33 (3H, s).

Example 111

Methyl[5-chloro-2-(4-ethyl-3-fluoropyridine-2-carbonyl)-1H-indol-3-yl]acetate

The title compound was prepared according to the procedure described in Example 57 from methyl trans-5-chloro-2-(penylsulfonylamino)cinnamate (Example 36, step 3) and 2-bromoacetyl-4-ethyl-3-fluoropyridine*.

* 2-Bromoacetyl-4-ethyl-3-fluoropyridine was prepared as follows;
$^1$H-NMR (CDCl$_3$) δ: 11.29 (1H, br s), 8.45 (1H, d, J=4.8 Hz), 7.64 (1H, d, J=1.8 Hz), 7.44 (1H, t, J=4.8 Hz), 7.38 (1H, d, J=8.9 Hz), 7.29 (1H, dd, J=2.0, 8.7 Hz), 4.21 (2H, s), 3.72 (3H, s), 2.81 (2H, q, J=7.6 Hz), 1.31 (3H, t, J=7.6 Hz).

4-Ethyl-3-fluoropyridine-N-oxide:

To a mixture of 4-ethyl-3-fluoropyridine (R. P. Dikinson et al., *Bioorg. Med. Chem. Lett.*, 1996, 6, 2031, 28.51 g, 205.9 mmol) and 30% hydrogen peroxide (30 ml) in acetic acid (300 ml) was heated at reflux temperature for 3 h. After cooling to room temperature, the resulting mixture was concentrated. The residue was diluted in dichloromethane (300 ml) and dried (MgSO$_4$). Removal of solvent gave 32.30 g (100%) of the title compound as an oil.
$^1$H-NMR (DMSO-d$_6$) δ: 8.43–8.46 (1H, m), 8.08 (1H, d, J=6.1 Hz), 7.38 (1H, dd, J=6.6, 9.7 Hz), 2.61 (2H, q, J=7.6 Hz), 1.17 (3H, t, J=7.6 Hz).

4-Ethyl-3-fluoro-2-pyridinecarbonitrile:

The title compound was prepared from 4-ethyl-3-fluoropyridine-N-oxide according to the procedure for preparing 4-chloro-2-pyridinecarbonitrile described in Example 33.
$^1$H-NMR (CDCl$_3$) δ: 8.42 (1H, d. J=4.8 Hz), 7.43 (1H, t, J=5.1 Hz), 2.78 (2H, q, J=7.6 Hz), 1.30 (3H, t, J=7.6 Hz).

2-Acetyl-4-ethyl-3-fluoropyridine:

The title compound was prepared from 4-ethyl-3-fluoro-2-pyridinecarbonitrile according to the procedure for preparing 2-acetyl-4-chloropyridine described in Example 33.
$^1$H-NMR (CDCl$_3$) δ: 8.376 (1H, d, J=4.6 Hz), 7.36 (1H, t, J=4.8 Hz), 2.76 (2H, q, J=7.6 Hz), 2.71 (3H, s), 1.28 (3H, t, J=7.6 Hz).

2-Bromoacetyl-4-ethyl-3-fluoropyridine:

The title compound was prepared from 2-acetyl-4-ethyl-3-fluoropyridine according to the procedure for preparing 2-bromoacetyl-4-ethylpyridine described in Example 57.
$^1$H-NMR (CDCl$_3$) δ: 8.38 (1H, d, J=4.6 Hz), 7.43 (1H, d, J=4.6 Hz), 4.75 (2H, s), 2.78 (2H, q, J=7.6 Hz), 1.29 (3H, t, J=7.6 Hz).

Example 112

[5-Chloro-2-(4-ethyl-3-fluoropyridine-2-carbonyl)-1H-indol-3-yl]acetic Acid

A stirred solution of methyl[5-chloro-2-(4-ethyl-3-fluoropyridine-2-carbonyl)-1H-indol-3-yl]acetate (Example 111, 391.2 mg, 1.044 mmol) in acetic acid (12 ml) and 2N aqueous HCl (4 ml) was heated at reflux temperature for 24 h. After cooling to room temperature, the resulting mixture was concentrated. The residue was diluted in THF (100 ml), dried (MgSO$_4$) and concentrated. The crude product was purified by recrystallization to afford 349.2 mg (93%) of the title compound.

MS (EI) m/z: 361 (M$^+$). m.p.: 208° C. IR (KBr) v: 3217, 1720, 1632, 1516, 1429, 1234, 1180, 1057 cm$^{-1}$. $^1$H-NMR (DMSO-d$_6$) δ: 11.78 (1H, br s), 8.35 (1H, d, J=4.8 Hz), 7.73 (1H, d, J=2.0 Hz), 7.56 (1H, t, J=5.1 Hz), 7.39 (1H, d, J=8.9 Hz), 7.22 (1H, dd, J=2.0, 8.9 Hz), 3.65 (2H, s), 2.65 (2H, q, J=7.6 Hz), 1.14 (3H, t, J=7.6 Hz).

Example 113

Methyl[6-chloro-2-(4-ethyl-3-fluoropyridine-2-carbonyl)-1H-indol-3-yl]acetate

The title compound was prepared according to the procedure described in Example 57 from methyl trans-4-chloro-2-(penylsulfonylamino)cinnamate (step 1 of Example 8, Method A).
$^1$H-NMR (CDCl$_3$) δ: 11.23 (1H, br s), 8.46 (1H, d, J=4.8 Hz), 7.60 (1H, d, J=9.2 Hz), 7.42–7.46 (2H, m), 7.10–7.14 (1H, m), 4.23 (2H, s), 3.71 (3H, s), 2.81 (2H, q, J=7.7 Hz), 1.31 (3H, t, J=7.7 Hz).

Example 114

[6-Chloro-2-(3-ethoxy-4-ethylpyridine-2-carbonyl)-1H-indol-3-yl]acetic Acid

The title compound was prepared according to the procedure described in Example 58 from methyl[6-chloro-2-(4-ethyl-3-fluoropyridine-2-carbonyl)-1H-indol-3-yl]acetate (Example 113).

m.p.: 165° C. IR (KBr) v: 3300, 2974, 1705, 1645, 1529, 1339, 1178 cm$^{-1}$. $^1$H-NMR (DMSO-d$_6$) δ: 11.65 (1H, br s), 8.32 (1H, d, J=4.6 Hz), 7.73 (1H, d, J=8.9 Hz), 7.47–7.52 (2H, m), 7.10 (1H, dd, J=1.8, 8.6 Hz), 3.89 (2H, q, J=6.9 Hz), 3.70 (2H, s), 2.72 (2H, q, J=7.6 Hz), 1.13–1.26 (6H, m).

Example 115

Methyl[6-chloro-2-(3-chloro-4-ethylpyridine-2-carbonyl)-1H-indol-3-yl]acetate

The title compound was prepared according to the procedure described in Example 57 from methyl trans-4-chloro- 2-(penylsulfonylamino)cinnamate (step 1 of Example 8, Method A) and 2-bromoacetyl-3-chloro-4-ethylpyridine hydrobromide*.

* 2-Bromoacetyl-3-chloro-4-ethylpyridine hydrobromide was prepared as follows;

$^1$H-NMR (CDCl$_3$) δ: 10.05 (1H, br s), 8.47 (1H, d, J=4.9 Hz), 7.53 (1H, d, J=8.7 Hz), 7.32–7.34 (2H, m), 7.05 (IR, dd, J=1.8, 8.7 Hz), 3.79 (2H, s), 3.61 (3H, s), 2.83 (2H, q, J=7.6 Hz), 1.28 (3H, t, J=7.6 Hz).

3-Chloro-4-ethylpyridine-N-oxide:

The title compound was prepared from 3-chloro-4-ethylpyridine (F. Marsais et al., *J. Organomet. Chem.*, 1981, 216, 139) according to the procedure for preparing 4-ethyl-3-fluoropyridine-N-oxide described in Example 111.

$^1$H-NMR (DMSO-d$_6$) δ: 8.46 (1H, d, J=1.8 Hz), 8.16 (1H, d, J=6.6 Hz), 7.40 (1H, dd, J=1.8, 6.6 Hz), 2.67 (2H, q, J=7.6 Hz), 1.14–1.19 (3H, m).

3-Chloro-4-ethyl-2-pyridinecarbonitrile:

The title compound was prepared from 3-chloro-4-ethylpyridine-N-oxide according to the procedure for preparing 4-chloro-2-pyridinecarbonitrile described in Example 33.

$^{11}$H-NMR (CDCl$_3$) δ: 8.50 (1H, d, J=4.9 Hz), 7.41 (1H, t, J=4.9 Hz), 2.84 (2H, q, J=7.4 Hz), 1.30 (3H, t, J=7.6 Hz).

2-Acetyl-3-chloro-4-ethylpyridine:

The title compound was prepared from 3-chloro-4-ethyl-2-pyridinecarbonitrile according to the procedure for preparing 2-acetyl-4-chloropyridine described in Example 33.

$^1$H-NMR (CDCl$_3$) δ: 8.41 (1H, d, J=4.8 Hz), 7.29 (1H, d, J=4.8 Hz), 2.83 (2H, q, J=7.6 Hz), 2.67 (3H, s), 1.27 (3H, t, J=7.6 Hz).

2-Bromoacetyl-3-chloro-4-ethylpyridine hydrobromide:

The title compound was prepared from 2-acetyl-3-chloro-4-ethylpyridine according to the procedure for preparing 2-bromo-4-methylpyridine hydrobromide described in step 2 of Example 31.

$^1$H-NMR (DMSO-d$_6$) δ: 8.55 (1H, d, J=4.9 Hz), 7.66 (1H, d, J=4.8 Hz), 4.93 (2H, s), 2.82 (2H, q, J=7.3 Hz), 1.21 (3H, t, J=7.4 Hz).

Example 116

[6-Chloro-2-(3-chloro-4-ethylpyridine-2-carbonyl)-1H-indol-3-yl]acetic Acid

The title compound was prepared according to the procedure described in Example 58 from methyl[6-chloro-2-(3-chloro-4-ethylpyridine-2-carbonyl)-1H-indol-3-yl]acetate (Example 115).

m.p.: 158° C. IR (KBr) ν: 3335, 1730, 1630, 1529, 1325, 1200 cm$^{-1}$. $^1$H-NMR (DMSO-d$_6$) δ: 11.83 (1H, br s), 8.54 (1H, d, J=4.8 Hz), 7.75 (1H, d, J=8.7 Hz), 7.63 (1H, d, J=4.9 Hz), 7.46 (1H, s), 7.12 (1H, dd, J=1.8, 8.7 Hz), 3.57 (2H, s), 2.82 (2H, q, J=7.4 Hz), 1.25 (3H, t, J=7.4 Hz).

Example 117

Methyl[5-chloro-2-(3-chloro-4-ethylpyridine-2-carbonyl)-1H-indol-3-yl]acetate

The title compound was prepared according to the procedure described in Example 57 from methyl trans-5-chloro-2-(penylsulfonylamino)cinnamate (Example 36, step 3) and 2-bromoacetyl-3-chloro-4-ethylpyridine hydrobromide (Preparation is described in Example 115).

$^1$H-NMR (CDCl$_3$) δ: 9.87 (1H, br s), 8.50 (1H, d, J=4.9 Hz), 7.64 (1H, s), 7.29–7.40 (3H, m), 3.86 (2H, s), 3.63 (3H, s), 2.88 (2H, q, J=7.6 Hz), 1.32 (3H, t, J=7.6 Hz).

Example 118

[5-Chloro-2-(3-chloro-4-ethylpyridine-2-carbonyl)-1H-indol-3-yl]acetic Acid

The title compound was prepared according to the procedure described in Example 58 from methyl[5-chloro-2-(3-chloro-4-ethylpyridine-2-carbonyl)-1H-indol-3-yl]acetate (Example 117).

m.p.: 220° C. IR (KBr) ν: 3341, 1695, 1626, 1533, 1458, 1429, 1229 cm$^{-1}$. $^1$H-NMR (DMSO-d$_6$) δ: 11.88 (1H, br s), 8.54 (1H, d, J=4.9 Hz), 7.82 (1H, s), 7.63 (1H, d, J=4.9 Hz), 7.46 (1H, d, J=8.9 Hz), 7.34 (1H, dd, J=2.0, 8.9 Hz), 3.60 (2H, s), 2.82 (2H, q, J=7.4 Hz), 1.25 (3H, t, J=7.4 Hz).

Example 119

Methyl[5-chloro-2-(4,6-dimethylpyridine-2-carbonyl)-1H-indol-3-yl]acetate

The title compound was prepared according to the procedure described in Example 57 from methyl trans-5-chloro-2-(phenylsulfonylamino)cinnamate (Example 36, step 3) and 2-bromoacetyl-4,6-dimethylpyridine*.

* 2-Bromoacetyl-3,4-dimethylpyridine was prepared from 2-acetyl-4,6-dimethylpyridine (Sundberg et al., *J. Am. Chem. Soc.*, 1969, 91, 658) according to the procedure for preparing 2-bromoacetyl-4-methylpyridine described in Example 57.

$^1$H-NMR (CDCl$_3$) δ: 12.73 (1H br s), 7.98 (1H, s), 7.67 (1H, br s), 7.42 (1H, d, J=8.9 Hz), 7.30 (1H, dd, J=1.8 and 8.7 Hz), 7.22 (1H, s), 4.27 (2H, s), 3.73 (3H, s), 2.70 (3H, s), 2.43 (3H, s). $^1$H-NMR (CDCl$_3$) δ: 7.72 (1H, s), 7.19 (1H, s), 5.13 (2H, s), 2.55 (3H, s), 2.38 (3H, s).

Example 120

[5-Chloro-2-(4,6-dimethylpyridine-2-carbonyl)-1H-indol-3-yl]acetic Acid

The title compound was prepared according to the procedure described in Example 58 from methyl[5-chloro-2-(4,6-dimethylpyridine-2-carbonyl)-1H-indol-3-yl]acetate (Example 119).

MS (EI) m/z: 342 (M$^+$). m.p.: 233–235° C. IR (KBr) ν: 3288, 2919, 1742, 1630, 1599, 1529, 1333, 1232, 1180, 1067, 772 cm$^{-1}$. $^1$H-NMR (DMSO-d$_6$) δ: 11.99 (1H, br s), 7.69 (1H, s), 7.57 (1H, s), 7.52 (1H, d, J=8.9 Hz), 7.28 (1H, s), 7.18 (1H, dd, J=2.1, 8.9 Hz), 3.87 (2H, s), 2.49 (3H, s), 2.27 (3H, s).

Example 121

Methyl[6-chloro-2-(4,6-dimethylpyridine-2-carbonyl)-1H-indol-3-yl]acetate

The title compound was prepared according to the procedure described in Example 57 from methyl trans-4-chloro-2-(phenylsulfonylamino)cinnamate (step 1 of Example 8, Method A) and 2-bromoacetyl-4,6-dimethylpyridine (Preparation is described in Example 119).

$^1$H-NMR (CDCl$_3$) δ: 12.69 (1H, br s), 7.98 (1H, s), 7.62 (1H, d, J=8.7 Hz), 7.50 (1H, d, J=0.7 Hz), 7.22 (1H, s), 7.12 (1H, dd, J=1.6, 8.6 Hz), 4.30 (2H, s), 3.72 (3H, s), 2.70 (3H, s), 2.43 (3H, s).

Example 122

[6-Chloro-2-(4,6-dimethylpyridine-2-carbonyl-1H-indol-3-yl]acetic Acid

The title compound was prepared according to the procedure described in Example 58 from methyl[6-chloro-2-(4,6-dimethylpyridine-2-carbonyl)-1H-indol-3-yl]acetate (Example 121).

MS (EI) m/z: 342 (M$^+$). m.p.: 219–220° C. IR (KBr) ν: 3300,1701, 1639, 1603, 1535, 1225, 1180 cm$^{-1}$. $^1$H-NMR (DMSO-d$_6$) δ: 11.95 (1H, br s), 7.62 (1H, d, J=8.7 Hz), 7.58

(1H, d, J=1.3 Hz), 7.56 (1H, s), 7.27 (1H, s), 6.96 (1H, dd, J=2.0, 8.7 Hz), 3.87 (2H, s), 2.49 (3H, s), 2.26 (3H, s).

Example 123

Methyl[5,6-dichloro-2-(4-methylpyridine-2-carbonyl)-1H-indol-3-yl]acetate

Step 1. Methyl trans-4,5-Dichloro-2-nitrocinnamate

The title compound was prepared according to the procedure described in step 1 of Example 36 from 4,5-dichloro-2-nitrobenzaldehyde (J. Kenneth et al., *J. Med. Chem.*, 1968, 11, 946).

$^1$H-NMR (CDCl$_3$) δ: 8.20 (1H, s), 8.04 (1H, d, J=15.8 Hz), 7.72 (1H, s), 6.36 (1H, d, J=15.8 Hz).

Step 2. Methyl trans-2-Amino-4,5-dichlorocinnamate

The title compound was prepared according to the procedure described in step 2 of Example 36 from methyl trans-4,5-dichloro-2-nitrocinnamate (step 1).

$^1$H-NMR (CDCl$_3$) δ: 7.65 (1H, d, J=15.8 Hz), 7.42 (1H, s), 7.26 (1H, s), 6.81 (1H, s), 6.28 (1H, d, J=15.8 Hz).

Step 3. Methyl trans-4,5-Dichloro-2-(phenylsulfonylamino)cinnamate

The title compound was prepared according to the procedure described in step 1 of Example 8 (Method A) from methyl trans-2-amino-4,5-dichlorocinnamate (step 2).

$^1$H-NMR (CDCl$_3$) δ: 7.80–7.70 (2H, m), 7.60–7.40 (6H, m), 7.02 (1H, br s), 6.13 (1H, d, J=16.1 Hz), 3.79 (3H, s).

Step 4. Methyl[(5,6-dichloro-2-(4-methylpyridine-2-carbonyl)-1H-indol-3-yl]acetate The title compound was prepared according to the procedure described in Example 57 from methyl trans-4,5-dichloro-2-(phenylsulfonylamino)cinnamate (step 3) and 2-bromoacetyl-4-methylpyridine hydrobromide (Preparation is described in step 2 of Example 31).

$^1$H-NMR (DMSO-d$_6$) δ: 12.45 (1H, br s), 8.69 (1H, d, J=5.1 Hz). 8.14 (1H, s), 8.00–7.93 (2H, m), 7.59 (1H, d, J=4.3 Hz), 4.16 (2H, s), 3.59 (3H, s), 3.32 (3H, s).

Example 124

[5,6-Dichloro-2-(4-methylpyridine-2-carbonyl)-1H-indol-3-yl]acetic Acid

The titled compound was prepared according to the procedure described in Example 58 from methyl[5,6-dichloro-2-(4-methylpyridine-2-carbonyl)-1H-indol-3-yl]acetate (Example 123).

m.p.: 220–224° C. $^1$H-NMR (DMSO-d$_6$) δ: 12.41 (1H, s), 12.20 (1H, br s), 8.69 (1H, d, J=5.1 Hz), 8.11 (1H, s), 7.96–7.58 (2H, m), 7.58 (1H, d, J=4.8 Hz), 4.08 (2H, s), 2.47 (3H, s).

Example 125

Methyl[5-methyl-2-(4-methylpyridine-2-carbonyl)-1H-indol-3-yl]acetate

Step 1. Methyl trans-2-Amino-5-methylcinnamate

The title compound was prepared according to the procedure described in step 2 of Example 36 from methyl trans-5-methyl-2-nitrocinnamate (C. Venkatasubban, J. Annamalai Univ., 1933, 2, 227).

$^1$H-NMR (CDCl$_3$) δ: 7.82 (1H, d, J=15.8 Hz), 7.20–7.19 (1H, m), 7.01–6.98 (1H, m), 6.63 (1H, d, J=8.2 Hz), 6.35 (1H, d, J=15.8 Hz), 3.83 (2H, m), 3.80 (3H, s), 2.24 (3H, s).

Step 2. Methyl trans-5-Methyl-2-(phenylsulfonylamino)cinnamate

The title compound was prepared according to the procedure described in step 1 of Example 8 (Method A) from methyl trans-2-amino-5-methylcinnamate (step 1).

$^1$H-NMR (CDCl$_3$) δ: 7.70–7.67 (2H, m), 7.55–7.38 (4H, m), 7.26–7.14 (3H, m), 6.55 (1H, br s), 6.14(1H, d, J=16.0 Hz), 3.77(3H, s), 2.33 (3H, s).

Step 3. Methyl[5-methyl-2-(4-methylpyridine-2-carbonyl)-1H-indol-3-yl]acetate The title compound was prepared according to the procedure described in Example 57 from methyl trans-5-methyl-2-(phenylsulfonylamino)cinnamate (step 2) and 2-bromoacetyl-4-methylpyridine hydrobromide (Preparation is described in step 2 of Example 31).

$^1$H-NMR (CDCl$_3$) δ: 12.32 (1H, br s), 8.61 (1H, d, J=5.0 Hz), 8.17 (1H, s), 7.46 (1H, s), 7.40 (1H, d, J=8.6 Hz), 7.33–7.32 (1H, m), 7.22–7.19 (1H, m), 4.31 (2H, s), 3.72 (3H, s), 2.46 (6H, m).

Example 126

[5-Methyl-2-(4-methylpyridine-2-carbonyl-1H-indol-3-yl]acetic Acid

The title compound was prepared according to the procedure described in Example 58 from methyl[5-methyl-2-(4-methylpyridine-2-carbonyl)-1H-indol-3-yl]acetate (Example 125).

m.p.: 220–226° C. IR (KBr) ν: 3736, 3649, 1697, 1533, 1508, 1398, 1194, 802 cm$^{-1}$. $^1$H-NMR (DMSO-d$_6$) δ: 12.08 (1H, br s), 8.69 (1H, d, J=4.8 Hz), 7.94 (1H, s), 7.56–7.49 (3H, m), 7.17 (1H, dd, J=8.4 Hz), 4.05 (2H, s), 2.46 (3H, s), 2.40 (3H, s).

Example 127

Methyl[5-fluoro-2-(4-methylpyridine-2-carbonyl)-1H-indol-3-yl]acetate

Step 1. Methyl trans-5-Fluoro-2-nitrocinnamate

The title compound was prepared according to the procedure described in step 1 of Example 36 from 5-fluoro-2-nitrobenzaldehyde.

$^1$H-NMR (CDCl$_3$) δ: 8.17–8.10 (2H, m), 7.32–7.19 (2H, m), 6.36 (1H, d, J=15.8 Hz), 3.84 (3H, s).

Step 2. Methyl trans-5-Fluoro-2-aminocinnamate

The title compound was prepared according to the procedure described in step 2 of Example 36 from methyl trans-5-fluoro-2-nitrocinnamate (step 1).

$^1$H-NMR (CDCl$_3$) δ: 7.77 (1H, dd, J=15.8, 1.5 Hz), 7.10–7.06 (1H, m), 6.94–6.87 (1H, m), 6.68–6.63 (1H, m), 6.33 (1H, d, J=15.8 Hz), 3.85 (2H, m), 3.81 (3H, s).

Step 3. Methyl trans-5-Fluoro-2-(phenylsulfonylamino)cinnamate

The title compound was prepared according to the procedure described in step 1 of Example 8 (Method A) from methyl trans-5-fluoro-2-aminocinnamate (step 2).

$^1$H-NMR (CDCl$_3$) δ: 7.68–7.65 (2H, m), 7.55–7.49 (2H, m), 7.44–7.33 (3H, m), 7.18–7.13 (1H, m), 7.10–7.04 (1H, m), 6.10 (1H, d, J=15.8 Hz), 3.78 (3H, s).

Step 4. Methyl[5-fluoro-2-(4-methylpyridine-2-carbonyl)-1H-indol-3-yl]acetate

The title compound was prepared according to the procedure described in Example 57 from methyl trans-5-fluoro-2-(phenylsulfonylamino)cinnamate (step 3).

$^1$H-NMR (CDCl$_3$) δ: 12.46 (1H, br s), 8.58–8.56 (1H, m), 8.12 (1H, s), 7.43–7.39 (1H, m), 7.33–7.26 (2H, m), 7.14–7.06 (1H, m), 4.26 (2H, s), 3.74 (3H, s), 2.45 (3H, s).

Example 128

[5-Fluoro-2-(4-methylpyridine-2-carbonyl)-1H-indol-3-yl]acetic acid

The title compound was prepared according to the procedure described in Example 58 from methyl[5-fluoro-2-(4- methylpyridine-2-carbonyl)-1H-indol-3-yl]acetate (Example 127).

m.p.: 223° C. (decomposed). IR (KBr) ν: 1705, 1643, 1570, 1277, 1227, 1204, 1186 cm$^{-1}$. $^1$H-NMR (DMSO-d$_6$) δ: 12.28 (1H, br s), 8.70 (1H, d, J=4.9 Hz), 7.95 (1H, s), 7.71–7.66 (1H, m), 7.58–7.52 (2H, m), 7.25–7.17 (1H, m), 4.06 (2H, s), 2.47 (3H, s).

Example 129

Methyl[5-methoxy-2-(4-methylpyridine-2-carbonyl)-1H-indol-3-yl]acetate

Step 1. Methyl trans-5-Methoxy-2-nitrocinnamate

The title compound was prepared according to the procedure described in step 1 of Example 36 from 5-methoxy-2-nitrobenzaldehyde.

$^1$H-NMR (CDCl$_3$) δ: 8.21 (1H, d, J=15.8 Hz), 8.16–8.12 (1H, m), 7.00–6.96 (2H, m), 6.30 (1H, d, J=15.8 Hz), 3.93 (3H, s), 3.83 (3H, s).

Step 2. Methyl trans-5-Methoxy-2-aminocinnamate

The title compound was prepared according to the procedure described in step 2 of Example 36 from methyl trans-5-methoxy-2-nitrocinnamate (step 1).

$^1$H-NMR (CDCl$_3$) δ: 7.83 (1H, d, J=15.8 Hz), 6.92–6.91 (1H, m), 6.82 (1H, dd, J=8.7, 2.8 Hz), 6.66 (1H, d, J=8.7 Hz), 6.35 (1H, d, J=15.8 Hz), 3.80 (3H, s), 3.76 (3H, s).

Step 3. Methyl trans-5-Methoxy-2-(phenylsulfonylamino)cinnamate

The title compound was prepared according to the procedure described in step 1 of Example 8 (Method A) from methyl trans-5-methoxy-2-aminocinnamate (step 2).

$^{11}$H-NMR (CDCl$_3$) δ: 7.67–7.64 (2H, m), 7.54–7.37 (4H, m), 7.24 (1H, d, J=8.7 Hz), 6.95 (1H, d, J=2.8 Hz), 6.89 (1H, dd, J=8.7, 2.8 Hz), 6.82 (1H, br s), 6.10 (1H, d, J=15.8 Hz), 3.81 (3H, s), 3.77 (3H, s).

Step 4. Methyl[5-methoxy-2-(4-methylpyridine-2-carbonyl)-1H-indol-3-yl]acetate

The title compound was prepared according to the procedure described in Example 57 from methyl trans-5-methoxy-2-(phenylsulfonylamino)cinnamate (step 3).

$^1$H-NMR (CDCl$_3$) δ: 12.38 (1H, br s), 8.61 (1H, d, J=4.9 Hz), 8.17 (1H, s), 7.40 (1H, d, J=8.7 Hz), 7.34–7.32 (1H, m), 7.08–7.03 (2H, m), 4.31 (2H, s), 3.88 (3H, s), 3.73 (3H, s), 2.47 (3H, s).

Example 130

[5-Methoxy-2-(4-methylpyridine-2-carbonyl)-1H-indol-3-yl]acetic Acid

The titled compound was prepared according to the procedure described in Example 58 from methyl[5-methoxy-2-(4-methylpyridine-2-carbonyl)-1H-indol-3-yl]acetate (Example 129).

m.p.: 235° C. (decomposed). IR (KBr) ν: 1701, 1638, 1595, 1528, 1448, 1423, 1340, 1279, 1263, 1234, 1223, 1192, 1111 cm$^{-1}$. $^1$H-NMR (DMSO-d$_6$) δ: 12.11 (1H, br s), 8.69 (1H, d, J=4.9 Hz), 7.95 (1H, s), 7.58–7.55 (2H, m), 7.18 (1H, m), 7.02–6.98 (1H, m), 4.07 (2H, s), 3.79 (3H, s), 2.46 (3H, s).

Example 131

Methyl[6-methoxy-2-(4-methylpyridine-2-carbonyl)-1H-indol-3-yl]acetate

Step 1. Methyl trans-(4-Methoxy-2-nitro)cinnamate

A mixture of 4-bromo-3-nitroanisole (4.177 g, 18.0 mmol), methyl acrylate (3.24 ml, 36.0 ml), palladium(II) acetate (606.1 mg, 2.7 mmol), triphenylphosphine (1.416 g, 5.4 mmol), triethylamine (3.76 ml, 27.0 mmol) in DMF (45.0 ml) was stirred at 130° C. for 4 h. After cooling to ambient temperature, the mixture was concentrated. To the residue was added water (30 ml), and then the mixture was extracted with ethyl acetate-toluene (3:1, 40 ml). The aqueous layer was further extracted with ethyl acetate (2×30 ml). The combined organic layers were dried (MgSO$_4$) and concentrated to afford 6.42g (quant.) of the title compound as an brown oil.

$^1$H-NMR (CDCl$_3$) δ: 8.07–6.97 (4H, m), 6.31 (1H, d, 15.8 Hz), 3.90 (3H, s), 3.82 (3H, s).

Step 2. Methyl trans-2-Amino-4-methoxycinnamate

The title compound was prepared according to the procedure described in step 2 of Example 36 from methyl trans-(4-methoxy-2-nitro)cinnamate (step 1).

$^1$H-NMR (CDCl$_3$) δ: 7.80–6.21 (5H, m), 4.03 (2H, br s), 3.79 (6H, s).

Step 3. Methyl trans-4-Methoxy-2-(p-toluenesulfonylamino)cinnamate

The title compound was prepared according to the procedure described in step 1 of Example 8 (Method A) from methyl trans-4-methoxy-2-aminocinnamate (step 2).

$^1$H-NMR (CDCl$_3$) δ: 7.62–6.73 (9H, m), 6.07 (1H, d, 15.8 Hz), 3.80 (3H, s), 3.77 (3H, s), 2.37 (3H, s).

Step 4. Methyl[6-methoxy-2-(4-methylpyridine-2-carbonyl)-1H-indol-3-yl]acetate

The title compound was prepared according to the procedure described in Example 57 from methyl trans-4-methoxy-2-(p-toluenesulfonylamino)cinnamate (step 3) and 2-bromoacetyl-4-methylpyridine hydrobromide (Preparation is described in step 2 of Example 31).

$^1$H-NMR (CDCl$_3$) δ: 12.32 (1H, br s), 8.61 (1H, d, 4.94 Hz), 8.19–7.55 (2H, m), 7.34–6.82 (311, m), 4.31 (2H, s), 3.89 (3H, s), 3.72 (3H, s), 2.47 (3H, s).

Example 132

[6-Methoxy-2-(4-methylpyridine-2-carbonyl)-1H-indol-3-yl]acetic Acid

The title compound was prepared according to the procedure described in Example 9 (Method B) from methyl[6-methoxy-2-(4-methylpyridine-2-carbonyl)-1H-indol-3-yl]acetate (Example 131).

m.p.: 204° C. IR (KBr) ν: 3198, 1709, 1630, 1593, 1531, 1460, 1423, 1334, 1275, 1213, 1161, 1136, 1039, 1001 cm$^{-1}$. $^1$H-NMR (DMSO-d$_6$) δ: 12.11 (1H, br s), 8.68 (1H, d, 4.94 Hz), 7.94 (11H, m), 7.62 (1H, d, 8.88 Hz), 7.56–7.52 (1H, m), 7.14 (1H, d, 2.30 Hz), 6.76 (1H, dd, 8,88 Hz, 2.30 Hz), 4.05 (2H, s), 3.82 (3H, s), 2.47 (3H, s).

Example 133

Methyl[5-ethyl-2-(4-methylpyridine-2-carbonyl)-1H-indol-3-yl]acetate

Step 1. Methyl trans-5-Ethyl-2-aminocinnamate

A mixture of 2-bromo-4-ethylaniline (1.0 g, 5.10 mmol), methyl acrylate (1.15 ml, 12.74 mmol), palladium(II) acetate (137 mg, 0.61 mmol), tri-o-tolylphosphine (745 mg, 2.45 mmol) and triethylamine (2.5 ml) in acetonitrile (10 ml) was heated at 110° C. After stirring for 2 h, methyl acrylate (0.6 ml, 6.37 mmol), palladium(II) acetate (69 mg, 0.30 mmol), tri-o-tolylphosphine (372 mg, 1.22 mmol), triethylamine (1.3 ml) were added and the mixture was stirred at 110° C. for 7 h. The solvent was removed and the residue was diluted with ethyl acetate (100 ml), washed with water (100 ml), dried (MgSO$_4$) and concentrated. The residue was purified by flash column chromatography eluting with ethyl acetate/hexane (1:5/1:4) to afford 793 mg (75.8%) of the title compound as yellow solids.

$^1$H-NMR (CDCl$_3$) δ: 7.83 (1H, d, J=15.8 Hz), 7.21 (1H, m), 7.04–7.01 (1H, m), 6.64 (1H, d, J=8.2 Hz), 6.36 (1H, d, J=15.8 Hz), 3.87 (2H, m), 3.80 (3H, s), 2.51 (2H, q, J=7.6 Hz), 1.19 (3H, t, J=7.6 Hz).

Step 2. Methyl trans-5-Ethyl-2-(phenylsulfonylamino) cinnamate

The title compound was prepared according to the procedure described in step 1 of Example 8 (Method A) from methyl trans-5-ethyl-2-aminocinnamate (step 1).

$^1$H-NMR (CDCl$_3$) δ: 7.70–7.48 (4H, m), 7.42–7.36 (2H, m), 7.29–7.26 (2H, m), 7.20–7.17 (2H, m), 6.14 (1H, d, J=15.8 Hz), 3.76 (3H, s), 2.62 (2H, q, J=7.6 Hz), 1.21 (3H, t, J=7.6 Hz).

Step 3. Methyl[5-ethyl-2-(4-methylpyridine-2-carbonyl)-1H-indol-3-yl]acetate

The title compound was prepared according to the procedure described in Example 57 from methyl trans-5-ethyl-2-(phenylsulfonylamino)cinnamate (step 2).

$^1$H-NMR (CDCl$_3$) δ: 12.32 (1H, br s), 8.59–8.57 (1H, m), 8.14 (1H, m), 7.47–7.39 (2H, m), 7.30–7.21 (2H, m), 4.32 (2H, s), 3.73 (3H, s), 2.75 (2H, q, J=7.6 Hz), 2.43 (3H, s), 1.27 (3H, t, J=7.6 Hz).

Example 134

[5-Ethyl-2-(4-methylpyridine-2-carbonyl)-1H-indol-3-yl]acetic Acid

The title compound was prepared according to the procedure described in Example 58 from methyl[5-ethyl-2-(4-methylpyridine-2-carbonyl)-1H-indol-3-yl]acetate (Example 133).

m.p.: 215° C. (decomposed). IR (KBr) ν: 1701, 1638, 1597, 1535, 1443, 1420, 1398, 1331, 1279, 1236, 1205 cm$^{-1}$. $^1$H-NMR (DMSO) δ: 12.09 (1H, br s), 8.69 (1H, d, J=4.9 Hz), 7.94 (1H, m), 7.58–7.51 (3H, m), 7.23–7.20 (1H, m), 4.06 (2H, s), 2.69 (2H, q, J=7.6 Hz), 2.46 (3H, s), 1.23 (3H, t, J=7.6 Hz).

Example 135

Methyl[5-ethyl-2-(4-ethylpyridine-2-carbonyl)-1H-indol-3-yl]acetate)

The title compound was prepared according to the procedure described in Example 57 from methyl trans-5-ethyl-2-(phenylsulfonylamino)cinnamate (Example 133, step 2) and 2-bromoacetyl-4-ethylpyridine (Preparation is described in Example 57).

$^1$H-NMR (CDCl$_3$) δ: 12.35 (1H, br s), 8.63 (1H, d, J=5.1 Hz), 8.20 (1H, m), 7.48 (1H, s), 7.42 (1H, d, J=8.6 Hz), 7.34 (1H, dd, J=5.1, 1.8 Hz), 7.26–7.22 (1H, m), 4.32 (2H, s), 3.73 (3H, s), 2.76 (4H, q, J=7.6 Hz), 1.30 (6H, t, J=7.6 Hz)

Example 136

[5-Ethyl-2-(4-ethylpyridine-2-carbonyl)-1H-indol-3-yl]acetic Acid

The title compound was prepared according to the procedure described in Example 58 from methyl[5-ethyl-2-(4-ethylpyridine-2-carbonyl)-1H-indol-3-yl]acetate (Example 135).

m.p.: 206.2° C. IR (KBr) ν: 1703, 1636, 1595, 1533, 1431, 1333, 1283, 1236, 1188, 1117cm$^{-1}$. $^1$H-NMR (DMSO-d$_6$) δ: 12.09 (1H, br s), 8.73 (1H, d, J=4.9 Hz), 7.97 (1H, s), 7.60–7.52 (3H, m), 7.22 (1H, d, J=8.6 Hz), 4.06 (2H, s), 2.82–2.65 (4H, m), 1.28–1.21 (6H, m).

Example 137

Methyl[6-ethyl-2-(4-Methylpyridine-2-carbonyl)-1H-indol-3-yl]acetate

Step 1. Methyl trans-(4-Acetyl-2-nitro)cinnamate

The title compound was prepared according to the procedure described in Example 131 from 4-bromo-3-nitroacetophenone and methyl acrylate.

$^1$H-NMR (CDCl$_3$) δ: 8.58–8.10 (3H, m), 7.77–7.74 (1H, m), 6.48–6.42 (1H, m), 3.85 (3H, s), 2.68 (3H, s).

Step 2. Methyl trans-4-(1-Hydroxyethyl)-2-nitrocinnamate

To a solution of methyl trans-4-acetyl-2-nitrocinnamate (462.2 mg, 1.854 mmol) in methanol (55 ml) was added sodium borohydride (176.3 mg, 4.66 mmol) at room temperature. After stirring for 10 min, the mixture was concentrated. The residue was diluted in dichloromethane (20 ml) and washed with brine (20 ml) The aqueous layer was extracted with dichloromethane (20 ml×2). The combined organic layers were dried (MgSO$_4$) and concentrated to afford 442 mg (quant.) of the title compound.

$^1$H-NMR (CDCl$_3$) δ: 8.12–6.33 (5H, m), 5.0 (1H, m), 3.83 (3H, s), 1.54 (3H, d, 9.56 Hz).

Step 3. Methyl trans-(4-Ethyl-2-nitro)cinnamate

To a mixture of sodium iodide (1.668 g, 11.1 mmol) and acetonitrile (581 μl, 11.1 mmol) was added chlorotrimethylsilane (1.41 ml, 11.1 mmol) at room temperature. After stirring for 10 min, a solution of methyl trans-4-(1-hydroxyethyl-2-nitro)cinnamate (563.6 mg, step 1) in hexane-toluene-acetonitrile (1:1:1, 6.0 ml) was added and the mixture was stirred for an additional 48 h. The reaction mixture was diluted with toluene-ethyl acetate (2:3, 25 ml) and poured into water (25 ml). The organic layer was separated and washed with 5% aqueous sodium thiosulfate (30 ml), brine (30 ml) and dried (MgSO$_4$). Removal of solvent gave 460 mg (quant.) of the title product as a brown oil.

$^1$H-NMR (CDCl$_3$) δ: 8.12–6.32 (5H, m), 3.83 (3H, s), 2.76 (2H, q, 7.59 Hz), 1.29 (3H, t, 7.59 Hz).

Step 4. Methyl trans-2-Amino-4-ethylcinnamate

The title compound was prepared according to the procedure described in step 2 of Example 36 from methyl trans-4-ethyl-2-nitrocinnamate (step 3).

$^1$H-NMR (CDCl$_3$) δ: 7.84–6.29 (5H, m), 3.80 (3H, s), 2.57 (2H, m), 1.21 (3H, t, 7.59 Hz).

Step 5. Methyl trans-4-Ethyl-2-(p-toluenesulfonylamino) cinnamate

The title compound was prepared according to the procedure described in step 1 of Example 8 (Method A) from methyl trans-2-amino-4-ethylcinnamate (step 4).

$^1$H-NMR (CDCl$_3$) δ: 7.57 (2H, d, 8.40 Hz), 7.46 (1H, d, 15.8 Hz), 7.39–7.08 (5H, m), 6.43 (1H, s), 6.43 (1H, d, 15.8 Hz), 3.78 (3H, s), 2.61 (2H, m), 2.37 (3H, s), 1.18 (3H, t, 7.75 Hz).

Step 6. Methyl[6-ethyl-2-(4-methylpyridine-2-carbonyl)-1H-indol-3-yl]acetate

The title compound was prepared according to the procedure described in Example 57 from methyl trans-4-ethyl-2-(p-toluenesulfonylamino)cinnamate (step 5) and 2-bromoacetyl-4-methylpyridine hydrobromide (Preparation is described in step 2 of Example 31).

$^1$H-NMR (CDCl$_3$) δ: 12.30 (1H, br s), 8.62 (1H, d, 4.94 Hz), 8.18–7.32 (4H, m), 7.05–7.02 (2H, m), 4.33 (2H, s), 3.72 (3H, s), 2.79 (2H, q, 7.59 Hz), 2.48 (3H, s), 1.31 (3H, t, 7.59 Hz).

Example 138

[6-Ethyl-2-(4-methylpyridine-2-carbonyl)-1H-indol-3-yl]acetic Acid

The title compound was prepared according to the procedure described in Example 9 (Method B) from methyl[6- ethyl-2-(4-methylpyridine-2-carbonyl)-1H-indol-3-yl]acetate (Example 137).

m.p.: 204–207° C. IR (KBr) ν: 3240, 1709, 1636, 1593, 1531, 1394, 1204, 1144, 1001 cm$^{-1}$. $^{1}$H-NMR (CDCl$_3$) δ: 12.07 (1H, br s), 8.69 (1H, d, 4.94 Hz), 7.93 (1H, m), 7.63(1H, d, 8.40 Hz), 7.55 (1H, m), 7.45 (1H, s), 7.00–6.96 (1H, m), 4.05 (2H, s), 2.73 (2H, q, 7.56 Hz), 2.46 (3H, s), 1.24 (3H, t, 7.56 Hz).

Example 139

Methyl[5-isopropyl-2-(4-methylpyridine-2-carbonyl)-1H-indol-3-yl]acetate

Step 1. Methyl trans-5-Isopropyl-2-aminocinnamate

The title compound was prepared according to the procedure described in step 1 of Example 133 from 2-bromo-4-isopropylaniline.

$^{1}$H-NMR (CDCl$_3$) δ: 7.83 (1H, d, J=15.8 Hz), 7.23 (1H, m), 7.08–7.05 (1H, m), 6.66 (1H, d, J=8.4 Hz), 6.37 (1H, d, J=15.8 Hz), 3.85 (2H, m), 3.81 (3H, s), 2.84–2.76 (1H, m), 1.21 (6H, m).

Step 2. Methyl trans-5-Isopropyl-2-(phenylsulfonylamino)cinnamate

The title compound was prepared according to the procedure described in step 1 of Example 8 (Method A) from methyl trans-5-isopropyl-2-aminocinnamate (step 1).

$^{1}$H-NMR (CDCl$_3$) δ: 7.71–7.68 (2H, m), 7.58 (1H, d, J=15.8 Hz), 7.51–7.20 (6H, m), 7.09 (1H, br, s), 6.16 (1H, d, J=15.8 Hz), 4.11 (3H, s), 2.94–2.83 (1H, m), 1.24–1.21 (6H, m).

Step 3. Methyl[5-isopropyl-2-(4-methylpyridine-2-carbonyl)-1H-indol-3-yl]acetate The title compound was prepared according to the procedure described in Example 57 from methyl trans-5-isopropyl-2-(phenylsulfonylamino)cinnamate (step 2).

$^{1}$H-NMR (CDCl$_3$) δ: 12.33 (11H, br s), 8.61 (1H, d, J=5.1 Hz), 8.17–8.16 (1H, m), 7.50–7.42 (2H, m), 7.33–7.26 (2H, m), 4.32 (2H, s), 3.73 (3H, s), 3.08–2.97 (1H, m), 2.46 (3H, s), 1.33–1.30 (6H, m).

Example 140

[5-Isopropyl-2-(4-methylpyridine-2-carbonyl)-1H-indol-3-yl]acetic Acid

The title compound was prepared according to the procedure described in Example 58 from methyl[5-isopropyl-2-(4-methylpyridine-2-carbonyl)-1H-indol-3-yl]acetate (Example 139).

m.p.: 213° C. (decomposed). IR (KBr)ν: 1717,1641, 1597,1537,1327,1273, 1196cm$^{-1}$. $^{1}$H-NMR (DMSO-d$_6$) δ: 12.10 (1H, br s), 8.70 (1H, d, J=4.9 Hz), 7.95–7.94 (1H, m), 7.59–7.54 (2H, m), 7.27 (1H, dd, J=8.6, 1.7 Hz), 4.07 (2H, s), 3.03 (1H, m), 2.46 (3H, s), 1.27–1.25 (6H, m).

Example 141

Methyl[2-(4-methylpyridine-2-carbonyl)-6-trifluoromethyl-1H-indol-3-yl]acetate

Step 1. Methyl trans-2-Amino-4-(trifluoromethyl)cinnamate

The title compound was prepared according to the procedure described in step 1 of Example 133 from 2-bromo-5-(trifluoromethyl)aniline.

$^{1}$H-NMR (CDCl$_3$) δ: 7.79 (1H, d, J=15.8 Hz), 7.46–7.43 (1H, m), 7.00–6.94 (2H, m), 6.41 (1H, d, J=15.8 Hz), 4.18 (2H, m), 3.82 (3H, m).

Step 2. Methyl trans-2-Phenylsulfonylamino-4-(trifluoromethyl)cinnamate

The title compound was prepared according to the procedure described in step 1 of Example 8 (Method A) from methyl trans-2-amino-4-(trifluoromethyl)cinnamate (step 1).

$^{1}$H-NMR (CDCl$_3$) δ: 7.77–7.68 (2H, m), 7.65–7.53 (4H, m), 7.47–7.41 (3H, m), 6.24 (1H, d, J=15.8 Hz), 3.80 (3H, s).

Step 3. Methyl[2-(4-methylpyridine-2-carbonyl)-6-trifluoromethyl-1H-indol-3-yl]acetate The title compound was prepared according to the procedure described in Example 57 from methyl trans-2-phenylsulfonylamino-4-(trifluoromethyl)cinnamate (step 2).

$^{1}$H-NMR (CDCl$_3$) δ: 12.74 (1H, br s), 8.58 (1H, d, J=4.9 Hz), 8.12 (1H, s), 7.81–7.74 (2H, m), 7.35–7.32 (2H, m), 4.32 (2H, s), 3.75 (3H, s), 2.46 (3H, s).

Example 142

[2-(4-Methylpyridine-2-carbonyl)-6-trifluoromethyl-1H-indol-3-yl]acetic Acid

The title compound was prepared according to the procedure described in Example 58 from methyl[2-(4-methylpyridine-2-carbonyl)-6-trifluoromethyl-1H-indol-3-yl]acetate (Example 141).

m.p.: 210–220° C. IR (KBr) ν: 1697, 1651, 1599, 1537, 1506, 1339, 1283, 1196, 1103, 1055 cm$^{-1}$. $^{1}$H-NMR (DMSO) δ: 12.62 (11H, br s), 8.71 (1H, d, J=4.9 Hz), 8.10 (1H, s), 7.99–7.97 (2H, m), 7.61–7.59 (11H, m), 7.39–7.36 (1H, m), 4.14 (2H, s), 2.48 (3H, s).

Example 143

Methyl[5-tert-butyl-2-(4-Methylpyridine-2-carbonyl)-1H-indol-3-yl]acetate

Step 1. Methyl trans-5-tert-Butyl-2-aminocinnamate

The title compound was prepared according to the procedure described in step 1 of Example 133 from 2-bromo-4-tert-butylaniline.

$^{1}$H-NMR (CDCl$_3$) δ: 7.85 (1H, d, 15.8 Hz), 7.38 (1H, d, 2.30 Hz), 7.23 (1H, dd, 8.56 Hz, 2.30 Hz), 6.67 (1H, d, 8.56 Hz), 6.37 (1H, d, 15.8 Hz), 3.87 (2H, br s), 3.81 (3H, s), 1.28 (9H, s).

Step 2. Methyl trans-5-tert-Butyl-2-(p-toluenesulfonylamino)cinnamate

The title compound was prepared according to the procedure described in step 1 of Example 8 (Method A) from methyl trans-5-tert-butyl-2-aminocinnamate and p-toluenesulfonyl chloride.

$^{1}$H-NMR (CDCl$_3$) δ: 7.60–7.20 (8H, m), 6.53 (1H, s), 6.17 (1H, d, 15.8 Hz), 3.79 (3H, s), 2.46 (3H, s), 1.29 (s, 9H).

Step 3. Methyl[5-tert-Butyl-2-(4-methylpyridine-2-carbonyl)-1H-indol-3-yl]acetate The compound was prepared according to the procedure described in Example of 57 from methyl trans-5-tert-butyl-2-(p-toluenesulfonylamino)cinnamate (step 2) and 2-bromoacetyl-4-methylpyridine hydrobromide (Preparation is described in step 2 of Example 31).

$^{1}$H-NMR (CDCl$_3$) δ: 12.33 (1H, br s), 8.63 (1H, d, 4.94 Hz), 8.18 (1H, m), 7.62–7.32 (4H, m), 4.43 (2H, s), 3.74 (3H, s), 2.47 (3H, s), 1.40 (s, 9H).

Example 144

[5-tert-Butyl-2-(4-methylpyridine-2-carbonyl)-1H-indol-3-yl]acetic Acid

The compound was prepared according to the procedure described in Example 9 (Method B) from methyl[5-tertbutyl-2-(4-methylpyridine-2-carbonyl)-1H-indol-3-yl]acetate (Example 143).

m.p.: 191° C. IR (KBr) ν: 2963, 1717, 1645, 1597, 1533, 1437, 1281, 1211, 1080, 1032, 1003 cm$^{-1}$. $^1$H-NMR (DMSO-d$_6$) δ: 12.10 (1H, br s), 7.70 (1H, d, 5.11 Hz), 7.95–7.44 (6H, m), 4.09 (2H, s), 2.46 (3H, s), 1.35 (9H, s).

Example 145

Methyl[2-(4-methylpyridine-2-carbonyl)-5-trifluoromethoxy-1H-indol-3-yl]acetate

Step 1. Methyl trans-2-Amino-5-(trifluoromethoxy)cinnamate

The title compound was prepared according to the procedure described in step 1 of Example 133 from 2-bromo-4-(trifluoromethoxy)aniline.

$^1$H-NMR (CDCl$_3$) δ: 7.74 (1H, d, 15.8 Hz), 7.23–7.02 (2H, m), 6.68 (1H, d, 8.72 Hz), 6.36 (1H, d, 15.8 Hz), 4.00 (2H, br s), 3.81 (3H, s).

Step 2. Methyl trans-2-2-Toluenesulfonylamino-5-(trifluoromethoxy)cinnamate

The title compound was prepared according to the procedure described in step 1 of Example 8 (Method A) from methyl trans-2-amino-4-(trifluoromethoxy)cinnamate (step 1) and p-toluenesulfonyl chloride.

$^1$H-NMR (CDCl$_3$) δ: 7.59–7.19 (8H, m), 6.76 (1H, s), 6.15 (1H, d, 15.8 Hz), 3.80 (3H, s), 2.39 (3H, s).

Step 3. Methyl[2-(4-methylpyridine-2-carbonyl)-5-trifluoromethoxy-1H-indol-3-yl]acetate The title compound was prepared according to the procedure described in Example 57 from methyl trans-2-p-toluenesulfonylamino-5-(trifluoromethoxy)cinnamate (step 2) and 2-bromoacetyl-4-methylpyridine hydrobromide (Preparation is described in step 2 of Example 31).

$^1$H-NMR (CDCl$_3$) δ: 12.7 (1H, br s), 8.64 (1H, d, 5.10 Hz), 8.19 (1H, m), 7.55–7.23 (4H, m), 4.30 (2H, s), 3.74 (3H, s), 2.49 (3H, s).

Example 146

[2-(4-Methyl-2-pyridine-2-carbonyl)-5-trifluoromethoxy-1H-indol-3-yl]acetic Acid The title compound was prepared according to the procedure described in Example 9 (Method B) from methyl[2-(4-methylpyridine-2-carbonyl)-5-trifluoromethoxy-1H-indol-3-yl]acetate (Example 145).

m.p.: 235–238° C. IR (KBr) ν: 3248, 1701, 1645, 1597, 1537, 1447, 1420, 1333, 1259, 1203, 1115, 1034, 1003 cm$^{-1}$. $^1$H-NMR (DMSO-d$_6$) δ: 12.40 (1H, br s), 8.71 (1H, d, 4.94 Hz), 7.97–7.96 (1H, m), 7.80–7.30 (4H, m), 4.09 (2H, s), 2.47 (3H, s).

Example 147

Methyl[2-(4-ethylpyridine-2-carbonyl)-5-trifluoromethoxy-1H-indol-3-yl]acetate

The title compound was prepared according to the procedure described in Example 57 from methyl trans-2-p-toluenesulfonylamino-5-(trifluoromethoxy)cinnamate (step 2 of Example 145) and 2-bromoacetyl-4-ethylpyridine (Preparation is described in Example 57).

$^1$H-NMR (CDCl$_3$) 67 : 8.66 (1H, d, 4.97 Hz), 8.22 (1H, br s), 7.55–7.26 (4H, m), 4.30 (2H, s), 3.74 (3H, s), 2.79 (2H, q, 7.59 Hz), 1.32 (3H, t, 7.59 Hz).

Example 148

[2-(4-Ethylpyridine-2-carbonyl)-5-trifluoromethoxy-1H-indol-3-yl]acetic Acid

The title compound was prepared according to the procedure described in Example 9 (Method B) from methyl[2-(4-ethylpyridine-2-carbonyl)-5-trifluoromethoxy-1H-indol-3-yl]acetate (Example 147).

m.p.: 223° C. IR (KBr) ν: 3271, 1697, 1645, 1597, 1539, 1423, 1400, 1337, 1258, 1198, 1117, 1028, 1003 cm$^{-1}$. $^1$H-NMR (DMSO-d$_6$) δ: 12.41 (1H, br s), 8.74 (1H, d, 4.94 Hz), 7.99 (1H, m), 7.80–7.75 (2H, m), 7.63–7.30 (2H, m), 4.10 (2H, s), 2.78 (2H, q, 7.59 Hz), 1.26 (3H, t, 7.59 Hz).

Example 149

Methyl[6-methyl-2-(4-methylpyridine-2-carbonyl)-1H-indol-3-yl]acetate

Step 1. Methyl trans-2-Amino-4-methylcinnamate

The title compound was prepared according to the procedure described in step 2 of Example 36 from methyl trans-4-methyl-2-nitrocinnamate.

$^1$H-NMR (CDCl$_3$) δ: 7.81 (1H, d, J=15.8 Hz), 7.30–7.26 (1H, m), 6.60–6.57 (1H, m), 6.52 (1H, m), 6.31 (1H, d, J=15.8 Hz), 3.92 (2H, br s), 3.79 (3H, s), 2.26 (2H, s).

Step 2. Methyl trans-4-Methyl-2-(phenylsulfonylamino)cinnamate

The title compound was prepared according to the procedure described in step 1 of Example 8 (Method A) from methyl trans-2-amino-4-methylcinnamate (step 1).

$^1$H-NMR (CDCl$_3$) δ: 7.72–7.68 (2H, m), 7.55–7.49 (1H, m), 7.44–7.34 (4H, m), 7.26–7.22 (1H, m), 7.07–7.04 (1H, m), 6.62 (1H, br s), 6.12 (1H, d, J=15.8 Hz), 3.76 (3H, s), 2.34 (3H, s).

Step 3. Methyl[6-methyl-2-(4-methylpyridine-2-carbonyl)-1H-indol-3-yl]acetate

The title compound was prepared according to the procedure described in Example 57 from methyl trans-4-methyl-2-(phenylsulfonylamino)cinnamate (step 2).

$^1$H-NMR (CDCl$_3$) δ: 12.26 (1H, br s), 8.61 (1H, d, J=4.9 Hz), 8.17 (1H, m), 7.58 (1H, d, J=8.4 Hz), 7.34–7.29 (2H, m), 7.01–6.98 (1H, m), 4.32 (2H, s), 3.72 (3H, s), 2.49 (3H, s), 2.47 (3H, s).

Example 150

[6-Methyl-2-(4-methylpyridine-2-carbonyl)-1H-indol-3-yl]Acetic Acid

The title compound was prepared according to the procedure described in Example 58 from methyl[6-methyl-2-(4-methylpyridine-2-carbonyl)-1H-indol-3-yl]acetate (Example 149).

m.p.: 208° C. (decomposed). IR (KBr) ν: 1707, 1638, 1593, 1531, 1277, 1205, 1142 cm$^{-1}$. $^1$H-NMR (DMSO-d$_6$) δ: 12.02 (1H, br s), 8.68 (1H, d, J=4.9 Hz), 7.93 (1H, s), 7.61 (1H, d, J=8.2 Hz), 7.56–7.54 (1H, m), 7.42 (1H, s), 6.96–6.93 (1H, m), 4.04 (2H, s), 2,46 (3H, s), 2.43 (3H, s).

Example 151

Methyl[2-(4-methylpyridine-2-carbonyl)-5-trifluoromethyl-1H-indol-3-yl]acetate

Step 1. Methyl trans-2-Amino-5-(trifluoromethyl)cinnamate

The title compound was prepared according to the procedure described in step 1 of Example 133 from 2-bromo-4-(trifluoromethyl)aniline.

$^1$H-NMR (CDCl$_3$) δ: 7.77 (1H, d, J=15.8 Hz), 7.61 (1H, s), 7.39 (1H, d, J=8.4 Hz), 6.74 (1H, d, J=8.4 Hz), 6.41 (1H, dd, J=15.8, 1.5 Hz), 4.29 (2H, m), 3.82 (3H, m).

Step 2. Methyl trans-2-Phenylsulfonylamino-5-(trifluoromethyl)cinnamate

The title compound was prepared according to the procedure described in step 1 of Example 8 (Method A) from methyl trans-2-amino-5-(trifluoromethyl)cinnamate (step 1).

¹H-NMR (CDCl₃) δ: 7.79–7.76 (2H, m), 7.66 (1H, m), 7.60–7.44 (6H, m), 7.06 (1H, br s), 6.26 (1H, d, J=15.8 Hz), 3.81 (3H, s).

Step 3. Methyl[2-(4-methylpyridine-2-carbonyl)-5-trifluoromethyl-1H-indol-3-yl]acetate The title compound was prepared according to the procedure described in Example 57 from methyl trans-2-phenylsulfonylamino-5-(trifluoromethyl)cinnamate (step 2).

¹H-NMR (CDCl₃) δ: 12.70 (1H, br s), 8.62 (1H, d, J=4.9 Hz), 8.17 (1H, s), 8.00 (1H, s), 7.61–7.54 (2H, m), 7.38–7.36 (1H, m), 4.34 (2H, s), 3.75 (3H, s), 2.48 (3H, s).

Example 152

[2-(4-Methylpyridine-2-carbonyl)-5-trifluoromethyl-1H-indol-3-yl]acetic Acid

The title compound was prepared according to the procedure described in Example 58 from methyl[2-(4-methylpyridine-2-carbonyl)-5-trifluoromethyl-1H-indol-3-yl]acetate (Example 151).

m.p.: 218–225° C. IR (KBr) ν: 1697, 1645, 1599, 1541, 1337, 1277, 1202, 1161, 1111, 1053 cm⁻¹. ¹H-NMR (DMSO-d₆) δ: 12.52 (1H, br s), 8.71 (1H, d, J=4.9 Hz), 8.23 (1H, s), 7.97 (1H, m), 7.85 (1H, d, J=8.9 Hz), 7.62–7.58 (2H, m), 4.16 (2H, s), 2.48 (3H, s).

Example 153

Methyl[2-(4-ethylpyridine-2-carbonyl)-5-trifluoromethyl-1H-indol-3-yl]acetate

The title compound was prepared according to the procedure described in Example 57 from methyl trans-2-phenylsulfonylamino-5-(trifluoromethyl)cinnamate (step 2 of Example 151) and 2-bromoacetyl-4-ethylpyridine (Preparation is described in Example 57).

¹H-NMR (CDCl₃) δ: 12.65 (1H, br s), 8.64 (1H, d, J=5.1 Hz), 8.21 (1H, m), 8.01 (1H, s), 7.61–7.52 (2H, m), 7.40–7.37 (1H, m), 4.34 (2H, s), 3.76 (3H, s), 2.78 (2H, q, J=7.6 Hz), 1.31 (3H, t, J=7.6 Hz).

Example 154

[2-(4-Ethylpyridine-2-carbonyl)-5-trifluoromethyl-1H-indol-3-yl]acetic Acid

The title compound was prepared according to the procedure described in Example 58 from methyl[2-(4-ethylpyridine-2-carbonyl)-5-trifluoromethyl-1H-indol-3-yl]acetate (Example 153).

m.p.: 203.6° C. IR (KBr) ν: 1703, 1647, 1599, 1537, 1340, 1202, 1105, 1051 cm⁻¹. ¹H-NMR (DMSO-d₆) δ: 12.52 (1H, br s), 8.74 (1H, d, J=5.1 Hz), 8.24 (1H, s), 8.00–7.99 (1H, m), 7.86 (1H, d, J=8.7 Hz), 7.64–7.58 (2H, m), 4.16 (2H, s), 2.79 (2H, q, J=7.6 Hz), 1.26 (3H, t, J=7.6 Hz).

Example 155

Methyl(2-benzoyl-1H-indol-3-yl)acetate
Step 1. Methyl trans-2-(Phenylsulfonylamino)cinnamate The title compound was prepared according to the procedure described in step 1 of Example 8 (Method A) from methyl trans-2-aminocinnamate.

¹H-NMR (CDCl₃) δ: 7.71–7.67 (2H, m), 7.58 (1H, d, J=15.8 Hz), 7.52–7.32 (6H, m), 7.28–7.22 (1H, m), 7.08 (1H, br s), 6.15 (1H, d, J=15.8 Hz), 3.78 (3H, s).

Step 2. Methyl(2-benzoyl-1H-indol-3-yl)acetate

The title compound was prepared according to the procedure described in Example 57 from methyl trans-2-(phenylsulfonylamino)cinnamate (step 1).

¹H-NMR (CDCl₃) δ: 8.91 (1H, br s), 7.80–7.77 (2H, m), 7.67–7.58 (2H, m), 7.53–7.48 (2H, m), 7.43–7.34 (2H, m), 7.21–7.15 (1H, m), 3.86 (2H, s), 3.65 (3H, s).

Example 156

(2-Benzoyl-1H-indol-3-yl)acetic Acid

The title compound was prepared according to the procedure described in Example 9 (Method B) from methyl(2-benzoyl-1H-indol-3-yl)acetate (Example 155).

m.p.: 194–196° C. IR (KBr) ν: 1713, 1597, 1541, 1450, 1402, 1267, 1180, 729 cm⁻¹. ¹H-NMR (DMSO-d₆) δ: 11.62 (1H, br s), 7.77–7.74 (2H, m), 7.69–7.66 (2H, m), 7.60–7.55 (2H, m), 7.48–7.45 (1H, m), 7.34–7.28 (1H, m), 7.13–7.08 (1H, m), 3.80 (2H, s).

Example 157

Methyl[2-(4-chlorobenzoyl)-6-methyl-1H-indol-3-yl]acetate

The title compound was prepared according to the procedure described in Example 57 from methyl trans-4-methyl-2-(phenylsulfonylamino)cinnamate (step 2 of Example 149) and 4-chlorophenacyl bromide.

¹H-NMR (CDCl₃) δ: 8.84 (1H, br s), 7.74–7.71 (2H, m), 7.53–7.45 (3H, m), 7.14 (1H, m), 7.03–7.00 (1H, m), 3.81 (2H, s), 3.65 (3H, s), 2.46 (3H, s).

Example 158

[2-(4-Chlorobenzoyl)-6-methyl-1H-indol-3-yl]acetic Acid

The title compound was prepared according to the procedure described in Example 58 from methyl[2-(4-chlorobenzoyl)-6-methyl-1H-indol-3-yl]acetate (Example 157).

m.p.: 193–195° C. IR (KBr) ν: 3302, 1697, 1587, 1335, 1263, 1090, 999, 770 cm⁻¹. ¹H-NMR (DMSO-d₆) δ: 11.47 (1H, br s), 7.76–7.73 (2H, m), 7.65–7.61 (2H, m), 7.57 (1H, d, J=8.4 Hz), 7.23 (1H, s), 6.96–6.93 (1H, m), 3.79 (2H, s), 2.42 (3H, s).

Example 159

[2-(4-Chlorobenzoyl)-5-methyl-1H-indol-3-yl]acetic Acid
Step 1. 2-(4-Chlorobenzoyl)-5-methyl-1-(phenylsulfonyl)indole The title compound was prepared according to the procedure described in step 2 of Example 2 (Method B) from 5-methyl-1-(phenylsulfonyl)indole (E. Wenkert, P. Moeller, and S. Piettre, *J. Am. Chem. Soc.*, 1988, 110, 7188–7194) and 4-chlorobenzoyl chloride.

¹H-NMR (CDCl₃) δ: 8.02–7.96 (3H, m), 7.96–7.88 (2H, m), 7.57–7.43 (5H, m), 7.33–7.25 (2H, m), 6.88 (1H, s), 2.41 (3H, s).

Step 2. 2-(4-Chlorobenzoyl)-5-methylindole

The title compound was prepared according to the procedure described in step 3 of Example 2 (Method B) from 2-(4-chlorobenzoyl)-5-methyl-1-(phenylsulfonyl)indole (step 1).

¹H-NMR (CDCl₃) δ: 9.43 (1H, br s), 7.94–7.91 (2H, m), 7.51–7.47 (3H, m), 7.37 (1H, d, J=8.4 Hz), 7.21 (1H, dd, J=8.4, 1.5 Hz), 7.04–7.03 (1H, m), 2.44 (3H, s).

Step 3. Diethyl α-Acetoxy-[2-(4-chlorobenzoyl)-5-methyl-1H-indol-3-yl]malonate

The title compound was prepared according to the procedure described in step 4 of Example 2 (Method B) from 2-(4-chlorobenzoyl)-5-methylindole (step 3).

$^1$H-NMR (CDCl$_3$) δ: 8.74 (11H, br s), 7.79 (2H, d, J=8.4 Hz), 7.67 (l1H, s), 7.42 (2H, d, J=8.4 Hz), 7.27–7.24 (1H, m), 7.14–7.11 (1H, m), 4.244.16 (4H, m), 2,45 (3H, s), 1.28–1.18 (6H, m).

Step 4. Diethyl[2-(4-chlorobenzoyl)-5-methyl-1H-indol-3-yl]malonate

The title compound was prepared according to the procedure described in step 5 of Example 2 (Method B) from diethyl α-acetoxy-[2-(4-chlorobenzoyl)-5-methyl-1H-indol-3-yl]malonate (step 3).

$^1$H-NMR (CDCl$_3$) δ: 8.80 (1H, br s), 7.73 (2H, d, J=8.4 Hz), 7.54 (1H, s), 7.47 (2H, d, J=8.4 Hz), 7.21–7.18 (1H, m), 7.13–7.10 (1H, m), 4.25–4.13 (4H, m), 2.42 (3H, s), 1.28–1.21 (6H, m).

Step 5. [2-(4-Chlorobenzoyl)-5-methyl-1H-indol-3-yl]acetic Acid

The title compound was prepared according to the procedure described in step 6 of Example 2 (Method B) from diethyl[2-(4-chlorobenzoyl)-5-methyl-1H-indol-3-yl]malonate (step 4).

m.p.: 194–197° C. IR (KBr) ν: 3308, 1695, 1609, 1529, 1402, 1263, 1223, 1088, 1015 cm$^{-1}$. $^1$H-NMR (DMSO-d$_6$) δ: 12.18 (1H, br s), 11.49 (1H, s), 7.77–7.73 (2H, m), 7.66–7.62 (2H, m), 7.45 (1H, s), 7.35 (1H, d, J=8.6 Hz), 7.15 (1H, dd, J=8.6, 1.5 Hz), 3.81 (2H, s), 2.39 (3H, s).

Example 160

Methyl[6-methoxy-2-(4-chlorobenzoyl)-1H-indol-3-yl]acetate

The title compound was prepared according to the procedure described in Example 57 from methyl trans-4-methoxy-3-p-toluenesulfonylamino)cinnamate (step 3 of Example 131) and 4-chlorophenacyl bromide.

$^1$H-NMR (CDCl$_3$) δ: 8.89 (1H, br s), 7.74–7.43 (5H, m), 6.86–6.77 (m, 2H), 3.85 (3H, s), 3.79 (3H, s), 3.65 (3H, s).

Example 161

[6-Methoxy-2-(4-chlorobenzoyl)-1H-indol-3-yl]acetic Acid

The title compound was prepared according to the procedure described in Example 9 (Method B) from methyl[6-methoxy-2-(4-chlorobenzoyl)-1H-indol-3-yl]acetate (Example 160).

m.p.: 193° C. IR (KBr) ν: 3308, 1701, 1628, 1603, 1526, 1427, 1335, 1271, 1205, 1148, 1092, 1032, 999 cm$^{-1}$. $^1$H-NMR (DMSO-d$_6$) δ: 11.43 (1H, br s), 7.75–7.56 (5H, m), 6.87 (1H, d, 2.13 Hz), 7.76 (1H, dd, 8.88 Hz, 2.13 Hz), 3.80 (3H, s), 3.79 (2H, s).

Example 162

[2-(4-Chlorobenzoyl)-6-trifluoromethyl-1H-indol-3-yl]acetic Acid

Step 1. 1-Phenylsulfonyl-6-(trifluoromethyl)indole

To a stirred mixture of 6-(trifluoromethyl)indole (500 mg, 2.70 mmol), 50% aqueous sodium hydroxide (5 ml), water (7 ml), and tetrabutylammonium bromide (87 mg, 0.27 mmol) was added a solution of phenylsulfonyl chloride (379 μl, 2.97 mmol) in toluene (5 ml) at room temperature. After stirring for 1 h, the organic layer was separated. The aqueous layer was extracted with ethyl acetate (50 ml). The combined organic layers were washed with saturated sodium bicarbonate (30 ml), water (30 ml), brine (30 ml), dried (MgSO$_4$), and concentrated to give 835 mg (95%) of the title compound.

$^1$H-NMR (CDCl$_3$) δ: 8.29 (1H, s), 7.91–7.88 (2H, m), 7.71 (1H, d, J=3.6 Hz), 7.64–7.54 (2H, m), 7.49–7.44 (3H, m), 6.72 (1H, d, J=3.6 Hz).

Step 2. 2-(4-Chlorobenzoyl)-1-phenylsulfonyl-6-(trifluoromethy)indole

The title compound was prepared according to the procedure described in step 2 of Example 2 (Method B) from 1-phenylsulfonyl-6-(trifluoromethyl)indole (step 1).

$^1$H-NMR (CDCl$_3$) δ: 8.42 (1H, s), 8.05–8.01 (2H, m), 7.92–7.89 (2H, m), 7.71–7.47 (7H, m), 6.95 (1H, s).

Step 3. 2-(4-Chlorobenzoyl)-6-(trifluoromethyl)indole

The title compound was prepared according to the procedure described in step 3 of Example 2 (Method B) from 2-(4-chlorobenzoyl)-1-phenylsulfonyl-6-(trifluoromethyl)indole (step 2).

$^1$H-NMR (CDCl$_3$) δ: 9.53 (1H, br s), 7.99–7.95 (2H, m), 7.85–7.79 (2H, m), 7.56–7.53 (2H, m), 7.42–7.39 (1H, m), 7.19–7.18 (1H, m).

Step 4. Diethyl α-Acetoxy-[2-(4-chlorobenzoyl)-6-(trifluoromethyl)-1H-indol-3-yl]malonate The title compound was prepared according to the procedure described in step 4 of Example 2 (Method B) from 2-(4-chlorobenzoyl)-6-(trifluoromethyl)indole (step 3).

$^1$H-NMR (CDCl$_3$) δ: 9.27 (1H, br s), 8.00 (1H, d, J=8.7 Hz), 7.78 (2H, d, J=8.6 Hz), 7.68 (1H, s), 7.45–7.39 (3H, m), 4.24–4.12 (4H, m), 1.74 (3H, s), 1.21–1.14 (6H, m).

Step 5. Diethyl[2-(4-chlorobenzoyl)-6-(trifluoromethyl)-1H-indol-3-yl]malonate

The title compound was prepared according to the procedure described in step 5 of Example 2 (Method B) from diethyl α-acetoxy-[2-(4-chlorobenzoyl)-6-trifluoromethyl)-1H-indol-3-yl]malonate (step 4).

$^1$H-NMR (CDCl$_3$) δ: 9.37 (1H, br s), 7.83 (1H, d, J=8.6 Hz), 7.77–7.73 (2H, m), 7.51–7.48 (3H, m), 7.33–7.30 (1H, m), 5.27 (1H, s), 4.25–4.06 (4H, m), 1.31–1.15 (6H, m).

Step 6. [2-(4-Chlorobenzoyl)-5-methyl-1H-indol-3-yl]acetic Acid

The title compound was prepared according to the procedure described in step 6 of Example 2 (Method B) from diethyl[2-(4-chlorobenzoyl)-6-(trifluoromethyl)-1H-indol-3-yl]malonate (step 5).

m.p.: 155–160° C. IR (KBr) ν: 3379, 1705, 1611, 1589, 1516, 1337, 1229, 1119, 1092, 1055 cm$^{-1}$. $^1$H-NMR (DMSO-d$_6$) δ: 12.09 (1H, br s), 7.96–7.93 (1H, m), 7,82–7.78 (3H, m), 7.68–7.64 (2H, m), 7.41–7.37 (1H, m), 3.86 (2H, s).

Example 163

Methyl[2-(4-chlorobenzoyl)-5-ethyl-1H-indol-3-yl]acetate

The title compound was prepared according to the procedure described in Example 57 from methyl trans-5-ethyl-2-(phenylsulfonylamino)cinnamate (Example 133, step 2).

$^1$H-NMR (CDCl$_3$) δ: 8.86 (1H, br s), 7.74–7.71 (2H, m), 7.48–7.41 (3H, m), 7.32–7.21 (2H, m), 3.85 (2H, s), 3.66 (3H, s), 2.75 (2H, q, J=7.6 Hz), 1.28 (3H, t, J=7.6 Hz)

Example 164

[2-4-Chlorobenzoyl)-5-ethyl-1H-indol-3-yl]acetic Acid

The title compound was prepared according to the procedure described in Example 58 from methyl[2-(4-chlorobenzoyl)-5-ethyl-1H-indol-3-yl]acetate (Example 163).

m.p.: 165–168° C. IR (KBr): 3321, 1693, 1605, 1531, 1221, 1088, 1011 cm$^{-1}$. $^1$H-NMR (DMSO-d$_6$) δ: 11.49 (1H, br s), 7.76–7.72 (2H, m), 7.65–7.61 (2H, m), 7.46 (1H, m), 7.36 (1H, d, J=8.6 Hz), 7.18 (1H, dd, J=8.6, 1.5 Hz), 3.81 (2H, s), 2.67 (2H, q, J=7.6 Hz), 1.21 (3H, t, J=7.6 Hz).

Example 165

Methyl[2-(4-chlorobenzoyl)-5-methoxy-1H-indol-3-yl]acetate

The title compound was prepared according to the procedure described in Example 57 from methyl trans-5-methoxy-2-(phenylsulfonylamino)cinnamate (Example 129, step 3).

$^1$H-NMR (CDCl$_3$) δ: 8.81 (1H, br s), 7.75–7.72 (2H, m), 7.49–7.46 (2H, m), 7.29 (1H, d, J=8.9 Hz), 7.04 (1H, dd, J=8.9, 2.5 Hz), 6.98 (1H, d, J=2.5 Hz), 3.86 (3H, s), 3.85 (2H, s), 3.67 (3H, s).

Example 166

[2-(4-Chlorobenzoyl)-5-methoxy-1H-indol-3-yl]acetic Acid

The title compound was prepared according to the procedure described in Example 58 from methyl[2-(4-chlorobenzoyl)-5-methoxy-1H-indol-3-yl]acetate (Example 165).

m.p.: 200–204° C. IR (KBr) ν: 3325, 1724, 1607, 1526, 1429, 1356, 1265, 1229, 1092, 1011 cm$^{-1}$. $^1$H-NMR (DMSO-d$_6$) δ: 11.46 (1H, br s), 7.74 (2H, d, J=8.6 Hz), 7.63 (2H, d, J=8.6 Hz), 7.35 (1H, d, J=8.9 Hz), 7.13 (1H, d, J=2.5 Hz), 6.96 (1H, dd, J=8.9, 2.5 Hz), 3.83 (2H, s), 3.77 (3H, s).

Example 167

Methyl[2-(4-chlorobenzoyl)-5-isopropyl-1H-indol-3-yl]acetate

The title compound was prepared according to the procedure described in Example 57 from methyl trans-5-isopropyl-2-(phenylsulfonylamino)cinnamate (Example 139, step 2).

$^1$H-NMR (CDCl$_3$) δ: 8.87 (1H, br s), 7.74–7.70 (2H, m), 7.49–7.44 (3H, m), 7.33–7.25 (2H, m), 3.85 (2H, s), 3.66 (3H, s), 3.07–2.96 (1H, m), 1.32–1.29 (6H, m).

Example 168

[2-(4-Chlorobenzoyl)-5-isopropyl-1H-indol-3-yl]acetic Acid

The title compound was prepared according to the procedure described in Example 58 from methyl[2-(4-chlorobenzoyl)-5-isopropyl-1H-indol-3-yl]acetate (Example 169).

m.p.: 197–200° C. IR (KBr) ν: 1697, 1609, 1533, 1429, 1348, 1265, 1090, 1011 cm$^{-1}$. $^1$H-NMR (DMSO-d$_6$) δ: 12.18 (1H, br s), 11.50 (1H, br s), 7.77–7.74 (2H, m), 7.65–7.62 (2H, m), 7.50 (1H, m), 7.40–7.37 (1H, m), 7.26–7.23 (1H, m), 3.83 (2H, s), 3.03–2.92 (1H, m), 1.26–1.24 (6H, m).

Example 169

Methyl[2-(4-chlorobenzoyl)-5-trifluoromethyl-1H-indol-3-yl]acetate

The title compound was prepared according to the procedure described in Example 57 from methyl trans-2-phenylsulfonylamino-5-(trifluoromethyl)cinnamate (Example 151, step 2).

$^1$H-NMR (CDCl$_3$) δ: 9.34 (1H, br s), 7.90 (1H, s), 7.77–7.70 (2H, m), 7.51–7.43 (3H, m), 7.33 (1H, d, J=8.7 Hz), 3.85 (2H, s), 3.66 (3H, s).

Example 170

[2-(4-Chlorobenzoyl)-5-trifluoromethyl-1-indol-3-yl]acetic Acid

The title compound was prepared according to the procedure described in Example 58 from methyl[2-(4-chlorobenzoyl)-5-trifluoromethyl-1H-indol-3-yl]acetate (Example 169).

m.p.: 198–200° C. IR (KBr) ν: 3317, 1697,1611, 1333, 1271, 1113, 1051, 1007 cm$^{-1}$. $^1$H-NMR (DMSO-d$_6$) δ: 12.08 (1H, br s), 8.18 (1H, s), 7.80–7.77 (2H, m), 7.68–7.57 (4H, m), 3.92 (2H, s).

Example 171

Methyl[2-(4-chlorobenzoyl)-5-trifluoromethoxy-1H-indol-3-yl]acetate

The title compound was prepared according to the procedure described in Example 57 from methyl trans-3-p-toluenesulfonylamino-5-(trifluoromethoxy)cinnamate (Example 145, step 2) and 4-chlorophenacyl bromide.

$^1$H-NMR (CDCl$_3$) δ: 8.93 (1H, br s), 7.76 (2H, d, 8.75 Hz), 7.52–7.40 (5H, m), 3.82 (2H, s), 3.68 (3H, s).

Example 172

[2-(4-Chlorobenzoyl)-5-trifluoromethoxy-1H-indol-3-yl]acetic Acid

The title compound was prepared according to the procedure described in Example 9 (Method B) from methyl[2-(4-chlorobenzoyl)-5-trifluoromethoxy-1H-indol-3-yl]acetate (Example 171).

m.p.: 195° C. IR (KBr) ν: 3339, 1705, 1622, 1589, 1533, 1435, 1342, 1256, 1225, 1177, 1092, 1013 cm$^{-1}$. $^1$H-NMR (DMSO-d$_6$) δ: 11.91 (1H, br s), 7.80–7.64 (5H, m), 7.55 (1H, d, 8.91 Hz), 7.32–7.24 (m, 1H), 3.87 (2H, s).

Example 173

Methyl[6-chloro-2-(2-methoxybenzoyl)-1H-indol-3-yl]acetate

Step 1. Methyl 2-[6-Chloro-2-(2-methoxybenzoyl)-1H-indol-3-yl]acetate

The title compound was prepared according to the procedure described in Example 57 from methyl trans 4-chloro-2-(phenylsulfonylamino)cinnamate (step 1 of Example 8, Method A) and 2-methoxyphenacyl bromide.

$^1$H-NMR (CDCl$_3$) δ: 9.02 (1H, br s), 7.60–7.46 (2H, m), 7.42–7.34 (2H, m), 7.15–6.99 (3H, m), 3.78 (3H, s), 3.66 (2H, s), 3.60 (3H, m).

Example 174

[6-Chloro-2-(2-methoxybenzoyl)-1H-indol-3-yl]acetic Acid

The title compound was prepared according to the procedure described in Example 9 (Method B) from methyl[6-chloro-2-(2-methoxybenzoyl)-1H-indol-3-yl]acetate (Example 172).

m.p.: 214–217° C. IR (KBr) ν: 3398, 2939, 2642, 1711, 1680, 1624, 1537, 1461, 1315, 1230, 937 cm$^{-1}$. $^1$H-NMR (DMSO-d$_6$) δ: 11.61 (1H, s), 7.67 (1H, d, J=8.7 Hz), 7.60–7.51 (1H, m), 7.45 (1H, d, J=2.0 Hz), 7.28 (1H, dd, J=7.4, 1.6 Hz), 7.18 (1H, d, J=8.2 Hz), 7.12–7.04 (2H, m), 3.70 (3H, s), 3.60 (2H, s).

Example 175

Methyl[6-chloro-2-(3-methoxybenzoyl)-1H-indol-3-yl]acetate

The title compound was prepared according to the procedure described in Example 57 from methyl trans 4-chloro-2-(phenylsulfonylamino)cinnamate (step 1 of Example 8, Method A) and 3-methoxyphenacyl bromide.

$^1$H-NMR (CDCl$_3$) δ: 8.86 (1H, s), 7.57 (1H, d, J=8.7 Hz), 7.46–7.26 (4H, m), 7.19–7.12 (2H, m), 3.86 (3H, s), 3.83 (2H, s), 3.67 (3H, s).

Example 176

[6-Chloro-2-(3-methoxybenzoyl)-1H-indol-3-yl] acetic Acid

The title compound was prepared according to the procedure described in Example 9 (Method B) from methyl[6-chloro-2-(3-methoxybenzoyl)-1H-indol-3-yl]acetate (Example 175).

m.p.: 227–231° C. IR (KBr) ν: 3354, 2933, 2636, 1709, 1607, 1569, 1427, 1321, 1269, 1218, 1049 cm$^{-1}$. $^1$H-NMR (DMSO-d$_6$) δ: 11.76 (1H, s), 7.72 (1H, d, J=8.6 Hz), 7.54–7.45 (2H, m), 7.35–7.22 (3H, m), 7.16–7.10 (1H, m), 3.83 (3H, s), 3.79 (2H, s).

Example 177

Methyl[6-chloro-2-(3-benzyloxybenzoyl)-1H-indol-3-yl]acetate

The title compound was prepared according to the procedure described in Example 57 from methyl trans 4-chloro-2-(phenylsulfonylamino)cinnamate (step 1 of Example 8, Method A) and 3-benzyloxyphenacyl bromide (A. Hernandez et al., J. Org. Chem., 1994, 59, 1058).

$^1$H-NMR (CDCl$_3$) δ: 8.79 (1H, s), 7.56 (1H, d, J=8.6 Hz), 7.46–7.33 (9H, m), 7.26–7.19 (1H, m), 7.16 (1H, dd, J=8.6, 1.8 Hz), 5.12 (2H, s), 3.82 (2H, s), 3.64 (3H, s).

Example 178

[6-Chloro-2-(3-benzyloxybenzoyl)-1H-indol-3-yl] acetic Acid

The title compound was prepared according to the procedure described in Example 9 (Method B) from methyl 2-[6-chloro-2-(3-benzyloxybenzoyl)-1H-indol-3-yl]acetate (Example 177).

m.p.: 174–177° C. IR (KBr) ν: 3308, 3028, 2897, 1697, 1612, 1566, 1444, 1328, 1269, 1223, 732 cm$^{-1}$. $^1$H-NMR (DMSO-d$_6$) δ: 11.76 (1H, s), 7.71 (1H, d, J=8.6 Hz), 7.54–7.30 (10H, m), 7.13 (1H, dd, J=8.6, 1.6 Hz), 5.18 (2H, s), 3.78 (2H, s).

Example 179

Methyl[6-chloro-2-(3-hydroxybenzoyl)-1H-indol-3-yl]acetate

A mixture of methyl[6-chloro-2-(3-benzyloxybenzoyl)-1H-indol-3-yl]acetate (Example 177, 0.37 g, 0.85 mmol) and 10% palladium-charcoal (80 mg) in ethyl acetate-methanol (5:1, 30 ml) was stirred under hydrogen atmosphere for 2.5 h. The mixture was filtered thorough a pad of Celite and the filtrate was concentrated. The solids were washed with dichloromethane (10 ml) to afford 70mg (24%) of the title compound as white solids.

$^1$H-NMR (CDCl$_3$) δ: 10.36 (1H, br s), 9.06 (1H, s), 7.55 (1H, d, J=8.7 Hz), 7.50–7.46 (1H, m), 7.36–7.22 (3H, m), 7.15–7.05 (2H, m), 3.89 (2H, s), 3.65 (3H, s).

Example 180

[6-Chloro-2-(3-hydroxybenzoyl)-1H-indol-3-yl] acetic Acid

The title compound was prepared according to the procedure described in Example 9 (Method B) from methyl[6-chloro-2-(3-hydroxybenzoyl)-1H-indol-3-yl]acetate (Example 179).

m.p.: 213–215° C. IR (KBr) ν: 3311, 3069, 1715, 1624, 1583, 1529, 1448, 1325, 1278, 1220, 761 cm$^{-1}$. $^1$H-NMR (DMSO-d$_6$) δ: 11.71 (1H, s), 9.86 (1H, br s), 7.71 (1H, d, J=8.6 Hz), 7.47 (1H, d, J=1.5 Hz), 7.41–7.32 (1H, m), 7.20–7.02 (4H, m), 3.82 (2H, s).

Example 181

Methyl[6-chloro-2-(4-benzyloxybenzoyl-1H-indol-3-yl]acetate

The title compound was prepared according to the procedure described in Example 57 from methyl trans 4-chloro-2-(phenylsulfonylamino)cinnamate (step 1 of Example 8, Method A) and 4-benzyloxyphenacyl bromide (A. Brossi et al., J. Heterocycl. Chem., 1965, 2, 310).

$^1$H-NMR (CDCl$_3$) δ: 8.87 (1H, br s), 7.81 (2H, d, J=8.6 Hz), 7.55 (1H, d, J=8.7 Hz), 7.48–7.32 (6H, m), 7.14 (1H, dd, J=8.7, 1.8 Hz), 7.06 (2H, d, J=8.6 Hz), 5.16 (2H, s), 3.86 (2H, s), 3.65 (3H, s).

Example 182

[6-Chloro-2-(4-benzyloxybenzoyl)-1H-indol-3-yl] acetic Acid

The title compound was prepared according to the procedure described in Example 9 (Method B) from methyl 2-[6-chloro-2-(4-benzyloxybenzoyl)-1H-indol-3-yl]acetate (Example 181).

m.p.: 220–222° C. IR (KBr) ν: 3331, 3013, 2914, 1717, 1699, 1599, 1564, 1508, 1253, 1167, 941 cm$^{-1}$. $^1$H-NMR (DMSO-d$_6$) δ: 11.72 (1H, s), 7.76 (2H, d, J=8.9 Hz), 7.69 (1H, d, J=8.4 Hz), 7.52–7.32 (6H, m), 7.17 (2H, d, J=8.9 Hz), 7.11 (1H, dd, J=8.4, 2.2 Hz), 5.23 (2H, s), 3.81 (2H, s).

Example 183

Methyl[6-chloro-2-(4-hydroxybenzoyl)-1H-indol-3-yl]acetate

The title compound was prepared according to the procedure described in Example 179 from methyl[6-chloro-2-(4-benzyloxybenzoyl)-1H-indol-3-yl]acetate (Example 181).

$^1$H-NMR (acetone-d$_6$) δ: 10.82 (1H, br s), 9.21 (1H, br s), 7.75 (2H, d, J=8.7 Hz), 7.71 (1H, d, J=8.7 Hz), 7.56 (1H, d, J=2.0 Hz), 7.13 (1H, dd, J=8.7, 2.0 Hz), 6.97 (2H, d, J=8.7 Hz), 3.95 (2H, s), 3.59 (3H, s).

Example 184

[6-Chloro-2-(4-hydroxybenzoyl)-1H-indol-3-yl] acetic Acid

The title compound was prepared according to the procedure described in Example 9 (Method B) from methyl[6- chloro-2-(4-hydroxybenzoyl)-1H-indol-3-yl]acetate (Example 183).

m.p.: 231–234° C. IR (KBr) ν: 3250 3120, 2822, 1734, 1618, 1539, 1456, 1321, 1236, 1120, 1060cm$^{-1}$. $^1$H-NMR (DMSO-d$_6$) δ: 11.58 (1H, br s), 7.63–7.53 (3H, m), 7.35 (1H, d, J=1.9 Hz), 7.00 (1H, dd, J=8.6, 1.9 Hz), 6.80 (2H, d, J=8.9 Hz), 3.69 (2H, s).

Example 185

Methyl[6-chloro-2-(4-isopropoxybenzoyl)-1H-indol-3-yl]acetate

To a stirred solution of methyl[6-chloro-2-(4-hydroxybenzoyl)-1H-indol-3-yl]acetate (Example 183, 0.15 g, 0.44 mmol) in DMF (5 ml) was added sodium hydride (15 mg, 0.46 mmol) at room temperature under nitrogen atmosphere. After 5min., 2-iodopropane (78 mg) was added and the mixture was stirred for 7 h. The mixture was quenched with 2N aqueous HCl (20 ml), and extracted with ethyl acetate (50 ml). The extract was washed with water (30 ml) and brine (30 ml), dried (MgSO$_4$), and concentrated. The residue was purified by flash column chromatography eluting with ethyl acetate-hexane (1:2) to afford 72 mg (43%) of the title compound as white solids.

$^1$H-NMR (CDCl$_3$) δ: 8.81 (1H, br s), 7.80 (2H, d, J=8.9 Hz), 7.56 (1H, d, J=8.7 Hz), 7.41 (1H, d, J=1.8 Hz), 7.15 (1H, dd, J=8.7, 1.8 Hz), 6.95 (2H, d, J=8.9 Hz), 4.67 (1H, heptet, J=6.1 Hz), 3.87 (2H, s), 3.67 (3H, s) 1.39 (6H, d, J=6.1 Hz).

Example 186

[6-Chloro-2-(4-isopropoxybenzoyl)-1H-indol-3-yl]acetic Acid

The title compound was prepared according to the procedure described in Example 9 (Method B) from methyl[6-chloro-2-(4-isopropoxybenzoyl)-1H-indol-3-yl]acetate (Example 185).

m.p.: 216–218° C. IR (KBr) ν: 3304, 2972, 2881, 1707, 1614, 1596, 1560, 1508, 1311, 1261, 1163cm$^{-1}$. $^1$H-NMR (DMSO-d$_6$) δ: 11.71 (1H, br s), 7.75 (2H, d, J=8.9 Hz), 7.69 (1H, d, J=8.6 Hz), 7.46 (1H, d, J=2.0 Hz), 7.12 (1H, dd, J=8.6, 2.0 Hz), 7.07 (2H, d, J=8.9 Hz), 4.78 (1H, heptet, J=5.9 Hz), 3.82 (2H, s) 1.32 (6H, d, J=5.9 Hz).

Example 187

Methyl[6-chloro-2-(4-phenylbenzoyl)-1H-indol-3-yl]acetate

The title compound was prepared according to the procedure described in Example 57 from methyl trans 4-chloro-2-(phenylsulfonylamino)cinnamate (step 1 of Example 8, Method A) and 4-phenylphenacyl bromide.

$^1$H-NMR (CDCl$_3$) δ: 8.91 (1H, br s), 7.88 (2H, d, J=8.1 Hz), 7.73 (2H, d, J=8.1Hz), 7.68–7.38 (7H, m), 7.16 (1H, dd, J=8.1, 1.8 Hz), 3.89 (2H, s), 3.66 (3H, s).

Example 188

[6-Chloro-2-(4-phenylbenzoyl)-1H-indol-3-yl]acetic Acid

The title compound was prepared according to the procedure described in Example 9 (Method B) from methyl[6-chloro-2-(4-phenylbenzoyl)-1H-indol-3-yl]acetate (Example 187).

m.p.: 228–231° C. IR (KBr ) ν: 3317, 3030, 2868, 1707, 1620, 1600, 1527, 1431, 1323, 1256, 1194 cm$^{-1}$. $^1$H-NMR (DMSO-d$_6$) δ: 11.81 (1H, s), 7.89 (2H, d, J=8.6 Hz), 7.87 (2H, d, J=8.6 Hz), 7.82–7.72 (3H, m), 7.58–7.40 (4H, m), 7.14 (1H, dd, J=8.6, 1.8 Hz), 3.87 (2H, s).

Example 189

Methyl[6-chloro-2-(4-trifluoromethoxybenzoyl)-1H-indol-3-yl]acetate

The title compound was prepared according to the procedure described in Example 57 from methyl trans 4-chloro-2-(phenylsulfonylamino)cinnamate (step 1 of Example 8, Method A) and 4-(trifluoromethoxy)phenacyl bromide*.

* 4-(Trifluoromethoxy)phenacyl bromide was prepared as follows;

$^1$H-NMR (CDCl$_3$) δ: 8.85 (1H, br s), 7.85 (2H, d, J=8.9 Hz), 7.57 (1H, d, J=8.6 Hz), 7.40 (1H, d, J=1.8 Hz), 7.35 (2H, d, J=8.9 Hz), 7.16 (1H, dd, J=8.6, 1.8 Hz), 3.80 (2H, s), 3.65 (3H, s).

A mixture of 4-(trifluoromethoxy)acetophenone (0.52 g, 2.55 mmol) and tetrabutylammonium tribromide (1.35 , 2.80 mmol) in dichloromethane-methanol (1:1, 8 ml) was stirred for 18 h and then concentrated. The residue was diluted with ethyl acetate (50 ml), washed with water (50 ml), brine (50 ml), and dried (MgSO$_4$). Removal of solvent gave 0.36 g (50%) of the title compound as a yellow oil.

tlc: Rf=0.47 (hexane-ethyl acetate=10:1).

Example 190

[6-Chloro-2-(4-trifluoromethoxybenzoyl)-1H-indol-3-yl]acetic Acid

The title compound was prepared according to the procedure described in Example 9 (Method B) from methyl[6-chloro-2-(4-trifluoromethoxybenzoyl)1H-indol-3-yl]acetate (Example 189).

m.p.: 166–168° C. IR (KBr) ν: 3315, 3219, 1719, 1699, 1616, 1527, 1508, 1254, 1221, 1167, 943 cm$^{-1}$. $^1$H-NMR (DMSO-d$_6$) δ: 11.79 (1H, s), 7.88 (2H, d, J=8.6 Hz), 7.75 (1H, d, J=8.9 Hz), 7.56 (2H, d, J=8.6 Hz), 7.47 (1H, d, J=1.8 Hz), 7.14 (1H, dd, J=8.9, 1.8 Hz), 3.85 (2H, s).

Example 191

Methyl[5-chloro-2-(4-trifluoromethoxybenzoyl)-1H-indol-3-yl]acetate

The title compound was prepared according to the procedure described in Example 8 (Method B) from methyl trans 5-chloro-2-(phenylsulfonylamino)cinnamate (Example 36, step 3) and 4-(trifluoromethoxy)phenacyl bromide (Preparation is described in Example 189).

$^1$H-NMR (CDCl$_3$) δ: 8.92 (1H, br s), 7.85 (2H, d, J=8.7 Hz), 7.61 (1H, br s), 7.38–7.28 (4H, m), 3.79 (2H, s), 3.67 (3H, s).

Example 192

[5-Chloro-2-(4-trifluoromethoxybenzoyl)-1H-indol-3-yl]acetic Acid

The title compound was prepared according to the procedure described in Example 9 (Method B) from methyl[5-chloro-2-(4-trifluoromethoxybenzoyl)-1H-indol-3-yl]acetate (Example 191).

m.p.: 186.7° C. IR (KBr) ν: 3332, 3086, 2925, 1697, 1610, 1408, 1259, 1217, 1161, 1007, 941 cm$^{-1}$. $^1$H-NMR (DMSO-d$_6$) δ: 11.85 (1H, br s), 7.89 (2H, d, J=8.7 Hz), 7.81 (1H, d, J=2.1 Hz), 7.60–7.53 (2H, m), 7.48 (1H, d, J=8.7Hz), 7.32 (1H, dd, J=8.7, 2.1 Hz), 3.86 (2H, s).

Example 193

Methyl[6-chloro-2-(4-methoxybenzoylpnenol-3-yl] acetate

The title compound was prepared according to the procedure described in Example 57 from methyl trans 5-chloro-2-(phenylsulfonylamino)cinnamate (Example 36, step 3) and 4-methoxyphenacyl bromide.

$^1$H-NMR (CDCl$_3$) δ: 8.86 (1H, s), 7.82 (2H, d, J=8.9 Hz), 7.63–7.60 (1H, m), 7.37–7.26 (2H, m), 6.99 (2H, d, J=8.9 Hz), 3.90 (3H, s), 3.84 (2H, s), 3.69(3H, s).

Example 194

[5-Chloro-2-(4-methoxybenzoyl)-1H-indol-3-yl] acetic Acid

The title compound was prepared according to the procedure described in Example 9 (Method B) from methyl[5-chloro-2-(4-methoxybenzoyl)-1H-indol-3-yl]acetate (Example 193).

m.p.: 232–235° C. IR (KBr) ν: 3312, 2833, 2621, 1701, 1599, 1510, 1454, 1263, 1167, 1001, 777 cm$^{-1}$. $^1$H-NMR (DMSO-d$_6$) δ: 11.78 (1H, s), 7.78 (2H, d, J=8.9 Hz), 7.75 (1H, d, J=2.0 Hz), 7.47 (1H, d, J=8.7 Hz), 7.29 (1H, dd, J=8.7, 2.0 Hz), 7.11 (2H, d, J=8.9 Hz), 3.88 (3H, s), 3.82 (2H, s).

Example 195

Methyl[6-chloro-2-(4-nitrobenzoyl)-1H-indol-3-yl] acetate

The title compound was prepared according to the procedure described in Example 57 from methyl trans 4-chloro-2-(phenylsulfonylamino)cinnamate (step 1 of Example 8, Method A) and 4-nitrophenacyl bromide.

$^1$H-NMR (CDCl$_3$) δ: 8.92 (1H, br s), 8.37 (2H, d, J=8.9 Hz), 7.93 (2H, d, J=8.9 Hz), 7.57 (1H, d, J=8.7 Hz), 7.40 (1H, d, J=1.8 Hz), 7.18 (1H, dd, J=8.7, 1.8 Hz), 3.73 (2H, s), 3.65 (3H, s).

Example 196

[6-Chloro-2-(4-nitrobenzoyl)-1H-indol-3-yl]acetic Acid

The title compound was prepared according to the procedure described in Example 9 (Method B) from methyl[6-chloro-2-(4-nitrobenzoyl)-1H-indol-3-yl]acetate (Example 195).

m.p.: 218.9° C. (decomposed). IR (KBr) ν: 3365, 3101, 2846, 1718, 1699, 1647, 1537, 1348, 1255, 1227, 852 m$^{-1}$. $^1$H-NMR (DMSO-d$_6$) δ: 11.84 (1H, s), 8.38 (2H, d, J=8.9 Hz), 7.97 (2H, d, J=8.9 Hz), 7.78 (1H, d, J=8.6 Hz), 7.48 (1H, d, J=2.0 Hz), 7.15 (1H, dd, J=8.6, 2.0 Hz), 3.83 (2H, s).

Example 197

Methyl[6-chloro-2-[(4-methylsulfonyl)benzoyl]-1H-indol-3-yl]acetate

The title compound was prepared according to the procedure described in Example 57 from 4-(methylsulfonyl) phenacyl bromide.

$^1$H-NMR (CDCl$_3$) δ: 9.10 (1H, br s), 8.08 (2H, d, J=8.6 Hz), 7.93 (2H, d, J=8.3 Hz), 7.57 (1H, d, J=8.7 Hz), 7.37 (1H, br), 7.20–7.10 m(1H, m), 3.78 (2H, s), 3.64 (3H, s), 3.12 (3H, s).

Example 198

[6-Chloro-2-[(4-methylsulfonyl)benzoyl-1H-indol-3-yl]acetic Acid

The title compound was prepared according to the procedure described in Example 9 (method B) from methyl[6-chloro-2-(4-methylsulfonyl)benzoyl-1H-indol-3-yl]acetate (Example 197).

m.p.: 241° C. (decomposed). IR (KBr) ν: 3330, 1713, 1614, 1524, 1230, 1150, 941, 781 cm$^1$. $^1$H-NMR (DMSO-d$_6$) δ: 11.83 (1H, s), 8.12 (2H, d, J=8.3 Hz), 7.96 (2H, d, J=8.3 Hz), 7.78 (1H, d, J=8.7 Hz), 7.48 (1H, d, J=1.8 Hz), 7.15 (1H, dd, J=1.8, 8.7 Hz), 3.85 (2H, s), 3.33 (3H, s).

Example 199

Methyl[6-Chloro-2-[4-(methylsulfonylamino) benzoyl]-1H-indol-3-yl]acetate

The title compound was prepared according to the procedure described in Example 8 (Method B) from methyl trans-4-chloro-2-(phenylsulfonylamino)cinnamate (step 1 of Example 8, Method A) and 4-(methylsulfonylamino) phenacyl bromide*.

\* 4-(Methylsulfonylamino)phenacyl bromide was prepared from (4-acetylphenyl)methanesulfonamide (R. Lis, et al., *J. Org. Chem.*, 1987, 52, 4377) according to the procedure for preparing 4-(trifluoromethoxy)phenacyl bromide described in Example 189.

$^1$H-NMR (CDCl$_3$) δ: 8.86 (1H, br s), 7.82 (2H, d, J=8.72 Hz), 7.58 (1H, d, J=8.72 Hz), 7.42–7.15(4H, m), 6.80(1H, br s), 3.83 (2H, s), 3.67(3H, s), 3.13 (3H, s). $^1$H-NMR (CDCl$_3$) δ: 8.01 (2H, d, 8.72 Hz), 7.28 (2H, d, 8.72 Hz), 4.40 (2H, s), 3.13 (2H, s).

Example 200

[6-Chloro-2-[4-(methylsulfonylamino)benzoyl]-1H-indol-3-yl]acetic Acid

The title compound was prepared according to the procedure described in Example 9 (Method B) from methyl[6-chloro-2-[4-(methylsulfonylamino)benzoyl]-1H-indol-3-yl] acetate (Example 199).

m.p.: 207–210° C. IR (KBr) ν: 3333, 3248, 1715, 1603, 1570, 1529, 1508, 1394, 1323, 1259, 1231, 1159, 1061 cm$^{-1}$. $^1$H-NMR (DMSO-d$_6$) δ: 11.6 (1H, br s), 7.76 (2H, d, J=8.88 Hz), 7.71 (1H, d, J=8.56 Hz), 7.46 (1H, 1.65 Hz), 7.12 (1H, dd, J=8.56 Hz, 1.65 Hz), 3.81 (2H, s), 3.13 (3H, s).

Example 201

[6-Chloro-2-(2-chlorobenzoyl)-1H-indol-3-yl]acetic Acid

Step 1. 6-Chloro-2-(2-chlorobenzoyl)-1-(phenylsulfonyl) indole

The title compound was prepared according to the procedure described in step 2 of Example 1 (Method B) from 6-chloro-1-(phenylsulfonyl)indole (step 1 of Example 1, Method B) and 2-chlorobenzoyl chloride. The crude product was used for the next step without further purification.

tlc: Rf=0.25 (hexane-ethyl acetate=4:1).

Step 2. 6-Chloro-2-(2-chlorobenzoyl)indole

The title compound was prepared according to the procedure described in step 3 of Example 1 (Method B) from 6-chloro-2-(2-chlorobenzoyl)-1-(phenylsulfonyl)indole (step 1). The crude product was used for the next step without further purification.

tlc: Rf =0.37 (hexane-ethyl acetate=4:1)

Step 3. Diethyl α-Acetoxy-2-[6-chloro-2-(2-chlorobenzoyl)-1H-indol-3-yl]malonate The title compound was prepared according to the procedure described in step 4 of Example 1 (Method B) from 6-chloro-2-(2-chlorobenzoyl)indole (step 2).

$^1$H-NMR (CDCl$_3$) δ: 8.61 (1H, br s), 7.79(1H, d, J=8.88 Hz), 7.52–7.33 (5H, m), 7.15 (1H, dd, J=1.97 Hz, 8.88 Hz), 4.26 (4H, m), 2.02 (3H, s), 1.22 (6H, t, J=7.07 Hz).

Step 4. Diethyl[6-chloro-2-(2-chlorobenzoyl)-1H-indol-3-yl]malonate

The title compound was prepared according to the procedure described in step 5 of Example 1 (Method B) from diethyl α-acetoxy-[6-chloro-2-(2-chlorobenzoyl)-1H-indol-3-yl]malonate (step 3).

$^1$H-NMR (CDCl$_3$) δ: 8.95 (1H, br s), 7.75 (1H, d, J=8.88 Hz), 7.53–7.39 (5H, m), 4.83 (1H, s), 4.15 (4H, m), 1.20 (6H, t, J=7.26 Hz).

Step 5. 2-[6-Chloro-2-(2-chlorobenzoyl)-1H-indol-3-yl] acetic Aid

The compound was prepared according to the procedure described in step 6 of Example 1 (Method B) from diethyl [6-chloro-2-(2-chlorobenzoyl)-1H-indol-3-yl]malonate (step 4).

m.p.: 138–140_C. IR (KBr) ν: 3315, 1713, 1632, 1564, 1526, 1435, 1325, 1254, 1215, 1151, 1061 cm$^{-1}$. $^1$H-NMR (DMSO-d$_6$) δ: 11.67 (1H, s), 7.61(1H, d, J=8.72), 7.51–7.34 (5H, m), 7.50 (1H, dd, J=1.97, 8.72 Hz), 3.75 (2H, s).

Example 202

[6-Chloro-2-(2,4-dichlorobenzoyl)-1H-indol-3-yl] acetic Acid

Step 1. 6-Chloro-2-(2,4-dichlorobenzoyl)-1-(phenylsulfonyl)indole

The title compound was prepared according to the procedure described in step 2 of Example 1 (Method B) from 6-chloro-1-(phenylsulfonyl)indole (step 1 of Example 1, Method B) and 2,4-dichlorobenzoyl chloride. The crude product was used for the next step without further purification.

tlc: Rf =0.34 (hexane-ethyl acetate =4:1).

Step 2. 6-Chloro-2-(2,4-dichlorobenzoyl)indole

The title compound was prepared according to the procedure described in step 3 of Example 1 (Method B) from 6-chloro-2-(2,4-dichlorobenzoyl)-1-(phenylsulfonyl)indole (step 1). The crude product was used for the next step without further purification.

tlc: Rf=0.45 (hexane-ethyl acetate=4:1)

Step 3. Diethyl α-Acetoxy-[6-chloro-2-(2,4-dichlorobenzoyl)-1H-indol-3-yl]malonate The title compound was prepared according to the procedure described in step 4 of Example 1 (Method B) from 6-chloro-2-(2,4-dichlorobenzoyl)indole (step 2).

$^1$-NMR (CDCl$_3$) δ: 8.92 (1H, br s), 7.79–7.11(6H, m), 4.24 (4H, m), 2.02 (3H, s), 1.22 (6H, t, J=7.10 Hz).

Step 4. Diethyl[6-chloro-2-(2,4-dichlorobenzoyl)-1H-indol-3-yl]malonate

The title compound was prepared according to the procedure described in step 5 of Example 1 from diethyl α-acetoxy-[6-chloro-2-(2,4-dichlorobenzoyl)-1H-indol-3-yl]malonate (step 3).

$^1$H-NMR (CDCl$_3$) δ: 8.92 (1H, br s), 7.75 (1H, d, J=8.92 Hz), 7.55–7.36 (4H, m), 7.13 (1H, dd, 8.92 Hz, 1.81 Hz), 4.85 (1H, s), 4.17 (4H, m), 1.21 (6H, t, J=7.10 Hz).

Step 5. [6-Chloro-2-(2,4-dichlorobenzoyl)-1H-indol-3-yl] acetic Acid

The title compound was prepared according to the procedure described in step 6 of Example 1 (method B) from diethyl 2-[6-chloro-2-(2,4-dichlorobenzoyl)-1H-indol-3-yl] malonate (step 4).

m.p.: 190–192° C. IR (KBr) ν: 3304, 1709, 1630, 1589, 1526, 1427, 1321, 1231, 1150, 1061 cm$^1$. $^1$H-NMR (DMSO-d$_6$) δ: 11.66 (1H, s), 7.72 (1H, d, J=2.00 Hz), 7.64 (1H, d, 8.91 Hz), 751–7.33 (3H, m), 7.01 (1H, dd, J=2.00, 8.91 Hz), 3.61 (2H, s).

Example 203

Methyl[6-chloro-2-(4-chloro-3-fluorobenzoyl)-1H-indol-3-yl]acetate

The title compound was prepared according to the procedure described in Example 57 from methyl trans-4-chloro-2-(phenylsulfonylamino)cinnamate (step 1 of Example 8, Method A) and 4-chloro-3-fluorophenacyl bromide* .

* 4-chloro-3-fluorophenacylbromide was prepared as follows;

$^1$H-NMR (CDCl$_3$) δ: 8.87 (1H, br s), 7.65–7.36 (4H, m), 7.17 (1H, dd, J=8.72 Hz, 1.81 Hz), 3.80 (2H, s), 3.68 (3H, s).

4-Acetyl-1-chloro-2-fluorobenzene:

To a solution of 1-bromo-4-chloro-3-fluorobenzene (2.09 g, 10 mmol) in dry diethyl ether (12.0 ml) was added a solution of n-BuLi (1.55M in hexane, 6.77ml, 10.5 mmol) at −78° C. under nitrogen atmosphere. The mixture was allowed to warm to −20_C stirred for 45 min. A solution of N,N-dimethylacetamide (1.04 ml, 11.2 mmol) in diethyl ether (1.5 ml) was added and the mixture stirred for an additional 1 h. The mixture was then allowed to warm to room temperature. After stirring for 3 h, the reaction mixture was poured into saturated aqueous ammonium chloride (20 ml) and extracted with diethyl ether (30 ml×3). The combined organic layers were washed with 2N aqueous HCl (20 ml), saturated aqueous sodium bicarbonate (20 ml), brine (20 ml), and dried (MgSO$_4$). Removal of solvent gave the title compound as a yellow oil (quant.).

$^1$H-NMR (CDCl$_3$) δ: 7.75–7.09 (3H, m), 2.59 (3H, s).

4-Chloro-3-fluorophenacyl Bromide:

The title compound was prepared from 4-acetyl-1-chloro-2-fluorobenzene according to the procedure for preparing 4-(trifluoromethoxy)phenacyl bromide described in Example 189.

$^1$H-NMR (CDCl$_3$) δ: 7.79–7.71 (2H, m), 7.58–7.52 (1H, m), 4.38 (2H, s).

Example 204

[6-Chloro-2-(4-chloro-3-fluorobenzoyl)-1H-indol-3-yl]acetic Acid

The title compound was prepared according to the procedure described in Example 9 (Method B) from methyl[6-chloro-2-(4-methylsulfonylaminophenacyl)-1H-indol-3-yl] acetate (Example 203).

m.p.: 179–182° C. MS (EI) m/z: 365 (M$^+$). $^1$H-NMR (DMSO-d$_6$) δ: 11.80 (1H, br s), 7.85–7.48 (5H, m), 7.14 (1H, dd, J=8.72 Hz, 1.97 Hz), 3.84 (2H, s).

Example 205

Methyl[6-chloro-2-(4-cyanobenzoyl)-1H-indol-3-yl] acetate

The title compound was prepared according to the procedure described in Example 8 (Method B) from methyl trans-4-chloro-2-(phenylsulfonylamino)cinnamate (step 1 of Example 8, Method A) and 4-cyanophenacyl bromide.

$^1$H-NMR (CDCl$_3$) δ: 8.88 (1H, br s), 7.89–7.80 (4H, m), 7.58 (1H, d, J=8.75 Hz), 7.41 (1H, d, 1.65 Hz), 7.18 (1H, dd, 8.75 Hz, 1.65 Hz), 3.74 (2H, s), 3.36 (3H, s).

Example 206

Methyl[6-chloro-2-[4-(bromo)benzoyl-1H-indol-3-yl]acetate

The title compound was prepared according to the procedure described in Example 57 from methyl trans 4-chloro-2-(phenylsulfonylamino)cinnamate (step 1 of Example 8, Method A) and 4-bromophenacyl bromide.

$^1$H-NMR (CDCl$_3$) δ: 8.89 (1H, br s), 7.66 (4H, s), 7.55 (1H, d, J=8.6 Hz), 7.36 (1H, d, J=1.6 Hz), 7.15 (1H, dd, J=8.6, 1.6 Hz), 3.81 (2H, s), 3.66 (3H, s).

Example 207

Methyl[6-chloro-2-[4-(2-thienyl)benzoyl]-1H-indol-3-yl]acetate

A mixture of methyl[6-chloro-2-(4-bromobenzoyl)-1H-indol-3-yl]acetate (Example 206, 0.40 g, 0.98 mmol), thiophene-2-boronic acid (0.14 g, 1.08 mmol), saturated aqueous sodium bicarbonate (4 ml), and dichlorobis(triphenylphosphine)palladium(II) (70 mg, 0.098 mmol) in DME (15 ml) was refluxed for 3 h. The mixture was poured into water (30 ml), and extracted with ethyl acetate (50 ml×2). The combined extracts were washed with brine (50 ml), dried (MgSO$_4$), and concentrated. The residue was purified by flash column chromatography eluting with ethyl acetate-hexane (1:6) to afford 0.33 g (83%) of the title compound as yellow solids.

$^1$H-NMR (CDCl$_3$) δ: 8.88 (1H, br s), 7.83 (2H, d, J=8.2 Hz), 7.75 (2H, d, J=8.2 Hz), 7.58 (1H, d, J=8.6 Hz), 7.46 (1H, dd, J=3.6, 1.2 Hz), 7.42–7.38 (2H, m), 7.19–7.12 (2H, m), 3.87 (2H, s), 3.67 (3H, s).

Example 208

[6-Chloro-2-[4-(2-thienyl)benzoyl]-1H-indol-3-yl] acetic Acid

The title compound was prepared according to the procedure described in Example 9 (Method B) from methyl[6-chloro-2-[4-(2-thienyl)benzoyl]-1H-indol-3-yl]acetate (Example 207).

m.p.: 246–249° C. IR (KBr) ν: 3319, 3068, 2628, 1705, 1610, 1593, 1427, 1323, 1257, 1186, 941 cm$^{-1}$. $^1$H-NMR (DMSO-d$_6$) δ: 11.79 (1H, s), 7.87 (2H, d, J=8.6 Hz), 7.82 (2H, d, J=8.6 Hz), 7.77–7.68 (3H, m), 7.48 (1H, d, J=1.5 Hz), 7.26–7.20 (1H, m), 7.13 (1H, dd, J=8.6, 2.0 Hz), 3.86 (2H, s).

Example 209

Methyl[6-chloro-2-[4-(2-furyl)benzoyl]-1H-indol-3-yl]acetate

The title compound was prepared according to the procedure described in Example 207 from methyl[6-chloro-2-(4-bromobenzoyl)-1H-indol-3-yl]acetate (Example 206) and furan-2-boronic acid.

$^1$H-NMR (CDCl$_3$) δ: 8.90 (1H, br s), 7.83 (2H, d, J=8.7 Hz), 7.80 (2H, d, J=8.7 Hz), 7.60–7.54 (2H, m), 7.40 (1H, d, J=1.8Hz), 7.15 (1H, dd, J=8.6, 1.8 Hz), 6.83 (1H, d, J=3.5 Hz), 6.57–6.52 (1H, m), 3.86 (2H, s), 3.66 (3H, s).

Example 210

[6-Chloro-2-[4-(2-furyl)benzoyl]-1H-indol-3-yl] acetic Acid

The title compound was prepared according to the procedure described in Example 9 (Method B) from methyl[6-chloro-2-[4-(2-furyl)benzoyl]-1H-indol-3-yl]acetate (Example 209).

m.p.: 230–232° C. IR (KBr) ν: 3315, 2873, 2630, 1709, 1616, 1597, 1527, 1431, 1321, 1257, 1232 cm$^{-1}$. $^1$H-NMR (DMSO-d$_6$) δ: 11.80 (1H, s), 7.93–7.79 (3H, m), 7.83 (2H, d, J=8.1 Hz), 7.73 (1H, d, J=8.6 Hz), 7.48 (1H, d, J=1.8 Hz), 7.21 (1H, d, J=3.5 Hz), 7.14 (1H, dd, J=8.6, 1.8 Hz), 6.72–6.66 (1H, m), 3.84 (2H, s).

Example 211

Methyl[6-chloro-2-[4-(3-pyridyl)benzoyl]-1H-indol-3-yl]acetate

The title compound was prepared according to the procedure described in Example 207 from methyl[6-chloro-2-(4-bromobenzoyl)-1H-indol-3-yl]acetate (Example 206) and pyridine-3-boronic acid.

$^1$H-NMR (CDCl$_3$) δ: 8.95 (1H, br s), 8.90 (1H, d, J=2.5 Hz), 8.69–8.65 (1H, m), 7.98–7.92 (1H, m), 7.92 (2H, d, J=8.6 Hz), 7.73 (2H, d, J=8.6 Hz), 7.59 (1H, d, J=8.7 Hz), 7.48–7.40 (2H, m), 7.17 (1H, dd, J=8.7, 1.8 Hz), 3.88 (2H, s), 3.67 (3H, s).

Example 212

[16-Chloro-2-[4-(3-pyridyl)benzoyl]-1H-indol-3-yl] acetic Acid

The title compound was prepared according to the procedure described in Example 9 (Method B) from methyl[6-chloro-2-[4-(3-pyridyl)benzoyl]-1H-indol-3-yl]acetate (Example 211).

m.p.: 194.8° C. IR (KBr) ν: 3224, 2960, 1604, 1568, 1527, 1382, 1321, 1259, 1004, 920 cm$^{-1}$. $^1$H-NMR (CD$_3$OD) δ: 8.93–8.89 (1H, m), 8.57 (1H, dd, J=4.8, 1.5 Hz), 8.24–8.17 (1H, m), 7.98 (2H, d, J=8.6 Hz), 7.85 (2H, d, J=8.6 Hz), 7.68 (1H, d, J=8.6 Hz), 7.60–7.53 (1H, m), 7.46–7.42 (1H, m), 7.04 (1H, dd, J=8.6, 1.8 Hz), 3.67 (2H, s).

Example 213

Methyl[6-chloro-2-[4-(2-thiazolyl)benzoyl]-1H-indol-3-yl]acetate

To a stirred solution of thiazole (0.11 g, 1.23 mmol) in diethyl ether (4 ml) was added n-BuLi (1.55M in hexane, 0.79ml) at −78° C. under nitrogen atmosphere. After stirring for 30 min., zinc chloride (1.0M in diethyl ether, 3.7 ml, 3.7 mmol) was added, and the mixture stirred at 0° C. for 30 min. To the resulting mixture was added palladium catalyst prepared in THF (5 ml) by the treatment of a suspension of dichlorobis(triphenylphosphine)palladium(II) (0.22 g, 0.31 mmol) with n-BuLi (1.55M in hexane, 0.39 ml). Methyl[6-chloro-2-(4-bromobenzoyl)-1H-indol-3-yl]acetate (Example 206, 0.25 g, 0.61 mmol) was added to the mixture. The reaction mixture was heated at reflux temperature for 4 h., poured into water (50 ml), and extracted with ethyl acetate (50 ml). The combined extracts were washed with brine (50 ml), dried (MgSO$_4$), and concentrated. This crude product was purified by flash column chromatography eluting with ethyl acetate-hexane (1:3) to afford 0.18 g (72%) of the title compound as yellow solids.

$^1$H-NMR (DMSO-d$_6$) δ: 11.87 (1H, br s), 8.16 (2H, d, J=8.4 Hz), 8.04 (1H, d, J=3.1 Hz), 7.93 (1H, d, J=3.1 Hz), 7.86 (2H, d, J=8.4 Hz), 7.77 (1H, d, J=8.6 Hz), 7.49 (1H, d, J=1.6 Hz), 7.15 (1H, dd, J=8.6, 1.6 Hz), 3.97 (2H, s), 3.54 (3H, s).

Example 214

[6-Chloro-2-[4-(2-thiazolyl)benzoyl]-1H-indol-3-yl] acetic Acid

The title compound was prepared according to the procedure described in Example 9 (Method B) from methyl[6-chloro-2-[4-(2-thiazolyl)benzoyl]-1H-indol-3-yl]acetate (Example 213).

m.p.: 230–233° C. IR (KBr) ν: 3331, 3126, 2546, 1693, 1635, 1535, 1350, 1313, 1213, 1150, 912 cm$^{-1}$. $^1$H-NMR (DMSO-d$_6$) δ: 11.82 (1H, s), 8.15 (2H, d, J=8.6 Hz), 8.04 (1H, d, J=3.3 Hz), 7.93 (1H, d, J=3.3 Hz), 7.88 (2H, d, J=8.6 Hz), 7.75 (1H, d, J=8.7 Hz), 7.49 (1H, d, J=2.0 Hz), 7.14 (1H, dd, J=8.7, 2.0 Hz), 3.86 (2H, s).

Example 215

Methyl[6-chloro-2-(3-bromobenzoyl)-1H-indol-3-yl] acetate

The title compound was prepared according to the procedure described in Example 57 from methyl trans 4-chloro-2-(phenylsulfonylamino)cinnamate (step 1 of Example 8, Method A) and 3-bromophenacyl bromide.

$^1$H-NMR (CDCl$_3$) δ: 8.91 (1H, br s), 7.93–7.87 (1H, m), 7.77–7.67 (2H, m), 7.57 (1H, d, J=8.7 Hz), 7.43–7.35 (2H, m), 7.19–7.13 (1H, m), 3.78 (2H, s), 3.69 (3H, s).

Example 216

Methyl[6-chloro-2-[3-(2-furyl)benzoyl]-1H-indol-3-yl]acetate

The title compound was prepared according to the procedure described in Example 207 from methyl[6-chloro-2-(3-bromobenzoyl)-1H-indol-3-yl]acetate (Example 215) and furan-2-boronic acid.

$^1$H-NMR (CDCl$_3$) δ: 8.93 (1H, br s), 8.05–8.01 (1H, m), 7.94–7.88 (1H, m), 7.68–7.62 (1H, m), 7.60–7.47 (3H, m), 7.45–7.41 (1H, m), 7.16 (1H, dd, J=8.6, 1.6 Hz), 6.74 (1H, d, J=3.3 Hz), 6.52–6.47 (1H, m), 3.80 (2H, s), 3.57 (3H, s).

Example 217

[6-Chloro-2-[3-(2-furyl)benzoyl]-1H-indol-3-yl] acetic Acid

The title compound was prepared according to the procedure described Example 9 (Method B) from methyl[6-chloro-2-[3-(2-furyl)benzoyl]-1H-indol-3-yl]acetate (Example 216).

m.p.: 246–249° C. IR (KBr) ν: 3310, 2984, 2632, 1695, 1624, 1568, 1327, 1227, 1062, 806, 739 cm$^{-1}$. $^1$H-NMR (DMSO-d$_6$) δ: 11.81 (1H, s), 8.05–7.96 (2H, m), 7.82–7.77 (1H, m), 7.74 (1H, d, J=8.7 Hz), 7.68–7.61 (2H, m), 7.49 (1H, d, J=2.0 Hz), 7.14 (1H, dd, J=8.7, 2.0Hz), 7.09 (1H, d, J=3.3 Hz), 6.66–6.61 (1H, m), 3.83 (2H, s).

Example 218

Methyl dl-2-[6-Chloro-2-(4-chlorobenzoyl)-1H-indol-3-yl]propionate

Step 1. Methyl[-tert-butoxycarbonyl-2-(4-chlorobenzoyl)-6-methyl-1H-indol-3-yl]acetate To a stirred suspension of methyl[2-(4-chlorobenzoyl)-6-methyl-1H-indol-3-yl]acetate (Example 8, Method B, 2.0 g, 5.5 mmol) in dichloromethane (20 ml) was added di-tert-butyl dicarbonate (2.4 g, 11 mmol) and 4-dimethylaminopyridine (670 mg, 5.5 mmol) at room temperature. After stirring for 5 min, the mixture was poured into 10% citric acid (200 ml) and extracted with dichloromethane (200 ml). The extract was washed with water (200 ml), brine (200 ml), dried (MgSO$_4$), and concentrated. The residue was purified by flash column chromatography eluting with ethyl acetate-hexane (1:4) to afford 2.3 g (90%) of the title compound as a yellow solids.

$^1$H-NMR (CDCl$_3$) δ: 8.26 (1H, d, J=2.2 Hz), 7.74 (2H, d, J=8.6 Hz), 7.53 (1H, d, J=8.6 Hz), 7.44 (2H, d, J=8.6 Hz), 7.32 (1H, dd, J=1.6, 8.4 Hz), 3.72 (2H, s), 3.56 (3H, s), 1.30 (9H, s).

Step 2. Methyl[1-tert-butoxycarbonyl-2-(4-chlorobenzoyl)-6-methyl-1H-indol-3-yl]propionate To a stirred solution of methyl[1-tert-butoxycarbonyl-2-(4-chlorobenzoyl)-6-methyl-1H-indol-3-yl]acetate (step 1, 200 mg, 0.43 mmol) in THF (3 ml) was added a solution of lithium bis(trimethylsilyl)amide in THF (1 M, 0.5 ml) at −78° C. After stirring for 0.5 h, iodomethane (0.14 ml, 2.2 mmol) was added at that temperature. The mixture was allowed to warm to −10° C. and stirred for an additional 0.5 h. The resulting mixture was poured into saturated aqueous ammonium chloride (50 ml) and extracted with diethyl ether (50 ml). The extract was washed with water (50 ml), brine (50 ml), dried (MgSO$_4$) and concentrated. The residue was purified by TLC developing with ethyl acetate-hexane (1:4) to afford 146 mg (71%) of the title compound as a colorless oil.

$^1$H-NMR (CDCl$_3$) δ: 8.28 (1H, d, J=1.9 Hz), 7.75 (2H, d, J=8.4 Hz), 7.59 (1H, d, J=8.4 Hz), 7.44 (2H, d, J=8.6 Hz), 7.28 (1H, dd, J=1.9, 8.4 Hz), 3.86 (1H, q, J=7.3 Hz), 3.54 (3H, s), 1.54 (3H, d, J=7.3 Hz), 1.30 (9H, s).

Step 3. Methyl dl-[2-(4-Chlorobenzoyl)-6-methyl-1H-indol-3-yl]propionate

Methyl[1-tert-butoxycarbonyl-2-(4-chlorobenzoyl)-6-methyl-1H-indol-3-yl]propionate (step 2, 270 mg, 0.72 mmol) was dissolved in trifluoroacetic acid (5 ml). After siring for 10 min, the mixture was concentrated. To the residue was added saturated sodium bicarbonate (30 ml), and then the mixture was extracted with ethyl acetate (100 ml). The extract was washed with water (50 ml) brine (50 ml), dried (MgSO$_4$), and concentrated. The residue was purified by flash column chromatography eluting with ethyl acetate-hexane (1:3) to afford 210 mg (78%) of yellow solids.

$^1$H-NMR (CDCl$_3$) δ: 8.89 (1H, br), 7.78 (2H, d, J=8.7 Hz), 7.67 (1H, d, J=8.7 Hz), 7.50 (2H, d, J=8.6 Hz), 7.40–7.37 (1H, m), 7.11 (1H, dd, J=1.8, 8.7 Hz), 4.20 (1H, q, J=7.2 Hz), 3.64 (3H, s), 1.54 (3H, d, J=7.2 Hz).

Example 219 dl-2-[2-(4-Chlorobenzoyl)-6-chloro-1H-indol-3-yl] proprionic Acid

The title compound was prepared according to the procedure described in Example 9 (Method B) from methyl dl-[2-(4-chlorobenzoyl)-6-methyl-1H-indol-3-yl]propionate (Example 218).

$^1$H-NMR (CDCl$_3$) δ: 8.77 (1H, br s), 7.82 (2H, d, J=8.6 Hz), 7.75 (1H, d, J=8.7 Hz), 7.53 (2H, d, J=8.6 Hz), 7.40 (1H, br), 7.13 (1H, dd, J=1.8, 8.7 Hz), 4.29 (1H, q, J=7.2 Hz), 1.61 (3H, d, J=7.2 Hz).

Example 220

Methyl[5-chloro-2-(isoquinoline-3-carbonyl)-1H-indol-3-yl)acetate

The title compound was prepared according to the procedure described in Example 57 from methyl trans-5-chloro- 2-(phenylsulfonylamino)cinnamate (Example 36, step 3) and 3-bromoacetylisoquinoline hydrobromide*.

* 3-Bromoacetylisoquinoline hydrobromide was prepared from 3-acetylisoquinoline (D. L. Klayman et al., Arzneim. Forsch., 1986, 36, 10) according to the method of H. McKennis, Jr., L. B. Turnbull, E. R. Bowman, and E. Tamaki (in J. Org. Chem., 1963, 28, 383–387).

$^1$H-NMR (CDCl$_3$) δ: 12.72 (1H, br s), 9.37 (1H, s), 8.80 (1H, s), 8.15–8.02 (2H, m), 7.87–7.76 (2H, m), 7.69 (1H, d, J=2.0 Hz), 7.48 (1H, d, J=8.9 Hz), 7.32 (1H, dd, J=2.0, 8.7 Hz), 4.33 (2H, s), 3.76 (3H, s). $^1$H-NMR (DMSO-d$_6$) δ: 9.49 (1H, s), 8.68 (1H, s), 8.34–8.26 (2H, m), 7.99–7.88 (2H, m), 5.14 (2H, s).

Example 221

[5-Chloro-2-(isoquinoline-3-carbonyl)-1H-indol-3-yl]acetic Acid

The title compound was prepared according to the procedure described in Example 58 from methyl[5-chloro-2-(isoquinoline-3-carbonyl)-1H-indol-3-yl]acetate (Example 219).

MS (EI) m/z: 364 (M$^+$). m.p.: 239–240° C. IR (KBr) ν: 3277, 1699, 1641, 1531, 1329, 1202, 1059, 961, 787 cm$^{-1}$. $^1$H-NMR (DMSO-d$_6$) δ: 12.46 (1H, br s), 9.56 (1H, s), 8.69 (1H, s), 8.39–8.26 (2H, m), 7.99–7.90 (2H, m), 7.87 (1H, d, J=2.1 Hz), 7.72 (1H, d, J=8.7 Hz), 7.35 (1H, dd, J=2.1, 8.9 Hz), 4.13 (2H, s).

Example 222

Methyl[6-chloro-2-(isoquinoline-3-carbonyl)-1H-indol-3-yl]acetate

The title compound was prepared according to the procedure described in Example 57 from methyl trans-4-chloro-2-(phenylsulfonylamino)cinnamate (step 1 of Example 8, Method A) and 3-bromoacetylisoquinoline (Preparation is described in Example 220).

$^1$H-NMR (CDCl$_3$) δ: 12.69 (1H, br s), 9.38 (1H, s), 8.81 (1H, s), 8.16–8.04 (2H, m), 7.88–7.77 (2H, m), 7.65 (1H, d, J=8.9 Hz), 7.57 (1H, d, J=2.0 Hz), 7.15 (1H, dd, J=2.0 and 8.7 Hz), 4.36 (2H, s), 3.75 (3H, s).

Example 223

[6-Chloro-2-(isoquinoline-3-carbonyl)-1H-indol-3-yl]acetic Acid

The title compound was prepared according to the procedure described in Example 58 from methyl[6-chloro-2-(isoquinoline-3-carbonyl)-1H-indol-3-yl]acetate (Example 222).

MS (EI) m/z: 364 (M$^+$). m.p.: 236–237° C. IR (KBr) ν: 3229, 1709, 1641, 1618, 1531, 1198, 793 cm$^{-1}$. $^1$H-NMR (DMSO-d$_6$) δ: 12.43 (1H, br s), 9.56 (1H, s), 8.70 (1H, s), 8.41–8.26 (2H, m), 7.99–7.87 (2H, m), 7.82 (1H, d, J=8.7 Hz), 7.77 (1H, d, J=1.5 Hz), 7.14 (1H, dd, J=2.0, 8.6 Hz), 4.14 (2H, s).

Example 224

Methyl[5-chloro-2-(5-methylisoxazole-3-carbonyl)-1H-indol-3-yl]acetate

The title compound was prepared according to the procedure described in Example 57 from methyl trans-5-chloro-2-(phenylsulfonylamino)cinnamate (Example 36, step 3) and 3-bromoacetyl-5-methylisoxazole (M. D. Amici et al., J. Org. Chem., 1989, 54, 2646).

$^1$H-NMR (CDCl$_3$) δ: 10.75 (1H, br s), 7.68 (1H, br s), 7.42 (1H, d, J=8.2 Hz), 7.34 (1H, dd, J=1.8, 9.1 Hz), 6.60 (1H, s), 4.25 (2H, s), 3.74 (3H, s), 2.56 (3H, s).

Example 225

[5-Chloro-2-(5-methylisoxazole-3-carbonyl)-1H-indol-3-yl]acetic Acid

The title compound was prepared according to the procedure described in Example 58 from methyl[5-chloro-2-(5-methylisoxazole-3-carbonyl)-1H-indol-3-yl]acetate (Example 224).

MS (EI) m/z: 318 (M$^+$). m.p.: 253–255° C. IR (KBr) ν: 3379, 1699, 1639, 1539, 1425, 1259, 1207, 1059, 804 cm$^{-1}$. $^1$H-NMR (DMSO-d$_6$) δ: 11.76 (1H, br s), 7.81 (1H, d, J=2.0 Hz), 7.59 (1H, d, J=8.9 Hz), 7.29 (1H, dd, J=2.0, 8.7 Hz), 6.67 (1H, s), 4.00 (2H, s), 2.49 (3H, s).

Example 226

Methyl[6-chloro-2-(5-methylisoxazole-3-carbonyl)-1H-indol-3-yl]acetate

The title compound was prepared according to the procedure described in Example 57 from methyl trans-4-chloro-2-(phenylsulfonylamino)cinnamate (step 1 of Example 8, Method A) and 3-bromoacetyl-5-methylisoxazole (M. D. Amici et al., J. Org. Chem., 1989, 54, 2646).

$^1$H-NMR (CDCl$_3$) δ: 10.70 (1H, br s), 7.62 (1H, d, J=8.7 Hz), 7.49 (1H, d, J=1.8 Hz), 7.15 (1H, dd, J=1.8 and 8.7 Hz), 6.60 (1H, br s), 4.27 (2H, s), 3.72 (3H, s), 2.56 (3H, s).

Example 227

[6-Chloro-2-(5-methylisoxazole-3-carbonyl)-1H-indol-3-yl]acetic Acid

The title compound was prepared according to the procedure described in Example 58 from methyl[6-chloro-2-(5-methylisoxazole-3-carbonyl)-1H-indol-3-yl]acetate (Example 226).

MS (EI) m/z: 318 (M$^+$). m.p.: 227–229° C. IR (KBr) ν: 3331, 1713, 1645, 1543, 1404, 1259, 1202, 891, 804 cm$^{-1}$. $^1$H-NMR (DMSO-d$_6$) δ: 11.70 (1H, br s), 7.74 (1H, d, J=8.7 Hz), 7.62 (1H, d, J=1.3 Hz), 7.07 (1H, dd, J=1.8, 8.6 Hz), 6.67 (1H, br s), 4.01 (2H, s), 2.49 (3H, s).

Example 228

Methyl[5-chloro-2-(4-methyl-1,2,3-thiadiazole-5-carbonyl)-1H-indol-3-yl]acetate

The title compound was prepared according to the procedure described in Example 57 from methyl trans-5-chloro-2-(phenylsulfonylamino)cinnamate (Example 36, step 3) and 5-bromoacetyl-4-methyl-1,2,3-thiadiazole hydrobromide*.

* 5-Bromoacetyl-4-methyl-1,2,3-thiadiazole hydrobromide was prepared as follows;

$^1$H-NMR (CDCl$_3$) δ: 9.00 (1H, br s), 7.63 (1H, br s), 7.34 (1H, dd, J=1.8, 8.9 Hz), 7.28 (1H, d. J=8.9 Hz), 3.81 (2H, s), 3.66 (3H, s), 2.78 (3H, s).

N-Methoxy-N-methyl-4-methyl-1,2,3-thiadiazole-5-carboxamide:

To a solution of 1,2,3-thiadiazole-5-carbonyl chloride (10.00 g, 61.5 mmol) and N,O-dimethylhydroxylamine hydrochloride (7.20 g, 73.8 mmol) in dichloromethane (200 ml) was added triethylamine (20.6 ml, 147.6 mmol) at 0° C. After stirring for 2 h at room temperature, the mixture was diluted with dichloromethane (300 ml), washed with water (200 ml×2) and dried (MgSO$_4$). Removal of solvent gave 11.31 g (98%) of the title compound as brown crystals.

$^1$H-NMR (CDCl$_3$) δ: 3.75 (3H, s), 3.40 (3H, s), 3.01 (3H, s),

5-Acetyl-4-methyl-1,2,3-thiadiazole:

To a solution of N-methoxy-N-methyl-4-methyl-1,2,3-thiadiazole-5-carboxamide (11.31 g, 60.4 mmol) in THF (100 ml) was added 2M diethyl ether solution of methylmagnesium iodide (45.3 ml, 90.6 mmol) over 0.5 h at 0° C. The mixture was allowed to warm to room temperature and stirred for 3 h. The mixture was quenched with saturated aqueous ammonium chloride (100 ml) and then extracted with diethyl ether (200 ml×2). The extracts were dried (MgSO$_4$) and concentrated to give 7.49 g (87%) of the title compound as a pale brown oil.

$^1$H-NMR (CDCl$_3$) δ: 2.96 (3H, s), 2.67 (3H, s).

5-Bromoacetyl-4-methyl-1,2,3-thiadiazole:

To a solution of 5-acetyl-4-methyl-1,2,3-thiadiazole (1.00 g, 7.03 mmol) in chloroform (20 ml) was added dropwise a solution of bromine (1.24 g, 7.73 mmol) in chloroform (10 ml) over 0.5 h at room temperature. The mixture was heated at reflux temperature for 2 h. After cooling to room temperature, the mixture was made basic with saturated aqueous sodium bicarbonate and extracted with dichloromethane (100 ml×2). The extracts were dried (Na$_2$SO$_4$) and concentrated to give 1.55 g (100%) of the title compound as a brown oil.

$^1$H-NMR (CDCl$_3$) δ: 4.28 (2H, s), 2.98 (3H, s).

Example 229

[5-Chloro-2-(4-methyl-1,2,3-thiadiazole-5-carbonyl)-1H-indol-3-yl]acetic Acid

A mixture of methyl[5-chloro-2-(4-methyl-1,2,3-thiadiazole-5-carbonyl)-1H-indol-3-yl]acetate (Example 228, 190 mg, 0.54 mmol), 2N aqueous HCl (4 ml), and acetic acid (20 ml) was heated at reflux temperature for 2 h. After cooling to room temperature, the mixture was concentrated. The crystalline residue was diluted with THF (100 ml) and dried (MgSO$_4$) and concentrated. The residual solids were washed with ethyl acetate gave 145 mg (79%) of the title compound as yellow solids.

MS (EI) m/z: 335 (M$^+$). m.p.: 229–230° C. IR (KBr) ν: 3300, 1715, 1622, 1526, 1329, 1261, 1204, 1063, 1009, 822 cm$^{-1}$. $^1$H-NMR (DMSO-d$_6$) δ: 11.92 (1H, br s), 7.89 (1H, d, J=2.0 Hz), 7.48 (1H, d, J=8.9 Hz), 7.36 (1H, dd, J=2.0, 8.9 Hz), 3.95 (2H, s), 2.63 (3H, s).

Example 230

Methyl[6-chloro-2-(4-methyl-1,2,3-thiadiazole-5-carbonyl)-1H-indol-3-yl]acetate

The title compound was prepared according to the procedure described in Example 57 from methyl trans-4-chloro-2-(phenylsulfonylamino)cinnamate (step 1 of Example 8, Method A) and 5-bromoacetyl-4-methyl-1,2,3-thiadiazole (Preparation is described in Example 228).

tlc: Rf=0.56 (ethyl acetate/hexane=1:2).

Example 231

[6-Chloro-2-(4-methyl-1,2,3-thiadiazole-5-carbonyl)-1H-indol-3-yl]acetic Acid

The title compound was prepared according to the procedure described in Example 229 from methyl[6-chloro-2-(4-methyl-1,2,3-thiadiazole-5-carbonyl)-1H-indol-3-yl]acetate (Example 230).

MS (EI) m/z: 335 (M$^+$). m.p.: 215–216° C. IR (KBr) ν: 3300, 1709, 1645, 1531, 1327, 1211, 1065, 922, 789 cm$^{-1}$. 1H-NMR (DMSO-d$_6$) δ: 12.35 (1H, br s), 11.86 (1H, br s), 7.82 (1H, d, J=8.7 Hz), 7.47 (1H, d, J=1.8 Hz), 7.17 (1H, dd, J=1.8, 8.6 Hz), 3.93 (2H, s), 2.63 (3H, s).

Example 232

Methyl[5-chloro-2-(5-methylthiazole-2-carbonyl)-1H-indol-3-yl]acetate

The title compound was prepared according to the procedure described in Example 57 from methyl trans-5-chloro-2-(phenylsulfonylamino)cinnamate (Example 36, step 3) and 2-bromoacetyl-5-methylthiazole hydrobromide*.

* 2-Bromoacetyl-5-methylthiazole was prepared from 2-acetyl-5-methylthiazole (Metzger et al., Bull. Soc. Chim. Fr., 1953, 702) according to the method of H. McKennis, Jr., L. B. Tumbull, E. R. Bowman, and E. Tamaki (in J. Org. Chem., 1963, 28, 383–387).

$^1$H-NMR (CDCl$_3$) δ: 11.74 (1H, br s), 7.76 (1H, d, J=1.1 Hz), 7.67 (1H, d, J=1.8), 7.43 (1H, d, J=8.7 Hz), 7.32 (1H, dd, J=2.0, 8.7 Hz), 4.28 (2H, s), 3.73 (3H, s), 2.62 (3H, d, J=1.0 Hz). $^1$H-NMR (DMSO-d$_6$) δ: 7.91 (1H, d, J=1.2 Hz), 4.87 (2H, s), 2.58 (3H, d, J=0.8 Hz).

Example 233

[5-Chloro-2-(5-methylthiazole-2-carbonyl)-1H-indol-3-yl]acetic Acid

The title compound was prepared according to the procedure described in Example 58 from methyl[5-chloro-2-(5-methylthiazole-2-carbonyl)-1H-indol-3yl]acetate (Example 232).

MS (EI) m/z: 334 (M$^+$). m.p.: 231–233° C. IR (KBr) ν: 3348, 1699, 1630, 1541, 1404, 1333, 1271, 1057, 1003, 804 cm$^1$. $^1$H-NMR (DMSO-d$_6$) δ: 12.05 (1H, br s), 8.04 (1H, s), 7.88 (1H, br s), 7.77 (1H, d, J=8.7 Hz), 7.35 (1H, br d, J=8.9 Hz), 4.15 (2H, s), 2.63 (3H, s).

Example 234

Methyl[6-chloro-2-(5-methylthiazole-2-carbonyl)-1H-indol-3-yl]acetate

The title compound was prepared according to the procedure described in Example 57 from methyl trans-4-chloro-2-(phenylsulfonylamino)cinnamate (step 1 of Example 8, Method A) and 2-bromoacetyl-5-methylthiazole (Preparation is described in Example 232).

$^1$H-NMR (CDCl$_3$) δ: 11.73 (1H, br s), 7.77 (1H, s), 7.62 (1H, d, J=8.2 Hz), 7.51 (1H, br s), 7.14 (1H, br d, J=8.7 Hz), 4.31 (2H, s), 3.72 (3H, s), 2.62 (3H, s).

Example 235

[6Chloro-2-(5-methylthiazole-2-carbonyl)-1H-indol-3-yl]acetic Acid

The title compound was prepared according to the procedure described in Example 58 from methyl[6-chloro-2-(5-methylthiazole-2-carbonyl)-1H-indol-3-yl]acetate (Example 234).

MS (EI) m/z: 334 (M$^+$). m.p.: 225–226° C. IR (KBr) ν: 3277, 1707, 1630, 1541, 1398, 1350, 1231, 1219, 1138, 878, 800 cm$^1$. $^1$H-NMR (DMSO-d$_6$) δ: 12.25 (1H,. br s), 11.99 (1H, br s), 8.04 (1H, s), 7.82 (1H, s), 7.81 (1H, d, J=9.0 Hz), 7.13 (1H, br d, J=8.7 Hz), 4.15 (2H, s), 2.63 (3H, s).

Example 236

[6-Chloro-2-(2-thienyl)carbonylindol-3-yl]acetic Acid

Step 1. 6-Chloro-2-(2-thienylcarbonyl)-1-(phenylsulfonyl)indole

The title compound was prepared according to the procedure described in step 2 of Example 2 (Method B) from 6-chloro-1-(phenylsulfonyl)indole (step 1 of Example 2, Method B) and 2-thienoyl chloride.

$^1$H-NMR (CDCl$_3$) δ: 8.13–8.16 (3H, m), 7.77–7.80 (2H, m), 7.50–7.63 (4H, m), 7.29 (1H, dd, J=1.8, 8.4 Hz), 7.19 (1H, t, J=5.4 Hz), 7.03 (1H, s).

Step 2. 6-Chloro-2-(2-thienylcarbonyl)indole

The title compound was prepared according to the procedure described in step 3 of Example 2 (Method B) from 6-chloro-2-(2-thienylcarbonyl)-1-(phenylsulfonyl)indole (step 1).

$^1$H-NMR (CDCl$_3$) δ: 10.96 (1H, br s), 8.01 (1H, dd, J=1.2, 3.8 Hz), 7.73 (1H, dd, J=1.2, 4.9 Hz), 7.64 (1H, d, J=8.6 Hz), 7.54–7.55 (1H, m), 7.35–7.37 (1H, m), 7.23 (1H, dd, J=3.8, 4.9 Hz), 7.10 (1H, dd, J=1.8, 8.6 Hz).

Step 3. Diethyl α-Acetoxy-[6-chloro-2-(2-thienylcarbonyl)-1H-indol-3-yl]malonate The title compound was prepared according to the procedure described in step 4 of Example 2 (Method B) from 6-chloro-2-(2-thienylcarbonyl)indole (step 2).

$^1$H-NMR (CDCl$_3$) δ: 8.93 (1H, br s), 7.82 (1H, d, J=8.9 Hz), 7.76 (1H, d, J=4.9 Hz), 7.55 (1H, d, J=3.8 Hz), 7.39 (1H, d, J=1.8 Hz), 7.11–7.18 (2H, m), 4.16–4.31 (4H, m), 1.87 (3H, s), 1.17–1.32 (6H, m).

Step 4. Diethyl[6-chloro-2-(2-thienylcarbonyl)-1H-indol-3-yl]malonate

The title compound was prepared according to the procedure described in step 5 of Example 2 (Method B) from diethyl α-acetoxy[6-chloro-2-(2-thienylcarbonyl)-1H-indol-3-yl]malonate (step 3).

$^1$H-NMR (CDCl$_3$) δ: 9.27 (1H, br s), 7.71–7.75 (2H, m), 7.60–7.66 (1H, m), 7.05–7.17 (3H, m), 5.56 (1H, s), 4.07–4.26 (4H, m), 1.20–1.28 (6H, m).

Step 5. [6-Chloro-2-(2-thienylcarbonyl)-1H-indol-3-yl]acetic Acid

The title compound was prepared according to the procedure described in step 6 of Example 2 (Method B) from diethyl[6-chloro-2-(2-thienylcarbonyl)-1H-indol-3-yl]malonate (step 4).

MS (EI) m/z: 319 (M$^+$). m.p.: 177–178° C. IR (KBr) ν: 3323, 1701, 1593, 1568, 1524, 1435, 1412, 1323, 1258, 1229, 920 cm$^{-1}$. 1-NMR (DMSO-d$_6$) δ: 12.25 (1H, br s), 11.85 (1H, br s), 8.13 (1H, d, J=4.9 Hz), 7.89 (IRH, d, J=3.6 Hz), 7.74 (1H, d, J=8.7 Hz), 7.51 (1H, d, J=1.8 Hz), 7.34 (1H, t, J=4.8Hz), 7.15 (1H, dd, J=1.8, 8.7 Hz), 3.96 (2H, s).

Example 237

Methyl[6-chloro-2-[3-(1-hydroxy-1-methylethyl)-2-furoyl]-1H-indol-3-yl]acetate The reaction was carried out according to the procedure described in Example 57 from methyl trans-4-chloro-2-(penylsulfonylamino)cinnamate (step 1 of Example 8, Method A) and 2-chloroacethyl-3-(1-hydroxy-1-methylethyl)furan*.

* 2-Chloroacethyl-3-(1-hydroxy-1-methylethyl)furan was prepared as follows;

$^1$H-NMR (CDCl$_3$) δ: 9.89 (1H, br s), 7.59 (1H, d, J=1.6 Hz), 7.53 (1H, d, J=8.7 Hz), 7.34 (1H, d, J=1.5 Hz), 7.08 (1H, dd, J=1.6, 8.7 Hz), 6.57 (1H, d, J=1.8 Hz), 6.39 (1H, br s), 4.22 (2H, s), 3.73 (3H, s), 1.57 (6H, s).

To a solution of 2-(3-furyl)-2-propanol (T. M. Bargar et al., *J. Med. Chem.*, 1986, 29, 315., 2.0 g, 15.85 mmol) in THF (100 ml) was added a solution of n-butyllithium in hexane (1.55M, 30.7 ml, 47.55 mmol) at –78° C. After stirring for 1 h, 2-chloro-N-methoxy-N-methylacetamide (6.54 g, 47.55 mmol) was added at 0° C. Saturated aqueous ammonium chloride (100 ml) was added to the mixture and the organic layer was separated. The organic layer was washed with water (100 ml×2) and brine (50 ml) and dried (MgSO$_4$). After removal of the solvent, the residue was purified by flash chromatography eluting with ethyl acetate/hexane (1:4) to afford 1.03 g (32%) of the title compound as an oil.

$^1$H-NMR (CDCl$_3$) δ: 7.52 (1H, d, J=1.8 Hz), 6.56 (1H, d, J=1.8 Hz), 5.51 (1H, s), 4.74 (2H, s), 1.56 (6H, s).

Example 238

[6-Chloro-2-[3-(1-hydroxy-1-methylethyl)-2-furoyl]1H-indol-3-yl]acetic Acid

The title compound was prepared according to the procedure described in Example 58 from methyl[6-chloro-2-[3-(1-hydroxy-1-methylethyl)-2-furoyl]-1H-indol-3-yl]acetate (Example 237).

MS (EI) m/z: 361 (M$^+$). m.p.: 229–230° C. IR (KBr) ν: 3270, 2980, 1270, 1591, 1564, 1522, 1398, 1302, 1263, 1200, 785 cm$^1$. $^1$H-NMR (DMSO-d$_6$) δ: 11.78 (1H, br s), 7.97 (1H, d, J=1.6 Hz), 7.77 (1H, d,. J=8.6 Hz), 7.56 (1H, d, J=1.5 Hz), 7.13 (1H, dd, J=1.8, 8.6 Hz), 6.87 (1H, d, J=1.6 Hz), 5.69(1H, br s), 3.96 (2H, s), 1.53 (6H, s).

Example 239

Methyl[6-chloro-2-[3-methoxymethyl-2-furoyl]-1H-indol-3-yl]acetate

The title compound was prepared according to the procedure described in Example 57 from methyl trans-4-chloro-2-(penylsulfonylamino)cinnamate (step 1 of Example 8, Method A) and 2-chloroacetyl-3-(methoxymethyl)furan*.

* 2-Chloroacetyl-3-(methoxymethyl)furan was prepared from 3-(methoxymethyl)furan (N. Greeves et al., *Synthesis*, 1993, 1109) according to the procedure for preparing 2-chloroacethyl-3-(1-hydroxy-1-methylethyl)furan described in Example 237.

$^1$H-NMR (CDCl$_3$) δ: 9.81 (1H, br s), 7.60 (1H, d, J=1.6 Hz), 7.56 (1H, d, J=8.7 Hz), 7.40 (1H, d, J=1.5 Hz), 7.10 (1H, dd, J=1.8, 8.7 Hz), 6.79 (1H, d, J=1.6 Hz), 4.81 (2H, s), 4.26 (2H, s), 3.74 (3H, s), 3.48 (3H, s). $^1$H-NMR (CDCl$_3$) δ: 7.52 (1H, d, J=1.8 Hz), 6.74 (1H, d, J=1.8 Hz), 4.73 (2H, s), 4.62 (2H, s), 3.44 (3H, s).

Example 240

[6-Chloro-2-[3-methoxymethyl-2-furoyl]-1H-indol-3-yl]acetic Acid

The title compound was prepared according to the procedure described in Example 58 from methyl[6-chloro-2-(3-methoxymethyl-2-furoyl)-1H-indol-3-yl]acetate (Example 239).

MS (EI) m/z: 347 (M$^+$). m.p.: 212–213° C. IR (KBr) ν: 3373, 3221, 1720, 1601, 1576, 1529, 1205, 1173, 1115, 1088 cm$^{-1}$. $^1$H-NMR (DMSO-d$_6$) δ: 11.72 (1H, br s), 8.04 (1H, d, J=1.6 Hz), 7.76 (1H, d, J=8.7 Hz), 7.59 (1H, d, J=1.5 Hz), 7.12 (1H, dd, J=1.8, 8.7 Hz), 6.86 (1H, d, J=1.6 Hz), 4.70 (2H, s), 4.02 (2H, s), 3.36 (3H, s).

Example 241

[6-Chloro-2-(1-methylimidazole-2-carbonyl)-1H-indol-3-yl]acetic Acid

Step 1. Methyl[6-chloro-1-ethoxycarbonyl-2-(1-methylimidazole-2-carbonyl)indolin-3-yl]acetate The title compound was prepared according to the procedure described in step 2 of Example 31 from methyl trans-4-chloro-2-(ethoxycarbonylamino)cinnamate (Example 31, step 1) and 2-bromoacetyl-1-methylimidazole hydrobromide*.

* 2-bromoacetyl-1-methylimidazole hydrobromide was prepared from 2-acetyl-1-methylimidazole according to the procedure for preparing 2-bromoacetyl-4-methylpyridine hydrobromide described in step 2 of Example 31.

MS (EI) m/z: 405 (M+). $^1$H-NMR (DMSO-d$_6$) δ: 7.69 (1H, s), 7.27 (1H, s), 4.68 (2H, s), 3.81 (3H, s).

Step 2. [6-Chloro-1-ethoxycarbonyl-2-(1-methylimidazole-2-carbonyl)indol-3-yl]acetic acid The title compound was prepared according to the procedure described in step 3 of Example 31 from methyl[6-chloro-1-ethoxycarbonyl-2-(1-methylimidazole-2-carbonyl)indolin-3-yl]acetate (step 1).

m.p.: 235.5° C. IR (KBr) ν: 3238, 1695, 1630, 1538, 1402, 1229, 1146 cm$^{-1}$. $^1$H-NMR (CDCl$_3$) δ: 12.3 (1H, br s), 7.64 (1H, d, J=8.7 Hz), 7.50 (1H, d, J=1.8 Hz), 7.41 (1H, s), 7.16 (1H, s), 7.09 (1H, dd, J=1.8, 8.6 Hz), 4.25 (2H, s), 4.13 (3H, s).

Example 242

Methyl[6-chloro-2-(1-methylimidazole-2-carbonyl)-1H-indol-3-yl]acetate

To a stirred solution of [6-chloro-2-(1-methylimidazole-2-carbonyl)indol-3-yl]acetic acid (Example 241, 65 mg, 0.21 mmol) in methanol (10 ml) was added (trimethylsilyl)diazomethane (1.0 M solution in hexanes, 1.05 ml, 2.1 mmol) at room temperature. After stirring for 19 h, the mixture was concentrated. The residue was purified by TLC developing with ethyl acetate-hexane (1:2) to afford 20 mg (23%) of the title compound as yellow solids.

$^1$H-NMR (CDCl$_3$) δ: 12.35 (1H, br s), 7.59 (1H, d, J=8.0 Hz), 7.49 (1H, d, J=1.5 Hz), 7.24 (1H, s), 7.11 (1H, dd, J=1.7, 8.1 Hz), 7.08 (1H, s), 4.30 (2H, s), 4.12 (3H, s), 3.71 (3H, s).

Example 243

Methyl[5-chloro-2-(1-methylimidazole-2-carbonyl)-1H-indol-3-yl]acetate

The title compound was prepared according to the procedure described in Example 57 from methyl trans-5-chloro-2-(phenylsulfonylamino)cinnamate (Example 36, step 3) and 2-bromoacetyl-1-methylimidazole hydrobromide (Preparation is described in Example 241).

$^1$H-NMR (DMSO-d$_6$) δ: 12.28 (1H, br s), 7.85 (1H, s), 7.77 (1H, d, J=8.7 Hz), 7.66 (1H, s), 7.33–7.29 (2H, m), 4.21 (2H, s), 4.03 (3H, s), 3.60 (3H, s).

Example 244

[5-Chloro-2-(1-methylimidazole-2-carbonyl)-1H-indol-3-yl]acetic Acid

The title compound was prepared according to the procedure described in Example 58 from methyl[5-chloro-2-(1-methylimidazol-2-carbonyl)-1H-indol-3-yl]acetate (Example 243).

m.p.: 230–233° C. $^1$H-NMR (DMSO-d$_6$) δ: 12.50 (1H, br s), 7.84 (1H, s), 7.76 (1H, d, J=13.2 Hz), 7.66 (1H, s), 7.35–7.7.28 (2H, m), 4.15 (2H, s), 4.06 (3H, s).

Example 245

Methyl[5-chloro-2-(imidazole-2-carbonyl)-1H-indol-3-yl]acetate

Step 1. Methyl[5-chloro-2-[]-[2-(trimethylsilyl)ethoxymethyl]imidazole-2-carbonyl]-1H-indol-3-yl]acetate The title compound was prepared according to the procedure described in Example 57 from methyl trans-5-chloro-2-(phenylsulfonylamino)cinnamate (Example 36, step 3) and 2-chloroacetyl-1-[2-(trimethylsilyl)ethoxymethyl]imidazole.*

* 2-chloroacetyl-1-[2-(trimethylsilyl)ethoxymethyl]imidazole was prepared as follows;

$^1$H-NMR (CDCl$_3$) d: 12.38 (1H, br s), 7.66 (1H, s), 7.46–7.38 (2H, m), 7.34–7.29 (2H, m), 5.95 (2H, s), 4.29 (2H, s), 3.73 (3H, s), 3.66 (2H, t, J=8.0 Hz), 0.98 (2H, t, J=8.0 Hz), 0.03 (9H, s).

To a stirred solution of 1-[2-(trimethylsilyl)ethoxymethyl]imidazole (Jeffrey P. Whitten et al., *J. Org. Chem.*, 51, 1891 (1986), 3.0 g, 15 mmol) in THF (30 ml) was added dropwise n-BuLi (1.55 M in n-hexane, 11.0 ml, 17 mmol) at −78° C. and the mixture was stirred for 1 h. To the resulting mixture was added 2-chloro-N-methoxy-N-methylacetamide (2.4 g, 17 mmol) at that temperature. The mixture was allowed to warm to 0° C. and stirred at for an additional 2 h. The mixture was poured into water (50 ml) and extracted with ethyl acetate (80 ml), dried (MgSO$_4$) and concentrated. The residual brown oil was purified by flash column chromatography eluting with ethyl acetate/hexane (1:4) to afford 1.2 g (32%) of the title compound as a yellow oil.

$^1$H-NMR (CDCl$_3$) d: 7.39 (1H, s), 7.25 (1H, s), 5.81 (2H, s), 4.96 (2H, s), 3.60 (2H, t, J=8.2 Hz), 0.95 (2H, t, J=8.2 Hz), 0.02 (9H, s).

Step 2. Methyl[5-chloro-2-(imidazole-2-carbonyl)-1H-indol-3-yl]acetate

To a solution of methyl[5-chloro-2-[1-[2-(trimethylsilyl)ethoxymethyl]imidazole-2-carbonyl]-1H-indol-3-yl]acetate (step 1, 300 mg, 0.67 mmol) in methanol (10 ml) was added 2N aqueous HCl (7 ml) and the mixture was refluxed for 1.5 h. After cooling to room temperature, the mixture was concentrated. To the residue was added saturated aqueous sodium bicarbonate (10 ml) and then the mixture was concentrated. The residual yellow solids were dissolved in THF (100 ml) and dried (MgSO$_4$). Removal of solvent afforded 220 mg (100%) of the title compound as yellow solids.

$^1$H-NMR (CDCl$_3$) d: 12.16 (1H, br s), 10.80 (1H, br s), 7.68 (1H, s), 7.50–7.28 (5H, m), 4.29 (2H, s), 3.70 (3H, s).

Example 246

[5-Chloro-2-(imidazole-2-carbonyl)-1H-indol-3-yl]acetic Acid

The title compound was prepared according to the procedure described in Example 58 from methyl[5-chloro-2-(imidazole-2-carbonyl)-1H-indol-3-yl]acetate (Example 245).

m.p.: 253–254° C. $^1$H-NMR (DMSO-d$_6$) δ: 12.28 (1H, br s), 7.84 (1H, d, J=2.0 Hz), 7.80 (1H, d, J=9.1 Hz), 7.32 (1H, dd, J=2.0, 9.1 Hz), 4.17 (2H, s).

Example 247

Methyl[6-chloro-2-(imidazole-2-carbonyl)-1H-indol-3-yl]acetate

Step 1. Methyl[6-chloro-2-[1-[2-(trimethylsilyl)ethoxymethyl]imidazole-2-carbonyl]-1H-indol-3-yl]acetate The title compound was prepared according to the procedure described in Example 57 from methyl trans-4-chloro- 2-(phenylsulfonylamino)cinnamate (Step 1 of Example 8, Method A) and 2-chloroacetyl-1-[2-(trimethylsilyl) ethoxymethyl]imidazole (Preparation is described in step 1 of Example 245).

$^1$H-NMR (CDCl$_3$) δ: 12.34, (1H, br s), 7.61 (1H, d, J=8.6 Hz), 7.52 (1H, d, J=1.6 Hz), 7.40 (1H, d, J=1.4 Hz), 7.31 (1H, d, J=1.4 Hz), 7.13 (1H, dd, J=1.6, 8.6 Hz), 5.95 (2H, s), 4.32 (2H, s), 3.72 (3H, s), 3.67 (2H, t, J=8.0 Hz), 1.00 (2H, t, J=8.0 Hz), 0.02 (9H, s).

Step 2. Methyl[5-chloro-2-(imidazole-2-carbonyl)-1H-indol-3-yl]acetate

The title compound was prepared according to the procedure described in step 2 of Example 245 from methyl[6-chloro-2-[1-[2-(trimethylsilyl)ethoxymethyl]imidazole-2-carbonyl]-1H-indol-3-yl]acetate (step 1).

$^1$H-NMR (CDCl$_3$) δ: 12.50 (1H, br s), 7.68–7.48 (2H, m), 7.40–7.30 (1H, m), 7.19–7.06 (1H, m), 6.97–6.92 (1H, m), 4.30 (2H, s), 3.67 (3H, s).

Example 248

[6-Chloro-2-(imidazole-2-carbonyl)-1H-indol-3-yl] acetic Acid

The title compound was prepared according to the procedure described in Example 58 from methyl[6-chloro-2-(imidazole-2-carbonyl)-1H-indol-3-yl]acetate (Example 247).

m.p.: 252–253° C. $^1$H-NMR (DMSO-d$_6$) δ: 13.63 (1H, br s), 12.40–12.15 (2H, br), 7.88 (1H, d, J=1.8 Hz), 7.78 (1H, d, J=8.6 Hz), 7.59 (1H, s), 7.40 (1H, s), 7.11 (1H dd, J=1.8, 8.6 Hz), 4.18 (2H, s).

Example 249

Methyl[5-chloro-2-(4-methylthiazole-2-carbonyl)-1H-indol-3-yl]acetate

The title compound was prepared according to the procedure described in Example 57 from methyl trans-5-chloro-2-(phenylsulfonylamino)cinnamate (Example 36, step 3) and 2-bromoacetyl-4-methylthiazole hydrobromide (Cowden, William B. et al., *Aust. J. Chem.*, 1985, 38, 1257).

$^1$H-NMR (DMSO-d$_6$) δ: 12.02 (1H, br s), 7.93–7.85 (2H, m), 7.75 (1H, d, J=8.9 Hz), 7.38 (1H, dd, J=2.0, 8.9 Hz), 4.23 (2H, s), 3.60 (3H, s), 2.61 (3H, s).

Example 250

[5-Chloro-2-(4-methylthiazole-2-carbonyl)-1H-indol-3-yl]acetic Acid

The title compound was prepared according to the procedure described in Example 58 from methyl[5-chloro-2-(4-methylthiazole-2-carbonyl)-1H-indol-3-yl]acetate (Example 249).

m.p.: 218–220° C. $^1$H-NMR (DMSO-d$_6$) δ: 11.97 (1H, br s), 7.89 (1H, d, J=2.0 Hz), 7.75 (1H, d, J=8.7 Hz), 7.37 (1H, dd, J=2.0, 8.7 Hz), 4.13 (2H, s), 2.62 (3H, s).

Example 251

Methyl[5-chloro-2-(1-methylpyrrole-2-carbonyl)-1H-indol-3-yl]acetate

The title compound was prepared according to the procedure described in Example 8 (Method B) from methyl trans-5-chloro-2-(phenylsulfonylamino)cinnamate (Example 36, step 3) and 2-chloroacetyl-1-methylpyrrole (P. D. Croce et al., *Synthesis*, 1990, 212).

$^1$H-NMR (DMSO-d$_6$) δ: 11.8 (1H, br s), 7.80 (1H, br s), 7.55 (1H, d, J=8.6 Hz), 7.40–7.32 (2H, m), 6.95–6.90 (1H, m), 6.35–6.26 (1H, m), 4.00 (2H, s), 3.43 (3H, s), 2.50 (3H, s).

Example 252

[5-Chloro-2-(1-methylpyrrole-2-carbonyl)-1H-indol-3-yl]acetic Acid

A mixture of methyl[5-chloro-2-(1-methylpyrrole-2-carbonyl)-1H-indol-3-yl]acetate (Example 251, 250 mg, 0.79 mmol) and potassium carbonate (900 mg, 6.4 mmol) in methanol-water (1:1, 40 ml) was heated at reflux temperature for 1 h. After cooling to room temperature, the mixture was concentrated. The residue was neutralized with 2N aqueous HCl and extracted with ethyl acetate (50 ml×2) The combined extracts were dried (MgSO$_4$) and concentrated. The residual solids were recrystallized from ethyl acetate/hexane to afford 40 mg (23%) of the title compound as pale yellow solids.

mp: 203–205° C. $^1$H-NMR (DMSO-d$_6$) δ: 11.56 (1H, br s), 7.57 (1H, s), 7.33 (1H, d, J=8.6 Hz), 7.20–7.10 (2H, m), 6.72 (1H, s), 6.10 (1H, s), 3.81 (2H, s), 2.52 (3H, s).

Example 253

Methyl[5-chloro-2-(2-methylimidazole-4-carbonyl)-1H-indol-3-yl]acetate

The title compound was prepared according to the procedure described in Example 8 (Method B) from methyl trans-5-chloro-2-(phenylsulfonylamino)cinnamate (Example 36, step 3) and 4-bromoacetyl-2-methylimidazole (Deady, Leslie W. et al., *Aust. J. Chem.*, 1981, 34, 1295).

$^1$H-NMR (DMSO-d$_6$) δ: 12.04 (1H br s), 8.51 (1H, s), 7.86 (1H, d, J=2.0 Hz), 7.71 (1H, d, J=8.9 Hz), 7.34 (1H, dd, J=2.0, 8.9 Hz), 4.17 (2H, s), 3.59 (3H, s), 2.71 (3H, s).

Example 254

[5-Chloro-2-(2-methylimidazole-4-carbonyl)-1H-indol-3-yl]acetic Acid

The title compound was prepared according to the procedure described in Example 58 from methyl[5-chloro-2-(2-methylimidazole-4-carbonyl)-1H-indol-3-yl]acetate (Example 253).

m.p.: 237–238° C. $^1$H-NMR (DMSO-d$_6$) δ: 12.03 (1H, br), 12.00 (1H, s), 8.49 (1H, s), 7.83 (1H, d, J=2.0 Hz), 7.70 (1H, d, J=8.9 Hz), 7.34 (1H, dd, J=2.0, 8.9 Hz), 4.09 (2H, s), 2.87 (3H, s).

Example 255

Methyl[5-chloro-2-(thiazole-5-carbonyl)-1H-indol-3-yl]acetate

The title compound was prepared according to the procedure described in Example 57 from methyl trans-5-chloro-2-(phenylsulfonylamino)cinnamate (Example 36, step 3) and 5-bromoacetylthiazole hydrobromide*.

* 5-bromoacetylthiazole hydrobromide was prepared from 5-acetylthiazole according to the procedure for preparing 2-bromoacetyl-4-methylpyridine hydrobromide described in step 2 of Example 31.

$^1$H-NMR (CDCl$_3$) d: 12.05 (1H, br s), 9.51 (1H, s), 8.62 (1H, s), 7.85 (1H, d, J=1.9 Hz), 7.55(1H, d, J=8.7 Hz), 7.35 (1H, dd, J=1.9, 8.7 Hz), 4.09(2H, s), 3.59(3H, s). $^1$H-NMR (DMSO-d$_6$) δ: 9.49 (1H, s), 8.34 (1H, s) 4.91 (2H, s).

Example 256

[5-Chloro-2-(thiazole-5-carbonyl-1H-indol-3-yl] acetic Acid

The title compound was prepared according to the procedure described in Example 58 from methyl[5-chloro-2-(thiazole-5-carbonyl)-1H-indol-3-yl]acetate (Example 255).

m.p.: 175–180° C. $^1$H-NMR (DMSO-d$_6$) δ: 11.80 (1H, br s), 9.48 (1H, s), 8.74 (1H, s), 7.78 (1H, s), 7.48 (1H, d, J=8.7 Hz), 7.30 (1H, d, J=8.9 Hz), 3.81 (2H, s).

Example 257

Methyl[6-chloro-2-(4-methylthiazole-2-carbonyl)-1H-indol-3-yl]acetate

The title compound was prepared according to the procedure described in Example 8 (Method B) from methyl trans-4-chloro-2-(phenylsulfonylamino)cinnamate (Step 1 of Example 8, Method A) and 2-bromoacetyl-4-methylthiazole hydrobromide (Cowden, William B. et al., *Aust. J. Chem.*, 1985, 38, 1257).

$^1$H-NMR (DMSO-d$_6$) δ: 11.95 (1H, br s), 7.90 (1H, s), 7.84 (1H, d, J=8.7 Hz), 7.84 (1H, d, J=2.0 Hz), 7.15 (1H, d, J=2.0 Hz), 4.24 (2H, s), 3.60 (3H, s), 2.62 (3H, s).

Example 258

[6-Chloro-2-(4-methylthiazole-2-carbonyl)-1H-indol-3-yl]acetic Acid

The title compound was prepared according to the procedure described in Example 58 from methyl[6-chloro-2-(4methylthiazole-2-carbonyl)-1H-indol-3-yl]acetate (Example 257).

m.p.: 239–240° C. $^1$H-NMR (DMSO-d$_6$) δ: 11.80 (1H, br s), 7.75 (1H, s), 7.68 (1H, d, J=8.4 Hz), 7.67 (1H, d, J=2.0 Hz), 7.02 (1H, dd, J=2.0, 8.4 Hz), 4.03 (2H, s), 2.49 (3H, s).

Example 259

Methyl[5-chloro-2-[3-(ethoxycarbonyl)isoxazole-5-carbonyl]-1H-indol-3-yl]acetate The title compound was prepared according to the procedure described in Example 8 (Method B) from methyl trans-5-chloro-2-(phenylsulfonylamino)cinnamate (Example 36, step 3) and ethyl-5-bromoacetyl)isoxazole-3-carboxylate.

$^1$H-NMR (DMSO-d$_6$) δ: 12.07 (1H, br s), 7.93 (1H, d, J=1.9 Hz), 7.70 (1H, s), 7.39 (1H, dd, J=1.9, 12.8 Hz), 7.62 (1H, d, J=12.8 Hz), 4.44 (2H, q, J=7.1 Hz), 4.15 (2H, s), 3.60 (3H, s), 1.37 (3H, t, J=7.1 Hz).

Example 260

[5-Chloro-2-[3-(carboxy)isoxazole-5-carbonyl]-1H-indol-3-yl]acetic Acid

To a solution of methyl[5-chloro-2-[3-(ethoxycarbonyl) isoxazole-5-carbonyl]-1H-indol-3-yl]acetate (Example 259, 314 mg, 0.80 mmol) in acetic acid (20 ml) was added 2N aqueous HCl (6.0 ml) and the mixture was heated at 110° C. for 5 h. The mixture was then cooled to room temperature and concentrated. The residual yellow solids were washed with ethyl acetate and recrystallized from ethyl acetate/hexane to afford 120 mg (43%) of the title compound as pale yellow solids.

m.p.: 200–205° C. $^1$H-NMR (DMSO-d$_6$) δ: 12.01 (1H, s), 7.91 (1H, s), 7.65–7.56 (2H, m), 7.39 (1H, d, J=8.9 Hz), 4.06 (2H, s).

Example 261

Methyl[6-chloro-2-cyclopropanecarbonyl-1H-indol-3-yl]acetate

The title compound was prepared according to the procedure described in Example 57 from methyl trans-4-chloro-2-(phenylsulfonylamino)cinnamate (step 1 of Example 8, Method A) and bromomethyl cyclopropyl ketone*.

*Bromomethylcyclopropyl ketone was prepared from cyclopropyl methyl ketone according to the procedure for preparing 4-(trifluoromethoxy)phenacyl bromide described in Example 189.

$^1$H-NMR (CDCl$_3$) δ: 9.55 (1H, br s), 7.58 (1H, d, J=8.56 Hz), 7.26 (1H, d, J=1.97 Hz) 7.10 (1H, dd, J=8.56 Hz, 1.97 Hz), 4.17 (2H, s), 3.73 (3H, s), 2.58–2.49 (1H, m), 1.30–1.25 (2H, m), 1.09–1.02 (2H, m). $^1$H-NMR (CDCl$_3$) δ: 3.91 (2H, s), 2.65 (1H, t, 6.94 Hz), 1.20–0.98 (4H, m).

Example 262

[6-Chloro-2-cyclopropanecarbonyl-1H-indol-3-yl] acetic Acid

The title compound was prepared according to the procedure described in Example 9 (Method B) from methyl 2-(6-chloro-2-cyclopropanecarbonyl-1H-indol-3-yl)acetate (Example 261).

m.p.: 207–210_° C. IR (KBr) ν: 3304, 3013, 1709, 1624, 1566, 1443, 1414, 1387, 1340, 1286, 1248, 1217, 1200, 1157, 1057, 1045, 1022 cm$^{-1}$. $^1$H-NMR (DMSO-d$_6$) δ: 11.98 (1H, br s), 7.75 (1H, d, J=8.75 Hz), 7.48 (1H, d, J=1.81 Hz) 7.11 (1H, dd, J=8.75 Hz, 1.81 Hz), 4.08 (2H, s), 2.73 (1H, quintet, 6.24 Hz), 1.07 (4H, d, 6.24 Hz).

Example 263

Methyl[6-chloro-2-cyclobutanecarbonyl-1H-indol-3-yl]acetate

The title compound was prepared according to the procedure described in Example 57 from methyl trans-4-chloro-2-(phenylsulfonylamino)cinnamate (step 1 of Example 8, Method A) and bromomethyl cyclobutyl ketone*.

*Bromomethylcyclobutyl ketone was prepared from cyclobutyl methyl ketone according to the procedure for preparing 4-(trifluoromethoxy)phenacyl bromide described in Example 189.

$^1$H-NMR (CDCl$_3$) δ: 9.35 (1H, br s), 7.53 (1H, d, J=8.72 Hz), 7.18 (1H, d, J=1.65 Hz) 7.07 (1H, dd, J=8.72 Hz, 1.65 Hz), 4.10 (2H, s), 3.77 (3H, s), 3.72 (1H, m), 2.44–1.86 (6H, m). $^1$H-NMR (CDCl$_3$) δ: 3.88 (2H, s), 3.60 (1H, m), 2.33–1.80 (6H, m)

Example 264

[6-Chloro-2-cyclobutanecarbonyl-1H-indol-3-yl] acetic Acid

The title compound was prepared according to the procedure described in Example 9 (Method B) from methyl 2-(6-chloro-2-cyclobutanecarbonyl-1H-indol-3-yl)acetate (Example 263).

m.p.: 225–228° C. IR (KBr) ν: 3303, 2954, 1705, 1632, 1564, 1529, 1437, 1412, 1335, 1242, 1213, 1188, 1157, 1056, 1024 cm$^{-1}$. $^1$H-NMR (DMSO-d$_6$) δ: 11.63 (1H, br s), 7.71 (1H, d, J=8.72 Hz), 7.46 (1H, d, J=1.81 Hz), 7.09 (1H, dd, J=8.72 Hz, 1.81 Hz), 4.04 (2H, s), 2.30–1.78 (7H, m).

Example 265

Methyl[5-(tert-butyl)-2-(4-chlorobenzoyl)-1H-indol-3-yl]acetate

The title compound was prepared according to the procedure described in Example 57 from methyl trans-5-tert-butyl-2-(p-toluenesulfonylamino)cinnamate (Example 143, step 2) and 4-chlorophenacyl bromide.

$^1$H-NMR (CDCl$_3$) δ: 8.82 (1H, br s), 7,8–7.31 (7H, m), 3.87 (2H, s), 3.67 (3H, s), 1.38 (9H, s).

Example 266

[5-(tert-Butyl)-2-(4-chlorobenzoyl)-1H-indol-3-yl]acetic Acid

The title compound was prepared according to the procedure described in Example 9 (Method B) from methyl[5-tert-butyl-2-(4-chlorobenzoyl)-1H-indol-3-yl]acetate (Example 265).

m.p.: 171° C. IR (KBr) ν: 3241, 2963, 1699, 1634, 1589/1541, 1394, 1331, 1222, 1091, 1011 cm$^{-1}$; $^1$H-NMR (DMSO-d$_6$) δ: 11.48 (1H, br s), 7.78–7.37 (7H, m), 3.85 (2H, s), 1.34 (9H, s).

Example 267

[6-Chloro-2-(4-methylpyridine-2-carbonyl-1H-indol-3-yl]-N,N-dimethylacetamide The title compound was prepared according to the procedure described in Example 43 from [6-chloro-2-(4-methylpyridine-2-carbonyl)-1H-indol-3-yl]acetic acid (Example 31).

m.p.: 208° C. (decompose). IR (KBr): 3233, 1655, 1638, 1524, 1398, 1200, 1134 cm$^{-1}$. $^1$H-NMR (CDCl$_3$) δ: 12.54 (1H, br s), 8.62 (1H, d, J=5.0 Hz), 8.15 (1H, br), 7.79 (1H, d, J=8.7 Hz), 7.49 (1H, d, J=1.8 Hz), 7.40–7.30 (1H, m), 7.09 (1H, dd, J=1.8, 8.7 Hz), 4.43 (2H, s), 3.16 (3H, s), 2.98 (3H, s), 2.48 (3H, s).

Example 268

[6-Chloro-2-(4-methylpyridine-2-carbonyl)-1H-indol-3-yl]-N-methylacetamide

The title compound was prepared according to the procedure described in Example 43 from [6-chloro-2-(4-methylpyridine-2-carbonyl)-1H-indol-3-yl]acetic acid (Example 31) and methylamine hydrochloride.

m.p.: 231° C. IR (KBr) ν: 3306, 1643, 1595, 1560, 1526, 1277, 1202, 797 cm$^{-1}$. $^1$H-NMR (CDCl$_3$) δ: 12.45 (1H, br), 8.64 (1H, d, J=4.9 Hz), 8.19 (1H. br), 7.85 (1H, d, J=8.6 Hz), 7.50 (1H, br), 7.40 (1H, br d, J=4.6 Hz), 7.15 (1H, dd, J=1.6, 8.9 Hz), 6.67 (1H, br), 4.14 (2H, s), 2.73 (3H, d, J=4.8 Hz), 2.51 (3H, s).

Example 269

[5-Chloro-2-(4-methylpyridine-2-carbonyl)-1H-indol-3-yl]-N-(2-hydroxyethyl)acetamide The title compound was prepared according to the procedure described in Example 43 from [5-chloro-2-(4-methylpyridine)-1H-indol-3-yl]acetic acid (Example 36) and 2-aminoethanol.

MS (EI) m/z: 371 (M$^+$). m.p.: 195.9° C. $^1$H-NMR (DMSO-d$_6$) δ: 12.28 (1H, br s), 8.69 (1H, d, J=4.9 Hz), 7.94 (1H, br s), 7.78 (2H, m), 7.66 (1H, d, J=8.7 Hz), 7.56 (1H, m), 7.31 (1H, dd, J=2.0 Hz, 8.7 Hz), 3.94 (2H, s), 3.09 (2H, dd, J=5.93 Hz, 11.86 Hz), 2.47 (3H, s).

Example 270

[5-Chloro-2-(4-methylpyridine-2-carbonyl)-1H-indol-3-yl]-N-methoxyacetamide

The title compound was prepared according to the procedure described in Example 43 from [5-chloro-2-(4-methylpyridine)-1H-indol-3-yl]acetic acid (Example 36) and O-mthylhydroxylamine hydrochloride.

MS (EI) m/z: 357 (M$^+$). $^1$H-NMR (CDCl$_3$) δ: 12.53 (1H, br s), 9.54 (1H, br s), 8.65 (1H, d, J=5.1 Hz), 8.19 (1H, br s), 7.92 (1H, br s), 7.42 (2H, m), 7.34 (1H, dd, J=1.7 Hz, 8.9 Hz), 4.01 (2H, s), 3.74 (3H, s), 2.52 (3H, s).

Example 271

2-[5-Chloro-2-(4-methylpyridine-2-carbonyl)-1H-indol-3-yl]-1-(1-piperazinyl)-1-ethanone Step 1. 2-[5-Chloro-2-(4-methylpyridine-2-carbonyl)-1H-indol-3-yl]-1-(4-tert-butoxycarbonyl-1-piperazinyl)-1-ethanone The title compound was prepared according to the procedure described in Example 43 from [5-chloro-2-(4-methylpyridine)-1H-indol-3-yl]acetic acid (Example 36) and tert-butyl 1-piperadinecarboxylate.

$^1$H-NMR (CDCl$_3$) δ: 12.61 (1H, br s), 8.62 (1H, d, J=5.1 Hz), 8.14 (1H, br s), 7.84 (1H, s), 7.42 (1H, d, J=8.7 Hz), 7.37 (br d, 1H, J=4.9 Hz), 7.30 (1H, dd, J=2.0 Hz, 8.9 Hz), 4.42 (2H, s), 3.66 (4H, m), 2.50 (3H, s), 1.64 (4H, m), 1.46 (9H, s).

Step 2. 2-[5-Chloro-2-(4-methylpyridine-2-carbonyl)-1H-indol-3-yl]-1-(1-piperazinyl)-1-ethanone To a solution of [5-chloro-2-(4-methylpyridine-2-carbonyl)-1H-indol-3-yl]-N-(4-tert-butoxycarbonylpiperadino)acetamide (step 1, 152.6 mg, 0.042 mmol) in THF (1 ml) was added dropwise trifluoroacetic acid (2 ml) at 0° C. The mixture was stirred at room temperature for 1.5 h and then concentrated. The residue was diluted with dichloromethane (25 ml), washed with saturated aqueous sodium bicarbonate (25 ml). The aqueous layer was extracted with dichloromathane (25 ml×2). The combined organic layers were dried (Na$_2$SO$_4$) and concentrated. The residue was purified by flash column chlomatographyon eluting with methanol/dichloromathane (1:10) to afford 80.8 mg of the title compound as yellow crystals.

MS (EI) m/z: 396 (M$^+$). m.p.:. 205.0° C. IR (KBr) ν: 3244, 1647, 1595, 1525, 1429, 1205 cm$^{-1}$. $^1$H-NMR (DMSO-d$_6$) δ: 12.28 (1H, br s), 8.68 (1H, d, J=4.9 Hz), 7.90 (1H, br s), 7.81 (1H, br s), 7.65 (1H, d, J=8.9 Hz), 7.56 (br d, 1H, J=4.1 Hz), 7.31 (1H, dd, J=1.8 Hz, 8.9 Hz), 4.15 (2H, br s), 3.50–3.15 (4H, m), 2.70–2.55 (4H, m), 2.46 (3H, s).

Example 272

[5-Chloro-2-(4-methylpyridine-2-carbonyl)-1H-indol-3-yl]-N-(2-aminoethyl)acetamide Step 1. [5-Chloro-2-(4-methylpyridine-2-carbonyl)-1H-indol-3-yl]-N-(2-tert-butoxycarbonylaminoethyl)acetamide The title compound was prepared according to the procedure described in Example 43 from [5-chloro-2-(4-methylpyridine)-1H-indol-3-yl]acetic acid (Example 36) and N-(2-aminoethyl)carbamic acid tert-butyl ester.

$^1$H-NMR (CDCl$_3$) δ: 12.29 (1H, br s), 8.68 (1H, d, J=4.9 Hz), 7.94 (1H, br s), 7.78 (2H, m), 7.67 (1H, d, J=8.9 Hz), 7.57 (1H, br d, J=4.9 Hz), 7.32 (dd, 1H, J=2.0 Hz, 8.7 Hz), 6.73 (1H, m), 3.94 (2H, s), 3.05–2.95 (4H, m), 2.47 (3H, s), 1.35 (9H, s).

Step 2. [5-Chloro-2-(4-methylpyridine-2-carbonyl)-1H-indol-3-yl]-N-(2-aminoethyl)acetamide The title compound was prepared according to the procedure described in step 2 of Example 273 from [5-chloro-2-(4-methylpyridine-2-carbonyl)-1H-indol-3-yl]-N-(2-tert-butoxycarbonylaminoethyl)acetamide (step 1).

MS (EI) m/z: 370 (M$^+$). m.p.: 165.7° C. IR (KBr) ν: 3346, 2927, 1665, 1627, 1593, 1515, 1435, 1267, 1207 cm$^{-1}$. $^1$H-NMR (DMSO-d$_6$) δ: 12.28 (1H, br s), 8.69 (1H, d, J=4.9 Hz), 7.93 (1H, br s), 7.80–7.76 (2H, m), 7.66 (1H, d, J=8.9

Hz), 7.57 (1H, m), 7.31 (dd, 1H, J=2.0 Hz, 8.9 Hz), 3.94 (2H, s), 3.01 (2H, q, J=5.77 Hz), 2.55–2.45 (2H, m), 2.47 (3H, s).

Example 273

2-[5-Chloro-2-(4-methylpyridine-2-carbonyl)-1H-indol-3-yl-1-(3-amino-1-pyrrolidinyl)-1-ethanone Step 1. 2-[5-Chloro-2-(4-methylpyridine-2-carbonyl)-1H-indol-3-yl]-1-[3-(tert-butoxycarbonylamino)-1-pyrrolidinyl]-1-ethanone The title compound was prepared according to the procedure described in Example 43 from [5-chloro-2-(4-methylpyridine)-1H-indol-3-yl]acetic acid (Example 36) and 3-(tert-butoxycarbonylamino)pyrrolidine.

$^1$H-NMR (CDCl$_3$) δ: 12.56 (1H, br s), 8.62 (1H, d, J=4.9 Hz), 8.18 (1H, br s), 7.78 (1H, br s), 7.42 (1H, d, J=8.9 Hz), 7.35 (1H, br d, J=4.9 Hz), 7.29 (2H, m), 4.89 (1H, br d, J=25.05), 4.36–3.45 (7H, m), 2.48 (3H, s), 2.35–1.80 (2H, m), 1.46 (9H, s).

Step 2. 2-[5-Chloro-2-(4-methylpyridine-2-carbonyl)-1H-indol-3-yl]-1-(3-amino-1-pyrrolidinyl)-1-ethanone The title compound was prepared according to the procedure described in step 2 of Example 271 from 2-[5-chloro-2-(4-methylpyridine-2-carbonyl)-1H-indol-3-yl]-1-[3-(tert-butoxycarbonylamino)-1-pyrrolidinyl]-1-ethanone (step 1).

MS (EI) m/z: 396 (M$^+$). m.p.: 179.2° C. IR (KBr) v: 3238, 2876, 1638, 1595, 1526, 1423, 1203 cm$^{-1}$; $^1$H-NMR (DMSO-d$_6$) δ: 12.26 (1H, br s), 8.68 (1H, d, J=4.9 Hz), 7.89 (1H, br s), 7.81 (1H, d, J=1.81 Hz), 7.65 (1H, d, J=8.9 Hz), 7.55 (1H, br d, J=5.1 Hz), 7.31 (dd, 1H, J=2.0 Hz, 8.7 Hz), 4.07 (1H, s), 4.05 (1H, s), 3.70–2.90 (5H, m), 2.46 (3H, s), 2.10–1.80 (1H, m), 1.75–1.45 (1H, m).

Example 274

Methyl[6-chloro-2-(4-chlorobenzoyl)-5-fluoro-1H-indol-3-]acetate

Step 1. Methyl trans-2-Amino-4-chloro-5-fluorocinnamate

The title compound was prepared according to the procedure described in step 1 of Example 133 from 2-bromo-5-chloro-4-fluoroaniline (JP 01311056 A2, Nippon Kayaku Co., Ltd., Japan).

$^1$H-NMR (CDCl$_3$) δ: 7.69 (1H, d, J=15.8 Hz), 7.15 (1H, d, J=9.7 Hz), 6.74 (1H, d, J=6.4 Hz), 6.31 (1H, d, J=15.8 Hz), 3.81 (3H, s).

Step 2. Methyl trans-4-Chloro-5-fluoro-2-(phenylsulfonylamino)cinnamate

The title compound was prepared according to the procedure described in step 1 of Example 8 (Method A) from methyl trans-2-amino-4-chloro-5-fluorocinnamate (step 1).

$^1$H-NMR (CDCl$_3$) δ: 7.71–7.68 (1H, m), 7.57–7.40 (6H, m), 7.23 (1H, d, J=9.4 Hz), 6.09 (1H, d, J=15.8 Hz), 3.77 (3H, s).

Step 3. Methyl[6-Chloro-2-(4-chlorobenzoyl)-5-fluoro-1H-indol-3-yl]acetate

The title compound was prepared according to the procedure described in Example 57 from methyl trans-4-chloro-5-fluoro-2-(phenylsulfonylamino)cinnamate (step 2).

$^1$H-NMR (CDCl$_3$) δ: 9.05 (1H, br.s), 7.74 (2H, d, J=8.7 Hz), 7.49 (2H, d, J=8.7 Hz), 7.35–7.32 (2H, m), 3.77 (2H, s), 3.66 (3H, s).

Example 275

[6-Chloro-2-(4-chlorobenzoyl)-5-fluoro-1H-indol-3-yl]Acetic Acid

The title compound was prepared according to the procedure described in Example 58 from methyl[6-chloro-2-(4-chlorobenzoyl)-5-fluoro-1H-indol-3-yl]acetate.

m.p.: 215–220° C. IR (KBr) v: 1709, 1626, 1585, 1529, 1456, 1439, 1279, 1250 cm$^{-1}$. $^1$H-NMR (DMSO-d$_6$) δ: 11.85 (1H, br.s), 7.79–7.75 (3H, m), 7.67–7.63 (2H, m), 7.60–7.58 (1H, m), 3.83 (2H, s).

Example 276

Methyl[6-chloro-5-fluoro-2-(4-Methylpridine-2-carbonyl)-1H-indol-3-yl]acetate

The title compound was prepared according to the procedure described in Example 57 from methyl trans-4-chloro-5-fluoro-2-(phenylsulfonylamino)cinnamate (Example 274, step 2).

$^1$H-NMR (CDCl$_3$) δ: 12.54 (1H, br.s), 8.58 (1H, d, J=4.9 Hz), 8.14 (1H, m), 7.56–7.53 (1H, m), 7.39–7.34 (2H, m), 4.25 (2H, s), 3.75 (3H, s), 2.48 (3H, s).

Example 277

[6-Chloro-5-fluoro-2-(4-methylpyridine-2-carbonyl)-1H-indol-3-yl]acetic Acid

The title compound was prepared according to the procedure described in Example 58 from methyl[6-chloro-5-fluoro-2-(4-methylpyridine-2-carbonyl)-1H-indol-3-yl]acetate (Example 276).

mp: 219.5° C. IR (KBr) v: 1732, 1709, 1647, 1597, 1529, 1279, 1252, 1204 cm$^{-1}$. $^1$H-NMR (DMSO-d$_6$) δ: 12.35 (1H, br.s), 8.70 (1H, d, J=5.1 Hz), 7.96 (1H, s), 7.87 (1H, d, J=6.6 Hz), 7.81 (1H, d, J=10.1 Hz), 7.59–7.58 (1H, m), 4.05 (2H, s), 2.47 (3H, s).

Example 278

Methyl[6-chloro-2-[4-(1-hydroxyethyl)pyridine-2-carbonyl]-1H-indol-3-yl]acetate

Step 1. Methyl[6-chloro-2-[4-(1-(tert-buthyldimethylsilyloxy)ethyl]pyridine-2-carbonyl]-1H-indol-3-yl]acetate The title compound was prepared according to the procedure described in Example 57 from methyl trans-4-chloro-2-(penylsulfonylamino)cinnamate (step 1 of Example 8, Method A) and 2-bromoacetyl-4-[1-(tert-butyldimethylsilyloxy)ethyl]pyridine*.

* 2-Bromoacetyl-4-[1-(tert-butyldimethylsilyloxy)ethyl]pyridine was prepared as follows;

$^1$H-NMR (CDCl$_3$) δ: 12.49 (1H, br s), 8.71 (1H, d, J=4.9 Hz), 8.24 (1H, d, J=1.5 Hz), 7.61–7.63 (2H, m), 7.53 (1H, d, J=1.8 Hz), 7.13 (1H, dd, J=1.8, 8.7 Hz), 4.96 (1H, q, J=6.4 Hz), 4.32 (2H,s), 3.73 (3H, s), 1.45 (3H, d, J=6.4 Hz), 0.93 (9H, s), 0.10 (3H, s), 0.03 (3H, s).

4-[1-(Trimethylsilyoxy)ethyl]-2-pyridinecarbonitrile:

The title compound was prepared from 4-(1-hydroxyethyl)pyridine-N-oxide (C. W. Muth et al., *J. Heterocycl. Chem.*, 1972, 9, 1299) according to the procedure for preparing 4-chloro-2-pyridinecarbonitrile described in Example 33.

$^1$H-NMR (CDCl$_3$) δ: 8.64 (1H, d, J=5.1 Hz), 7.69–7.70 (1H, m), 7.45–7.48 (1H, m), 4.88 (2H, q, J=6.4 Hz), 1.43 (3H, d, J=6.6 Hz), 0.14 (9H, s).

4-[1-(tert-Butyldimethylsilyloxy)ethyl]-2-pyridinecarbonitrile:

To a solution of 4-[1-(trimethylsilyoxy)ethyl]-2-pyridinecarbonitrile (39.04 g, 0.1624 mol) in THF (200 ml) was added a solution of tetrabutylammonium fluoride in THF (1M, 178.6 ml, 0.1786 mol) at room temperature. After stirring for 0.5 h, the mixture was concentrated. The residue was diluted with ethyl acetate (300 ml) and washed with water (200 ml). The aqueous layer was then extracted with dichloromethane (200 ml×2). The combined organic layers were dried (MgSO₄) and concentrated. The residual oil was dissolved in DMF (200 ml). To the solution was added tert-butyldimethylsilylchloride (36.72 g, 0.2436 mol) and imidazole (22.11 g, 0.3248 mol) at room temperture. After stirring for 19 h, diethyl ether (500 ml) and water (200 ml) were added to the mixture and the organic layer was separated. The organic layer was washed with water (100 ml×2), dried (MgSO₄) and concentrated. The residue was purified by flash column chromatography eluting with ethyl acetate/hexane (1:20) to give 39.23 g (92%) of the title compound as an oil.

$^1$H-NMR (CDCl₃) δ: 8.64 (1H, d, J=5.1 Hz), 7.67–7.68 (1H, m), 7.46–7.48 (1H, m), 4.89 (1H, q, J=6.4 Hz), 1.42 (3H, d, J=6.4 Hz), 0.92 (9H, s), 0.10 (6H, s).

2-Acetyl-4-[1-(tert-butyldimethylsilyloxy)ethyl]pyridine:

The title compound was prepared from 4-[1-(tert-butyldimethylsilyloxy)ethyl]-2-pyridinecarbonitrile according to the procedure for preparing 2-acetyl-4-chloropyridine described Example 33.

$^1$H-NMR (CDCl₃) δ: 8.62 (1H, d, J=4.9 Hz), 7.95–7.96 (1H, m), 7.49–7.52 (1H, m), 4.91 (1H, q, J=6.4 Hz), 2.73 (3H, s), 1.41 (3H, d, J=6.4 Hz), 0.91 (9H, s), 0.10 (6H, s).

2-Bromoacety-4-[1-(tert-butyldimethylsilyloxy)ethyl]pyridine

The title compound was prepared according to the procedure for preparing 2-bromoacetyl-4-(tert-butyldimethylsilyloxymethyl)pyridine described in Example 95 from 2-acetyl-4-[1-(tert-butyldimethylsilyloxy)ethyl]pyridine.

Step 2. Methyl[6-chloro-2-[4-(1-hydroxyethyl)pyridine-2-carbonyl]-1H-indol-3-yl]acetate.

The title compound was prepared according to the procedure described in step 2 of Example 95 from methyl[6-chloro-2-[4-[1-(tert-buthyldimethylsilyloxy)ethyl]pyridine-2-carbonyl]-1H-indol-3-yl]acetate (step 1).

$^1$H-NMR (DMSO-d₆) δ: 12.34 (1H, br s), 8.77 (1H, d, J=5.1 Hz), 8.11 (1H, s), 7.81 (1H, d, J=8.7 Hz), 7.75 (1H, d, J=1.6 Hz), 7.70 (1H, dd, J=1.2, 4.9 Hz), 7.13 (1H, dd, J=1.8, 8.6 Hz), 5.61 (1H, d, J=4.6 Hz), 4.84–4.93 (1H, m), 4.17 (2H, s), 3.59 (3H, s), 1.39 (3H, d, J=6.4 Hz).

Example 279

[6-Chloro-2-[4-(1-hydroxyethyl)pyridine-2-carbonyl]-1H-indol-3-yl]acetic Acid

The title compound was prepared according to the procedure described in Example 58 from methyl[6-chloro-2-[4-(1-hydroxyethyl)pyridine-2-carbonyl]-1H-indol-3-yl]acetate (Example 278).

m.p.: 193–194° C. IR (KBr) ν: 3464, 1707, 1632, 1591, 1526, 1250, 1225, 1192, 1144, 914 cm$^{-1}$. $^1$H-NMR (DMSO-d₆) δ: 12.30 (1H, br s), 8.78 (1H, d, J=5.1 Hz), 8.11 (1H, s), 7.79 (1H, d, J=8.6 Hz), 7.74 (1H, d, J=1.6 Hz), 7.71 (1H, d, J=5.3 Hz), 7.12 (1H, dd, J=1.8, 8.7 Hz), 5.60 (1H, d, J=4.4 Hz), 4.84–4.93 (1H, m), 4.09 (2H, s), 1.39 (3H, d, J=6.6 Hz).

Example 280

[6-Chloro-2-(4-ethyl-3-fluoropyridine-2-carbonyl)-1-H-indol-3-yl]acetic Acid

The title compound was prepared according to the procedure described in Example 112 from methyl[6-chloro-2-(4-ethyl-3-fluoropyridine-2-carbonyl)-1H-indol-3-yl]acetate (Example 113).

m.p.; 193–194° C. IR (KBr) ν: 3256, 1707, 1645, 1529, 1420, 1227, 1180, 1159, 1153 cm$^{-1}$. MS (EI) m/z: 360 (M⁺).

$^1$H-NMR (DMSO-d₆) δ: 11.84 (1H, br s), 8.46 (1H, d, J=5.3 Hz), 7.77 (1H, d, J=8.7 Hz), 7.67 (1H, t, J=5.1 Hz), 7.51 (1H, d, J=1.8 Hz), 7.12 (1H, dd, J=1.8, 8.6 Hz), 3.74 (2H, s), 2.76 (2H, q, J=7.6 Hz), 1.25 (3H, t, J=7.6 Hz).

Example 281

[6-Chloro-2-(2-nitrobenzoyl)-1H-indol-3-yl]acetic Acid

Step 1. Polymer-bound trans 4-Chloro-2-(phenylsulfonylamino)cinnamate

To a mixture of Wang resin (200–400 mesh, 1.37 g, ca. 0.89 mmol) and trans 4-chloro-2-(phenylsulfonylamino)cinnamic acid (600 mg, 1.77 mmol) was added dichloromethane (10 ml) and N,N-diisopropylethylamine (1.86 ml, 10.7 mmol). The mixture was allowed to stand for 1h, and then 4-dimethylaminopyridine (22 mg, 0.18 mmol) and WSC (339 mg, 1.77 mmol) were added. The mixture was agitated for 18 h and filtrated. The residual resin was washed with water (20 ml×3), methanol (20 ml×3), acetone (20 ml×3), dichloromethane (20 ml×3) and dried to give 1.65 g of the title compound.

Step 2. [6-Chloro-2-(2-nitrobenzoyl)-1H-indol-3-yl]acetic Acid

To a mixture of polymer-bound trans 4-chloro-2-(phenylsulfonylamino)cinnamate (step 1, 100 mg, 53 μmol) and 2-nitrophenacyl bromide (39 mg, 0.16 mmol) in acetone (3 ml) was added potassium carbonate (37 mg, 0.27 mmol). The mixture was agitated for 18 h. and filtrated. The residual resin was washed with water (20 ml×3), acetone (20 ml×3), dichloromethane (20 ml×3) and THF (20 ml×2) and dried. The resin was diluted with THF (4 ml) and then DBU was added (40 μl, 0.27 mmol). After agitating for 6 h, the resin was filtered off and washed with THF (20 ml×3), acetone (20 ml×3) and dichloromethane (20 ml×3). To the resin was added 95% trifluoroacetic acid in dichloromethane (5 ml) and the mixture was agitated for 3 h. The mixture was filtered and the residue was washed with dichloromethane (20 ml×5). The filtrate was concentrated and the residue was purified by HPLC (MeOH/AcONH₄ aquous solution=60/40–90/10) to give 3.2 mg (17%) of the title compound.

MS (ESI) m/z: 359 (MH⁺).

Example 282

[6-Chloro-2-(2,4-dimethoxybenzoyl)-1H-indol-3-yl]acetic Acid

The title compound was prepared according to the procedure described in Example 281 from 4-chloro-2-(phenylsulfonylamino)cinnamic acid.

MS (ESI) mn/z: 374 (MH⁺).

Example 283

[6-Chloro-2-(4-difuluoromethoxybenzoyl)-1H-indol-3-yl]acetic Acid

The title compound was prepared according to the procedure described in Example 289 from 4-chloro-2-(phenylsulfonylamino)cinnamic acid.

MS (ESI) m/z: 380 (MH⁺).

Example 284

[6-Chloro-2-(2,5-dimethoxybenzoyl)-1H-indol-3-yl]acetic Acid

The title compound was prepared according to the procedure described in Example 281 from 4-chloro-2-(phenylsulfonylamino)cinnamic acid.

MS (ESI) m/z: 374 (MH⁺).

Example 285

Methyl[5-acetyl-2-(4-chlorobenzoyl)-1H-indol-3-yl] acetate

Step 1. 4-Acetyl-2-bromoaniline

To a stirred suspension of 4-acetamido-3-bromoacetophenone in ethanol (12 ml) was added dropwise hydrochloric acid (3 ml) at 0° C. The reaction mixture was stirred under reflux condition for 4.5 h. The mixture was cooled and concentrated. The residual solids were partitioned between saturated aqueous sodium bicarbonate (50 ml) and diethyl ether (50 ml). The aqueous layer was extracted with ethyl acetate (50 ml×2). The combined organic layers were dried (MgSO$_4$) and concentrated to afford 1.79 g (quant.) of the title compound as a brown oil.

$^1$H-NMR (CDCl$_3$) δ: 8.06 (1H, d, 1.97 Hz), 7.76–7.72 (1H, m), 6.74 (1H, d, 8.40 Hz), 4.60 (1H, br s), 2.50 (s, 3H).

Step 2. Methyl trans-(5-Acetyl-2-amino)cinnamate

The title compound was prepared according to the procedure described in step 1 of Example 133 from 4-acetyl-2-bromoaniline (step 1) and methyl acrylate.

$^1$H-NMR (CDCl$_3$) δ: 8.02 (1H, d, 2.13 Hz), 7.81–7.75 (2H, m), 6.70 (1H, d, 8.56 Hz), 6.44 (1H, d, 15.8 Hz), 4.55 (2H, br s), 3.81 (3H, s), 2.53 (3H, s).

Step 3. Methyl trans-5-Acetyl-2-(p-toluenesulfonylamino) cinnamate

The title compound was prepared according to the procedure described in step 1 of Example 8 (Method A) from methyl trans-(5-acetyl-2-amino)cinnamate (step 2) and p-toluenesulfonyl chloride.

$^1$H-NMR (CDCl$_3$) δ: 8.01 (1H, d, 2.00 Hz), 7.89 (1H, dd, 8.59 Hz, 1.97 Hz), 7.68–7.22 (7H, m), 6.30 (1H, s), 6.15 (1H, d, 15.8 Hz), 3.81 (3H, s), 2.57 (3H, s), 2.38 (3H, s).

Step 4. Methyl[5-acetyl-2-(4-chlorobenzoyl)-1H-indol-3-yl] acetate

The title compound was prepared according to the procedure described in Example 57 from methyl trans-5-acetyl-3-(p-toluenesulfonylamino)cinnamate (step 3) and 4-chlorophenacyl bromide.

$^1$H-NMR (CDCl$_3$) δ: 9.2 (1H, br s), 8.34–7.75 (4H, m), 7.52–7.45 (3H, m), 3.89 (2H, s), 3.69 (3H, s), 2.68 (3H, s).

Example 286

[5-Acetyl-2-(4-chlorobenzoyl)-1H-indol-3-yl]acetic Acid

The title compound was prepared according to the procedure described in Method B of Example 9 from methyl [5-acetyl-2-(4-chlorobenzoyl)-1H-indol-3-yl]acetate (Example 285).

m.p.: 225° C. IR (KBr) v: 3281, 1703, 1666, 1643, 1614, 1574, 1539, 1452, 1425, 1402, 1364, 1263, 1240, 1178, 1092, 1011, 959 cm$^{-1}$. $^1$H-NMR (DMSO-d$_6$) δ: 12.01 (1H, br s), 8.49 (1H, br s), 7.93–7.89 (1H, m), 7.78 (2H, d, 8.56 Hz), 7.65 (d, 2H, 8.56 Hz), 7.52 (1H, d, 8.72 Hz), 3.93 (2H, s), 2.63 (3H, s).

Example 287

Methyl[6-fluoro-2-(4-Methylpridine-2-carbonyl)-1H-indol-3-yl]acetate

Step 1. Methyl trans-(4-Fluoro-2-nitro)cinnamate

The title compound was prepared according to the procedure described in step 1 of Example 133 from 3-fluoro-6-iodonitrobenzene and methyl acrylate.

$^1$H-NMR (CDCl$_3$) δ: 8.67 (1H, d, 15.8 Hz), 7.78 (1H, dd, 8.07 Hz, 2.65 Hz), 7.68–7.63 (2H, m), 6.34 (1H, d, 15.8 Hz), 3.84 (3H, s).

Step 2. Methyl trans-(2-Amino-4-fluoro)cinnamate

The title compound was prepared according to the procedure described in step 2 of Example 36 from methyl trans-(4-fluoro-2-nitro)cinnamate (step 1).

$^1$H-NMR (CDCl$_3$) δ: 7.75 (1H, d, 15.8 Hz), 7.37–7.31 (1H, m), 6.50–6.37 (2H, m), 6.32–6.26 (1H, m), 4.13 (2H, br s), 3.80 (3H, s).

Step 3. Methyl trans-4-Fluoro-2-(p-toluenesulfonylamino) cinnamate

The title compound was prepared according to the procedure described in step 1 of Example 8 (Method A) from methyl trans-(2-amino-4-fluoro)cinnamate (step 2).

$^1$H-NMR (CDCl$_3$) δ: 7.64 (1H, d, 8.40 Hz), 7.46–7.19 (4H, m), 6.94–6.87 (1H, m), 6.77 (1H, s), 6.16–6.10 (1H, m), 3.79 (3H, s), 2.38 (3H, s).

Step 4. Methyl[6-fluoro-2-(4-methylpridine-2-carbonyl)-1H-indol-3-yl]acetate

The title compound was prepared according to the procedure described in Example 57 from methyl trans-4-fluoro-2-(p-toluenesulfonylamino)cinnamate (step 3).

$^1$H-NMR (CDCl$_3$) δ: 12.49 (1H, br s), 8.61 (1H, d, 4.94 Hz), 8.17–7.61 (2H, m), 7.36–7.14 (2H, m), 6.98–6.90 (1H, m), 4.31 (2H, s), 3.73 (3H, s), 2.47 (3H, s).

Example 288

[6-Fluoro-2-(4-methylpridine-2-carbonyl)-1H-indol-3-yl]acetic Acid

The title compound was prepared according to the procedure described in Example 9 (Method B) from methyl[6-fluoro-2-(4-methylpyridine-2-carbonyl)-1H-indol-3-yl] acetate (Example 287).

m.p.: 208° C. IR (KBr) v: 3238, 1701, 1638, 1597, 1533, 1398, 1281, 1211, 1132, 1003 cm$^{-1}$. $^1$H-NMR (CDCl$_3$) δ: 12.28 (1H, br s), 8.70 (1H, d, 4.94 Hz), 7.96 (1H, s), 7.83–7.77 (1H, m), 7.57 (1H, d, 4.94 Hz), 7.42 (1H, dd, 10.2 Hz, 2.13 Hz), 7.03–6.95 (1H, m), 4.09 (2H, s), 2.47 (3H, s).

Example 289

Methyl[6-fluoro-2-(4-chlorobenzoyl)-1H-indol-3-yl] acetate

The title cornpound was prepared according to the procedure described in Example 57 from methyl trans-4-fluoro-3-(p-toluenesulfonylamino)cinnamate (step 3 of Example 287) and 4-chlorophenacylbromide.

$^1$H-NMR (CDCl$_3$) δ: 9.10 (1H, br s), 7.76–7.71 (2H, m), 7.60–7.54 (2H, m), 7.50–7.45 (2H, m), 7.04–6.90 (2H, m), 3.81 (2H, s), 3.66 (3H, s).

Example 290

[6-Fluoro-2-(4-chlorobenzoyl)-1H-indol-3-yl]acetic Acid

The title compound was prepared according to the proceduie described in Example 9 (Method B) from methyl[6-fluoro-2-(4-chlorobenzoyl)-1H-indol-3-yl]acetate (Example 289).

m.p.: 214° C. IR (KBr) v: 3335, 1699, 1618, 1605, 1587, 1531, 1425, 1327, 1267, 1231, 1134, 1094, 1001 cm$^{-1}$. $^1$H-NMR (DMSO-d$_6$) δ: 11.73 (1H, br s), 7.78–7.63 (5H, m), 7.17 (1H, dd, 9.72 Hz, 2.13 Hz), 7.04–6.96 (1H, m), 3.84 (2H, s).

Example 291

[2-(4-Methylpyridine-2-carbonyl)-5-methylthio-1H-indol-3-yl]acetic Acid

Step 1. Methyl trans-(2-Amino-5-methylthio)cinnamate

The title compound was prepared according to the procedure described in step 1 of Example 133 from 2-bromo-4-methylthioxyaniline (JP80-122756) and methyl acrylate.

¹H-NMR (CDCl₃) δ: 7.77 (1H, d, 15.8 Hz), 7.38 (1H, d, 2.13 Hz), 7.19 (1H, dd, 8.40 Hz, 2.13 Hz), 6.66 (1H, d, 8.40 Hz), 6.36 (1H, d, 15.8 Hz), 3.97 (1H, br s), 3.80 (3H, s), 2.43 (3H, s).

Step 2. Methyl trans-2-p-Toluenesulfonylamino-5-methylthiocinnamate

The title compound was prepared according to the procedure described in step 1 of Example 8 from methyl trans-(2-amino-4-methylthio)cinnamate (step 1) and p-toluenesulfonyl chloride.

¹H-NMR (CDCl₃) δ: 7.81 (2H, d, 8.40 Hz), 7.56–6.91 (8H, m), 6.13 (1H, d, 15.6 Hz), 3.79 (3H, s), 2.46 (3H, s), 2.39 (3H, s).

Step 3. Methyl[2-(4-methylpyridine-2-carbonyl)-5-methylthio-1H-indol-3-yl]acetate The title compound was prepared according to the procedure described in Example 57 from methyl trans-2-p-toluenesulfonylamino-5-methylthiocinnamate (step 2) and 2-bromoacetyl-4-methylpyridine hydrobromide (Preparation is described in step 2 of Example 31).

¹H-NMR (CDCl₃) δ: 12.47 (1H, br s), 8.62 (1H, d, 4.78 Hz), 8.19–8.17 (1H, m), 7.65–7.62 (1H, m), 7.47–7.30 (3H, m), 4.31 (2H, s), 3.73 (3H, s), 2.48 (3H, s).

Example 292

[2-(4-Methylpyridine-2-carbonyl)-5-methylthio-1H-indol-3-yl]acetic Acid

The title compound was prepared according to the procedure described in Method B of Example 9 from methyl [2-(4-methylpyridine-2-carbonyl)-5-methylthio-1H-indol-3-yl]acetate (Example).

¹H-NMR (DMSO-d₆) δ: 12.22 (1H, br s), 8.70 (1H, d, 4.62 Hz), 7.95–7.17 (4H, m), 4.08 (2H, s), 2.47 (3H, s), 2.35 (3H, s). MS (EI) m/z: 340 (M⁺).

Example 293

3-[4-Chloro-2-(toluene-4-sulfonylamino)-phenyl]-acrylic Acid Ethyl Ester

To 3-(2-amino-4-chloro-phenyl)-acrylic acid ethyl ester (18.0g, 79.8 mmol) in dichloromethane (144 ml) was added pyridine (9.04 ml, 112 mmol) and p-toluenesulfonyl chloride (16.0g, 83.9 mmol). The reaction was stirred at room temperature for 18 hours and poured into 1N hydrochloric acid (150 ml). The layers were separated and the organic layer was dried over magnesium sulfate, filtered, and concentrated. The resulting solid was slurried in hexanes and filtered to afford 3-[4-chloro-2-(toluene-4-sulfonylamino)-phenyl]-acrylic acid ethyl ester (28.3g, 93%). mp=124–127° C. ¹H NMR (300 MHz, CDCl₃) d 1.35 (t, 3, J=7.2), 2.40 (s, 3), 4.27 (q, 2, J=7.2), 6.12 (dd, 1, J=15.9, 0.9), 7.20–7.39 (m, 4), 7.39 (d, 1, J=8.6), 7.48–7.53 (m, 2), 7.62 (d, 2, J=8.3). ¹³C NMR (75 MHz, CDCl₃) d 15.50, 22.79, 62.24, 122.48, 127.98, 128.49, 129.34, 129.50, 131.05, 136.82, 137.00, 137.73, 138.93, 145.55, 167.59. IR 3214, 1694, 1631, 1318, 1167 cm⁻¹. Analysis calculated for C₁₈H₁₈ClNO₄S: C, 56.91; H, 4.78; N, 3.69. Found: C, 57.10; H, 5.08; N, 3.70.

Example 294

[6-Chloro-2-(4-chloro-benzoyl)-1H-indol-3-yl]-acetic Acid

To a solution of 3-[4-chloro-2-(toluene-4-sulfonylamino)-phenyl]-acrylic acid ethyl ester (13.0g, 34.2 mmol) in N,N-dimethylacetamide (120 ml) was added potassium carbonate (9.45 g, 68.4 mmol) and 2-bromo-4'-chloroacetophenone (8.78 g, 37.6 mmol) and the reaction was stirred at room temperature for 15 minutes. 1N Sodium hydroxide (130 ml) was added and the reaction mixture was heated to 100° C. for 8 hours. The reaction mixture was cooled to room temperature and poured into a separatory funnel and washed with methyl t-butyl ether (2×200 ml). The aqueous layer was acidified to pH 1 with 6N hydrochloric acid and was extracted with ethyl acetate (150 ml). The solvent was removed under reduced pressure and to the resulting oil was added isopropyl alcohol (24 ml) and water (48 ml). A solid precipitated and the slurry was stirred 12 hours. The precipitate was filtered, washed with water, and dried to provide [6-chloro-2-(4-chloro-benzoyl)-1H-indol-3-yl]-acetic acid (9.73 g, 82%). mp 181–183° C. ¹H NMR (400 MHz, d₆-DMSO) d 3.79 (s, 2), 7.08 (dd, 1, J=8.5, 1.9), 7.42 (d, 1, J=1.9), 7.60 (d, 2, J=8.5), 7.62–7.73 (m, 3), 11.74 (bs, 1), 12.22 (bs, 1). ¹³C NMR (75 MHz, d₆-DMSO) d 31.74, 113.25, 118.00, 121.93, 123.96, 127.69, 130.10, 131.30, 132.02, 133.59, 138.02, 138.37, 138.58, 173.20, 188.29. IR 3314, 1710, 1700, 1618, 1522, 1323, 1227, 1093, 941 cm⁻¹. Analysis calculated for C₁₇H₁₁Cl₂NO₃: C, 58.64; H, 3.18; N, 4.02. Found: C, 58.58; H, 3.22; N, 3.93.

Example 295

3-{4-Chloro-2-[[2-(4-chloro-phenyl)-2-oxo-ethyl]-(toluene-4-sulfonyl)-amino]-phenyl}-acrylic Acid Ethyl Ester To a solution of 3-[4-chloro-2-(toluene-4-sulfonylamino)-phenyl]-acrylic acid ethyl ester (3.00 g, 7.90 mmol) in N,N-dimethylacetamide (15.0 ml) was added potassium carbonate (2.18 g, 15.8 mmol) and 2-bromo-4'-chloroacetophenone (2.03 g, 8.69 mmol). The reaction was stirred for 30 minutes, poured into 1N hydrochloric acid (30 ml) and extracted with methyl f-butyl ether (2×30 ml). The organic extracts were dried over magnesium sulfate, filtered, concentrated to a low volume. Hexanes was added and a solid precipitated. The precipitate was filtered to provide 3-{4-chloro-2-[[2-(4-chloro-phenyl)-2-oxo-ethyl]-(toluene-4-sulfonyl)-amino]-phenyl}-acrylic acid ethyl ester (3.19 g, 76%). mp=162–165° C. ¹H NMR (300 MHz, CDCl₃) d 1.38 (t, 3, J=7.2), 2.47 (s, 3), 4.28 (q, 2, J=7.2), 5.00 (bs, 2), 6.23 (d, 1, J=16.0), 7.29–7.36 (m, 4), 7.47 (d, 2, J=8.7), 7.54 (d, 1, J=8.4), 7.59 (d, 2, J=8.3), 7.74 (d, 1, J=16.0), 7.88 (d, 2, J=8.7). ¹³C NMR (75 MHz, CDCl₃) d 14.33, 21.62, 57.72, 60.66, 112.49, 120.69, 128.07, 129.21, 129.58, 129.70, 131.22, 132.80, 133.83, 134.80, 135.84, 138.55, 139.28, 140.38, 144.46, 166.02, 191.70. IR 1720, 1698, 1590, 1338, 1313, 1179, 1161, 1089 cm⁻¹. Analysis calculated for C₂₆H₂₃Cl₂NO₅S: C, 58.65; H, 4.35; N, 2.63. Found: C, 58.74; H, 4.56; N, 2.72.

Example 296 cis- and trans-[6-Chloro-2-(4-chloro-benzoyl)-1-(toluene-4-sulfonyl)-2,3-dihydro-1H-indol-3-yl]-acetic Acid Ethyl Ester To 3-{4-chloro-2-[[2-(4-chloro-phenyl)-2-oxo-ethyl]-(toluene-4-sulfonyl)-amino]-phenyl}-acrylic acid ethyl ester (1.00 g, 1.88 mmol) in N,N-dimethylacetamide (5.0 ml) was added potassium carbonate (0.520 g, 3.76 mmol). The reaction mixture was stirred for four hours, poured in 1N hydrochloric acid (30 ml) and extracted with methyl 1-butyl ether (2×30 ml). The organic extracts were dried with magnesium sulfate, filtered, and concentrated. The resulting solid was purified by chromatography on silica gel (ethyl acetate/hexanes 20/80) to provide [6-chloro-2-(4-chloroenzoyl)-1-(toluene-4-sulfonyl)-2,3-dihydro-1H- indol-3-yl]-acetic acid ethyl ester as a 1 to 9 mixture of cis and trans isomers (0.488 g, 49%). Some of the $^1$H NMR (300 MHz, CDCl$_3$) significant signals are: d 1.09 (t, J=7.2), 1.19 (t, J=7.2), 2.44 (s), 5.40 (d, J=4.0), 5.99 (d, J=9.7), 6.92 (dd, J=8.1, 1.1), 7.04 (dd, J=8.1, 1.9), 7.52 (d, J=8.4), 7.57 (d, J=1.9), 7.73 (d, J=8.3), 7.99 (d, J=8.6). Lc-MS analysis was performed on the mixture of diastereoisomers and indicated to products with identical mass of 531 (M+H$^+$).

Example 297

[6-Chloro-2-(4-chloro-benzoyl)-1H-indol-3-yl]-acetic Acid Ethyl Ester

To a solution of 3-[4-chloro-2-(toluene-4-sulfonylamino)-phenyl]-acrylic acid ethyl ester (3.00 g, 7.90 mmol) in N,N-dimethylacetamide (15.0 ml) was added potassium carbonate (2.18 g, 15.8 mmol) and 2-bromo-4'-chloroacetophenone (2.03 g, 8.69 mmol). The reaction was stirred 30 minutes and 1,8-diazabicyclo[5.4.0]undec-7-ene (3.54 ml, 23.7 mmol) was added. The reaction mixture was stirred one hour, poured into 1N hydrochloric acid (30 ml) and extracted with methyl t-butyl ether (2×30 ml). The organic extracts were dried with magnesium sulfate, filtered, and concentrated to provide a solid which was slurried in a mixture of methyl t-butyl ether and hexanes to afford [6-chloro-2-(4-chloro-benzoyl)-1H-indol-3-yl]-acetic acid ethyl ester (2.42 g, 81%). mp=186–188° C. $^1$H NMR (300 MHz, CDCl$_3$) d 1.27 (t, 2, J=7.1), 3.80 (s, 2), 4.11 (q, 2, J=7.1), 7.15 (ddd, 1, J=8.5, 1.7, 0.5), 7.28–7.30 (m, 1), 7.48 (d, J=8.3), 7.54–7.57 (m, 1), 7.77 (d, 2, J=8.3), 9.16 (bs, 1). $^{13}$C NMR (75 MHz, CDCl$_3$) d 15.42, 32.29, 62.45, 113.27, 117.60, 122.99, 123.23, 127.85, 130.12, 131.77, 133.61, 137.86, 138.13, 140.10, 172.45, 188.25. IR 3305, 1732, 1618, 1323 cm$^{-1}$. Analysis calculated for C$_{19}$H$_{15}$Cl$_2$NO$_3$: C, 60.65; H, 4.02; N, 3.72. Found: C, 60.70; H, 3.97; N, 3.71.

Example 298

[6-Chloro-2-(4-chloro-benzoyl)-1H-indol-3-yl]-acetic Acid

To a solution of [6-chloro-2-(4-chloro-benzoyl)-1H-indol-3-yl]-acetic acid ethyl ester (200 mg, 0.532 mmol) in methanol (2 ml) and water (0.8 ml) was added sodium hydroxide (137 mg, 3.43 mmol). The reaction mixture was stirred 24 hours, and was concentrated to a low volume. Water (4 ml) was added, the material was transferred to a separatory funnel and was washed with dichloromethane (5 ml). The aqueous layer was acidified to pH 1 with 1N hydrochloric acid and was extracted with ethyl acetate (15 ml). The organic layer was dried over magnesium sulfate, filtered, and concentrate to afford [6-chloro-2-(4-chloro-benzoyl)-1H-indol-3-yl]-acetic acid (150 mg, 81%). The $^1$H NMR spectrum was identical with the one obtained for the compound prepared by the method described in example 2.

The chemical structures of the compounds prepared in the Examples 1 to 292 are summarized in the following tables.

TABLE

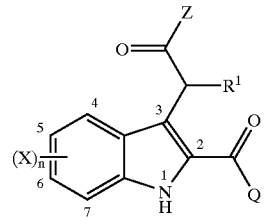

| Ex. # | (X)$_n$ | R$^1$ | Z | Q |
|---|---|---|---|---|
| 1 | 6-Cl | H | ethoxy | phenyl |
| 2 | 6-Cl | H | OH | phenyl |
| 3 | 6-Cl | H | ONa | phenyl |
| 4 | 6-Cl | H | OH | 2-methylphenyl |
| 5 | 6-Cl | H | OH | 3-methylphenyl |
| 6 | 6-Cl | H | OH | 4-methylphenyl |
| 7 | 6-Cl | H | OH | 3-chlorophenyl |
| 8 | 6-Cl | H | methoxy | 4-chlorophenyl |
| 9 | 6-Cl | H | OH | 4-chlorophenyl |
| 10 | 6-Cl | H | OH | 3-fluorophenyl |
| 11 | 6-Cl | H | OH | 4-fluorophenyl |
| 12 | 6-Cl | H | OH | 3-bromophenyl |
| 13 | 6-Cl | H | OH | 4-bromophenyl |
| 14 | 6-Cl | H | OH | 3-CF$_3$-phenyl |
| 15 | 6-Cl | H | OH | 4-CF$_3$-phenyl |
| 16 | 6-Cl | H | OH | 3,4-dichlorophenyl |
| 17 | 4-Cl | H | OH | phenyl |
| 18 | 5-Cl | H | OH | 3-methylphenyl |
| 19 | 5-Cl | H | OH | 4-chlorophenyl |
| 20 | 5-Cl | H | OH | 3-chlorophenyl |
| 21 | 5-F | H | OH | 4-chlorophenyl |
| 22 | 5-F | H | OH | 3-chlorophenyl |
| 23 | 5-methoxy | H | OH | 3-methylphenyl |
| 24 | 7-Cl | H | OH | phenyl |
| 25 | 4,5-di-Cl | H | OH | phenyl |
| 26 | 4,6-di-Cl | H | OH | phenyl |
| 27 | 5,6-di-Cl | H | OH | phenyl |
| 28 | 6-Cl (racemic) | methyl | OH | phenyl |

TABLE-continued

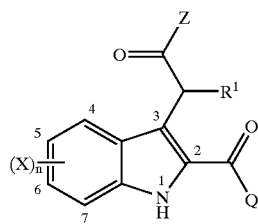

| Ex. # | $(X)_n$ | $R^1$ | Z | Q |
|---|---|---|---|---|
| 29 (less polar antipode) | 6-Cl | methyl | OH | phenyl |
| 30 (more polar antipode) | 6-Cl | methyl | OH | phenyl |
| 31 | 6-Cl | H | OH | 4-methyl-2-pyridyl |
| 32 | 6-Cl | H | OH | 5-methyl-2-pyridyl |
| 33 | 6-Cl | H | methoxy | 4-chloro-2-pyridyl |
| 34 | 6-Cl | H | OH | 4-chloro-2-pyridyl |
| 35 | 6-Cl | H | OH | 2-pyridyl |
| 36 | 5-Cl | H | OH | 4-methyl-2-pyridyl |
| 37 | 5-Cl | H | methoxy | 6-methyl-2-pyridyl |
| 38 | 5-Cl | H | OH | 6-methyl-2-piridyl |
| 39 | 6-Cl | H | OH | 1-methyl-2-imidazolyl |
| 40 | 5-Cl | H | methoxy | 2-thiazolyl |
| 41 | 5-Cl | H | OH | 2-thiazolyl |
| 42 | 6-Cl | H | methoxy | phenyl |
| 43 | 6-Cl | H | dimethylamino | phenyl |
| 44 | 6-Cl | H | methylamino | phenyl |
| 45 | 6-Cl | H | amino | phenyl |
| 46 | 6-Cl | H | N-methoxy-N-methylamino | phenyl |
| 47 | 6-Cl | H | piperidino | phenyl |
| 48 | 6-Cl | H | 4-methyl-1-piperazinyl | phenyl |
| 49 | 6-Cl | H | 2-cyanoethylamino | phenyl |
| 50 | 6-Cl | H | 2-HO-ethylamino | phenyl |
| 51 | 6-Cl | H | morpholino | phenyl |
| 52 | H | H | OH | 4-chlorophenyl |
| 53 | 6-Cl | H | OH | 2-furyl |
| 54 | 6-Cl | H | OH | cyclohexyl |
| 55 | 6-Cl | H | OH | 4-methoxyphenyl |
| 56 | 6-Cl | H | methoxy | 4-methoxyphenyl |
| 57 | 6-Cl | H | methoxy | 4-ethyl-2-pyridyl |
| 58 | 6-Cl | H | OH | 4-ethyl-2-pyridyl |
| 59 | 5-Cl | H | methoxy | 4-ethyl-2-pyridyl |
| 60 | 5-Cl | H | OH | 4-ethyl-2-pyridyl |
| 61 | 6-Cl | H | methoxy | 4-isopropyl-2-pyridyl |
| 62 | 6-Cl | H | OH | 4-isopropyl-2-pyridyl |
| 63 | 5-Cl | H | methoxy | 4-isopropyl-2-pyridyl |
| 64 | 5-Cl | H | OH | 4-isopropyl-2-pyridyl |
| 65 | 6-Cl | H | methoxy | 4-n-propyl-2-pyridyl |
| 66 | 6-Cl | H | OH | 4-n-propyl-2-pyridyl |
| 67 | 5-Cl | H | methoxy | 4-n-propyl-2-pyridyl |
| 68 | 5-Cl | H | OH | 4-n-propyl-2-pyridyl |
| 69 | 6-Cl | H | methoxy | 4-tert-butyl-2-pyridyl |
| 70 | 6-Cl | H | OH | 4-tert-butyl-2-pyridyl |
| 71 | 5-Cl | H | methoxy | 4-tert-butyl-2-pyridyl |
| 72 | 5-Cl | H | OH | 4-tert-butyl-2-pyridyl |
| 73 | 6-Cl | H | methoxy | 3-methyl-2-pyridyl |
| 74 | 6-Cl | H | OH | 3-methyl-2-pyridyl |
| 75 | 5-Cl | H | methoxy | 3-methyl-2-pyridyl |
| 76 | 5-Cl | H | OH | 3-methyl-2-pyridyl |
| 77 | 6-Cl | H | methoxy | 6-methyl-2-pyridyl |
| 78 | 6-Cl | H | OH | 6-methyl-2-pyridyl |
| 79 | 5-Cl | H | methoxy | 5-methyl-2-pyridyl |
| 80 | 5-Cl | H | OH | 5-methyl-2-pyridyl |
| 81 | 6-Cl | H | methoxy | 5-$CF_3$-2-pyridyl |
| 82 | 6-Cl | H | OH | 5-$CF_3$-2-pyridyl |
| 83 | 5-Cl | H | methoxy | 5-$CF_3$-2-pyridyl |
| 84 | 5-Cl | H | OH | 5-$CF_3$-2-pyridyl |
| 85 | 5-Cl | H | methoxy | 5-Cl-2-pyridyl |
| 86 | 5-Cl | H | OH | 5-Cl-2-pyridyl |
| 87 | 6-Cl | H | methoxy | 5-Cl-2-pyridyl |
| 88 | 6-Cl | H | OH | 5-Cl-2-pyridyl |
| 89 | 5-Cl | H | methoxy | 4-Cl-2-pyridyl |
| 90 | 5-Cl | H | OH | 4-Cl-2-pyridyl |

TABLE-continued

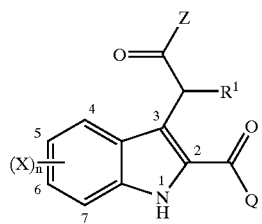

| Ex. # | (X)$_n$ | R$^1$ | Z | Q |
|---|---|---|---|---|
| 91 | 6-Cl | H | methoxy | 3-pyridyl |
| 92 | 6-Cl | H | OH | 3-pyridyl |
| 93 | 6-Cl | H | methoxy | 4-pyridyl |
| 94 | 6-Cl | H | OH | 4-pyridyl |
| 95 | 6-Cl | H | methoxy | 4-hydroxymethyl-2-pyridyl |
| 96 | 6-Cl | H | OH | 4-hydroxymethyl-2-pyridyl |
| 97 | 5-Cl | H | methoxy | 4-hydroxymethyl-2-pyridyl |
| 98 | 5-Cl | H | OH | 4-hydroxymethyl-2-pyridyl |
| 99 | 5-Cl | H | methoxy | 3,4-dimethyl-2-pyridyl |
| 100 | 5-Cl | H | OH | 3,4-dimethyl-2-pyridyl |
| 101 | 5-Cl | H | methoxy | 4,5-dimethyl-2-pyridyl |
| 102 | 5-Cl | H | OH | 4,5-dimethyl-2-pyridyl |
| 103 | 6-Cl | H | methoxy | 4,5-dimethyl-2-pyridyl |
| 104 | 6-Cl | H | OH | 4,5-dimethyl-2-pyridyl |
| 105 | 6-Cl | H | methoxy | 4-methoxy-2-pyridyl |
| 106 | 6-Cl | H | OH | 4-methoxy-2-pyridyl |
| 107 | 5-Cl | H | methoxy | 4-methoxy-2-pyridyl |
| 108 | 5-Cl | H | OH | 4-methoxy-2-pyridyl |
| 109 | 6-Cl | H | methoxy | 3,5-dimethyl-2-pyridyl |
| 110 | 6-Cl | H | OH | 3,5-dimethyl-2-pyridyl |
| 111 | 5-Cl | H | methoxy | 3-F-4-ethyl-2-pyridyl |
| 112 | 5-Cl | H | OH | 3-F-4-ethyl-2-pyridyl |
| 113 | 6-Cl | H | methoxy | 3-F-4-ethyl-2-pyridyl |
| 114 | 6-Cl | H | OH | 3-C$_2$H$_5$O-4-ethyl-2-pyridyl |
| 115 | 6-Cl | H | methoxy | 3-Cl-4-ethyl-2-pyridyl |
| 116 | 6-Cl | H | OH | 3-Cl-4-ethyl-2-pyridyl |
| 117 | 5-Cl | H | methoxy | 3-Cl-4-ethyl-2-pyridyl |
| 118 | 5-Cl | H | OH | 3-Cl-4-ethyl-2-pyridyl |
| 119 | 5-Cl | H | methoxy | 4,6-dimethyl-2-pyridyl |
| 120 | 5-Cl | H | OH | 4,6-dimethyl-2-pyridyl |
| 121 | 6-Cl | H | methoxy | 4,6-dimethyl-2-pyridyl |
| 122 | 6-Cl | H | OH | 4,6-dimethyl-2-pyridyl |
| 123 | 5,6-di-Cl | H | methoxy | 4-methyl-2-pyridyl |
| 124 | 5,6-di-Cl | H | OH | 4-methyl-2-pyridyl |
| 125 | 5-methyl | H | methoxy | 4-methyl-2-pyridyl |
| 126 | 5-methyl | H | OH | 4-methyl-2-pyridyl |
| 127 | 5-F | H | methoxy | 4-methyl-2-pyridyl |
| 128 | 5-F | H | OH | 4-methyl-2-pyridyl |
| 129 | 5-methoxy | H | methoxy | 4-methyl-2-pyridyl |
| 130 | 5-methoxy | H | OH | 4-methyl-2-pyridyl |
| 131 | 6-methoxy | H | methoxy | 4-methyl-2-pyridyl |
| 132 | 6-methoxy | H | OH | 4-methyl-2-pyridyl |
| 133 | 5-ethyl | H | methoxy | 4-methyl-2-pyridyl |
| 134 | 5-ethyl | H | OH | 4-methyl-2-pyridyl |
| 135 | 5-ethyl | H | methoxy | 4-ethyl-2-pyridyl |
| 136 | 5-ethyl | H | OH | 4-ethyl-2-pyridyl |
| 137 | 6-ethyl | H | methoxy | 4-methyl-2-pyridyl |
| 138 | 6-ethyl | H | OH | 4-methyl-2-pyridyl |
| 139 | 5-isopropyl | H | methoxy | 4-ethyl-2-pyridyl |
| 140 | 5-isopropyl | H | OH | 4-methyl-2-pyridyl |
| 141 | 6-CF$_3$ | H | methoxy | 4-methyl-2-pyridyl |
| 142 | 6-CF$_3$ | H | OH | 4-methyl-2-pyridyl |
| 143 | 5-tert-butyl | H | methoxy | 4-methyl-2-pyridyl |
| 144 | 5-tert-butyl | H | OH | 4-methyl-2-pyridyl |
| 145 | 5-CF$_3$O | H | methoxy | 4-methyl-2-pyridyl |
| 146 | 5-CF$_3$O | H | OH | 4-methyl-2-pyridyl |
| 147 | 5-CF$_3$O | H | methoxy | 4-ethyl-2-pyridyl |
| 148 | 5-CF$_3$O | H | OH | 4-ethyl-2-pyridyl |
| 149 | 6-methyl | H | methoxy | 4-methyl-2-pyridyl |
| 150 | 6-methyl | H | OH | 4-methyl-2-pyridyl |
| 151 | 5-CF$_3$ | H | methoxy | 4-methyl-2-pyridyl |
| 152 | 5-CF$_3$ | H | OH | 4-methyl-2-pyridyl |
| 153 | 5-CF$_3$ | H | methoxy | 4-ethyl-2-pyridyl |
| 154 | 5-CF$_3$ | H | OH | 4-ethyl-2-pyridyl |
| 155 | H | H | methoxy | phenyl |

TABLE-continued

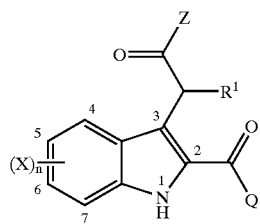

| Ex. # | (X)$_n$ | R$^1$ | Z | Q |
|---|---|---|---|---|
| 156 | H | H | OH | phenyl |
| 157 | 6-methyl | H | methoxy | 4-chlorophenyl |
| 158 | 6-methyl | H | OH | 4-chlorophenyl |
| 159 | 5-methyl | H | OH | 4-chlorophenyl |
| 160 | 6-methoxy | H | methoxy | 4-chlorophenyl |
| 161 | 6-methoxy | H | OH | 4-chlorophenyl |
| 162 | 6-CF$_3$ | H | OH | 4-chlorophenyl |
| 163 | 5-ethyl | H | methoxy | 4-chlorophenyl |
| 164 | 5-ethyl | H | OH | 4-chlorophenyl |
| 165 | 5-methoxy | H | methoxy | 4-chlorophenyl |
| 166 | 5-methoxy | H | OH | 4-chlorophenyl |
| 167 | 5-isopropyl | H | methoxy | 4-chlorophenyl |
| 168 | 5-isopropyl | H | OH | 4-chlorophenyl |
| 169 | 5-CF$_3$ | H | methoxy | 4-chlorophenyl |
| 170 | 5-CF$_3$ | H | OH | 4-chlorophenyl |
| 171 | 5-CF$_3$O | H | methoxy | 4-chlorophenyl |
| 172 | 5-CF$_3$O | H | OH | 4-chlorophenyl |
| 173 | 6-Cl | H | methoxy | 2-methoxyphenyl |
| 174 | 6-Cl | H | OH | 2-methoxyphenyl |
| 175 | 6-Cl | H | methoxy | 3-methoxyphenyl |
| 176 | 6-Cl | H | OH | 3-methoxyphenyl |
| 177 | 6-Cl | H | methoxy | 3-benzyloxyphenyl |
| 178 | 6-Cl | H | OH | 3-benzyloxyphenyl |
| 179 | 6-Cl | H | methoxy | 3-hydroxyphenyl |
| 180 | 6-Cl | H | OH | 3-hydroxyphenyl |
| 181 | 6-Cl | H | methoxy | 4-benzyloxyphenyl |
| 182 | 6-Cl | H | OH | 4-benzyloxyphenyl |
| 183 | 6-Cl | H | methoxy | 4-hydroxyphenyl |
| 184 | 6-Cl | H | OH | 4-hydroxyphenyl |
| 185 | 6-Cl | H | methoxy | 4-isopropoxyphenyl |
| 186 | 6-Cl | H | OH | 4-isopropoxyphenyl |
| 187 | 6-Cl | H | methoxy | 4-biphenyl |
| 188 | 6-Cl | H | OH | 4-biphenyl |
| 189 | 6-Cl | H | methoxy | 4-CF$_3$O-phenyl |
| 190 | 6-Cl | H | OH | 4-CF$_3$O-phenyl |
| 191 | 5-Cl | H | methoxy | 4-CF$_3$O-phenyl |
| 192 | 5-Cl | H | OH | 4-CF$_3$O-phenyl |
| 193 | 5-Cl | H | methoxy | 4-methoxyphenyl |
| 194 | 5-Cl | H | OH | 4-methoxyphenyl |
| 195 | 6-Cl | H | methoxy | 4-nitrophenyl |
| 196 | 6-Cl | H | OH | 4-nitrophenyl |
| 197 | 6-Cl | H | methoxy | 4-methyl-S(O)$_2$-phenyl |
| 198 | 6-Cl | H | OH | 4-methyl-S(O)$_2$-phenyl |
| 199 | 6-Cl | H | methoxy | 4-methyl-S(O)$_2$-NH-phenyl |
| 200 | 6-Cl | H | OH | 4-methyl-S(O)$_2$-NH-phenyl |
| 201 | 6-Cl | H | OH | 2-chlorophenyl |
| 202 | 6-Cl | H | OH | 2,4-dichlorophenyl |
| 203 | 6-Cl | H | methoxy | 3-F-4-Cl-phenyl |
| 204 | 6-Cl | H | OH | 3-F-4-Cl-phenyl |
| 205 | 6-Cl | H | methoxy | 4-cyanophenyl |
| 206 | 6-Cl | H | methoxy | 4-bromophenyl |
| 207 | 6-Cl | H | methoxy | 4-(2-thienyl)phenyl |
| 208 | 6-Cl | H | OH | 4-(2-thienyl)phenyl |
| 209 | 6-Cl | H | methoxy | 4-(2-furyl)phenyl |
| 210 | 6-Cl | H | OH | 4-(2-furyl)phenyl |
| 211 | 6-Cl | H | methoxy | 4-(3-pyridyl)phenyl |
| 212 | 6-Cl | H | OH | 4-(3-pyridyl)phenyl |
| 213 | 6-Cl | H | methoxy | 4-(2-thiazolyl)phenyl |
| 214 | 6-Cl | H | OH | 4-(2-thiazolyl)phenyl |
| 215 | 6-Cl | H | methoxy | 3-bromophenyl |
| 216 | 6-Cl | H | methoxy | 3-(2-furyl)phenyl |
| 217 | 6-Cl | H | OH | 3-(2-furyl)phenyl |
| 218 | 6-Cl | methyl | methoxy | 4-chlorophenyl |
| 219 | 6-Cl | methyl | OH | 4-chlorophenyl |
| 220 | 5-Cl | H | methoxy | isoquinolin-3-yl |

TABLE-continued

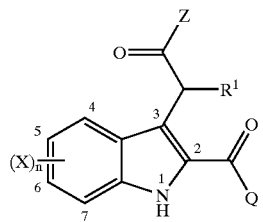

| Ex. # | (X)$_n$ | R$^1$ | Z | Q |
|---|---|---|---|---|
| 221 | 5-Cl | H | OH | isoquinolin-3-yl |
| 222 | 6-Cl | H | methoxy | isoquinolin-3-yl |
| 223 | 6-Cl | H | OH | isoquinolin-3-yl |
| 224 | 5-Cl | H | methoxy | 5-methyl-3-isoxazolyl |
| 225 | 5-Cl | H | OH | 5-methyl-3-isoxazolyl |
| 226 | 6-Cl | H | methoxy | 5-methyl-3-isoxazolyl |
| 227 | 6-Cl | H | OH | 5-methyl-3-isoxazolyl |
| 228 | 5-Cl | H | methoxy | 4-methyl-5-(1,2,3-thiadiazolyl) |
| 229 | 5-Cl | H | OH | 4-methyl-5-(1,2,3-thiadiazolyl) |
| 230 | 6-Cl | H | methoxy | 4-methyl-5-(1,2,3-thiadiazolyl) |
| 231 | 6-Cl | H | OH | 4-methyl-5-(1,2,3-thiadiazolyl) |
| 232 | 5-Cl | H | methoxy | 5-methyl-2-thiazolyl |
| 233 | 5-Cl | H | OH | 5-methyl-2-thiazolyl |
| 234 | 6-Cl | H | methoxy | 5-methyl-2-thiazolyl |
| 235 | 6-Cl | H | OH | 5-methyl-2-thiazolyl |
| 236 | 6-Cl | H | OH | 2-thienyl |
| 237 | 6-Cl | H | methoxy | 3-(HO)(CH$_3$)$_2$C-2-furyl |
| 238 | 6-Cl | H | OH | 3-(HO)(CH$_3$)$_2$C-2-furyl |
| 239 | 6-Cl | H | methoxy | 3-methoxymethyl-2-furyl |
| 240 | 6-Cl | H | OH | 3-methoxymethyl-2-furyl |
| 241 | 6-Cl | H | OH | 1-methyl-2-imidazolyl |
| 242 | 6-Cl | H | methoxy | 1-methyl-2-imidazolyl |
| 243 | 5-Cl | H | methoxy | 1-methyl-2-imidazolyl |
| 244 | 5-Cl | H | OH | 1-methyl-2-imidazolyl |
| 245 | 5-Cl | H | methoxy | 2-imidazolyl |
| 246 | 5-Cl | H | OH | 2-imidazolyl |
| 247 | 6-Cl | H | methoxy | 2-imidazolyl |
| 248 | 6-Cl | H | OH | 2-imidazolyl |
| 249 | 5-Cl | H | methoxy | 4-methyl-2-thiazolyl |
| 250 | 5-Cl | H | OH | 4-methyl-2-thiazolyl |
| 251 | 5-Cl | H | methoxy | 1-methyl-2-pyrrolyl |
| 252 | 5-Cl | H | OH | 1-methyl-2-pyrrolyl |
| 253 | 5-Cl | H | methoxy | 2-methyl-4-thiazolyl |
| 254 | 5-Cl | H | OH | 2-methyl-4-thiazolyl |
| 255 | 5-Cl | H | methoxy | 5-thiazolyl |
| 256 | 5-Cl | H | OH | 5-thiazolyl |
| 257 | 6-Cl | H | methoxy | 4-methyl-2-thiazolyl |
| 258 | 6-Cl | H | OH | 4-methyl-2-thiazolyl |
| 259 | 5-Cl | H | methoxy | 3-carboxyl-5-isoxazolyl |
| 260 | 5-Cl | H | OH | 3-carboxyl-5-isoxazolyl |
| 261 | 6-Cl | H | methoxy | cyclopropyl |
| 262 | 6-Cl | H | OH | cyclopropyl |
| 263 | 6-Cl | H | methoxy | cyclobutyl |
| 264 | 6-Cl | H | OH | cyclobutyl |
| 265 | 5-tert-butyl | H | methoxy | 4-chlorophenyl |
| 266 | 5-tert-butyl | H | OH | 4-chlorophenyl |
| 267 | 6-Cl | H | dimethylamino | 4-methyl-2-pyridyl |
| 268 | 6-Cl | H | methylamino | 4-methyl-2-pyridyl |
| 269 | 5-Cl | H | HO—(CH$_2$)$_2$—NH— | 4-methyl-2-pyridyl |
| 270 | 5-Cl | H | methoxyamino | 4-methyl-2-pyridyl |
| 271 | 5-Cl | H | 1-piperazinyl | 4-methyl-2-pyridyl |
| 272 | 5-Cl | H | H$_2$N—(CH$_2$)$_2$—NH— | 4-methyl-2-pyridyl |
| 273 | 5-Cl | H | 3-amino-1-pyrrolidinyl | 4-methyl-2-pyridyl |
| 274 | 5-F,6-Cl | H | methoxy | 4-chlorophenyl |
| 275 | 5-F,6-Cl | H | OH | 4-chlorophenyl |
| 276 | 5-F,6-Cl | H | methoxy | 4-methyl-2-pyridyl |
| 277 | 5-F,6-Cl | H | OH | 4-methyl-2-pyridyl |
| 278 | 6-Cl | H | methoxy | 4-(HO)(H$_3$C)CH-2-pyridyl |
| 279 | 6-Cl | H | OH | 4-(HO)(H$_3$C)CH-2-pyridyl |
| 280 | 6-Cl | H | OH | 4-ethyl-3-F-2-pyridyl |
| 281 | 6-Cl | H | OH | 2-nitrophenyl |
| 282 | 6-Cl | H | OH | 2,4-dimethoxyphenyl |
| 283 | 6-Cl | H | OH | 4-CHF$_2$O-phenyl |
| 284 | 6-Cl | H | OH | 2,5-dimethoxyphenyl |
| 285 | 5-acetyl | H | methoxy | 4-Cl-phenyl |

TABLE-continued

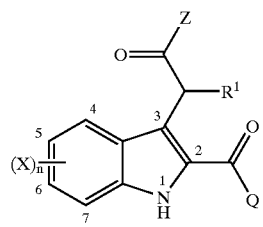

| Ex. # | (X)$_n$ | R$^1$ | Z | Q |
|---|---|---|---|---|
| 286 | 5-acetyl | H | OH | 4-Cl-phenyl |
| 287 | 6-F | H | methoxy | 4-methyl-2-pyridyl |
| 288 | 6-F | H | OH | 4-methyl-2-pyridyl |
| 289 | 6-F | H | methoxy | 4-Cl-phenyl |
| 290 | 6-F | H | OH | 4-Cl-phenyl |
| 291 | 5-CH$_3$S— | H | methoxy | 4-methyl-2-pyridyl |
| 292 | 5-CH$_3$S— | H | OH | 4-methyl-2-pyridyl |

What is claimed is:

1. A compound of the following formula:

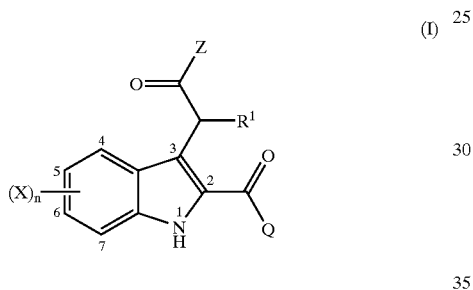

or the pharmaceutically acceptable salts thereof wherein
Z is OH, $C_{1-6}$ alkoxy, —NR$^2$R$^3$ or a group of the formula (II) or (III):

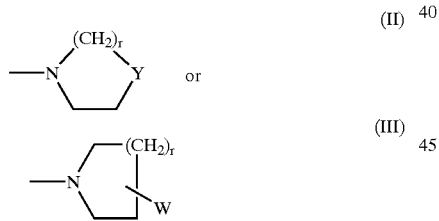

wherein r is 1, 2, 3 or 4, Y is a direct bond, O, S or NR$^4$, and W is OH or —NR$^2$R$^3$;

Q is selected from the following:
(a) phenyl optionally substituted with one, two or three substituents independently selected from
  (a-1) halo, $C_{1-4}$ alkyl, halo-substituted $C_{1-4}$ alkyl, OH, $C_{1-4}$ alkoxy, halo-substituted $C_{1-4}$ alkoxy, $C_{1-4}$ alkylthio, NO$_2$, NH$_2$, di-($C_{1-4}$ alkyl)amino, $C_{1-4}$ alkylamino, CN, HO—($C_{1-4}$)alkyl, $C_{1-4}$ alkoxy-$C_{1-4}$ alkyl, $C_{1-4}$ alkylsulfonyl, aminosulfonyl, —NH$_2$S(O)$_2$NR$^2$R$^3$, acetyl, —COOH, —C(O)O—$C_{1-4}$ alkyl, $C_{1-4}$ alkylsulfonylamino and $C_{3-7}$ cycloalkyl,
  (a-2) aryl or —O—(CH$_2$)$_n$-aryl, and the aryl or aryl moiety being optionally substituted with one, two or three substituents independently selected from halo, $C_{1-4}$ alkyl, halo-substituted $C_{1-4}$ alkyl, OH, $C_{1-4}$ alkoxy, halo-substituted $C_{1-4}$ alkoxy, $C_{1-4}$ alkylthio, NO$_2$, NH$_2$, di-($C_{1-4}$ alkyl)amino, $C_{1-4}$ alkylamino and CN,
  (a-3) 5-membered monocyclic aromatic group optionally substituted with one, two or three substituents independently selected from halo, $C_{1-4}$ alkyl, halo-substituted $C_{1-4}$ alkyl, OH, $C_{1-4}$ alkoxy, halo-substituted $C_{1-4}$ alkoxy, $C_{1-4}$ alkylthio, NO$_2$, NH$_2$, di-($C_{1-4}$ alkyl)amino, $C_{1-4}$ alkylamino and CN,
  (a-4) 6-membered monocyclic aromatic group optionally substituted with one, two or three substituents independently selected from halo, $C_{1-4}$ alkyl, halo-substituted $C_{1-4}$ alkyl, OH, $C_{1-4}$ alkoxy, halo-substituted $C_{1-4}$ alkoxy, $C_{1-4}$ alkylthio, NO$_2$, NH$_2$, di-($C_{1-4}$ alkyl)amino, $C_{1-4}$ alkylamino and CN,
(b) a 6-membered monocyclic aromatic group containing one, two, three or four nitrogen atom(s), and said monocyclic aromatic group being optionally substituted with one, two or three substituents independently selected from the above group (a-1), (a-2), (a-3) and (a-4),
(c) a 5-membered monocyclic aromatic group containing one heteroatom selected from O, S and N and optionally containing one, two or three nitrogen atom(s) in addition to said heteroatom, and said monocyclic aromatic group being optionally substituted with one, two or three substituents independently selected from the above group (a-1), (a-2), (a-3) and (a-4);
(d) $C_{3-7}$ cycloalkyl optionally substituted with one or two substituents independently selected from OH, $C_{1-4}$ alkyl, halo and halo-substituted $C_{1-4}$ alkyl; and
(e) a benzo-fuzed heterocycle optionally substituted with one, two or three substituents independently selected from the group (a-1);

R$^1$ is hydrogen, $C_{1-4}$ alkyl or halo;
R$^2$ and R$^3$ are independently H, OH, $C_{1-4}$ alkoxy, $C_{1-4}$ alkyl or $C_{1-4}$ alkyl substituted with halo, OH, $C_{1-4}$ alkoxy, NH$_2$ or CN;
R$^4$ is hydrogen or $C_{1-4}$ alkyl;
X is independently selected from halo, $C_{1-4}$ alkyl, halo-substituted $C_{1-4}$ alkyl, OH, $C_{1-4}$ alkoxy, halo-substituted $C_{1-4}$ alkoxy, $C_{1-4}$ alkylthio, NO$_2$, NH$_2$, di-($C_{1-4}$ alkyl)amino, $C_{1-4}$ alkylamino, CN, HO—

193

($C_{1-4}$)alkyl, $C_{1-4}$ alkoxy-$C_{1-4}$ alkyl, $C_{1-4}$ alkylsulfonyl, aminosulfonyl, —$NH_2S(O)_2NR^2NR^3$, acetyl, —COOH, —C(O)O—$C_{1-4}$ alkyl, $C_{1-4}$ alkylsulfonylamino and $C_{3-7}$ cycloalkyl; and n is 0, 1, 2, 3 or 4.

2. A compound according to claim 1, wherein

Z is OH, $C_{1-6}$ alkoxy, dimethylamino, methylamino, amino, N-methoxy-N-methylamino, 2-cyanoethylamino, 2-hydroxyethylamino, pyrrolidinyl, piperidino, piperazinyl, N-methylpiperazinyl, morpholino, methoxyamino, piperazinyl, aminoPyrrolidinyl or aminoethylamino.

3. A compound according to claim 2, wherein

Z is OH or $C_{1-6}$ alkoxy; and

Q is selected from the following:
(a) phenyl optionally substituted with one, two or three substituents independently selected from
   (a-1) halo, $C_{1-4}$ alkyl, halo-substituted $C_{1-4}$ alkyl, OH, $C_{1-4}$ alkoxy, halo-substituted $C_{1-4}$ alkoxy, $C_{1-4}$ alkylthio, $NO_2$, $NH_2$, di-($C_{1-4}$ alkyl)amino, $C_{1-4}$ alkylamino, CN, HO—($C_{1-4}$)alkyl, $C_{1-4}$ alkoxy-$C_{1-4}$ alkyl, $C_{1-4}$ alkylsulfonyl, aminosulfonyl, —$NH_2S(O)_2NR^2R^3$, acetyl, —COOH, —C(O)O—$C_{1-4}$ alkyl, $C_{1-4}$ alkylsulfonylamino and $C_{3-7}$ cycloalkyl,
   (a-2) aryl or —O—$(CH_2)_n$-aryl, and the aryl or aryl moiety being optionally substituted with one, two or three substituents independently selected from halo, $C_{1-4}$ alkyl, halo-substituted $C_{1-4}$ alkyl, OH, $C_{1-4}$ alkoxy, halo-substituted $C_{1-4}$ alkoxy, $C_{1-4}$ alkylthio, $NO_2$, $NH_2$, di-($C_{1-4}$ alkyl)amino, $C_{1-4}$ alkylamino and CN,
   (a-3) 5-membered monocyclic aromatic group optionally substituted with one, two or three substituents independently selected from halo, $C_{1-4}$ alkyl, halo-substituted $C_{1-4}$ alkyl, OH, $C_{1-4}$ alkoxy, halo-substituted $C_{1-4}$ alkoxy, $C_{1-4}$ alkylthio, $NO_2$, $NH_2$, di-($C_{1-4}$ alkyl)amino, $C_{1-4}$ alkylamino and CN,
   (a-4) 6-membered monocyclic aromatic group optionally substituted with one, two or three substituents independently selected from halo, $C_{1-4}$ alkyl, halo-substituted $C_{1-4}$ alkyl, OH, $C_{1-4}$ alkoxy, halo-substituted $C_{1-4}$ alkoxy, $C_{1-4}$ alkylthio, $NO_2$, $NH_2$, di-($C_{1-4}$ alkyl)amino, $C_{1-4}$ alkylamino and CN,
(b) a 6-membered monocyclic aromatic group containing one, two, three or four nitrogen atom(s), and said monocyclic aromatic group being optionally substituted with one, two or three substituents independently selected from the above group (a-1), (a-2), (a-3) and (a-4),
(c) a 5-membered monocyclic aromatic group containing one heteroatom selected from O, S and N and optionally containing one, two or three nitrogen atom(s) in addition to said heteroatom, and said monocyclic aromatic group being optionally substituted with one, two or three substituents independently selected from the above group (a-1), (a-2), (a-3) and (a-4);
(d) $C_{3-7}$ cycloalkyl selected from cyclopropyl, cyclobutyl, cyclopentyl and cyclohexyl, and the said cycloalkyl being optionally substituted with one substituent selected from OH, methyl, ethyl, propyl, F, Cl and $CF_3$; and
(e) a benzo-fuzed heterocycle selected from quinolyl, isoquinolyl, cinnolinyl, quinoxalinyl, benzoimidazolyl, benzothiazolyl, benzoxazolyl, benzofuranyl; benzothiophenyl and indolyl, and the benzo-fuzed heterocycle being optionally substituted with one, two, or three substituents independently selected from the group (a-1).

4. A compound according to claim 3, wherein

Q is selected from the following:
(a) phenyl optionally substituted with one, two or three substituents independently selected from
   (a-1) halo, $C_{1-4}$ alkyl, halo-substituted $C_{1-4}$ alkyl, OH, $C_{1-4}$ alkoxy, halo-substituted $C_{1-4}$ alkoxy, $C_{1-4}$ alkylthio, $NO_2$, $NH_2$, di-($C_{1-4}$ alkyl)amino, $C_{1-4}$ alkylamino, CN, HO—($C_{1-4}$)alkyl, $C_{1-4}$ alkoxy-$C_{1-4}$ alkyl, $C_{1-4}$ alkylsulfonyl, aminosulfonyl, —$NH_2S(O)_2NR^2R^3$, acetyl, —COOH, —C(O)O—$C_{1-4}$ alkyl, $C_{1-4}$ alkylsulfonylamino and $C_{3-7}$ cycloalkyl,
   (a-2) aryl or —O—$(CH_2)_n$-aryl, and the aryl or aryl moiety being optionally substituted with one, two or three substituents independently selected from halo, $C_{1-4}$ alkyl, halo-substituted $C_{1-4}$ alkyl, OH, $C_{1-4}$ alkoxy, halo-substituted $C_{1-4}$ alkoxy, $C_{1-4}$ alkylthio, $NO_2$, $NH_2$, di-($C_{1-4}$ alkyl)amino, $C_{1-4}$ alkylamino and CN,
   (a-3) 5-membered monocyclic aromatic group optionally substituted with one, two or three substituents independently selected from halo, $C_{1-4}$ alkyl, halo-substituted $C_{1-4}$ alkyl, OH, $C_{1-4}$ alkoxy, halo-substituted $C_{1-4}$ alkoxy, $C_{1-4}$ alkylthio, $NO_2$, $NH_2$, di-($C_{1-4}$ alkyl)amino, $C_{1-4}$ alkylamino and CN,
   (a-4) 6-membered monocyclic aromatic group optionally substituted with one, two or three substituents independently selected from halo, $C_{1-4}$ alkyl, halo-substituted $C_{1-4}$ alkyl, OH, $C_{1-4}$ alkoxy, halo-substituted $C_{1-4}$ alkoxy, $C_{1-4}$ alkylthio, $NO_2$, $NH_2$, di-($C_{1-4}$ alkyl)amino, $C_{1-4}$ alkylamino and CN,
(b) a 6-membered monocyclic aromatic group containing one, two, three or four nitrogen atom(s), and said monocyclic aromatic group being optionally substituted with one, two or three substituents independently selected from the above group (a-1), (a-2), (a-3) and (a-4);
(c) a 5-membered monocyclic aromatic group containing one heteroatom selected from O, S and N and optionally containing one, two or three nitrogen atom(s) in addition to said heteroatom, and said monocyclic aromatic group being optionally substituted with one, two or three substituents independently selected from the above group (a-1), (a-2), (a-3) and (a-4);
(d) cyclopropyl, cyclobutyl and cyclohexyl; and
(e) quinolyl or isoquinolyl, and said quinolyl or isoquinolyl being optionally substituted with one substituent selected from the group halo, $C_{1-4}$ alkyl, $NH_2$, OH, $C_{1-4}$ alkoxy and $C_{1-4}$ halo-substituted alkyl.

5. A compound according to claim 4, wherein

Z is OH, $C_{1-6}$ alkoxy;

Q is selected from the following:
(a) phenyl optionally substituted with one, two or three substituents independently selected from
   (a-1) halo, $C_{1-4}$ alkyl, halo-substituted $C_{1-4}$ alkyl, OH, $C_{1-4}$ alkoxy, halo-substituted $C_{1-4}$ alkoxy, $C_{1-4}$ alkylthio, $NO_2$, $NH_2$, di-($C_{1-4}$ alkyl)amino, $C_{1-4}$ alkylamino, CN, HO—($C_{1-4}$)alkyl, $C_{1-4}$ alkoxy-$C_{1-4}$ alkyl, $C_{1-4}$ alkylsulfonyl, aminosulfonyl, —$NH_2S(O)_2NR^2R^3$, acetyl, —COOH, —C(O)O—$C_{1-4}$ alkyl, $C_{1-4}$ alkylsulfonylamino and $C_{3-7}$ cycloalkyl, (a-2) aryl or —O—$(CH_2)_n$-aryl, and the aryl or aryl moiety being optionally substituted with one, two or three substituents independently selected from halo, $C_{1-4}$ alkyl, halo-substituted $C_{1-4}$ alkyl, OH, $C_{1-4}$ alkoxy, halo-substituted $C_{1-4}$ alkoxy, $C_{1-4}$ alkylthio, $NO_2$, $NH_2$, di-($C_{1-4}$ alkyl)amino, $C_{1-4}$ alkylamino and CN, (a-3) 5-membered monocyclic aromatic group optionally substituted with one, two or three substituents independently selected from halo, $C_{1-4}$ alkyl, halo-substituted $C_{1-4}$ alkyl, OH, $C_{1-4}$ alkoxy, halo-substituted $C_{1-4}$ alkoxy, $C_{1-4}$ alkylthio, $NO_2$, $NH_2$, di-($C_{1-4}$ alkyl)amino, $C_{1-4}$ alkylamino and CN, (a-4) 6-membered monocyclic aromatic group optionally substituted with one, two or three substituents independently selected from halo, $C_{1-4}$ alkyl, halo-substituted $C_{1-4}$ alkyl, OH, $C_{1-4}$ alkoxy, halo-substituted $C_{1-4}$ alkoxy, $C_{1-4}$ alkylthio, $NO_2$, $NH_2$, di-($C_{1-4}$ alkyl)amino, $C_{1-4}$ alkylamino and CN, (b) a 6-membered monocyclic aromatic group containing one, two, three or four nitrogen atom(s), and said monocyclic aromatic group being optionally substituted with one, two or three substituents independently selected from the above group (a-1), (a-2), (a-3) and (a-4), (c) a 5-membered monocyclic aromatic group containing one heteroatom selected from O, S and N and optionally containing one, two or three nitrogen atom(s) in addition to said heteroatom, and said monocyclic aromatic group being optionally substituted with one, two or three substituents independently selected from the above group (a-1), (a-2), (a-3) and (a-4); and (e) isoquinolyl;

$R^1$ is hydrogen or $C_{1-4}$ alkyl;

$R^2$ and $R^3$ are independently H or methyl;

X is independently selected from halo, $C_{1-4}$ alkyl, halo-substituted $C_{1-4}$ alkyl, OH, $C_{1-4}$ alkoxy, halo-substituted $C_{1-4}$ alkoxy, $C_{1-4}$ alkylthio, $NO_2$, $NH_2$, di-($C_{1-4}$ alkyl)amino, $C_{1-4}$ alkylamino, CN, HO—$(C_{1-4})$alkyl, $C_{1-4}$ alkoxy-$C_{1-4}$ alkyl, $C_{1-4}$ alkylsulfonyl, aminosulfonyl, —$NH_2S(O)_2NR^2NR^3$, acetyl, —$COOR^4$, $C_{1-4}$ alkylsulfonylamino and $C_{3-7}$ cycloalkyl; and n is 0, 1, 2, or 3.

6. A compound according to claim 5, wherein

Z is OH, methoxy, ethoxy, n-propoxy, iso-propoxy, n-butoxy, iso-butoxy or tert-butoxy;

Q is selected from the following:
  (a) phenyl optionally substituted with one or two substituents independently selected from
    (a-1) halo, $C_{1-4}$ alkyl, halo-substituted $C_{1-4}$ alkyl, OH, $C_{1-4}$ alkoxy, halo-substituted $C_{1-4}$ alkoxy, $C_{1-4}$ alkylthio, HO—$(C_{1-4})$alkyl, $C_{1-4}$ alkoxy-$C_{1-4}$ alkyl, —COOH, $C_{1-4}$ alkylsulfonylamino, nitro, $C_{1-4}$ alkylsulfonyl and cyano,
    (a-2) phenyl or benzyloxy, and the phenyl or phenyl moiety of benzyloxy being optionally substituted with one substituent selected from $C_{1-4}$ alkyl, halo-substituted $C_{1-4}$ alkyl, halo, OH, $C_{1-4}$ alkoxy, halo-substituted $C_{1-4}$ alkoxy and $NH_2$,
    (a-3) 5-membered monocyclic aromatic group selected from imidazolyl, thiazolyl, furyl, thienyl, pyrrolyl, tetrazolyl, triazolyl, oxazolyl, isoxazolyl, thiadiazolyl and pyrazolyl, and the 5-membered monocyclic aromatic group optionally being substitued with one substituent selected from $C_{1-4}$ alkyl, halo-substituted $C_{1-4}$ alkyl, halo, OH, $C_{1-4}$ alkoxy, halo-substituted $C_{1-4}$ alkoxy and $NH_2$,
    (a-4) 6-membered monocyclic aromatic group selected from pyridyl, pyrazinyl, pyrimidinyl and pyridazinyl, and the 6-membered monocyclic aromatic group optionally being substitued with one substituent selected from $C_{1-4}$ alkyl, halo-substituted $C_{1-4}$ alkyl, halo, OH, $C_{1-4}$ alkoxy, halo-substituted $C_{1-4}$ alkoxy and $NH_2$, (b) a 6-membered monocyclic aromatic group selected from pyridyl, pyrazinyl, pyrimidinyl and pyridazinyl, and said monocyclic aromatic group being optionally substituted with one or two substituents independently selected from the above group (a-1), (a-2), (a-3) and (a-4), (c) a 5-membered monocyclic aromatic group selected from imidazolyl, thiazolyl, fiiryl, thienyl, pyrrolyl, tetrazolyl, triazolyl, oxazolyl, isoxazolyl, thiadiazolyl and pyrazolyl, and said monocyclic aromatic group being optionally substituted with one or two substituents independently selected from the above group (a-1), (a-2), (a-3) and (a-4);

$R^1$ is hydrogen, methyl, ethyl, n-propyl, iso-propyl, n-butyl, iso-butyl or tert-butyl;

X is independently selected from halo, $C_{1-4}$ alkyl, halo-substituted $C_{1-4}$ alkyl, OH, $C_{1-4}$ alkoxy, halo-substituted $C_{1-4}$ alkoxy, $C_{1-4}$ alkylthio, $NO_2$, $NH_2$, di-($C_{1-4}$ alkyl)amino, $C_{1-4}$ alkylamino, CN, HO-$(C_{1-4})$ alkyl, $C_{1-4}$ alkoxy-$C_{1-4}$ alkyl, $C_{1-4}$ alkylsulfonyl and aminosulfonyl; and n is 0, 1, 2, or 3.

7. A compound according to claim 6, wherein

Z is OH, methoxy, ethoxy, n-propoxy, iso-propoxy, n-butoxy, iso-butoxy or tert-butoxy;

Q is selected from the following:
  (a) phenyl optionally substituted with one or two substituents independently selected from
    (a-1) fluoro, chloro, bromo, iodo, methyl, ethyl, propyl, butyl, $CH_2F$, $CHF_2$, $CF_3$, methoxy, ethoxy, n-propoxy, n-butoxy, isopropoxy, $CH_2F$—O—, $CHF_2$—O—, $CF_3$—O—, methylthio, ethylthio, hydroxymethyl, methoxymethyl, methoxyethyl, ethoxymethyl, hydroxy, nitro, methylsulfonyl, cyano, $(HO)(H_3C)_2C$—, acetyl and methylsulfonylamino,
    (a-2) phenyl or benzyloxy, and the phenyl or phenyl moiety of benzyloxy being optionally substituted with one substituent selected from methyl, ethyl, propyl, $CF_3$, F, Cl, OH, methoxy, ethoxy and $NH_2$,
    (a-3) 5-membered inonocyclic aromatic group selected from furyl, thienyl and pyrrolyl, and the 5-membered monocyclic aromatic group optionally being substituted with one substituent selected from methyl, ethyl, propyl, $CF_3$, F, Cl, OH, methoxy, ethoxy and $NH_2$,
    (a-4) pyridyl optionally substituted with one substituent selected from methyl, ethyl, propyl, $CF_3$, F, Cl, OH, methoxy, ethoxy and $NH_2$, (b) pyridyl optionally substituted with one, two or three substituents independently selected from the above group (a-1), (a-1), (a-2), (a-3) and (a-4), (c) imidazolyl, thiazolyl, furyl, thienyl, isoxazolyl, 1,2,3-thiadiazolyl or pyrrolyl, and said imidazolyl, thiazolyl, furyl, thienyl, isoxazolyl, 1,2,3-thiadiazolyl or pyrrolyl being optionally substituted with one or two substituents independently selected from the above group (a-1), (a-2), (a-3) and (a-4);

$R^1$ is hydrogen, methyl, ethyl, n-propyl, iso-propyl;

X is independently selected from fluoro, chloro, bromo, methyl, ethyl, propyl, butyl, $CH_2F$, $CHF_2$, $CF_3$, methoxy, CFO or ethoxy; and n is 0, 1 or 2.

8. A compound according to claim 7, wherein

Z is OH, ethoxy or methoxy; Q is phenyl, chlorophenyl, fluorophenyl, bromophenyl, methylphenyl, methoxyphenyl, (furyl)phenyl, trifluoromethylphenyl, trifluoromethoxyphenyl, pyridyl, methylpyridyl, ethylpyridyl, propylpyridyl, dimethylpyridyl, chloropyridyl, fluoropyridyl, trifluoromethylpyridyl, methoxypyridyl, (ethyl)(ethoxy)pyridyl, (chloro)(ethyl)pyridyl, thiazolyl, methylthiazolyl, furyl, methoxymethylfuryl, isoquinolyl, cyclohexyl, methoxyphenyl, (fluoro)(ethyl)pyridyl, dimethylpyridyl or (ethoxy)(ethyl)pyridyl;

$R^1$ is hydrogen; X is fluoro, chloro, methyl, ethyl, isopropyl, tert-butyl, $CF_3$ or methoxy; and n is 1 or 2.

9. A compound according to claim 8, wherein

Z is OH, ethoxy or methoxy; Q is phenyl, chlorophenyl, pyridyl, methylpyridyl, ethylpyridyl, propylpyridyl or chloropyridyl; $R^1$ is hydrogen; X is fluoro, chloro, methyl or $CF_3$; and n is 1 or 2.

10. A compound according to claim 1, selected from ethyl(2-benzoyl-6-chloro-1H-indol-3-yl)acetate;
(2-benzoyl-6-chloro-1H-indol-3-yl)acetic acid;
(2-benzoyl-6-chloro-1H-indol-3-yl)acetic acid, sodium salt;
[6-chloro-2-(2-methylbenzoyl)-1H-indol-3-yl]acetic acid;
[6-chloro-2-(3-methylbenzoyl)-1H-indol-3-yl]acetic acid;
[6-chloro-2-(4-methylbenzoyl)-1H-indol-3-yl]acetic acid;
[6-chloro-2-(3-chlorobenzoyl)-1H-indol-3-yl]acetic acid;
methyl[6-chloro-2-(4-chlorobenzoyl)-1H-indol-3-yl]acetate;
[6-chloro-2-(4-chlorobenzoyl)-1H-indol-3-yl]acetic acid;
[6-chloro-2-(3-fluorobenzoyl)-1H-indol-3-yl]acetic acid;
[6-chloro-2-(4-fluorobenzoyl)-1H-indol-3-yl]acetic acid;
[2-(3-bromobenzoyl)-6-chloro-1H-indol-3-yl]acetic acid;
[2-(4-bromobenzoyl)-6-chloro-1H-indol-3-yl]acetic acid;
[6-chloro-2-(3-trifluoromethylbenzoyl)-1H-indol-3-yl]acetic acid;
[6-chloro-2-(4-trifluoromethylbenzoyl)-1H-indol-3-yl]acetic acid;
[6-chloro-2-(3,4-dichloro benzoyl)-1H-indol-3-yl]acetic acid;
(2-benzoyl-4-chloro-1H-indol-3-yl)acetic acid;
[5-chloro-2-(3-methylbenzoyl)-1H-indol-3-yl]acetic acid;
[5-chloro-2-(4-chlorobenzoyl)-1H-indol-3-yl]acetic acid;
[5-chloro-2-(3-chlorobenzoyl)-1H-indol-3-yl]acetic acid;
[2-(4-chlorobenzoyl)-5-fluoro-1H-indol-3-yl]acetic acid;
[2-(3-chlorobenzoyl)-5-fluoro-1H-indol-3-yl]acetic acid;
[5-methoxy-2-(3-methylbenzoyl)-1H-indol-3-yl]acetic acid;
(2-benzoyl-7-chloro-1H-indol-3-yl)acetic acid;
(2-benzoyl-4,5-dichloro-1H-indol-3-yl)acetic acid;
(2-benzoyl-4,6-dichloro-1H-indol-3-yl)acetic acid;
(2-benzoyl-5,6-dichloro-1H-indol-3-yl)acetic acid;
dl-2-(2-benzoyl-6-chloro-1H-indol-3-yl)propanoic acid;
less polar antipode, 2-(2-benzoyl-6-chloro-1H-indol-3-yl)propanoic acid;
more polar antipode, 2-(2-benzoyl-6-chloro-1H-indol-3-yl)propanoic acid;
[6-chloro-2-(4-methylpyridine-2-carbonyl)-1H-indol-3-yl]acetic acid;
[6-chloro-2-(5-methylpyridine-2-carbonyl)-1H-indol-3-yl]acetic acid;
methyl[6-chloro-2-(4-chloropyridine-2-carbonyl)-1H-indol-3-yl]acetate;
[6-chloro-2-(4-chloropyridine-2-carbonyl)-1H-indol-3-yl]acetic acid;
[6-chloro-2-(pyridine-2-carbonyl)-1H-indol-3-yl]acetic acid;
[5-chloro-2-(4-methylpyridine-2-carbonyl)-1H-indol-3-yl]acetic acid;
methyl[5-chloro-2-(6-methylpyridine-2-carbonyl)-1H-indol-3-yl]acetate;
[5-chloro-2-(6-methylpyridine-2-carbonyl)-1H-indol-3-yl]acetic acid;
[6-chloro-2-(1-methylimidazole-2-carbonyl)-1H-indol-3-yl]acetic acid;
methyl[5-chloro-2-(thiazole-2-carbonyl)-1H-indol-3-yl]acetate;
[5-chloro-2-(thiazole-2-carbonyl)-1H-indol-3-yl]acetic acid;
methyl(2-benzoyl-6-chloro-1H-indol-3-yl)acetate;
(2-benzoyl-6-chloro-1H-indol-3-yl)-N,N-dimethylacetamide;
(2-benzoyl-6-chloro-1H-indol-3-yl)-N-methylacetamide;
(2-benzoyl-6-chloro-1H-indol-3-yl)acetamide;
(2-benzoyl-6-chloro-1H-indol-3-yl)-N-methoxy-N-methylacetamide;
2-(2-benzoyl-6-chloro-1H-indol-3-yl)-1-piperidino-1-ethanone;
2-(2-benzoyl-6-chloro-1H-indol-3-yl)-1-(4-methyl-1-piperazinyl)-1-ethanone;
(2-benzoyl-6-chloro-1H-indol-3-yl)-N-(2-cyanoethyl)acetamide;
(2-benzoyl-6-chloro-1H-indol-3-yl)-N-(2-hydroxyethyl)acetamide;
2-(2-benzoyl-6-chloro-1H-indol-3-yl)-1-morpholino-1-ethanone;
[2-(4-chlorobenzoyl)-1H-indol-3-yl]acetic acid;
[6-chloro-2-(2-furylcarbonyl)-1H-indol-3-yl]acetic acid;
[6-chloro-2-(cyclohexanecarbonyl)-1H-indol-3-yl]acetic acid;
methyl[6-chloro-2-(4-methoxybenzoyl)-1H-indol-3-yl]acetate;
[6-chloro-2-(4-methoxybenzoyl)-1H-indol-3-yl]acetic acid;
methyl[6-chloro-2-(4-ethylpyridine-2-carbonyl)-1H-indol-3-yl]acetate;
[6-chloro-2-(4-ethylpyridine-2-carbonyl)-1H-indol-3-yl]acetic acid;

methyl[5-chloro-2-(4-ethylpyridine-2-carbonyl)-1H-indol-3-yl]acetate;
[5-chloro-2-(4-ethylpyridine-2-carbonyl)-1H-indol-3-yl]acetic acid;
methyl[6-chloro-2-(4-isopropylpyridine-2-carbonyl)-1H-indol-3-yl]acetate;
[6-chloro-2-(4-isopropylpyridine-2-carbonyl)-1H-indol-3-yl]acetic acid;
methyl[5-chloro-2-(4-isopropylpyridine-2-carbonyl)-1H-indol-3-yl]acetate;
[5-chloro-2-(4-isopropylpyridine-2-carbonyl)-1H-indol-3-yl]acetic acid;
methyl[6-chloro-2-(4-propylpyridine-2-carbonyl)-1H-indol-3-yl]acetate;
[6-chloro-2-(4-propylpyridine-2-carbonyl)-1H-indol-3-yl]acetic acid;
methyl[5-chloro-2-(4-propylpyridine-2-carbonyl)-1H-indol-3-yl]acetate;
[5-chloro-2-(4-propylpyridine-2-carbonyl)-1H-indol-3-yl]acetic acid;
methyl[2-(4-tert-butylpyridine-2-carbonyl)-6-chloro-1H-indol-3-yl]acetate;
[2-(4-tert-butylpyridine-2-carbonyl)-6-chloro-1H-indol-3-yl]acetic acid;
methyl[2-(4-tert-butylpyridine-2-carbonyl)-5-chloro-1H-indol-3-yl]acetate;
[2-(4-tert-butylpyridine-2-carbonyl)-5-chloro-1H-indol-3-yl]acetic acid;
methyl[6-chloro-2-(3-methylpyridine-2-carbonyl)-1H-indol-3-yl]acetate;
[6-chloro-2-(3-methylpynidine-2-carbonyl)-1H-indol-3-yl]acetic acid;
methyl[5-chloro-2-(3-methylpyridine-2-carbonyl)-1H-indol-3-yl]acetate,
[5-chloro-2-(3-methylpyridine-2-carbonyl)-1H-indol-3-yl]acetic acid;
methyl[6-chloro-2-(6-methylpyridine-2-carbonyl)-1H-indol-3-yl]acetate;
[6-chloro-2-(6-methylpyridine-2-carbonyl)-1H-indol-3-yl]acetic acid;
methyl[5-chloro-2-(5-methylpyridine-2-carbonyl)-1H-indol-3-yl]acetate;
[5-chloro-2-(5-methylpyridine-2-carbonyl)-1H-indol-3-yl]acetic acid;
methyl[6-chloro-2-[5-(trifluoromethyl)pyridine-2-carbonyl]-1H-indol-3-yl]acetate;
[6-chloro-2-[5-(trifluoromethyl)pyridine-2-carbonyl]-1H-indol-3-yl]acetic acid;
methyl[5-chloro-2-[5-(trifluoromethyl)pyridine-2-carbonyl]-1H-indol-3-yl]acetate;
[5-chloro-2-[5-(trifluoromethyl)pyridine-2-carbonyl]-1H-indol-3-yl]acetic acid;
methyl[5-chloro-2-(5-chloropyridine-2-carbonyl)-1H-indol-3-yl]acetate;
[5-chloro-2-(5-chloropyridine-2-carbonyl)-1H-indol-3-yl]acetic acid;
methyl[6-chloro-2-(5-chloropyridine-2-carbonyl)-1H-indol-3-yl]acetate;
[6-chloro-2-(5-chloropyridine-2-carbonyl)-1H-indol-3-yl]acetic acid;
methyl[5-chloro-2-(4-chloropyridine-2-carbonyl)-1H-indol-3-yl]acetate;
[5-chloro-2-(4-chloropyridine-2-carbonyl)-1H-indol-3-yl]acetic acid;
methyl[6-chloro-2-(pyridine-3-carbonyl)-1H-indol-3-yl]acetate;
[6-chloro-2-(pyridine-3-carbonyl)-1H-indol-3-yl]acetic acid;
methyl[6-chloro-2-(pyridine-4-carbonyl)-1H-indol-3-yl]acetate;
[6-chloro-2-(pyridine-4-carbonyl)-1H-indol-3-yl]acetic acid;
methyl[6-chloro-2-[4-(hydroxymethyl)pyridine-2-carbonyl]-1H-indol-3-yl]acetate;
[6-chloro-2-[4-(hydroxymethyl)pyridine-2-carbonyl]-1H-indol-3-yl]acetic acid;
methyl[5-chloro-2-[4-(hydroxymethyl)pyridine-2-carbonyl]-1H-indol-3-yl]acetate;
[5-chloro-2-[4-(hydroxymethyl)pyridine-2-carbonyl]-1H-indol-3-yl]acetic acid;
methyl[5-chloro-2-(3,4-dimethylpyridine-2-carbonyl)-1H-indol-3-yl]acetate;
[5-chloro-2-(3,4-dimethylpyridine-2-carbonyl)-1H-indol-3-yl]acetic acid;
methyl[5-chloro-2-(4,5-dimethylpyridine-2-carbonyl)-1H-indol-3-yl]acetate;
[5-chloro-2-(4,5-dimethylpyridine-2-carbonyl)-1H-indol-3-yl]acetic acid;
methyl[6-chloro-2-(4,5-dimethylpyridine-2-carbonyl)-1H-indol-3-yl]acetate;
[6-chloro-2-(4,5-dimethylpyridine-2-carbonyl)-1H-indol-3-yl]acetic acid;
methyl[6-chloro-2-(4-methoxypyridine-2-carbonyl)-1H-indol-3-yl]acetate;
[6-chloro-2-(4-methoxypyridine-2-carbonyl)-1H-indol-3-yl]acetic acid;
methyl[5-chloro-2-(4-methoxypyridine-2-carbonyl)-1H-indol-3-yl]acetate;
[5-chloro-2-(4-methoxypyridine-2-carbonyl)-1H-indol-3-yl]acetic acid;
methyl[6-chloro-2-(3,5-dimethylpyridine-2-carbonyl)-1H-indol-3-yl]acetate;
[6-chloro-2-(3,5-dimethylpyridine-2-carbonyl)-1H-indol-3-yl]acetic acid;
methyl[5-chloro-2-(4-ethyl-3-fluoropyridine-2-carbonyl)-1H-indol-3-yl]acetate;
[5-chloro-2-(4-ethyl-3-fluoropyridine-2-carbonyl)-1H-indol-3-yl]acetic acid;
methyl[6-chloro-2-(4-ethyl-3-fluoropyridine-2-carbonyl)-1H-indol-3-yl]acetate;
[6-chloro-2-(3-ethoxy-4-ethylpyridine-2-carbonyl)-1H-indol-3-yl]acetic acid;
methyl[6-chloro-2-(3-chloro-4-ethylpyridine-2-carbonyl)-1H-indol-3-yl]acetate;
[6-chloro-2-(3-chloro-4-ethylpyridine-2-carbonyl)-1H-indol-3-yl]acetic acid;
methyl[5-chloro-2-(3-chloro-4-ethylpyridine-2-carbonyl)-1H-indol-3-yl]acetate;
[5-chloro-2-(3-chloro-4-ethylpyridine-2-carbonyl)-1H-indol-3-yl]acetic acid;
methyl[5-chloro-2-(4,6-dimethylpyridine-2-carbonyl)-1H-indol-3-yl]acetate;
[5-chloro-2-(4,6-dimethylpyridine-2-carbonyl)-1H-indol-3-yl]acetic acid;

methyl[6-chloro-2-(4,6-dimethylpyridine-2-carbonyl)-1H-indol-3-yl]acetate;
[6-chloro-2-(4,6-dimethylpyridine-2-carbonyl)-1H-indol-3-yl]acetic acid;
methyl[5,6-dichloro-2-(4-methylpyridine-2-carbonyl)-1H-indol-3-yl]acetate;
[5,6-dichloro-2-(4-methylpyridine-2-carbonyl)-1H-indol-3-yl]acetic acid;
methyl[5-methyl-2-(4-methylpyridine-2-carbonyl)-1H-indol-3-yl]acetate;
[5-methyl-2-(4-methylpyridine-2-carbonyl)-1H-indol-3-yl]acetic acid;
methyl[5-fluoro-2-(4-methylpyridine-2-carbonyl)-1H-indol-3-yl]acetate;
[5-fluoro-2-(4-methylpyridine-2-carbonyl)-1H-indol-3-yl]acetic acid;
methyl[5-methoxy-2-(4-methylpyridine-2-carbonyl)-1H-indol-3-yl]acetate;
[5-methoxy-2-(4-methylpyridine-2-carbonyl)-1H-indol-3-yl]acetic acid;
methyl[6-methoxy-2-(4-methylpyridine-2-carbonyl)-1H-indol-3-yl]acetate;
[6-methoxy-2-(4-methylpyridine-2-carbonyl)-1H-indol-3-yl]acetic acid;
methyl[5-ethyl-2-(4-methylpyridine-2-carbonyl)-1H-indol-3-yl]acetate;
[5-ethyl-2-(4-methylpyridine-2-carbonyl)-1H-indol-3-yl]acetic acid;
methyl[5-ethyl-2-(4-ethylpyridine-2-carbonyl)-1H-indol-3-yl]acetate;
[5-ethyl-2-(4-ethylpyridine-2-carbonyl)-1H-indol-3-yl]acetic acid;
methyl[6-ethyl-2-(4-methylpyridine-2-carbonyl)-1H-indol-3-yl]acetate;
[6-ethyl-2-(4-methylpyridine-2-carbonyl)-1H-indol-3-yl]acetic acid;
methyl[5-isopropyl-2-(4-methylpyridine-2-carbonyl)-1H-indol-3-yl]acetate;
[5-isopropyl-2-(4-methylpyridine-2-carbonyl)-1H-indol-3-yl]acetic acid;
methyl[2-(4-methylpyridine-2-carbonyl)-6-trifluoromethyl-1H-indol-3-yl]acetate;
[2-(4-methylpyridine-2-carbonyl)-6-trifluoromethyl-1H-indol-3-yl]acetic acid;
methyl[5-tert-butyl-2-(4-methylpyridine-2-carbonyl)-1H-indol-3-yl]acetate;
[5-tert-butyl-2-(4-methylpyridine-2-carbonyl)-1H-indol-3-yl]acetic acid;
methyl[2-(4-methylpyridine-2-carbonyl)-5-trifluoromethoxy-1H-indol-3-yl]acetate;
[2-(4-methyl-2-pyridine-2-carbonyl)-5-trifluoromethoxy-1H-indol-3-yl]acetic acid;
methyl[2-(4-ethylpyridine-2-carbonyl)-5-trifluoromethoxy-1H-indol-3-yl]acetate;
[2-(4-ethylpyridine-2-carbonyl)-5-trifluoromethoxy-1H-indol-3-yl]acetic acid;
methyl[6-methyl-2-(4-methylpyridine-2-carbonyl)-1H-indol-3-yl]acetate;
[6-methyl-2-(4-methylpyridine-2-carbonyl)-1H-indol-3-yl]acetic acid;
methyl[2-(4-methylpyridine-2-carbonyl)-5-trifluoromethyl-1H-indol-3-yl]acetate;
[2-(4-methylpyridine-2-carbonyl)-5-trifluoromethyl-1H-indol-3-yl]acetic acid;
methyl[2-(4-ethylpyridine-2-carbonyl)-5-trifluoromethyl-1H-indol-3-yl]acetate;
[2-(4-ethylpyridine-2-carbonyl)-5-trifluoromethyl-1H-indol-3-yl]acetic acid;
methyl(2-benzoyl-1H-indol-3-yl)acetate;
(2-benzoyl-1H-indol-3-yl)acetic acid;
methyl[2-(4-chlorobenzoyl)-6-methyl-1H-indol-3-yl]acetate;
[2-(4-chlorobenzoyl)-6-methyl-1H-indol-3-yl]acetic acid;
[2-(4-chlorobenzoyl)-5-methyl-1H-indol-3-yl]acetic acid;
methyl[6-methoxy-2-(4-chlorobenzoyl)-1H-indol-3-yl]acetate;
[6-methoxy-2-(4-chlorobenzoyl)-1H-indol-3-yl]acetic acid;
[2-(4-chlorobenzoyl)-6-trifluoromethyl-1H-indol-3-yl]acetic acid;
methyl[2-(4-chlorobenzoyl)-5-ethyl-1H-indol-3-yl]acetate;
[2-(4-chlorobenzoyl)-5-ethyl-1H-indol-3-yl]acetic acid;
methyl[2-(4-chlorobenzoyl)-5-methoxy-1H-indol-3-yl]acetate;
[2-(4-chlorobenzoyl)-5-methoxy-1H-indol-3-yl]acetic acid;
methyl[2-(4-chlorobenzoyl)-5-isopropyl-1H-indol-3-yl]acetate;
[2-(4-chlorobenzoyl)-5-isopropyl-1H-indol-3-yl]acetic acid;
methyl[2-(4-chlorobenzoyl)-5-trifluoromethyl-1H-indol-3-yl]acetate;
[2-(4-chlorobenzoyl)-5-trifluoromethyl-1H-indol-3-yl]acetic acid;
methyl[2-(4-chlorobenzoyl)-5-trifluoromethoxy-1H-indol-3-yl]acetate;
[2-(4-chlorobenzoyl)-5-trifluoromethoxy-1H-indol-3-yl]acetic acid;
methyl[6-chloro-2-(2-methoxybenzoyl)-1H-indol-3-yl]acetate;
[6-chloro-2-(2-methoxybenzoyl)-1H-indol-3-yl]acetic acid;
methyl[6-chloro-2-(3-methoxybenzoyl)-1H-indol-3-yl]acetate;
[6-chloro-2-(3-methoxybenzoyl)-1H-indol-3-yl]acetic acid;
methyl[6-chloro-2-(3-yoxybylenzoyl)-1H-indol-3-yl]acetate;
[6-chloro-2-(3-benzyloxybenzoyl)-1H-indol-3-yl]acetic acid;
methyl[6-chloro-2-(3-hydroxybenzoyl)-1H-indol-3-yl]acetate;
[6-chloro-2-(3-hydroxybenzoyl)-1H-indol-3-yl]acetic acid;
methyl[6-chloro-2-(4-benzoxybenzyloyl)-1H-indol-3-yl]acetate;
[6-chloro-2-(4-benzyloxybenzoyl)-1H-indol-3-yl]acetic acid;
methyl[6-chloro-2-(4-hydroxybenzoyl)-1H-indol-3-yl]acetate;

[6-chloro-2-(4-hydroxybenzoyl)-1H-indol-3-yl]acetic acid;
methyl[6-chloro-2-(4-isopropoxybenzoyl)-1H-indol-3-yl]acetate;
[6-chloro-2-(4-isopropoxybenzoyl)-1H-indol-3-yl]acetic acid;
methyl[6-chloro-2-(4-phenylbenzoyl)-1H-indol-3-yl]acetate;
[6-chloro-2-(4-phenylbenzoyl)-1H-indol-3-yl]acetic acid;
methyl[6-chloro-2-(4-trifluoromethoxybenzoyl)-1H-indol-3-yl]acetate;
[6-chloro-2-(4-trifluoromethoxybenzoyl)-1H-indol-3-yl]acetic acid;
methyl[5-chloro-2-(4-trifluoromethoxybenzoyl)-1H-indol-3-yl]acetate;
[5-chloro-2-(4-trifluoromethoxybenzoyl)-1H-indol-3-yl]acetic acid;
methyl[5-chloro-2-(4-methoxybenzoyl)-1H-indol-3-yl]acetate;
[5-chloro-2-(4-methoxybenzoyl)-1H-indol-3-yl]acetic acid;
methyl(6-chloro-2-(4-nitrobenzoyl)-1H-indol-3-yl]acetate;
[6-chloro-2-(4-nitrobenzoyl)-1H-indol-3-yl]acetic acid;
methyl[6-chloro-2-[(4-methylsulfonyl)benzoyl]-1H-indol-3-yl]acetate;
[6-chloro-2-[(4-methylsulfonyl)benzoyl]-1H-indol-3-yl]acetic acid;
methyl(6-chloro-2-[4-(methylsulfonylamino)benzoyl]-1H-indol-3-yl]acetate;
[6-chloro-2-[4-(methylsulfonylamino)benzoyl]-1H-indol-3-yl]acetic acid;
[6-chloro-2-(2-chlorobenzoyl)-1H-indol-3-yl]acetic acid;
[6-chloro-2-(2,4-dichlorobenzoyl)-1H-indol-3-yl]acetic acid;
methyl[6-chloro-2-(4-chloro-3-fluorobenzoyl)-1H-indol-3-yl]acetate;
[6-chloro-2-(4-chloro-3-fluorobenzoyl)-1H-indol-3-yl]acetic acid;
methyl[6-chloro-2-(4-cyanobenzoyl)-1H-indol-3-yl]acetate;
methyl[6-chloro-2-[4-bromobenzoyl]-1H-indol-3-yl]acetate;
methyl[6-chloro-2-[4-(2-thienyl)benzoyl]-1H-indol-3-yl]acetate;
[6-chloro-2-[4-(2-thienyl)benzoyl]-1H-indol-3-yl]acetic acid;
methyl[6-chloro-2-[4-(2-furyl)benzoyl]-1H-indol-3-yl]acetate;
[6-chloro-2-[4-(2-furyl)benzoyl]-1H-indol-3-yl]acetic acid;
methyl[6-chloro-2-[4-(3-pyridyl)benzoyl]-1H-indol-3-yl]acetate;
[6-chloro-2-[4-(3-pyridyl)benzoyl]-1H-indol-3-yl]acetic acid;
methyl[6-chloro-2-[4-(2-thiazolyl)benzoyl]-1H-indol-3-yl]acetate;
[6-chloro-2-[4-(2-thiazolyl)benzoyl]-1H-indol-3-yl]acetic acid;
methyl[6-chloro-2-(3-bromobenzoyl)-1H-indol-3-yl]acetate;
methyl[6-chloro-2-[3-(2-furyl)benzoyl]-1H-indol-3-yl]acetate;
[6-chloro-2-[3-(2-furyl)benzoyl]-1H-indol-3-yl]acetic acid;
methyl dl-2-[6-chloro-2-(4-chlorobenzoyl)-1H-indol-3-yl]propionate;
dl-2-[2-(4-chlorobenzoyl)-6-chloro-1H-indol-3-yl]propionic acid;
methyl[5-chloro-2-(isoquinoline-3-carbonyl)-1H-indol-3-yl]acetate;
[5-chloro-2-(isoquinoline-3-carbonyl)-1H-indol-3-yl]acetic acid;
methyl[6-chloro-2-(isoquinoline-3-carbonyl)-1H-indol-3-yl]acetate;
[6-chloro-2-(isoquinoline-3-carbonyl)-1H-indol-3-yl]acetic acid;
methyl[5-chloro-2-(5-methylisoxazole-3-carbonyl)-1H-indol-3-yl]acetate;
[5-chloro-2-(5-methylisoxazole-3-carbonyl)-1H-indol-3-yl]acetic acid;
methyl[6-chloro-2-(5-methylisoxazole-3-carbonyl)-1H-indol-3-yl]acetate;
[6-chloro-2-(5-methylisoxazole-3-carbonyl)-1H-indol-3-yl]acetic acid;
methyl[5-chloro-2-(4-methyl-1,2,3-thiadiazole-5-carbonyl)-1H-indol-3-yl]acetate;
[5-chloro-2-(4-methyl-1,2,3-thiadiazole-5-carbonyl)-1H-indol-3-yl]acetic acid;
methyl[6-chloro-2-(4-methyl-1,2,3-thiadiazole-5-carbonyl)-1H-indol-3-yl]acetate;
[6-chloro-2-(4-methyl-1,2,3-thiadiazole-5-carbonyl)-1H-indol-3-yl]acetic acid;
methyl[5-chloro-2-(5-methylthiazole-2-carbonyl)-1H-indol-3-yl]acetate;
[5-chloro-2-(5-methylthiazole-2-carbonyl)-1H-indol-3-yl]acetic acid;
methyl[6-chloro-2-(5-methylthiazole-2-carbonyl)-1H-indol-3-yl]acetate;
[6-chloro-2-(5-methylthiazole-2-carbonyl)-1H-indol-3-yl]acetic acid;
[6-chloro-2-(2-thienyl)carbonylindol-3-yl]acetic acid;
methyl[6-chloro-2-[3-(1-hydroxy-1-methylethyl)-2-furoyl]-1H-indol-3-yl]acetate;
[6-chloro-2-[3-(1-hydroxy-1-methylethyl)-2-furoyl]-1H-indol-3-yl]acetic acid;
methyl[6-chloro-2-[3-methoxymethyl-2-furoyl]-1H-indol-3-yl]acetate;
[6-chloro-2-[3-methoxymethyl-2-furoyl]-1H-indol-3-yl]acetic acid;
[6-chloro-2-(1-methylimidazole-2-carbonyl)-1H-indol-3-yl]acetic acid;
methyl[6-chloro-2-(1-methylimidazole-2-carbonyl)-1H-indol-3-yl]acetate;
methyl[5-chloro-2-(1-methylimidazole-2-carbonyl)-1H-indol-3-yl]acetate;
[5-chloro-2(1-methylimidazole-2-carbonyl)-1H-indol-3-yl]acetic acid;
methyl[5-chloro-2-(imidazole-2-carbonyl)-1H-indol-3-yl]acetate;
[5-chloro -2-(imidazole-2-carbonyl)-1H-indol-3-yl]acetic acid;

methyl[6-chloro-2-(imidazole-2-carbonyl)-1H-indol-3-yl]acetate;
[6-chloro -2-(imidazole-2-carbonyl)-1H-indol-3-yl]acetic acid;
methyl[5-chloro-2-(4-methylthiazole-2-carbonyl)-1H-indol-3-yl]acetate;
[5-chloro-2-(4-methylthiazole-2-carbonyl)-1H-indol-3-yl]acetic acid;
methyl[5-chloro-2-(1-methylpyrrole-2-carbonyl)-1H-indol-3-yl]acetate;
[5-chloro-2-(1-methylpyrrole-2-carbonyl)-1H-indol-3-yl]acetic acid;
methyl[5-chloro-2-(2-methylimidazole-4-carbonyl)-1H-indol-3-yl]acetate;
[5-chloro-2-(2-methylimidazole-4-carbonyl)-1H-indol-3-yl]acetic acid;
methyl[5-chloro-2-(thiazole-5-carbonyl)-1H-indol-3-yl]acetate;
[5-chloro-2-(thiazole-5-carbonyl)-1H-indol-3-yl]acetic acid;
methyl[6-chloro-2-(4-methylthiazole-2-carbonyl)-1H-indol-3-yl]acetate;
[6-chloro-2-(4-methylthiazole-2-carbonyl)-1H-indol-3-yl]acetic acid;
methyl[5-chloro-2-[3-(ethoxycarbonyl)isoxazole-5-carbonyl]-1H-indol-3-yl]acetate;
[5-chloro-2-[3-(carboxy)isoxazole-5-carbonyl]-1H-indol-3-yl]acetic acid;
methyl[6-chloro-2-cyclopropanecarbonyl-1H-indol-3-yl]acetate;
[6-chloro-2-cyclopropanecarbonyl-1H-indol-3-yl]acetic acid;
methyl[6-chloro-2-cyclobutanecarbonyl-1H-indol-3-yl]acetate;
[6-chloro-2-cyclobutanecarbonyl-1H-indol-3-yl]acetic acid;
methyl[5-(tert-butyl)-2-(4-chlorobenzoyl)-1H-indol-3-yl]acetate;
[5-(tert-butyl)-2-(4-chlorobenzoyl)-1H-indol-3-yl]acetic acid;
[6-chloro-2-(4-methylpyridine-2-carbonyl)-1H-indol-3-yl]-N,N-dimethylacetamide;
[6-chloro-2-(4-methylpyridine-2-carbonyl)-1H-indol-3-yl]-N-methylacetamide;
[5-chloro-2-(4-methylpyridine-2-carbonyl)-1H-indol-3-yl]-N-(2-hydroxyethyl)acetamide;
[5-chloro-2-(4-methylpyridine-2-carbonyl)-1H-indol-3-yl]-N-methoxyacetamide;
2-[5-chloro-2-(4-methylpyridine-2-carbonyl)-1H-indol-3-yl]-1-piperazinyl-1-ethanone;
[5-chloro-2-(4-methylpyridine-2-carbonyl)-1H-indol-3-yl]-N-(2-aminoethyl)acetamide;
2-[5-chloro-2-(4-methylpyridine-2-carbonyl)-1H-indol-3-yl]-1-(3-amino-1-pyrrolidinyl)-1-ethanone;
[6-chloro-2-(4-chlorobenzoyl)-5-fluoro-1H-indol-3-yl]acetic acid;
methyl[6-chloro-5-fluoro-2-(4-methylpyridine-2-carbonyl)-1H-indol-3-yl]acetate;
[6-chloro-5-fluoro-2-(4-methylpyridine-2-carbonyl)-1H-indol-3-yl]acetic acid;
methyl[6-chloro-2-[4-(1-hydroxyethyl)pyridine-2-carbonyl]-1H-indol-3-yl]acetate;
[6-chloro-2-[4-(1-hydroxyethyl)pyridine-2-carbonyl]-1H-indol-3-yl]acetic acid;
[6-chloro-2-(4-ethyl-3-fluoropyridine-2-carbonyl)-1H-indol-3-yl]acetic acid;
[6-chloro-2-(2-nitrobenzoyl)-1H-indol-3-yl]acetic acid;
[6-chloro-2-(2,4-dimethoxybenzoyl)-1H-indol-3-yl]acetic acid;
[6-chloro-2-(4-difuluoromethoxybenzoyl)-1H-indol-3-yl]acetic acid;
[6-chloro-2-(2,5-dimethoxybenzoyl)-1H-indol-3-yl]acetic acid;
methyl[5-acetyl-2-(4-chlorobenzoyl)-1H-indol-3-yl]acetate;
[5-acetyl-2-(4-chlorobenzoyl)-1H-indol-3-yl]acetic acid;
methyl[6-chloro-2-(4-chlorobenzoyl)-5-fluoro-1H-indol-3-yl]acetate;
methyl[6-fluoro-2-(4-methylpyridine-2-carbonyl]-1H-indol-3-yl]acetate;
[6-fluoro-2-(4-methylpyridine-2-carbonyl)-1H-indol-3-yl]acetic acid;
methyl[6-fluoro-2-(4-chlorobenzoyl)-1H-indol-3-yl]acetate;
[6-fluoro-2-(4-chlorobenzoyl)-1H-indol-3-yl]acetic acid;
[2-(4-methylpyridine-2-carbonyl)-5-methylthio-1H-indol-3-yl]acetic acid;
[2-(4-methylpyridine-2-carbonyl)-5-methylthio-1H-indol-3-yl]acetic acid, and a salt thereof.

11. A compound according to claim 1 selected from
(2-benzoyl-6-chloro-1H-indol-3-yl)acetic acid;
[6-chloro-2-(3-chlorobenzoyl)-1H-indol-3-yl]acetic acid;
[6-chloro-2-(4-chlorobenzoyl)-1H-indol-3-yl]acetic acid;
[5-chloro-2-(4-chlorobenzoyl)-1H-indol-3-yl]acetic acid;
[5-chloro-2-(3-chlorobenzoyl)-1H-indol-3-yl]acetic acid;
[2-(4-chlorobenzoyl)-5-fluoro-1H-indol-3-yl]acetic acid;
(2-benzoyl-5,6-dichloro-1H-indol-3-yl)acetic acid;
[6-chloro-2-(4-methylpyridine-2-carbonyl)-1H-indol-3-yl]acetic acid;
[6-chloro-2-(5-methylpyridine-2-carbonyl)-1H-indol-3-yl]acetic acid;
methyl[6-chloro-2-(4-chloropyridine-2-carbonyl)-1H-indol-3-yl]acetate;
[6-chloro-2-(4-chloropyridine-2-carbonyl)-1H-indol-3-yl]acetic acid;
[6-chloro-2-(pyridine-2-carbonyl)-1H-indol-3-yl]acetic acid;
[5-chloro-2-(4-methylpyridine-2-carbonyl)-1H-indol-3-yl]acetic acid;
[6-chloro-2-(4-ethylpyridine-2-carbonyl)-1H-indol-3-yl]acetic acid;
methyl[5-chloro-2-(4-ethylpyridine-2-carbonyl)-1H-indol-3-yl]acetate;
[5-chloro-2-(4-ethylpyridine-2-carbonyl)-1H-indol-3-yl]acetic acid;
methyl[6-chloro-2-(4-isopropylpyridine-2-carbonyl)-1H-indol-3-yl]acetate;
[6-chloro-2-(4-isopropylpyridine-2-carbonyl)-1H-indol-3-yl]acetic acid;
methyl[6-chloro-2-(4-propylpyridine-2-carbonyl)-1H-indol-3-yl]acetate;
[6-chloro-2-(4-propylpyridine-2-carbonyl)-1H-indol-3-yl]acetic acid;

methyl[5-methyl-2-(4-methylpyridine-2-carbonyl)-1H-indol-3-yl]acetate;
[5-methyl-2-(4-methylpyridine-2-carbonyl)-1H-indol-3-yl]acetic acid;
methyl[2-(4-ethylpyridine-2-carbonyl)-5-trifluoromethyl-1H-indol-3-yl]acetate;
[2-(4-ethylpyridine-2-carbonyl)-5-trifluoromethyl-1H-indol-3-yl]acetic acid;
methyl[6-chloro-2-(4-methoxybenzoyl)-1H-indol-3-yl]acetate;
[6-chloro-2-(4-methoxybenzoyl)-1H-indol-3-yl]acetic acid;
methyl[5-chloro-2-(4-chloropyridine-2-carbonyl)-1H-indol-3-yl]acetate;
[5-chloro-2-(4-chloropyridine-2-carbonyl)-1H-indol-3-yl]acetic acid;
methyl[6-chloro-2-(4-methoxypyridine-2-carbonyl)-1H-indol-3-yl]acetate;
[6-chloro-2-(4-methoxypyridine-2-carbonyl)-1H-indol-3-yl]acetic acid;
methyl[5-chloro-2-(4-ethyl-3-fluoropyridine-2-carbonyl)-1H-indol-3-yl]acetate;
[5-chloro-2-(4-ethyl-3-fluoropyridine-2-carbonyl)-1H-indol-3-yl]acetatic acid;
methyl[5-fluoro-2-(4-methylpyridine-2-carbonyl)-1H-indol-3-yl]acetate;
[5-fluoro-2-(4-methylpyridine-2-carbonyl)-1H-indol-3-yl]acetic acid;
methyl[5-chloro-2-(4-methoxybenzoyl)-1H-indol-3-yl]acetate;
[5-chloro-2-(4-methoxybenzoyl)-1H-indol-3-yl]acetic acid;
methyl[6-chloro-2-(isoquinoline-3-carbonyl)-1H-indol-3-yl]acetate;
[6-chloro-2-(isoquinoline-3-carbonyl)-1H-indol-3-yl]acetic acid;
[6-chloro-5-fluoro-2-(4-methylpyridine-2-carbonyl)-1H-indol-3-yl]acetic acid;
methyl[6-chloro-2-[4-(1-hydroxyethyl)pyridine-2-carbonyl]-1H-indol-3-yl]acetate;
[6-chloro-2-[4-(1-hydroxyethyl)pyridine-2-carbonyl]-1H-indol-3-yl]acetic acid;
[6-chloro-2-(4-ethyl-3-fluoropyridine-2-carbonyl)-1H-indol-3-yl]acetic acid;
methyl[6-chloro-2-(5-chloropyridine-2-carbonyl)-1H-indol-3-yl]acetate;
[6-chloro-2-(5-chloropyridine-2-carbonyl)-1H-indol-3-yl]acetic acid;
methyl[6-methyl-2-(4-methylpyridine-2-carbonyl)-1H-indol-3-yl]acetate;
[6-methyl-2-(4-methylpyridine-2-carbonyl)-1H-indol-3-yl]acetic acid;
methyl[5-chloro-2-(isoquinoline-3-carbonyl)-1H-indol-3-yl]acetate;
[5-chloro-2-(isoquinoline-3-carbonyl)-1H-indol-3-yl]acetic acid;
[6-chloro-2-(4-chlorobenzoyl)-5-fluoro-1H-indol-3-yl]acetic acid;
methyl[6-chloro-5-fluoro-2-(4-methylpyridine-2-carbonyl)-1H-indol-3-yl]acetate, and a salt thereof.

12. A compound according to claim 10, selected from (2-benzoyl-6-chloro-1H-indol-3-yl)acetic acid;
[6-chloro-2-(3-chlorobenzoyl)-1H-indol-3-yl]acetic acid;
[6-chloro-2-(4-chlorobenzoyl)-1H-indol-3-yl]acetic acid;
[5-chloro-2-(4-chlorobenzoyl)-1H-indol-3-yl]acetic acid;
[5-chloro-2-(3-chlorobenzoyl)-1H-indol-3-yl]acetic acid;
[2-(4-chlorobenzoyl)-5-fluoro-1H-indol-3-yl]acetic acid;
(2-benzoyl-5,6-dichloro-1H-indol-3-yl)acetic acid;
[6-chloro-2-(4-methylpyridine-2-carbonyl)-1H-indol-3-yl]acetic acid;
[6-chloro-2-(5-methylpyridine-2-carbonyl)-1H-indol-3-yl]acetic acid;
[6-chloro-2-(4-chloropyridine-2-carbonyl)-1H-indol-3-yl]acetic acid;
[6-chloro-2-(pyridine-2-carbonyl)-1H-indol-3-yl]acetic acid;
[5-chloro-2-(4-methylpyridine-2-carbonyl)-1H-indol-3-yl]acetic acid;
[6-chloro-2-(4-ethylpyridine-2-carbonyl)-1H-indol-3-yl]acetic acid;
[5-chloro-2-(4-ethylpyridine-2-carbonyl)-1H-indol-3-yl]acetic acid;
[6-chloro-2-(4-isopropylpyridine-2-carbonyl)-1H-indol-3-yl]acetic acid;
[6-chloro-2-(4-propylpyridine-2-carbonyl)-1H-indol-3-yl]acetic acid;
[5-methyl-2-(4-methylpyridine-2-carbonyl)-1H-indol-3-yl]acetic acid;
[2-(4-ethylpyridine-2-carbonyl)-5-trifluoromethyl-1H-indol-3-yl]acetic acid;
[6-chloro-2-(4-methoxybenzoyl)-1H-indol-3-yl]acetic acid;
[5-chloro-2-(4-chloropyridine-2-carbonyl)-1H-indol-3-yl]acetic acid;
[6-chloro-2-(4-methoxypyridine-2-carbonyl)-1H-indol-3-yl]acetic acid;
[5-chloro-2-(4-ethyl-3-fluoropyridine-2-carbonyl)-1H-indol-3-yl]acetic acid;
[5-fluoro-2-(4-methylpyridine-2-carbonyl)-1H-indol-3-yl]acetic acid;
[5-chloro-2-(4-methoxybenzoyl)-1H-indol-3-yl]acetic acid;
[6-chloro-2-(isoquinoline-3-carbonyl)-1H-indol-3-yl]acetic acid;
[6-chloro-2-[4-(1-hydroxyethyl)pyridine-2-carbonyl]-1H-indol-3-yl]acetic acid;
[6-chloro-2-(4-ethyl-3-fluoropyridine-2-carbonyl)-1H-indol-3-yl]acetic acid;
[6-chloro-2-(5-chloropyridine-2-carbonyl)-1H-indol-3-yl]acetic acid;
[6-methyl-2-(4-methylpyridine-2-carbonyl)-1H-indol-3-yl]acetic acid;
[5-chloro-2-(isoquinoline-3-carbonyl)-1H-indol-3-yl]acetic acid;
[6-chloro-2-(4-chlorobenzoyl)-5-fluoro-1H-indol-3-yl]acetic acid,
and a salt thereof.

13. A pharmaceutical composition useful for the treatment of a medical condition in which prostaglandins are, implicated as pathogens, which comprises a compound of the formula (I) of claim 1, and a pharmaceutically inert carrier.

14. A method for the treatment of a medical condition in which prostaglandins are implicated as pathogens, in a mammalian subject, which comprises administering to said subject a pharmaceutical composition according to claim 13, wherein said medical condition is selected from the group consisting of pain, fever and inflammation associated with rheumatic fever, symptoms associated with influenza or other viral infections, common cold, low back and neck pain, dysmenorrhea, headache, toothache, sprains and strains, myositis, neuralgia, synovitis, arthritis including rheumatoid arthritis, degenerative joint disease including osteoarthritis, gout, ankylosing spondylitis, systemic lupus erythematosus, juvenile arthritis, bursitis, burns, and injury following surgical and dental procedures.

* * * * *